US012807722B2

(12) United States Patent
Mimoto et al.

(10) Patent No.: US 12,807,722 B2
(45) Date of Patent: Nov. 24, 2026

(54) Fc-γ-RIIb-SPECIFIC Fc ANTIBODY

(71) Applicant: Chugai Seiyaku Kabushiki Kaisha, Tokyo (JP)

(72) Inventors: Futa Mimoto, Shizuoka (JP); Taichi Kuramochi, Shizuoka (JP); Tomoyuki Igawa, Shizuoka (JP); Hitoshi Katada, Shizuoka (JP); Shojiro Kadono, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 825 days.

(21) Appl. No.: 17/846,672

(22) Filed: Jun. 22, 2022

(65) Prior Publication Data

US 2023/0174655 A1 Jun. 8, 2023

Related U.S. Application Data

(62) Division of application No. 14/001,218, filed as application No. PCT/JP2012/054624 on Feb. 24, 2012, now abandoned.

(30) Foreign Application Priority Data

Feb. 25, 2011 (JP) ................................ 2011-040923
Oct. 4, 2011 (JP) ................................ 2011-219835

(51) Int. Cl.

*C07K 16/00* (2006.01)
*C07K 16/08* (2006.01)
*C07K 16/18* (2006.01)
*C07K 16/28* (2006.01)
*C07K 16/30* (2006.01)

(52) U.S. Cl.

CPC .......... *C07K 16/2866* (2013.01); *C07K 16/08* (2013.01); *C07K 16/18* (2013.01); *C07K 16/303* (2013.01); *C07K 2317/524* (2013.01); *C07K 2317/72* (2013.01)

(58) Field of Classification Search

None
See application file for complete search history.

(56) References Cited

U.S. PATENT DOCUMENTS 4,689,299 A 8/1987 Insel et al.
5,585,089 A 12/1996 Queen et al.
5,827,733 A 10/1998 Lee et al.
5,994,524 A 11/1999 Matsushima et al.
6,024,956 A 2/2000 Matsushima et al.
6,025,158 A 2/2000 Gonzalez et al.
6,096,506 A 8/2000 Lee et al.
6,165,745 A 12/2000 Ward et al.
6,245,894 B1 6/2001 Matsushima et al.
6,344,443 B1 2/2002 Liu et al.
6,458,355 B1 10/2002 Hsei et al.
6,737,056 B1 5/2004 Presta
6,821,505 B2 11/2004 Ward
7,247,302 B1 7/2007 Rosok et al.
7,261,893 B2 8/2007 Geertruida et al.
7,282,568 B2 10/2007 Teeling et al.
7,317,091 B2 1/2008 Lazar et al.
7,320,789 B2 1/2008 Aghajanian et al.
7,371,826 B2 5/2008 Presta
7,632,499 B2 12/2009 Davies et al.
7,662,377 B2 2/2010 Umana et al.
7,662,925 B2 2/2010 Lazar et al.
7,670,600 B2 3/2010 Dall Acqua et al.
7,785,791 B2 8/2010 Presta (Continued)

FOREIGN PATENT DOCUMENTS

AU 2010206050 8/2010
AU 2011244851 11/2011

(Continued)

OTHER PUBLICATIONS

U.S. Appl. No. 18/450,863, Kakiuchi et al., filed Aug. 16, 2023.

(Continued)

*Primary Examiner* — Chun W Dahle
(74) *Attorney, Agent, or Firm* — Fish & Richardson P.C.

(57) ABSTRACT

An objective of the present invention is to provide a polypeptide containing an Fc region having maintained or decreased binding activities towards both allotypes of FcγRIIa, types H and R, and having enhanced FcγRIIb-binding activity in comparison with a parent polypeptide; a pharmaceutical composition containing the polypeptide; an agent for treating or preventing immunological inflammatory diseases that includes the pharmaceutical composition; a production method thereof; and a method for maintaining or decreasing binding activities towards both allotypes of FcγRIIa and enhancing the FcγRIIb-binding activity. Specifically, it is found that a polypeptide containing an antibody Fc region that has an alteration of substituting Pro at position 238 (EU numbering) with Asp or Leu at position 328 (EU numbering) with Glu enhances FcγRIIb-binding activity, and maintains or decreases binding activities towards both allotypes of FcγRIIa, types H and R. It is also found that a polypeptide containing an antibody Fc region that contains an alteration of substituting Pro at position 238 (EU numbering) with Asp and several other alterations, enhances FcγRIIb-binding activity, and maintains or decreases binding activities towards both allotypes of FcγRIIa, types H and R.

18 Claims, 16 Drawing Sheets

Specification includes a Sequence Listing.

(56) References Cited

U.S. PATENT DOCUMENTS

| | | | |
|---|---|---|---|
| 7,807,159 B2 | 10/2010 | Chin et al. | |
| 7,888,486 B2 | 2/2011 | Walsh et al. | |
| 7,951,917 B1 | 5/2011 | Arathoon et al. | |
| 7,960,512 B2 | 6/2011 | Stavenhagen et al. | |
| 8,101,720 B2 | 1/2012 | Lazar et al. | |
| 8,147,829 B2 | 4/2012 | Hariharan et al. | |
| 8,323,962 B2 | 12/2012 | Dall Acqua et al. | |
| 8,415,459 B2 | 4/2013 | Vallie et al. | |
| 8,524,867 B2 | 9/2013 | Bernett et al. | |
| 8,592,562 B2 | 11/2013 | Kannan et al. | |
| 8,604,174 B2 | 12/2013 | Babcook et al. | |
| 8,637,641 B2 | 1/2014 | Dahiyat et al. | |
| 8,735,545 B2 | 5/2014 | Lazar et al. | |
| 8,753,629 B2 | 6/2014 | Lazar et al. | |
| 8,802,820 B2 | 8/2014 | Chamberlain et al. | |
| 8,802,823 B2 | 8/2014 | Lazar et al. | |
| 9,029,515 B2 | 5/2015 | Pons et al. | |
| 9,051,373 B2 * | 6/2015 | Lazar | C07K 16/32 |
| 9,079,949 B1 | 7/2015 | Andrien, Jr. et al. | |
| 9,107,861 B1 | 8/2015 | Andrien, Jr. et al. | |
| 9,200,060 B2 | 12/2015 | Kannan et al. | |
| 9,605,061 B2 | 3/2017 | Lazar et al. | |
| 9,890,218 B2 | 2/2018 | Mimoto et al. | |
| 9,969,800 B2 | 5/2018 | Igawa et al. | |
| 10,000,560 B2 | 6/2018 | Ruike et al. | |
| 10,519,229 B2 | 12/2019 | Igawa et al. | |
| 10,738,111 B2 | 8/2020 | Ruike et al. | |
| 10,766,960 B2 | 9/2020 | Igawa et al. | |
| 10,919,953 B2 * | 2/2021 | Katada | A61P 29/00 |
| 11,053,308 B2 | 7/2021 | Kakiuchi et al. | |
| 11,142,563 B2 | 10/2021 | Igawa et al. | |
| 11,180,548 B2 | 11/2021 | Igawa et al. | |
| 11,267,868 B2 | 3/2022 | Mimoto et al. | |
| 11,359,009 B2 | 6/2022 | Ruike et al. | |
| 11,454,633 B2 | 9/2022 | Ruike et al. | |
| 11,780,912 B2 | 10/2023 | Kakiuchi et al. | |
| 11,820,793 B2 | 11/2023 | Igawa et al. | |
| 12,304,960 B2 * | 5/2025 | Igawa | A61K 47/6849 |
| 2002/0082396 A1 | 6/2002 | Matsushima et al. | |
| 2003/0077283 A1 | 4/2003 | Ye | |
| 2004/0001822 A1 | 1/2004 | Levanon et al. | |
| 2004/0001839 A1 | 1/2004 | Levanon et al. | |
| 2004/0002450 A1 | 1/2004 | Lazarovits et al. | |
| 2004/0110226 A1 | 6/2004 | Lazar et al. | |
| 2005/0032114 A1 | 2/2005 | Hinton et al. | |
| 2005/0260213 A1 | 11/2005 | Koenig et al. | |
| 2006/0134709 A1 | 6/2006 | Stavenhagen et al. | |
| 2006/0140934 A1 | 6/2006 | Gegg et al. | |
| 2006/0275283 A1 | 12/2006 | Van Vlijmen et al. | |
| 2007/0190056 A1 | 8/2007 | Kambadur et al. | |
| 2007/0231329 A1 | 10/2007 | Lazar et al. | |
| 2007/0248602 A1 | 10/2007 | Lazar et al. | |
| 2008/0044417 A1 | 2/2008 | Johnson et al. | |
| 2008/0050370 A1 | 2/2008 | Glaser et al. | |
| 2008/0051563 A1 | 2/2008 | Lazar et al. | |
| 2008/0138349 A1 | 6/2008 | Stavenhagen et al. | |
| 2008/0181890 A1 | 7/2008 | Lazar et al. | |
| 2008/0199471 A1 | 8/2008 | Bernett et al. | |
| 2009/0035836 A1 | 2/2009 | Datta et al. | |
| 2009/0042291 A1 | 2/2009 | Chu et al. | |
| 2009/0053211 A9 | 2/2009 | Lazar et al. | |
| 2009/0076251 A1 | 3/2009 | Koenig et al. | |
| 2009/0136485 A1 | 5/2009 | Chu et al. | |
| 2009/0324589 A1 | 12/2009 | Igawa et al. | |
| 2010/0098730 A1 | 4/2010 | Lowman et al. | |
| 2010/0099147 A1 | 4/2010 | Hariharan et al. | |
| 2010/0129365 A1 | 5/2010 | Kim et al. | |
| 2010/0183621 A1 | 7/2010 | Jure-Kunkel et al. | |
| 2010/0184959 A1 | 7/2010 | Guler-Gane et al. | |
| 2010/0249482 A1 | 9/2010 | Chung et al. | |
| 2010/0298542 A1 * | 11/2010 | Igawa | A61P 29/00 530/387.3 |
| 2010/0316641 A1 | 12/2010 | Dimitrov | |
| 2010/0331527 A1 | 12/2010 | Davis et al. | |
| 2011/0021755 A1 | 1/2011 | Lazar et al. | |
| 2011/0059093 A1 | 3/2011 | Bohrmann et al. | |
| 2011/0105724 A1 | 5/2011 | Clegg et al. | |
| 2011/0111406 A1 | 5/2011 | Igawa et al. | |
| 2011/0135662 A1 | 6/2011 | Finney et al. | |
| 2011/0223658 A1 | 9/2011 | Beliard et al. | |
| 2011/0229489 A1 | 9/2011 | Pons et al. | |
| 2012/0093818 A1 | 4/2012 | Jackson et al. | |
| 2012/0149876 A1 | 6/2012 | Kreudenstein et al. | |
| 2012/0189639 A1 | 7/2012 | Schebye et al. | |
| 2012/0237498 A1 | 9/2012 | Ahrens et al. | |
| 2012/0244578 A1 | 9/2012 | Kannan et al. | |
| 2012/0301488 A1 | 11/2012 | Zhang et al. | |
| 2013/0085074 A1 | 4/2013 | Walker et al. | |
| 2013/0085265 A1 | 4/2013 | Jackson et al. | |
| 2013/0101581 A1 | 4/2013 | Kuramochi et al. | |
| 2013/0131319 A1 | 5/2013 | Igawa et al. | |
| 2013/0142788 A1 | 6/2013 | Ashman et al. | |
| 2013/0209489 A1 | 8/2013 | Han et al. | |
| 2013/0247234 A1 | 9/2013 | McWhirter et al. | |
| 2013/0259876 A1 | 10/2013 | Murphy et al. | |
| 2013/0302399 A1 | 11/2013 | Feldhaus et al. | |
| 2014/0044730 A1 | 2/2014 | Yancopoulos et al. | |
| 2014/0082760 A1 | 3/2014 | McWhirter et al. | |
| 2014/0093496 A1 | 4/2014 | Mimoto et al. | |
| 2014/0105889 A1 | 4/2014 | Igawa et al. | |
| 2014/0112914 A1 | 4/2014 | Nezu et al. | |
| 2014/0112926 A1 | 4/2014 | Liu | |
| 2014/0127209 A1 | 5/2014 | Grabstein et al. | |
| 2014/0199294 A1 | 7/2014 | Mimoto et al. | |
| 2014/0227292 A1 | 8/2014 | Flanagan et al. | |
| 2014/0234340 A1 | 8/2014 | Igawa et al. | |
| 2014/0271459 A1 | 9/2014 | Dutzar et al. | |
| 2014/0294833 A1 | 10/2014 | Desjarlais et al. | |
| 2014/0335089 A1 | 11/2014 | Igawa et al. | |
| 2014/0356371 A1 | 12/2014 | Swergold et al. | |
| 2014/0363426 A1 | 12/2014 | Moore et al. | |
| 2014/0363428 A1 | 12/2014 | Igawa et al. | |
| 2015/0050269 A1 | 2/2015 | Igawa et al. | |
| 2015/0079088 A1 | 3/2015 | Lowman et al. | |
| 2015/0166636 A1 | 6/2015 | Igawa et al. | |
| 2015/0166654 A1 | 6/2015 | Igawa et al. | |
| 2015/0203577 A1 | 7/2015 | Igawa et al. | |
| 2015/0210763 A1 | 7/2015 | Kuramochi et al. | |
| 2015/0252107 A1 | 9/2015 | Stevis et al. | |
| 2015/0299296 A1 | 10/2015 | Katada et al. | |
| 2015/0299313 A1 | 10/2015 | Igawa et al. | |
| 2015/0344570 A1 | 12/2015 | Igawa et al. | |
| 2015/0353630 A1 | 12/2015 | Igawa et al. | |
| 2016/0039912 A1 | 2/2016 | Mimoto et al. | |
| 2016/0046693 A1 | 2/2016 | Igawa et al. | |
| 2016/0053023 A1 | 2/2016 | Rosenthal et al. | |
| 2016/0090425 A1 | 3/2016 | Rosenthal et al. | |
| 2016/0200807 A1 | 7/2016 | Ruike et al. | |
| 2016/0229908 A1 | 8/2016 | Igawa et al. | |
| 2016/0229915 A1 | 8/2016 | Igawa et al. | |
| 2016/0326237 A1 | 11/2016 | Rosenthal et al. | |
| 2017/0022270 A1 | 1/2017 | Igawa et al. | |
| 2017/0181987 A1 | 6/2017 | Camilla et al. | |
| 2018/0155451 A1 | 6/2018 | Mimoto et al. | |
| 2018/0258161 A1 | 9/2018 | Igawa et al. | |
| 2019/0112393 A1 | 4/2019 | Igawa et al. | |
| 2020/0181257 A1 | 6/2020 | Kuramochi et al. | |
| 2020/0317768 A1 | 10/2020 | Ruike et al. | |
| 2021/0261648 A1 | 8/2021 | Katada et al. | |
| 2021/0301011 A1 | 9/2021 | Kakiuchi et al. | |
| 2022/0242934 A1 | 8/2022 | Igawa et al. | |
| 2022/0389118 A1 | 12/2022 | Igawa et al. | |
| 2022/0411483 A1 | 12/2022 | Mimoto et al. | |
| 2023/0140797 A1 | 5/2023 | Igawa et al. | |
| 2023/0257470 A1 | 8/2023 | Igawa et al. | |
| 2023/0416371 A1 | 12/2023 | Katada et al. | |
| 2024/0043515 A1 | 2/2024 | Katada et al. | |

FOREIGN PATENT DOCUMENTS

| | | |
|---|---|---|
| AU | 2014250434 | 10/2015 |
| AU | 2015227424 | 10/2015 |
| AU | 2012222252 | 8/2016 |
| CA | 2815266 | 5/2012 |

(56) References Cited

FOREIGN PATENT DOCUMENTS

| | | | |
|---|---|---|---|
| CA | 2827923 | | 8/2012 |
| CA | 2908350 | | 10/2014 |
| CN | 1156460 | | 8/1997 |
| CN | 1291198 | | 4/2001 |
| CN | 1763097 | | 2/2006 |
| CN | 101001873 | | 7/2007 |
| CN | 101014619 | | 8/2007 |
| CN | 101230102 | | 7/2008 |
| CN | 101277976 | | 10/2008 |
| CN | 101282992 | | 10/2008 |
| CN | 100455598 | | 1/2009 |
| CN | 101479381 | | 7/2009 |
| CN | 101511871 | | 8/2009 |
| CN | 101932593 | | 12/2010 |
| CN | 102056946 | | 5/2011 |
| CN | 102149729 | | 8/2011 |
| CN | 102325793 | | 1/2012 |
| CN | 102918057 | | 2/2013 |
| CN | 102993304 | | 3/2013 |
| CN | 103097415 | | 5/2013 |
| CN | 103221426 | | 7/2013 |
| CN | 103492565 | | 1/2014 |
| CN | 103827300 | | 5/2014 |
| CN | 103975060 | | 8/2014 |
| CN | 102633880 | | 2/2015 |
| CN | 107108726 | | 8/2017 |
| CN | 105102618 | A | 11/2025 |
| CO | 07124506 | | 11/2007 |
| CO | 11080753 | | 6/2011 |
| CO | 13047993 | | 3/2013 |
| CO | 15075851 | | 4/2015 |
| EA | 004317 | | 2/2004 |
| EA | 2008/01027 | | 10/2008 |
| EP | 0 770 628 | B | 9/2006 |
| EP | 1 992 692 | A | 11/2008 |
| EP | 2 006 381 | A | 12/2008 |
| EP | 2 196 541 | A | 6/2010 |
| EP | 2 202 245 | A | 6/2010 |
| EP | 2 275 443 | A | 1/2011 |
| EP | 2 368 911 | A | 9/2011 |
| EP | 2 409 990 | A | 1/2012 |
| EP | 2 431 393 | A | 3/2012 |
| EP | 2 471 813 | A | 7/2012 |
| EP | 2 552 955 | A | 2/2013 |
| EP | 2 647 706 | A | 10/2013 |
| EP | 2 679 681 | A | 1/2014 |
| EP | 2 698 431 | A | 2/2014 |
| EP | 2 728 002 | A | 5/2014 |
| EP | 1 509 770 | B | 7/2014 |
| EP | 2 760 890 | A | 8/2014 |
| EP | 2 762 166 | A | 8/2014 |
| EP | 2 762 493 | A | 8/2014 |
| EP | 2 762 564 | A | 8/2014 |
| EP | 2 765 192 | A | 8/2014 |
| EP | 2 818 183 | A | 12/2014 |
| EP | 2 853 898 | A | 4/2015 |
| EP | 2 862 875 | A1 | 4/2015 |
| EP | 2 889 377 | A | 7/2015 |
| EP | 2 940 043 | A | 11/2015 |
| EP | 2 940 135 | A | 11/2015 |
| EP | 3 042 912 | A | 7/2016 |
| EP | 3 156 072 | A | 4/2017 |
| EP | 3 240 804 | A | 11/2017 |
| EP | 4 082 570 | A1 | 11/2022 |
| EP | 4 361 273 | A1 | 5/2024 |
| JP | H08-217799 | | 8/1996 |
| JP | 2638680 | | 8/1997 |
| JP | 2003-512019 | | 4/2003 |
| JP | 2005-510212 | | 4/2005 |
| JP | 2006-512407 | | 4/2006 |
| JP | 2006-517525 | | 7/2006 |
| JP | 2006-519583 | | 8/2006 |
| JP | 2006-524039 | | 10/2006 |
| JP | 3865418 | | 1/2007 |
| JP | 2007-252368 | | 10/2007 |
| JP | 2007-532139 | | 11/2007 |
| JP | 2008-505174 | | 2/2008 |
| JP | 2008-511292 | | 4/2008 |
| JP | 2008-514201 | | 5/2008 |
| JP | 2009-511067 | | 3/2009 |
| JP | 2009-511587 | | 3/2009 |
| JP | 2009-538273 | | 11/2009 |
| JP | 2009-540837 | | 11/2009 |
| JP | 2009-541352 | | 11/2009 |
| JP | 2010-500020 | | 1/2010 |
| JP | 2010-081866 | | 4/2010 |
| JP | 2010-514460 | | 5/2010 |
| JP | 2011-504096 | | 2/2011 |
| JP | 2012-512641 | | 6/2012 |
| JP | 4961501 | | 6/2012 |
| JP | 2013-518606 | | 5/2013 |
| JP | 2013-528354 | | 7/2013 |
| JP | 2013-531486 | | 8/2013 |
| JP | 2013-537425 | | 10/2013 |
| JP | 2014-504265 | A | 2/2014 |
| JP | 2014-055145 | | 3/2014 |
| JP | 2014-509857 | | 4/2014 |
| JP | 2014-514345 | | 6/2014 |
| JP | 2016-026190 | | 2/2016 |
| JP | 2016-505240 | | 2/2016 |
| JP | 2017-535244 | | 11/2017 |
| JP | 2018-517674 | | 7/2018 |
| JP | 6433297 | | 12/2018 |
| JP | 2019-523295 | | 8/2019 |
| JP | 6628966 | | 1/2020 |
| JP | 5048866 | | 10/2020 |
| KR | 10-0261941 | | 7/2000 |
| KR | 10-2011-0004435 | | 1/2011 |
| KR | 10-2011-0103431 | | 9/2011 |
| KR | 10-2012-0035192 | | 4/2012 |
| KR | 102014/0005864 | | 1/2014 |
| KR | 10-2014-0069332 | | 6/2014 |
| RU | 2236222 | | 9/2004 |
| RU | 2005/112742 | | 1/2006 |
| RU | 2318829 | | 3/2008 |
| RU | 2006/142852 | | 6/2008 |
| RU | 2337107 | | 10/2008 |
| RU | 2360925 | | 7/2009 |
| RU | 2390527 | | 5/2010 |
| RU | 2398777 | | 9/2010 |
| RU | 2009/112723 | | 10/2010 |
| RU | 2422460 | | 6/2011 |
| RU | 2010/150931 | | 6/2012 |
| SG | 192945 | | 9/2013 |
| TW | 416960 | | 1/2011 |
| TW | 2011/16625 | | 5/2011 |
| TW | 2012/02419 | | 1/2012 |
| TW | 2016/43190 | | 12/2016 |
| TW | 2017/12032 | | 4/2017 |
| TW | I605057 | | 11/2017 |
| TW | 2018/08331 | | 3/2018 |
| TW | 2018/08992 | | 3/2018 |
| TW | 2018/19409 | | 6/2018 |
| TW | I656133 | | 4/2019 |
| TW | 2020/39553 | | 11/2020 |
| WO | WO 91/13631 | | 9/1991 |
| WO | WO 92/07084 | | 4/1992 |
| WO | WO 94/21681 | | 9/1994 |
| WO | WO 95/14714 | | 6/1995 |
| WO | WO 96/02576 | | 2/1996 |
| WO | WO 97/34631 | | 9/1997 |
| WO | WO 98/05787 | | 2/1998 |
| WO | WO 99/40117 | | 8/1999 |
| WO | WO 99/51642 | | 10/1999 |
| WO | WO 99/58572 | | 11/1999 |
| WO | WO 00/15214 | | 3/2000 |
| WO | WO 00/42072 | | 7/2000 |
| WO | WO 01/70968 | | 9/2001 |
| WO | WO 02/09641 | | 2/2002 |
| WO | WO 02/60919 | | 8/2002 |
| WO | WO 03/27248 | | 4/2003 |
| WO | WO 03/74679 | | 9/2003 |
| WO | WO 2004/024890 | | 3/2004 |
| WO | WO 2004/029207 | | 4/2004 |

(56) References Cited

FOREIGN PATENT DOCUMENTS

WO WO 2004/037861 5/2004
WO WO 2004/039826 5/2004
WO WO 2004/058797 7/2004
WO WO 2004/063351 7/2004
WO WO 2004/099249 11/2004
WO WO 2004/108157 12/2004
WO WO 2005/023193 3/2005
WO WO 2005/047307 5/2005
WO WO 2005/047327 5/2005
WO WO 2005/056606 6/2005
WO WO 2005/056759 6/2005
WO WO 2005/059106 6/2005
WO WO 2005/066204 7/2005
WO WO 2005/077981 8/2005
WO WO 2005/092925 10/2005
WO WO 2005/094446 10/2005
WO WO 2005/115452 12/2005
WO WO 2006/004663 1/2006
WO WO 2006/015371 2/2006
WO WO 2006/019447 2/2006
WO WO 2006/020114 2/2006
WO WO 2006/023403 3/2006
WO WO 2006/023420 3/2006
WO WO 2006/031370 3/2006
WO WO 2006/036291 4/2006
WO WO 2006/036834 4/2006
WO WO 2006/047350 5/2006
WO WO 2006/050166 5/2006
WO WO 2006/053301 5/2006
WO WO 2006/071877 7/2006
WO WO 2006/072620 7/2006
WO WO 2006/076594 7/2006
WO WO 2006/083182 8/2006
WO WO 2006/083183 8/2006
WO WO 2006/083706 8/2006
WO WO 2006/085938 8/2006
WO WO 2006/085967 8/2006
WO WO 2006/088494 8/2006
WO WO 2006/102095 9/2006
WO WO 2006/105338 10/2006
WO WO 2006/106905 10/2006
WO WO 2006/113643 10/2006
WO WO 2006/116269 11/2006
WO WO 2006/130834 12/2006
WO WO 2006/133486 12/2006
WO WO 2007/001422 1/2007
WO WO 2007/008943 1/2007
WO WO 2007 022520 2/2007
WO WO 2007/024249 3/2007
WO WO 2007/024535 3/2007
WO WO 2007/041635 4/2007
WO WO 2007/044411 4/2007
WO WO 2007/044616 4/2007
WO WO 2007/047112 4/2007
WO WO 2007/047291 4/2007
WO WO 2007/047578 4/2007
WO WO 2007/092772 8/2007
WO WO 2007/114319 10/2007
WO WO 2007/114325 10/2007
WO WO 2007/121354 10/2007
WO WO 2007/150015 12/2007
WO WO 2007/150016 12/2007
WO WO 2008/002933 1/2008
WO WO 2008/003103 1/2008
WO WO 2008/017963 2/2008
WO WO 2008/022152 2/2008
WO WO 2008/030706 3/2008
WO WO 2008/036688 3/2008
WO WO 2008/091798 7/2008
WO WO 2008/091954 7/2008
WO WO 2008/092117 7/2008
WO WO 2008/098115 8/2008
WO WO 2008/031056 10/2008
WO WO 2008/121160 10/2008
WO WO 2008/130969 10/2008
WO WO 2008/150494 12/2008
WO WO 2009/000098 12/2008
WO WO 2009/000099 12/2008
WO WO 2009/026117 2/2009
WO WO 2009/032145 3/2009
WO WO 2009/032782 3/2009
WO WO 2009/041062 4/2009
WO WO 2009/041643 4/2009
WO WO 2009/058346 5/2009
WO WO 2009/058492 5/2009
WO WO 2009/062083 5/2009
WO WO 2009/086320 7/2009
WO WO 2009/095235 8/2009
WO WO 2009/125825 10/2009
WO WO 2009/131702 10/2009
WO WO 2009/137880 11/2009
WO WO 2009/139822 11/2009
WO WO 2009/155513 12/2009
WO WO 2010/033736 3/2010
WO WO 2010/045193 4/2010
WO WO 2010/058860 5/2010
WO WO 2010/070094 6/2010
WO WO 2010/077854 7/2010
WO WO 2010/085682 7/2010
WO WO 2010/107109 9/2010
WO WO 2010/107110 9/2010
WO WO 2010/136831 12/2010
WO WO 2010/151338 12/2010
WO WO 2011/008517 1/2011
WO WO 2011/021009 2/2011
WO WO 2011/091078 7/2011
WO WO 2011/100271 8/2011
WO WO 2011/107989 9/2011
WO WO 2011/108714 9/2011
WO WO 2011/111007 9/2011
WO WO 2011/122011 10/2011
WO WO-2011120134 A1 * 10/2011 .............. A61P 35/00
WO WO 2011/150008 12/2011
WO WO 2011/151432 12/2011
WO WO 2012/016227 2/2012
WO WO 2012/024242 2/2012
WO WO 2012/044831 4/2012
WO WO 2012/058768 5/2012
WO WO 2012/073985 6/2012
WO WO 2012/073992 6/2012
WO WO 2012/093704 7/2012
WO WO 2012/115241 8/2012
WO WO 2012/125850 9/2012
WO WO 2012/132067 10/2012
WO WO 2012/133782 10/2012
WO WO 2012/151199 11/2012
WO WO 2012/151481 11/2012
WO WO 2013/002362 1/2013
WO WO 2013/012733 1/2013
WO WO 2013/046704 4/2013
WO WO 2013/046722 4/2013
WO WO 2013/047729 4/2013
WO WO 2013/047748 4/2013
WO WO 2013/047752 4/2013
WO WO 2013/063702 5/2013
WO WO 2013/081143 6/2013
WO WO 2013/118858 8/2013
WO WO 2013/125667 8/2013
WO WO 2013/138680 9/2013
WO WO 2013/138681 9/2013
WO WO 2013/152001 10/2013
WO WO 2013/166099 11/2013
WO WO 2013/180200 12/2013
WO WO 2013/186719 12/2013
WO WO 2013/187495 12/2013
WO WO 2013/192240 12/2013
WO WO 2014/006217 1/2014
WO WO 2014/028354 2/2014
WO WO 2014/030728 2/2014
WO WO 2014/030750 2/2014
WO WO 2014/043344 3/2014
WO WO 2014/066744 5/2014
WO WO 2014/071206 5/2014
WO WO 2014/074532 5/2014

(56) References Cited

FOREIGN PATENT DOCUMENTS

| | | | |
|---|---|---|---|
| WO | WO 2014/100689 | | 6/2014 |
| WO | WO 2014/104165 | | 7/2014 |
| WO | WO 2014/114651 | | 7/2014 |
| WO | WO 2014/140366 | | 9/2014 |
| WO | WO 2014/144080 | | 9/2014 |
| WO | WO 2014/144577 | | 9/2014 |
| WO | WO 2014/144903 | | 9/2014 |
| WO | WO 2014/145159 | | 9/2014 |
| WO | WO 2014/145806 | | 9/2014 |
| WO | WO 2014/150983 | | 9/2014 |
| WO | WO 2014/163101 | | 10/2014 |
| WO | WO 2014/164959 | | 10/2014 |
| WO | WO 2014/177459 | A2 | 11/2014 |
| WO | WO 2014/182676 | | 11/2014 |
| WO | WO 2014/184384 | | 11/2014 |
| WO | WO 2014/186599 | | 11/2014 |
| WO | WO 2014/190441 | | 12/2014 |
| WO | WO 2015/022658 | | 2/2015 |
| WO | WO 2015/034000 | | 3/2015 |
| WO | WO 2015/042250 | | 3/2015 |
| WO | WO 2015/077491 | | 5/2015 |
| WO | WO 2015/083764 | | 6/2015 |
| WO | WO 2015/111008 | | 7/2015 |
| WO | WO 2015/134894 | | 9/2015 |
| WO | WO 2015/162590 | | 10/2015 |
| WO | WO 2015/190538 | | 12/2015 |
| WO | WO 2016/073853 | | 5/2016 |
| WO | WO 2016/073879 | | 5/2016 |
| WO | WO 2016/073906 | | 5/2016 |
| WO | WO 2016/092439 | | 6/2016 |
| WO | WO 2016/098357 | | 6/2016 |
| WO | WO 2016/125495 | | 8/2016 |
| WO | WO 2016/164358 | | 10/2016 |
| WO | WO 2016/168613 | | 10/2016 |
| WO | WO 2016/170176 | | 10/2016 |
| WO | WO 2016/194992 | | 12/2016 |
| WO | WO 2017/046994 | | 3/2017 |
| WO | WO 2017/049011 | | 3/2017 |
| WO | WO 2017/091719 | | 6/2017 |
| WO | WO 2017/104783 | | 6/2017 |
| WO | WO 2017/110981 | | 6/2017 |
| WO | WO 2017/120523 | | 7/2017 |
| WO | WO 2017/217525 | | 12/2017 |
| WO | WO 2017/218592 | | 12/2017 |
| WO | WO 2018/025982 | | 2/2018 |
| WO | WO 2018/146317 | A1 | 8/2018 |
| WO | WO 2019/098212 | | 5/2019 |
| WO | WO 2019/198807 | | 10/2019 |
| WO | WO 2020/032230 | | 2/2020 |
| WO | WO 2020/209318 | | 10/2020 |
| WO | WO 2020/230834 | | 11/2020 |
| WO | WO 2021/075479 | | 4/2021 |
| WO | WO 2021/131021 | A1 | 7/2021 |
| WO | WO 2021/162020 | | 8/2021 |
| WO | WO 2022/044248 | A1 | 3/2022 |
| WO | WO 2022/045276 | A1 | 3/2022 |
| WO | WO 2022/220275 | A1 | 10/2022 |
| WO | WO 2022/270611 | A1 | 12/2022 |

OTHER PUBLICATIONS

Yu et al., "How to select IgG subclasses in developing anti-tumor therapeutic antibodies," J Hematol Oncol, May 5, 2020, 13(1):45.
U.S. Appl. No. 14/127,576, filed Dec. 19, 2013, Mimoto et al.
U.S. Appl. No. 14/347,321, filed Mar. 26, 2014, Igawa et al.
U.S. Appl. No. 15/860,163, filed Jan. 2, 2018, Mimoto et al.
U.S. Appl. No. 15/963,449, filed Apr. 26, 2018, Ruike et al.
U.S. Appl. No. 15/963,455, filed Apr. 26, 2018, Ruike et al.
U.S. Appl. No. 15/976,288, filed May 10, 2018, Igawa et al.
U.S. Appl. No. 15/977,757, filed May 11, 2018, Igawa et al.
U.S. Appl. No. 16/065,192, filed Jun. 22, 2018, Ruike et al.
U.S. Appl. No. 16/323,142, filed Feb. 4, 2019, Kakiuchi et al.
U.S. Appl. No. 16/697,310, filed Nov. 27, 2019, Igawa et al.
U.S. Appl. No. 16/795,676, filed Feb. 20, 2020, Kuramochi et al.
U.S. Appl. No. 16/763,134, filed May 11, 2020, Feng et al.
U.S. Appl. No. 16/889,066, filed Jun. 1, 2020, Ruike et al.
U.S. Appl. No. 17/028,210, filed Sep. 22, 2020, Katada et al.
U.S. Appl. No. 17/046,395, filed Oct. 9, 2020, Fukuzawa et al.
U.S. Appl. No. 17/266,024, filed Feb. 4, 2021, Igawa et al.
U.S. Appl. No. 17/484,003, filed Sep. 24, 2021, Igawa et al.
"Blog entry," Thunder's Place, Jun. 1, 2014, retrieved from the Internet on May 23, 2018: https://www.thundersplace.org/male-supplements/the-chemical-pe thread-7.html92.
"Mouse GDF-8/Myostatin Propeptide Antibody," R&D Catalogue AF 1539, Feb. 6, 2018, XP055478493, retrieved from the Internet on May 25, 2018: https://resources.rndsystems.com/pdfs/datasheets/af1539.pdf.
"polyclonal human pro-Myostatin (aa 79-92) antibody," Immun Diagnostik Antibodies catalogue, Jun. 30, 2016, retrieved from the Internet on May 24, 2018: https://www.immundiagnostik.com/fileadmin/pdf/AK3004.pdf.
"Rabbit Antibody to Human pro-Myostatin (amino acids 79-92)," Meridian Life Science Inc, Nov. 13, 2015, XP055478289, retrieved from the Internet on May 24, 2018: https://meridianlifescience.com/biospecs/K24340R.pdf.
Abdiche et al., "Antibodies Targeting Closely Adjacent or Minimally Overlapping Epitopes Can Displace One Another," PLoS One, Jan. 6, 2017, 12(1):e0169535. doi: 10.1371/journal.pone.0169535.
Alignment sequences 1047 and 30, Jan. 26, 2021, 1 page (document cited in the office action dated Feb. 2, 2021 for EP 15869566.8).
Alignment sequences 472 and 24, Jan. 26, 2021, 1 page (document cited in the office action dated Feb. 2, 2021 for EP 15869566.8).
Almitairi et al., "Structure of the C1r-C1s interaction of the C1 complex of complement activation," Proc Natl Acad Sci USA, Jan. 23, 2018, 115(4):768-773. doi:10.1073/pnas.1718709115.
Amigorena et al., "Cytoplasmic domain heterogeneity and functions of IgG Fc receptors in B lymphocytes," Science, Jun. 1992, 256(5065):1808-1812.
Amigorena et al., "FcγRII expression in resting and activated B lymphocytes," Eur J Immunol, Aug. 1989, (8):1379-1385.
Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.
Arici, "Local Cytokines in Endometrial Tissue: The Role of Interleukin-8 in the Pathogenesis of Endometriosis," Ann NY Acad Sci, Mar. 2002, 955:101-109; panel discussions, pp. 118 and 396-406.
Arlaud et al., "A Study on the Structure and Interactions of the C1 Sub-Components C1r and C1s in the Fluid Phase," Biochim Biophys Acta, Nov. 6, 1980, 616(1):105-115.
Armour et al., "Differential binding to human FcγRIIa and FcγRIIb receptors by human IgG wildtype and mutant antibodies," Mol Immunol, Dec 2003, 40(9):585-593.
Ascierto et al., "Clinical Experiences With Anti-CD137 and Anti-PD1 Therapeutic Antibodies," Semin Oncol, Oct. 2010, 37(5):508-516. doi: 10.1053/j_seminoncol.2010.09.008.
Atwell et al., "Stable heterodimers from remodeling the domain interface of a homodimer using a phage display library," J Mol Biol, Jul. 4, 1997, 270(1):26-35.
Bally et al., "Identification of the C1q-binding Sites of Human C1r and C1s—A Refined Three-Dimensional Model of the C1 Complex of Complement," J Biol Chem, 2009, 284(29):19340-19348. doi:10.1074/jbcM109.004473.
Becker et al., "Prevention of postoperative abdominal adhesions by a sodium hyaluronate-based bioresorbable membrane: a prospective, randomized, double-blind multicenter study," J Am Coll Surg, Oct. 1996, 183(4):297-306.
Beljaars et al., "The preferential homing of a platelet derived growth factor receptor-recognizing macromolecule to fibroblast-like cells in fibrotic tissue," Biochemical Pharmacology, Oct. 2003, 66(7):1307-1317.
Binetruy-Tournaire et al., "Identification of a peptide blocking vascular endothelial growth factor (VEGF)-mediated angiogenesis," EMBO J, Apr. 3, 2000, 19(7):1525-1533.

(56) References Cited

OTHER PUBLICATIONS

Bjellqvist et al., "The focusing positions of polypeptides in immobilized pH gradients can be predicted from their amino acid sequences," Electrophoresis, Oct. 1993, 14(10):1023-1031.
Blank et al., "Decreased transcription of the human FCGR2B gene mediated by the −343 G/C promoter polymorphism and association with systemic lupus erythematosus," Hum Genet, Jul. 2005, 117(2-3):220-227. Epub May 14, 2005.
Bogdanovich et al., "Functional improvement of dystrophic muscle by myostatin blockade," Nature, Nov. 28, 2002, 420(6914):418-421.
Bonvin et al., "De novo isolation of antibodies with pH-dependent binding properties," mAbs, Mar.-Apr. 2015, 7(2):294-302.
Bork, "Powers and Pitfalls in Sequence Analysis: The 70% Hurdle," Genome Res, Apr. 2000, 10(4):398-400.
Borrok et al., "pH-dependent Binding Engineering Reveals an FcRn Affinity Threshold That Governs IgG Recycling," J Biol Chem, Feb. 13, 2015, 290(7):4282-4290. doi: 10.1074/jbcM114.603712. Epub Dec 23, 2014.
Boruchov et al., "Activating and inhibitory IgG Fc receptors on human DCs mediate opposing functions," J Clin Invest, Oct. 2005, 115(10):2914-2923. Epub Sep. 15, 2005.
Boumpas et al., "A short course of BG9588 (anti-CD40 ligand antibody) improves serologic activity and decreases hematuria in patients with proliferative lupus glomerulonephritis," Arthritis Rheum, Mar. 2003, 48(3):719-727.
Bowie et al., "Deciphering the Message in Protein Sequences: Tolerance to Amino Acid Substitutions," Science, Mar. 16, 1990, 247(4948):1306-1310.
Breitbart et al., "Highly Specific Detection of Myostatin Prodomain by an Immunoradiometric Sandwich Assay in Serum of Healthy Individuals and Patients," PLoS One, Nov. 15, 2013, 18(11):e80454. doi: 10.1371/journal.pone.0080454 eCollection 2013.
Brennand et al., "A cyclic peptide analogue of loop III of PDGF-BB causes an apoptosis in human fibroblasts," FEBS Lett, Dec 15, 1997, 419(2-3):166-170.
Brown et al., "Tolerance to Single, but Not Multiple, Amino Acid Replacements in Antibody $V_H$ CDR2," J Immunol, May 1996, 156(9):3285-3291.
Bruhns et al., "Specificity and affinity of human Fcγ receptors and their polymorphic variants for human IgG subclasses," Blood, Apr. 16, 2009, 113(16):3716-3725. doi: 10.1182/blood-2008-09-179754. Epub Nov. 18, 2008.
Bruhns, "Properties of mouse and human IgG receptors and their contribution to disease models," Blood, Jun. 14, 2012, 119(24):5640-5649. doi: 10.1182/blood-2012-01-380121. Epub Apr. 25, 2012.
Buckler, Section 2.4. "Library Selection," vol. 4—Molecular Medicine and Medicinal Chemistry, Antibody Drug Discovery, edited by Clive R. Wood, London: Imperial College Press, 2012, pp. 49-57.
Bulun, "Endometriosis," New Eng J Med, Jan. 2009, 360(3):268-279.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol, Nov. 1990, 111(5 Pt 1):2129-2138.
Burmeister et al., "Crystal structure of the complex of rat neonatal Fc receptor with Fc," Nature, Nov. 24, 1994, 372(6504):379-383.
Cartron et al., "Therapeutic activity of humanized anti-CD20 monoclonal antibody and polymorphism in IgG Fc receptor FcγRIIIa gene," Blood, Feb. 1, 2002, 99(3):754-758.
Cemerski et al., "Suppression of mast cell degranulation through a dual-targeting tandem IgE-IgG Fc domain biologic engineered to bind with high affinity to FcγRIIb," Immunol Lett, Mar. 30, 2012, 143(1):34-43. doi: 10.1016/j.imlet.2012.01.008. Epub Jan. 25, 2012.
Chamarthy et al., "Gene delivery to dendritic cells facilitated by a tumor necrosis factor alpha-competing peptide," The Mol Immunol, Jul. 2004, 41(8):741-749.
Chan et al., "Therapeutic antibodies for autoimmunity and inflammation," Nat Rev Immunol, May 2010, 10(5):301-316. doi: 10.1038/nri2761.
Chaparro-Riggers et al., "Increasing Serum Half-life and Extending Cholesterol Lowering in Vivo by Engineering Antibody with pH-sensitive Binding to PCSK9," J Biol Chem, Mar. 30, 2012, 287(14):11090-11097. doi: 10.1074/jbcM111.319764. Epub Jan. 31, 2012.
Chen et al., "Association of a transmembrane polymorphism of Fcγ receptor IIb (*FCGR2B*) with systemic lupus erythematosus in Taiwanese patients," Arthritis Rheum, Dec. 2006, 54(12):3908-3917.
Chen et al., "Enhancement and destruction of antibody function by somatic mutation: unequal occurrence is controlled by V gene combinatorial associations," EMBO J, Jun. 15, 1995, 14(12):2784-2794.
Chu et al., "Inhibition of B cell receptor-mediated activation of primary human B cells by coengagement of CD19 and FcγRIIb with Fc-engineered antibodies," Mol Immunol, Sep. 2008, 45(15):3926-3933. doi: 10.1016/j.molimm.2008.06.027. Epub Aug. 8, 2008.
Chu et al., "Reduction of total IgE by targeted coengagement of IgE B-cell receptor and FcγRIIb with Fc-engineered antibody," J Allergy Clin Immunol, Apr. 2012, 129(4):1102-1115. doi: 10.1016/j.jaci.2011.11.029. Epub Jan. 16, 2012.
Chuntharapai et al., "Isotype-dependent inhibition of tumor growth in vivo by monoclonal antibodies to death receptor 4," J Immunol, Apr. 2001, 166(8):4891-4898.
Clark, "IgG effector mechanisms," Chem Immunol, 1997, 65:88-110.
Clynes et al., "Fc receptors are required in passive and active immunity to melanoma," Proc Natl Acad Sci USA, Jan. 20, 1998, 95(2):652-656.
Clynes et al., "Inhibitory Fc receptors modulate in vivo cytotoxicity against tumor targets," Nat Med, Apr. 2000, 6(4):443-446.
Colman, "Effects of amino acid sequence changes on antibody-antigen interactions," Res Immunol, Jan. 1994, 145(1):33-36.
Cooper et al., "Variable domain-identical antibodies exhibit IgG subclass-related differences in affinity and kinetic constants as determined by surface plasmon resonance," Mol Immunol, Jun. 1994, 31(8):577-584.
Crowe et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol, Jan. 1992, 87(1):105-110.
Dagbay et al., "Structural basis of specific inhibition of extracellular activation of pro- or latent myostatin by the monoclonal antibody SRK-015," J Biol Chem, Apr. 17, 2020, 295(16):5404-5418.
Dall'Acqua et al., "Increasing the affinity of a human IgG1 for the neonatal Fc receptor: biological consequences," J Immunol, 2002, 169(9):5171-5180.
Dall'Acqua et al., "Properties of human IgGls engineered for enhanced binding to the neonatal Fc receptor (FcRn)," J Biol Chem, Aug. 18, 2006, 281(33):23514-23524. Epub Jun. 21, 2006.
Datta-Mannan et al., "Monoclonal antibody clearance. Impact of modulating the interaction of IgG with the neonatal Fc receptor," J Biol Chem, Jan. 19, 2007, 282(3):1709-1717. Epub Nov. 29, 2006.
Datta-Mannan et al., "FcRn Affinity-Pharmacokinetic Relationship of Five Human IgG4 Antibodies Engineered for Improved In Vitro FcRn Binding Properties in Cynomolgus Monkeys," Drug Metab Dispos, Aug. 2012, 40(8):1545-1555.
Davis et al., "SEEDbodies: fusion proteins based on strand-exchange engineered domain (Seed) $C_H3$ heterodimers in an Fc analogue platform for asymmetric binders or immunofusions and bispecific antibodies," Protein Eng Des Sel, Apr. 2010, 23(4):195-202. doi: 10.1093/protein/gzp094. Epub Feb. 4, 2010.
De Groot et al., "Reducing risk, improving outcomes: bioengineering less immunogenic protein therapeutics," Clin Immunol, May 2009, 131(2):189-201. doi: 10.1016/j.clim.2009.01.009. Epub Mar. 6, 2009.
Deambrosis et al., "Inhibition of CD40-CD154 costimulatory pathway by a cyclic peptide targeting CD154," J Mol Med, Feb. 2009, 87(2):181-197.

(56) References Cited

OTHER PUBLICATIONS

Declaration of Muramatsu Hiroyasu, signed Oct. 21, 2020, 5 pages (document cited in the office action dated Feb. 2, 2021 for EP 15869566.8).
Desai et al., "Fcγ receptor IIB on dendritic cells enforces peripheral tolerance by inhibiting effector T cell responses," J Immunol, May 2007, 178(10):6217-6226.
Devanaboyina et al., "The effect pH dependence of antibody-antigen interactions on subcellular trafficking dynamics," mAbs, Nov. 1, 2013, 5(6):851-859.
Dhodapkar et al., "Selective blockade of inhibitory Fcγ receptor enables human dendritic cell maturation with IL-12p70 production and immunity to antibody-coated tumor cells," Proc Natl Acad Sci USA, Feb. 22, 2005,102(8):2910-2915. Epub Feb. 9, 2005.
Di Stefano et al., "Role of Interleukin-8 in the Pathogenesis and Treatment of COPD," Chest, Sep. 2004, 126(3):676-678. doi: 10.1378/chest.126.3.676.
Diamond et al., "Somatic mutation of the T15 heavy chain gives rise to an antibody with autoantibody specificity," Proc Natl Acad Sci USA, Sep. 1984, 81(18):5841-5844.
Donnez et al., "Current thinking on the pathogenesis of endometriosis," Gynecol Obstet Invest, 2002, 54(Suppl 1):52-62.
Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-1233. doi: 10.1007/s00262-010-0846-9. Epub Mar. 25, 2010.
Duffau et al., "Platelet CD154 potentiates interferon-alpha secretion by plasmacytoid dendritic cells in systemic lupus erythematosus," Sci Transl Med, Sep. 1, 2010, 2(47):47ra63, pp. 1-21. doi: 10.1126/scitranslmed.3001001.
Edelman et al., "The Covalent Structure of an Entire γG Immunoglobulin Molecule," Proc Natl Acad Sci USA, May 1969, 63(1):78-85.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-118.
Examination Report No. 1 for AU 2013306700, issued on Jun. 7, 2018, 3 pages.
Faham et al., "Antigen-Containing Liposomes Engrafted with Flagellin-Related Peptides are Effective Vaccines That Can Induce Potent Antitumor Immunity and Immunotherapeutic Effect," J Immunol, Jul. 7, 2010, 185:1744-1754.
Fillipovic et al., Biochemical basis of human life activity, Vlados, 2005:38-43 (with English translation).
Fillipovich et al., Biochemical basis of human life activity, Vlados, 2005:49-50 (with English translation).
Flores et al., "Dominant Expression of the Inhibitory FcγRIIB Prevents Antigen Presentation by Murine Plasmacytoid Dendritic Cells," J Immunol, Dec 1, 2009, 183(11):7129-7139. doi: 10.4049/jimmunol.0901169.
Floto et al., "Loss of function of a lupus-associated FcγRIIb polymorphism through exclusion from lipid rafts," Nat Med, Oct. 2005, 11(10):1056-1058. Epub Sep. 18, 2005.
Fournier et al., "Activation of human peripheral IgM+ B cells is transiently inhibited by BCR-independent aggregation of FcγRIIB," J Immunol, Oct. 2008, 181(8):5350-5359.
Gal et al., "Early complement proteases: C1r, C1s and MASPs. A structural insight into activation and functions," Mol Immunol, 2009, 46(14):2745-2752. doi:10.1016/j.molimm.2009.04.026.
Gary et al., Chapter 8 "Making Antibodies in Bacteria," Making and Using Antibodies: A Practical Handbook, CRC Press, Taylor & Francis Group, 2006, pp. 157-177.
Gershoni et al., "Epitope Mapping—The First Step in Developing Epitope-Based Vaccines," BioDrugs, 2007, 21(3):145-156.
Ghetie et al., "Increasing the serum persistence of an IgG fragment by random mutagenesis," Nat Biotechnol, 1997, 15(7):637-640.
Giudice et al., "Endometriosis," Lancet, Nov. 2004, 364(9447):1789-1799.
Gonzalez et al., "BMP-1/Tolloid-like Metalloproteases Process Endorepellin, the Angiostatic C-terminal Fragment of Perlecan," J Biol Chem, Feb. 25, 2005, 280(8):7080-7087. Epub Dec 9, 2004.
Greenwood et al., "Structural motifs involved in human IgG antibody effector functions," Eur J Immunol, May 1993, 23(5):1098-1104.
Guilliams et al., "The function of Fcγ receptors in dendritic cells and macrophages," Nat Rev Immunol, Feb. 2014, 14(2):94-108. doi: 10.1038/nri3582. Epub Jan. 21, 2014.
Gunasekaran et al., "Enhancing antibody Fc heterodimer formation through electrostatic steering effects: applications to bispecific molecules and monovalent IgG," J Biol Chem, 2010, 285(25):19637-19646.
Guo, "Recurrence of endometriosis and its control," Hum Reprod Update, Jul.-Aug. 2009 15(4):441-461. Epub Mar. 2009.
Hamid et al., "Anti-programmed death-1 and anti-programmed death-ligand 1 antibodies in cancer therapy," Expert Opin Biol Ther, Jun. 2013, 13(6):847-861. doi: 10.1517/14712598.2013.770836. Epub Feb. 19, 2013.
Han et al., "Targeting the Myostatin Signaling Pathway to Treat Muscle Wasting Diseases," Curr Opin Support Palliat Care, Dec 2011, 5(4):334-341. doi: 10.1097/SPC0b013e32834bddf9.
Hanahan et al., "Hallmarks of Cancer: The Next Generation," Cell, Mar. 4, 2011, 144(5):646-674. doi: 10.1016/j.cell.2011.02.013.
Hanson et al., "Catalytic antibodies and their applications," Curr Opin Biotechnol, Dec 2005, 16(6):631-636. Epub Oct. 21, 2005.
Harvey et al., Chapter 2 "Antigens and Receptors," pp. 11-23 and Chapter 11 "Lymphocyte Effector Receptors," pp. 141-157, Lippincott's Illustrated Reviews: Immunology, 2$^{nd}$ ed., Nov. 30, 2013.
Hasemann et al., "Mutational Analysis of Arsonate Binding by a $CRI_{A+}$Antibody—$V_H$ and $V_L$ Junctional Diversity are Essential for Binding Activity," J Biol Chem, Apr. 25, 1991, 266(12):7626-7632.
Hess et al., "Cancer therapy with trifunctional antibodies: linking innate and adaptive immunity," Future Oncol, Jan. 2012, 8(1):73-85. doi: 10.2217/fon.11.138.
Hetian et al., "A Novel Peptide Isolated from a Phage Display Library Inhibits Tumor Growth and Metastasis by Blocking the Binding of Vascular Endothelial Growth Factor to Its Kinase Domain Receptor," J Biol Chem, Nov. 8, 2002, 277(45):43137-43142.
Heyman, "Feedback regulation by IgG antibodies," Immunol Lett, Aug. 2003, 88(2):157-161.
Hill et al., "The Myostatin Propeptide and the Follistatin-related Gene are Inhibitory Binding Proteins of Myostatin in Normal Serum," J Biol Chem, Oct. 25, 2002, 277(43):40735-40741. Epub Aug. 22, 2002.
Hinton et al., "An engineered human IgG1 antibody with longer serum half-life," J Immunol, 2006, 176(1):346-356.
Hjelm et al., "Antibody-mediated regulation of the immune response," Scand J Immunol, Sep. 2006, 64(3):177-184.
Holash et al., "VEGF-Trap: a VEGF blocker with potent antitumor effects," Proc Natl Acad Sci USA, Aug. 20, 2002, 99(17):11393-11398. Epub Aug. 12, 2002.
Hoodless et al., "Mechanism and function of signaling by the TGF beta superfamily," Curr Top Microbiol Immunol, 1998, 228:235-272.
Horton et al., "Potent in vitro and in vivo activity of an Fc-engineered anti-CD19 monoclonal antibody against lymphoma and leukemia," Cancer Res, Oct. 1, 2008, 68(19):8049-8057. doi: 10.1158/0008-5472. CAN-08-2268.
Houot et al., "Therapeutic effect of CD137 immunomodulation in lymphoma and its enhancement by $T^{reg}$ depletion," Blood, Oct. 15, 2009, 114(16):3431-3438. doi: 10.1182/blood-2009-05-223958. Epub Jul. 29, 2009.
Idusogie et al., "Engineered antibodies with increased activity to recruit complement," J Immunol, Feb. 15, 2001, 166(4):2571-2575.
Idusogie et al., "Mapping of the C1q binding site on rituxan, a chimeric antibody with a human IgG1 Fc," J Immunol, Apr. 15, 2000, 164(8):4178-4184.
Igawa et al., "Antibody Optimization Technologies for Developing Next Generation Antibody Therapeutics," Bio Industry, 2011, 28(7):15-21 (with English translation).

(56) References Cited

OTHER PUBLICATIONS

Igawa et al., "Antibody recycling by engineered pH-dependent antigen binding improves the duration of antigen neutralization," Nat Biotechnol, Nov. 2010, 28(11):1203-1207. doi: 10.1038/nbt.1691. Epub Oct. 17, 2010.
Igawa et al., "Engineered Monoclonal Antibody with Novel Antigen-Sweeping Activity In Vivo," PLoS One, May 7, 2013, 8(5):e63236, pp. 1-10. doi: 10.1371/journal.pone.0063236. Print 2013.
Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.
Igawa et al., "Sweeping antibody as a novel therapeutic antibody modality capable of eliminating soluble antigens from circulation," Immunol Rev, Mar. 2016, 270(1):132-151.
Igawa et al., "Engineering the variable region of therapeutic IgG antibodies," mAbs, May-Jun. 2011, 3(3):243-252. Epub May 1, 2011.
Igawa et al., "Reduced elimination of IgG antibodies by engineering the variable region," Protein Eng Des Sel, May 2010, 23(5):385-392. Epub Feb. 15, 2010.
Information Meeting on Antibody Engineering Technologies, Copyright ® Chugai Pharmaceutical Co., Ltd., Dec. 18, 2012.
Ito et al., "The His-probe method: effects of histidine residues introduced into the complementarity-determining regions of antibodies on antigen-antibody interactions at different pH values," FEBS Lett, 1992, 309:85-88.
Iwabe et al., "Pathogenetic significance of increased levels of interleukin-8 in the peritoneal fluid of patients with endometriosis," Fertil Steril, May 1998, 69(5):924-930.
James et al., "1.9 Å structure of the therapeutic antibody CAMPATH-1H fab in complex with a synthetic peptide antigen," J Mol Biol, Jun. 4, 1999, 289(2):293-301.
Janeway et al., Chapter 3 "Structure of the Antibody Molecule and Immunoglobulin Genes," Immunology, 3rd ed., Garland Publishing Inc, 1997, pp. 3:1-3:11.
Jaeger, Clinical Immunology and Allergology, M.: Meditsina, 2nd ed., 1990, 2:484-485 (with English translation).
Jefferis et al., "Interaction sites on human IgG-Fc for FcγR: current models," Immunol Lett, Jun. 3, 2002, 82(1-2):57-65.
Jones et al., "Growth factor receptor interplay and resistance in cancer," Endocr Relat Cancer, Dec 2006, 13 Suppl 1:S45-51.
Kabat et al., "Sequences of proteins of immunological interest," Diane publishing, 5th ed., 1991, vol. 1, pp. 679-687.
Kakita et al., "Isolation of a Human Monoclonal Antibody with Strong Neutralizing Activity against Diphtheria Toxin," Infect Immun, Jun. 2006, 74(6):3682-3683.
Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-29.
Kim et al., "Production of a Polyclonal Anti-Myostatin Antibody and the Effects of In Ovo Administration of the Antibody on Posthatch Broiler Growth and Muscle Mass," Poult Sci, Jun. 2006, 85(6):1062-1071.
Kim et al., "Production of a Polyclonal Anti-Myostatin Antibody and the Effects of In Ovo Administration of the Antibody on Posthatch Broiler Growth and Muscle Mass," Poult Sci, Jun. 2007, 86(6):1196-1205.
Kim et al., "Antibody Engineering for the Development of Therapeutic Antibodies," Mol Cells, 2005, 20(1):17-29.
Kim et al., Chapter 24 "Affinity Maturation of Monoclonal Antibodies by Multi-Site-Directed Mutagenesis," Methods Mol Biol, 2014, 1131:407-420. doi: 10.1007/978-1-62703-992-5_24.
King, "Preparation, structure and function of monoclonal antibodies," Applications and Engineering of Monoclonal Antibodies, CRC Press, 1998, pp. 2, 13-4.
King, Chapter 5 "Production of Monoclonal Antibodies," Applications and Engineering of Monoclonal Antibodies, Taylor & Francis, ISBN 0-203-21169-3, 2005, pp. 151-159, 162-164.
Kingsley et al., "The TGF-beta superfamily: new members, new receptors, and new genetic tests of function in different organisms," Genes Dev, Jan. 1994, 8(2):133-146.
Kohrt et al., "Stimulation of natural killer cells with a CD137-specific antibody enhances trastuzumab efficacy in xenotransplant models of breast cancer," J Clin Invest, Mar. 1, 2012, 122(3):1066-1075. doi: 10.1172/JCI61226. Epub Feb. 13, 2012.
Kontermann, "Dual targeting strategies with bispecific antibodies," mAbs, Mar.-Apr. 2012, 4(2):182-197. doi: 10.4161/mabs.4.2.19000. Epub Mar. 1, 2012.
Kraft et al., "Definition of an Unexpected Ligand Recognition Motif for αvβ6 Integrin," J Biol Chem, Jan. 1999, 274:1979-1985.
Lacroix et al., "Assembly and Enzymatic Properties of the Catalytic Domain of Human Complement Protease C1r," J Biol Chem, Sep. 28, 2001, 276(39):36233-36240. doi:10.1074/jbcM105688200.
Lazar et al., "Transforming Growth Factor a: Mutation of Aspartic Acid 47 and Leucine 48 Results in Different Biological Activities," Mol Cell Biol, Mar. 1988, 8(3):1247-1252.
Lazar et al., "Engineered antibody Fc variants with enhanced effector function," Proc Natl Acad Sci USA, Mar. 2006, 103(11):4005-4010. Epub Mar. 6, 2006.
Lee et al., "Genetic analysis of the role of proteolysis in the activation of latent myostatin," PLoS One, Feb. 20, 2008, 3(2):e1628. doi: 10.1371/journal.pone.0001628.
Lee et al., "Regulation of myostatin activity and muscle growth," Proc Natl Acad Sci USA, Jul. 31, 2001, 98(16):9306-9311. Epub Jul. 17, 2001.
Li et al., "Activation of the Proapoptotic Death Receptor DR5 by Oligomeric Peptide and Antibody Agonists," J Mol Biol, Aug. 2006, 361(3):522-536.
Li et al., "Apoptotic and antitumor activity of death receptor antibodies require inhibitory Fcγ receptor engagement," Proc Natl Acad Sci USA, Jul. 3, 2012, 109(27):10966-10971. doi: 10.1073/pnas.1208698109. Epub Jun. 20, 2012.
Li et al., "CD72 down-modulates BCR-induced signal transduction and diminishes survival in primary mature B lymphocytes," J Immunol, May 2006, 176(9):5321-5328.
Li et al., "Inhibitory Fcγ receptor engagement drives adjuvant and anti-tumor activities of agonistic CD40 antibodies," Science, Aug. 19, 2011, 333(6045):1030-1034. doi: 10.1126/science.1206954.
Li et al., "Antitumor activities of agonistic anti-TNFR antibodies require differential FcγRIIB coengagement in vivo," Proc Natl Acad Sci USA, Nov. 26, 2013, 110(48):19501-19506. doi: 10.1073/pnas.1319502110. Epub Nov. 11, 2013.
Liberti et al., "Antigenicity of Polypeptides (Poly-α-amino Acids). Physicochemical Studies of a Calcium-Dependent Antigen-Antibody Reaction," Biochemistry, Apr. 27, 1971, 10(9):1632-1616.
Liu et al., "Asymmetrical Fc engineering greatly enhances antibody-dependent cellular cytotoxicity (ADCC) effector function and stability of the modified antibodies," J Biol Chem, Feb. 7, 2014, 289(6):3571-3590. doi: 10.1074/jbcM113.513366. Epub Dec 5, 2013.
Lloyd et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.
MacCallum et al., "Antibody-antigen Interactions: Contact Analysis and Binding Site Topography," J Mol Biol, 1996, 262:732-745.
Mackay et al., "Selective dysregulation of the FcγIIB receptor on memory B cells in SLE," J Exp Med, Sep. 4, 2006, 203(9):2157-2164. Epub Aug. 21, 2006.
Malbec et al., "Antibodies against growth factor receptors can inhibit the proliferation of transformed cells via a cis-interaction with inhibitory FcR," Immunol Lett., Mar. 30, 2012;143(1):28-33.
Manger et al., "Fcγ receptor IIa polymorphism in Caucasian patients with systemic lupus erythematosus: association with clinical symptoms," Arthritis Rheum, Jul. 1998, 41(7):1181-1189.
Marino et al., "Prevention of systemic lupus erythematosus in MRL/lpr mice by administration of an immunoglobulin-binding peptide," Nat Biotechnol, Jul. 2000, 18(7):735-739.
Mariuzza et al., "The Structural Basis of Antigen-Antibody Recognition," Annu Rev Biophys Chem, Jun. 1987, 16:139-159.

(56) References Cited

OTHER PUBLICATIONS

Marvin et al., "Recombinant approaches to IgG-like bispecific antibodies," Acta Pharmacol Sin, Jun. 2005, 26(6):649-658.
Matsumiya et al., "Structural comparison of fucosylated and nonfucosylated Fc fragments of human immunoglobulin G1," J Mol Biol, May 4, 2007, 368(3):767-779. Epub Feb. 22, 2007.
Matsumoto et al., "Functional analysis of activated C1s, a subcomponent of the first component of human complement, by monoclonal antibodies," J Immunol, Nov. 1, 1986, 137(9):2907-2912.
Maurer et al., "Antigenicity of polypeptides (polyaamino acids): calcium-dependent and independent antibodies," J Immunol, Sep. 1970, 105(3):567-573.
Maxfield et al., "Endocytic Recycling," Nat Rev Mol Cell Biol, Feb. 2004, 5(2):121-132.
Maxwell et al., "Crystal structure of the human leukocyte Fc receptor, FcγRIIa," Nat Struct Biol, May 1999, 6(5):437-442.
Mazda et al., "Regulation of Muscle Homeostasis and Metabolism by the TGF-β Superfamily Cytokine, Myostatin/growth Differentiation Factor 8 (GDF8)," Journal of Kyoto Prefectural University of Medicine, 2013, 122(3):133-141.
McCroskery et al., "Improved muscle healing through enhanced regeneration and reduced fibrosis in myostatin-null mice," J Cell Sci, Aug. 1, 2005, 118(Pt 15):3531-3541.
McPherron et al., "Double muscling in cattle due to mutations in the myostatin gene," Proc Natl Acad Sci USA, Nov. 11, 1997, 94(23):12457-12461.
McPherron et al., "Regulation of skeletal muscle mass in mice by a new TGF-beta superfamily member," Nature, May 1, 1997, 387(6628):83-90.
Mendez-Fernandez et al., "The inhibitory FcγRIIb modulates the inflammatory response and influences atherosclerosis in male apo$E^{-/-}$ mice," Atherosclerosis, Jan. 2011, 214(1):73-80. doi: 10.1016/j.atherosclerosis.2010.10.018.
Meulenbroek et al., Chapter 2.3 "Properties of human IgG subclasses," Human IgG Subclasses: Useful Diagnostic Markers for Immunocompetence, published online by Sanquin, Amsterdam, The Netherlands, retrieved from the Internet on Mar. 23 and 24, 2017: <http://ednieuw.home.xs4all.nl/IgGsubclasses/subk123.htm>, 8 pages.
Meyer et al., "Bevacizumab immune complexes activate platelets and induce thrombosis in FCGR2A transgenic mice," J Thromb Haemost, Jan. 2009, 7(1):171-181. doi: 10.1111/j.1538-7836.2008.03212.x. Epub Oct. 30, 2008.
Mi et al., "Targeting the neonatal fc receptor for antigen delivery using engineered fc fragments," J Immunol, Dec 1, 2008, 181(11):7550-7561.
Mimoto et al., "Engineered antibody Fc variant with selectively enhanced FcγRIIb binding over both FcγRIIa$^{R131}$ and FcγRIIa$^{H131}$," Protein Eng Des Sel, Oct. 2013, 26(10):589-598. doi: 10.1093/protein/gzt022. Epub Jun. 5, 2013.
Mimoto et al., "Novel asymmetrically engineered antibody Fc variant with superior FcγR binding affinity and specificity compared with afucosylated Fc variant," mAbs, Mar.-Apr. 2013, 5(2):229-236. doi: 10.4161/mabs.23452. Epub Feb. 13, 2013.
Misawa et al., "Rapid and High-Sensitivity Cell-Based Assays of Protein—Protein Interactions Using Split Click Beetle Luciferase Complementation: An Approach to the Study of G-Protein-Coupled Receptors," Anal Chem, Feb. 24, 2010, 82(6):2552-2560. doi: 10.1021/ac100104Q.
Moore et al., "Engineered Fc variant antibodies with enhanced ability to recruit complement and mediate effector functions," mAbs, Mar.-Apr. 2010, 2(2):181-189.
Morgan et al., "The N-terminal end of the $C_H2$ domain of chimeric human IgGI anti-HLA-DR is necessary for C1q, FcγRI and FcγRIII binding," Immunology, Oct. 1995; 86(2):319-24.
Mortensen et al., "Structure and activation of C1, the complex initiating the classical pathway of the complement cascade," Proc Natl Acad Sci USA, Jan. 31, 2017, 114(5):986-991. doi: 10.1073/pnas.1616998114. Epub Jan. 19, 2017.
Muramatsu, "Latent myostatin specific elimination by sweeping antibody® is a novel therapeutic approach to improve muscle strength," Abstracts/Neuromuscular Disorders, 2019, 29(Supplement 1):S86, 1 page.
Murtaugh et al., "A Combinatorial Histidine Scanning Library Approach to Engineer Highly pH-Dependent Protein Switches," Protein Sci, Sep. 2011, 20(9):1619-1631. doi: 10.1002/pro.696. Epub Aug. 3, 2011.
Muta et al., "A 13-amino-acid motif in the cytoplasmic domain of FγRIIB modulates B-cell receptor signaling," Nature, Mar. 1994, 368(6466):70-73.
Nagaoka et al., "Single amino acid substitution in the mouse IgG1 Fc region induces drastic enhancement of the affinity to protein A," Protein Eng, Apr. 2003, 16(4):243-245. doi: 10.1093/proeng/gzg037.
Nakamura et al., "Fcγ receptor IIB-deficient mice develop Goodpasture's syndrome upon immunization with type IV collagen: a novel murine model for autoimmune glomerular basement membrane disease," J Exp Med, Mar. 2000, 191(5):899-906.
Nakamura et al., "Peptide mimics of epidermal growth factor (EGF) with antagonistic activity," Journal of Biotechnology, Mar. 2005, 116(3):211-219.
Natsume et al., "Engineered antibodies of IgG1/IgG3 mixed isotype with enhanced cytotoxic activities," Cancer Res, May 15, 2008, 68(10):3863-3872. doi: 10.1158/0008-5472.CAN-07-6297.
Nicholas et al., "Regulation of the immune response. I. Reduction in ability of specific antibody to inhibit long-lasting IgG immunological priming after removal of the Fc fragment," J Exp Med, Jun. 1969, 129(6):1183-1201.
Nimmerjahn et al., "Divergent immunoglobulin G subclass activity through selective Fc receptor binding," Science, Dec 2, 2005, 310(5753):1510-1512.
Nimmerjahn et al., "Fcγ receptors as regulators of immune responses," Nat Rev Immunol, Jan. 2008, 8(1):34-47.
Ohno et al., "Antigen-binding specificities of antibodies are primarily determined by seven residues of $V_H$," Proc Natl Acad Sci USA, May 1985, 82(9):2945-2949.
Okabe, "Proprietary Innovative Antibody Engineering Technologies in Chugai Pharmaceutical," Information meeting on Antibody Engineering Technologies, Dec 18, 2012.
Olferiev et al., "The role of activating protein 1 in the transcriptional regulation of the human FCGR2B promoter mediated by the −343 G → > C polymorphism associated with systemic lupus erythematosus," J Biol Chem, Jan. 19, 2007, 282(3):1738-1746. Epub Nov. 27, 2006.
OriGene Technologies, Inc., AP02123SU-N, Polyclonal Antibody to Myostatin (79-92)—Serum, Mar. 19, 2013, https://ml.acris-antibodies.com/pdf/AP02123SU-N.pdf.
Pace et al., "How to measure and predict the molar absorption coefficient of a protein," Protein Sci, Nov. 1995, 4(11):2411-2423.
Pakula et al., "Genetic Analysis of Protein Stability and Function," Annu Rev Genet, Dec. 1989, 23:289-310.
Patentee submission dated Jul. 16, 2015 (Response to Search Report filed on Jul. 16, 2015), 30 pages (document submitted by the Opponent on May 6, 2020 in the EPO opposition proceedings of EP 2 679 681).
Pavlou et al., "The therapeutic antibodies market to 2008," Eur J Pharm Biopharm, Apr. 2005, 59(3):389-396.
Petillot et al., "Analysis of the N-linked oligosaccharides of human C1s using electrospray ionisation mass spectrometry," FEBS Lett, Jan. 30, 1995, 358(3):323-328.
Pirruccello-Straub et al., "Blocking extracellular activation of myostatin as a strategy for treating muscle wasting," Scientific Reports, 2018, vol. 8, Article No. 2292, pp. 1-15.
Poosarla et al., "Computational de novo Design of Antibodies binding to a Peptide with High Affinity," Biotechn Bioeng, Jun. 2017, 114(6):1331-1342.
Prieto et al., "CTLA-4 Blockade with Ipilimumab: Long-term Follow-up of 177 Patients with Metastatic Melanoma," Clin Cancer Res, Apr. 1, 2012, 18(7):2039-2047. doi: 10.1158/1078-0432.CCR-11-1823. Epub Jan. 23, 2012.

(56) References Cited

OTHER PUBLICATIONS

Radaev et al., "The role of Fc glycosylation and the binding of peptide inhibitors," J Biol Chem, May 11, 2001, 276(19):16478-16483.
Radaev et al., "The structure of a human type III Fcγ receptor in complex with Fc," J Biol Chem, May 11, 2001, 276(19):16469-16477. Epub Jan. 31, 2001.
Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-14657.
Rajpal et al., "A general method for greatly improving the affinity of antibodies by using combinatorial libraries," Proc Natl Acad Sci USA, Jun. 14, 2005, 102(24):8466-8471. Epub Jun. 6, 2005.
Rao et al., "Novel cyclic and linear oligopeptides that bind to integrin β1 chain and either inhibit or costimulate T lymphocytes," Int Immunopharmacol, Mar. 2003, 3(3):435-443.
Rathanaswami et al., "Demonstration of an in vivo generated sub-picomolar affinity fully human monoclonal antibody to interleukin-8," Biochem Biophys Res Commun, 2005, 334(4):1004-1013.
Ravetch et al., "Immune inhibitory receptors," Science, Oct. 2000, 290(5489):84-89.
Reichert et al., "Monoclonal antibody successes in the clinic," Nat Biotechnol, Sep. 2005, 23(9):1073-1078.
Reverberi et al., "Factors affecting the antigen-antibody reaction," Blood Transfus, Nov. 2007, 5(4):227-240. doi: 10.2450/2007.0047-07.
Richards et al., "A peptide containing a novel FPGN CD40-binding sequence enhances adenoviral infection of murine and human dendritic cells," Eur J Biochem, May 2003, 270(10):2287-2294.
Richards et al., "Optimization of antibody binding to FcγRIIa enhances macrophage phagocytosis of tumor cells," Mol Cancer Ther, Aug. 2008, 7(8):2517-2527. doi: 10.1158/1535-7163.MCT-08-0201.
Riechelmann et al., "Adoptive therapy of head and neck squamous cell carcinoma with antibody coated immune cells: a pilot clinical trial," Cancer Immunol Immunother, Sep. 2007, 56(9):1397-1406. Epub Feb. 2, 2007.
Rivas et al., "Calcium-Linked Self-Association of Human Complement C1s," Biochemistry, Dec 1, 1992, 31(47):11707-11712.
Robles-Carrillo et al., "Anti-CD40L immune complexes potently activate platelets in vitro and cause thrombosis in FCGR2A transgenic mice," J Immunol, Aug. 1, 2010, 185(3):1577-1583. doi: 10.4049/jimmunol.0903888. Epub Jun. 28, 2010.
Roitt et al., "Antibodies and their Receptors," Immunology, Moscow, Mir, 2000, p. 110-111 (with what are believed to be the corresponding pages from an English version of Immunology).
Roitt et al., "Overview: Antibody—a flexible adaptor," Immunology, Moscow, Mir, 2000, p. 9 (with what are believed to be the corresponding pages from an English version of Immunology).
Roitt et al., Chapter 19 "Vaccination," Immunology, Moscow, Mir, 2000, pp. 373-374 (with English translation).
Rossi et al., "Classical complement pathway components C1r and C1s: purification from human serum and in recombinant form and functional characterization," Methods Mol Biol, 2014, 1100:43-60. doi: 10.1007/978-1-62703-724-2_4.
Rossi et al., "Baculovirus-mediated Expression of Truncated Modular Fragments from the Catalytic Region of Human Complement Serine Protease C1s," J Biol Chem, Jan. 9, 1998, 273(2):1232-1239. doi: 10.1074/jbc273.2.1232.
Rothe et al., "Recombinant proteins in rheumatology—recent advances," N Biotechnol, Sep. 2011, 28(5):502-510. doi: 10.1016/j.nbt.2011.03.019. Epub Apr. 5, 2011.
Rudikoff et al., "Single amino acid substitution altering antigen-binding specificity," Proc Natl Acad Sci USA, Mar. 1982, 79(6):1979-1983.
Russo et al., "The CXCL8/IL-8 chemokine family and its receptors in inflammatory diseases," Expert Rev Clin Immunol, May 2014, 10(5):593-619. doi: 10.1586/1744666X.2014.894886. Epub Mar. 29, 2014.
Safdari et al., "Antibody humanization methods—a review and update," Biotechnol Genet Eng Rev, 2013, 29:175-186.
Salmon et al., "FcγRIIA alleles are heritable risk factors for lupus nephritis in African Americans," J Clin Invest, Mar. 1996, 97(5):1348-1354.
Samuelsson et al., "Anti-inflammatory activity of IVIG mediated through the inhibitory Fc receptor," Science, Jan. 19, 2001, 291(5503):484-486.
Sazinsky et al., "Aglycosylated immunoglobulin G1 variants productively engage activating Fc receptor," Proc Natl Acad Sci USA, Dec. 23, 2008, 105(51):20167-20172. doi: 10.1073/pnas.0809257105. Epub Dec 12, 2008.
Scappaticci et al., "Arterial thromboembolic events in patients with metastatic carcinoma treated with chemotherapy and bevacizumab," J Natl Cancer Inst, Aug. 15, 2007, 99(16):1232-1239. Epub Aug. 8, 2007.
Schabowsky et al., "A Novel Form of 4-1BBL Has Better Immunomodulatory Activity than an Agonistic Anti-4-1BB Ab without Ab Associated Severe Toxicity," Vaccine, Dec 11, 2009, 28(2):512-522. doi: 10.1016/j.vaccine.2009.09.127. Epub Oct. 29, 2009.
Schlothauer et al., "Novel human IgG1 and IgG4 Fc-engineered antibodies with completely abolished immune effector functions," Protein Engineering, Design and Selection, Oct. 2016, 29(10):457-466, https://doi.org/10.1093/protein/gzw040.
Schroter et al., "A generic approach to engineer antibody pH-switches using combinatorial histidine scanning libraries and yeast display," mAbs, 2015, 7(1):138-51. doi:0.4161/19420862.2014.985993.
Seimetz et al., "Development and approval of the trifunctional antibody catumaxomab (anti-EpCAM x anti-CD3) as a targeted cancer immunotherapy," Cancer Treat Rev, Oct. 2010, 36(6):458-467. doi: 10.1016/j.ctrv.2010.03.001. Epub Mar. 27, 2010.
Shanmugam et al., "Synthetic Toll Like Receptor-4 (TLR-4) Agonist Peptides as a Novel Class of Adjuvants," PLoS ONE, Feb. 2012, 7(2):e30839.
Shi et al., "TNT003, an inhibitor of the serine protease C1s, prevents complement activation induced by cold agglutinins," Blood, Jun. 26, 2014, 123(26):4015-4022. doi: 10.1182/blood-2014-02-556027. Epub Apr. 2, 2014.
Shields et al., "High resolution mapping of the binding site on human IgG1 for FcγRI, FcγRII, FcγRIII, and FcRn and design of IgGI variants with improved binding to the FcγR," J Biol Chem, Mar. 2, 2001, 276(9):6591-6604. Epub Nov. 28, 2000.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-3473. Epub Nov. 8, 2002.
Siberil et al., "Molecular aspects of human FcγR interactions with IgG: functional and therapeutic consequences," Immunol Lett, Aug. 15, 2006, 106(2):111-118. Epub Jun. 12, 2006.
Sikkink et al., "Biochemical and aggregation analysis of Bence Jones proteins from different light chain diseases," Amyloid, Mar. 2008, 15(1):29-39.
Singer et al., "The Genetic Molecules," Genes & Genomes, Moscow, Mir, 1998, 1:63-64 (with what are believed to be the corresponding pages from an English version of Genes & Genomes).
Singer et al., Chapter 3 "The Logic and Machinery of Gene Expression," Genes & Genomes, Moscow, Mir, 1998, pp. 115-188 (with what are believed to be the corresponding pages from an English version of Genes & Genomes).
Smith et al., "FcγRIIB in autoimmunity and infection: evolutionary and therapeutic implications," Nat Rev Immunol, May 2010, 10(5):328-343. doi: 10.1038/nri2762.
Sondermann et al., "Molecular Basis for Immune Complex Recognition: A Comparison of Fc-Receptor Structures," J Mol Biol, Jun. 8, 2001, 309(3):737-749.
Sondermann et al., "Crystal structure of the soluble form of the human Fcγ-receptor IIb: a new member of the immunoglobulin superfamily at 1.7 Å resolution," EMBO J, Mar. 1, 1999, 18(5):1095-1103.

(56) References Cited

OTHER PUBLICATIONS

Sondermann et al., "The 3.2-Å crystal structure of the human IgG1 Fc fragment-FcγRIII complex," Nature, Jul. 20, 2000, 406(6793):267-273.

Stavenhagen et al., "Enhancing the potency of therapeutic monoclonal antibodies via Fc optimization," Adv Enzyme Regul, 2008, 48:152-164.

Stepanov, Chapter 4 "Primary Structure of Protein," Molecular biology. Structure and functions of proteins, M.: Nauka, 2005, pp. 61-62 (with English translation).

Stevenson et al., "A chimeric antibody with dual Fc regions (bisFabFc) prepared by manipulations at the IgG hinge," Anticancer Drug Des, Mar. 1989, 3(4):219-230.

Su et al., "Expression profile of FcγRIIb on leukocytes and its dysregulation in systemic lupus erythematosus," J Immunol, Mar. 2007, 178(5):3272-3280.

Summers et al., "Fine-tuning of dendritic cell biology by the TNF superfamily," Nat Rev Immunol, Apr. 10, 2012, 12(5):339-351. doi: 10.1038/nri3193.

Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol, Feb. 15, 2010, 184(4):1968-1976. doi: 10.4049/jimmunol.0903296. Epub Jan. 18, 2010.

Szlama et al., "Latent myostatin has significant activity and this activity is controlled more efficiently by WFIKKN1 than by WFIKKN2," FEBS J, Aug. 2013, 280(16):3822-3839. doi: 10.1111/febs.12377. Epub Jul. 5, 2013.

Tackenberg et al., "Impaired inhibitory Fcγ receptor IIB expression on B cells in chronic inflammatory demyelinating polyneuropathy," Proc Natl Acad Sci USA, Mar. 24, 2009, 106(12):4788-4792. doi: 10.1073/pnas.0807319106.

Tarantul, "Antibodies," Explanatory Biotechnological Dictionary—Russian—English, Moscow, 2009, p. 72 (with English translation).

Torres et al., "The immunoglobulin constant region contributes to affinity and specificity," Trend Immunol, 2008, 29(2):91-97.

Travis et al., "Isolation of Albumin from Whole Human Plasma and Fractionation of Albumin-Depleted Plasma," Biochem J, Aug. 1, 1976, 157(2):301-306.

Traxlmayr et al., "Integrin binding human antibody constant domains—probing the C-terminal structural loops for grafting the RGD motif," J Biotechnol, Sep. 10, 2011, 155(2):193-202. doi: 10.1016/j.jbiotec2011.06.042. Epub Jul. 8, 2011.

Tseng et al., "Probing the structure of C1 with an anti-C1s monoclonal antibody: the possible existence of two forms of C1 in solution," Mol Immunol, Jun. 1997, 34(8-9):671-679. doi: 10.1016/s0161-5890(97)00039-4.

Unkeless et al., "Structure and function of human and murine receptors for IgG," Annu Rev Immunol, 1988, 6:251-281.

Vaccaro et al., "Engineering the Fc region of immunoglobulin G to modulate in vivo antibody levels," Nat Biotechnol, Oct. 2005, 23(10):1283-1288. Epub Sep. 25, 2005.

Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-428.

Vercellini et al., "Postoperative oral contraceptive exposure and risk of endometrioma recurrence," Am J Obstet Gynecol, May 2008, 198(5):504.e1-504.e5. Epub Feb. 2008.

Veri et al., "Monoclonal antibodies capable of discriminating the human inhibitory Fcγ-receptor IIB (CD32B) from the activating Fcγ-receptor IIA (CD32A): biochemical, biological and functional characterization," Immunology, 2007, 121(3):392-404.

Veri et al., "Therapeutic control of B cell activation via recruitment of Fcγ receptor IIb (CD32B) inhibitory function with a novel bispecific antibody scaffold," Arthritis Rheum, Jul. 2010, 62(7):1933-1943. doi: 10.1002/art.27477.

Vidarsson et al., "IgG subclasses and allotypes: from structure to effector functions," Front Immunol, Oct. 20, 2014, 5(520):1-17. doi:10.3389/fimmu.2014.00520. eCollection 2014.

Vinay et al., "4-1BB signaling beyond T cells," Cell Mol Immunol, Jul. 2011, 8(4):281-284. doi: 10.1038/cmi. 2010. 82. Epub Jan. 10, 2011.

Wagner et al., "Loss of myostatin attenuates severity of muscular dystrophy in mdx mice," Ann Neurol, Dec. 2002, 52(6):832-836.

Wang et al., "Molecular Basis of Assembly and Activation of Complement Component C1 in Complex with Immunoglobulin G1 and Antigen," Mol Cell, Jul. 7, 2016, 63(1):135-145. doi: 10.1016/j.molcel.2016.05.016. Epub Jun. 16, 2016.

Wang et al., "Monoclonal Antibodies with Identical Fc Sequences Can Bind to FcRn Differentially with Pharmacokinetic Consequences," Drug Metabolism and Disposition, Sep. 2011, 39(9):1469-1477.

Warmerdam et al., "Molecular basis for a polymorphism of human Fcγ receptor II (CD32)," J Exp Med, Jul. 1990, 172(1):19-25.

Warmerdam et al., "The human low affinity immunoglobulin G Fc receptor IIC gene is a result of an unequal crossover event," J Biol Chem, Apr. 5, 1993, 268(10):7346-7349.

Warncke et al., "Different adaptations of IgG effector function in human and nonhuman primates and implications for therapeutic antibody treatment," J Immunol, May 1, 2012, 188(9):4405-4411. doi: 10.4049/jimmunol. 1200090. Epub Mar. 28, 2012.

Weiss et al., "Rapid mapping of protein functional epitopes by combinatorial alanine scanning," Proc Natl Acad Sci USA, Aug. 1, 2000, 97(16):8950-8954.

Wenink et al., "The inhibitory FcγIIb receptor dampens TLR4-mediated immune responses and is selectively up-regulated on dendritic cells from rheumatoid arthritis patients with quiescent disease," J Immunol, Oct. 1, 2009, 183(7):4509-4520. doi: 10.4049/jimmunol.0900153. Epub Sep. 4, 2009.

Wernersson et al., "IgG-mediated enhancement of antibody responses is low in Fc receptor γ chain-deficient mice and increased in Fc γ RII-deficient mice," J Immunol, Jul. 1999, 163(2):618-622.

Werwitzke et al., "Treatment of lupus-prone NZB/NZW $F_1$ mice with recombinant soluble Fcγ receptor II (CD32)," Ann Rheum Dis, Feb. 2008, 67(2):154-161. Epub Jun. 8, 2007.

Whittemore et al., "Inhibition of myostatin in adult mice increases skeletal muscle mass and strength," Biochem Biophys Res Commun, Jan. 24, 2003, 300(4):965-971.

Wilson et al., "An Fcγ receptor-dependent mechanism drives antibody-mediated target-receptor signaling in cancer cells," Cancer Cell, Jan. 18, 2011, 19(1):101-113. doi: 10.1016/j.ccr.2010.11.012.

Wines et al., "The IgG Fc Contains Distinct Fc Receptor (FcR) Binding Sites: The Leukocyte Receptors FcγRI and FcRγIIa Bind to a Region in the Fc Distinct from That Recognized by Neonatal FcR and Protein A," J Immunol, May 15, 2000, 164(10):5313-5318.

Wolfman et al., "Activation of latent myostatin by the BMP-1/tolloid family of metalloproteinases," Proc Natl Acad Sci USA, Dec 23, 2003, 100(26):15842-15846. Epub Dec 11, 2003.

Wozniak-Knopp et al., "Introducing antigen-binding sites in structural loops of immunoglobulin constant domains: Fc fragments with engineered HER2/neu-binding sites and antibody properties," Protein Eng Des Sel, Apr. 2010, 23(4):289-297. doi: 10.1093/protein/gzq005. Epub Feb. 11, 2010.

Wu et al., "Development of motavizumab, an ultra-potent antibody for the prevention of respiratory syncytial virus infection in the upper and lower respiratory tract," J Mol Biol, May 4, 2007, 368(3):652-665. Epub Feb. 20, 2007.

Wu et al., "Structure-based engineering of a monoclonal antibody for improved solubility," Protein Eng Des Sel, Aug. 2010, 23(8):643-651. doi: 10.1093/protein/gzq037. Epub Jun. 11, 2010.

Wu et al., "Structures of the CXCR4 Chemokine GPCR with Small-Molecule and Cyclic Peptide Antagonists," Science, Nov. 2010, 330:1066-1071.

Xi et al., "Increased survival and reduced renal injury in MRL/lpr mice treated with a human Fcγ receptor II (CD32) peptide," Immunology, May 2012, 136(1):46-53. doi: 10.1111/j.1365-2567.2012.03553.x.

Xiao et al., "A large library based on a novel (CH2) scaffold: Identification of HIV-1 inhibitors," Biochem Biophys Res Commun, Sep. 18, 2009, 387(2):387-392. doi: 10.1016/j.bbrc2009.07.044. Epub Jul. 15, 2009.

(56) References Cited

OTHER PUBLICATIONS

Xie et al., "A new format of bispecific antibody: highly efficient heterodimerization, expression and tumor cell lysis," J Immunol Methods, Jan. 2005, 296(1-2):95-101. Epub Nov. 19, 2004.
Xu et al., "FcγRs modulate cytotoxicity of anti-Fas antibodies: implications for agonistic antibody-based therapeutics," J Immunol, Jul. 2003, 171(2):562-568.
Yada et al., Chapter 2 "Antigens and Receptors," pp. 11-23 and Chapter 11 "Lymphocyte Effector Receptors," pp. 141-157, Lippincott's Illustrated Reviews: Immunology, $2^{nd}$ ed., Nov. 30, 2013 (with what are believed to be the corresponding pages from an English version of Lippincott's Illustrated Reviews: Immunology).
Yarilin, Chapter 3 "Molecular and cellular basis of adaptive immunity," Fundamentals of Immunology, M.: Medicina, 1999, pp. 172-174 (with English translation).
Yarilin, Chapter 3 "Molecular and cellular basis of adaptive immunity," Fundamentals of Immunology, M.: Medicina, 1999, pp. 181-184 (with English translation).
Yarilin, Fundamentals of Immunology, M:Medicina, 1999, pp. 169-172 and 354-358 (with English translation).
Yeung et al., "Engineering human IgG1 affinity to human neonatal Fc receptor: impact of affinity improvement on pharmacokinetics in primates," J Immunol, Jun. 15, 2009, 182(12):7663-7671. doi: 10.4049/jimmunol.0804182.
Ying et al., "Large Yellow Croaker MSTM-1 Prodomain Prokaryotic Expression Polyclonal Antibody Preparation and Antibody Function Identification," Chinese Journal of Cell Biology, Oct. 2014, 36(10):1344-1349 (with English Abstract).
Yuasa et al., "Deletion of fcγ receptor IIB renders H-$2^b$ mice susceptible to collagen-induced arthritis," J Exp Med, Jan. 1999, 189(1):187-194.
Zalevsky et al., "Enhanced antibody half-life improves in vivo activity," Nat Biotechnol, Feb. 2010, 28(2):157-159. doi: 10.1038/nbt.1601. Epub Jan. 17, 2010.
Zalevsky et al., "The impact of Fc engineering on an anti-CD19 antibody: increased Fcγ receptor affinity enhances B-cell clearing in nonhuman primates," Blood, 2009, 113(16):3735-3743. Epub Dec 24, 2008.
Zeidler et al., "Simultaneous activation of T cells and accessory cells by a new class of intact bispecific antibody results in efficient tumor cell killing," J Immunol, Aug. 1, 1999, 163(3):1246-1252.
Zhang et al., "Effective therapy for a murine model of human anaplastic large-cell lymphoma with the anti-CD30 monoclonal antibody, HeFi-1,does not require activating Fc receptors," Blood, Jul. 15, 2006;108(2):705-10. Epub Mar. 21, 2006.
Zhang et al., "Immune complex/Ig negatively regulate TLR4-triggered inflammatory response in macrophages through FcγRIIb-dependent PGE2 production," J Immunol, Jan. 1, 2009, 182(1):554-562.
Zheng et al., "Translational pharmacokinetics and pharmacodynamics of an FcRn-variant anti-CD4 monoclonal antibody from preclinical model to phase I study," Clin Pharmacol Ther, Feb. 2011, 89(2):283-290. doi: 10.1038/clpt.2010.311. Epub Dec 29, 2010.
Zimmers et al., "Induction of cachexia in mice by systemically administered myostatin," Science, May 24, 2002, 296(5572):1486-1488.
International Search Report and Written Opinion for App. Ser. No. PCT/JP2012/054624, mailed Apr. 3, 2013, 7 pages.
International Preliminary Report on Patentability for App. Ser. No. PCT/JP2012/054624, dated Aug. 27, 2013, 7 pages.
International Search Report for App. Ser. No. PCT/JP2012/075092, mailed Dec. 25, 2012, 4 pages.
International Preliminary Report on Patentability for App. Ser. No. PCT/JP2012/075092, dated Apr. 1, 2014, 10 pages.
International Preliminary Report on Patentability for App. Ser. No. PCT/JP2012/066665, dated Jan. 16, 2014, 10 pages.
International Search Report and Written Opinion for App. Ser. No. PCT/JP2012/066665, mailed Sep. 25, 2012, 10 pages.
International Search Report for App. Ser. No. PCT/JP2013/054461, mailed May 7, 2013, 7 pages.
International Preliminary Report on Patentability for App. Ser. No. PCT/JP2013/054461, dated Aug. 26, 2014, 6 pages.
International Search Report for App. Ser. No. PCT/JP2013/066428, mailed Aug. 6, 2013.
International Preliminary Report on Patentability for App. Ser. No. PCT/JP2013/066428, dated Dec. 16, 2014.
International Search Report for App. Ser. No. PCT/JP2013/072507, mailed Oct. 29, 2013, 4 pages.
International Preliminary Report on Patentability for App. Ser. No. PCT/JP2013/072507, dated Feb. 24, 2015, 6 pages.
International Search Report for App. Ser. No. PCT/JP2013/084809, mailed Apr. 1, 2014, 4 pages.
International Preliminary Report on Patentability for App. Ser. No. PCT/JP2013/084809, dated Jun. 30, 2015, 7 pages.
International Search Report for App. Ser. No. PCT/JP2014/059706, dated Jul. 15, 2014, 4 pages.
International Preliminary Report on Patentability for App. Ser. No. PCT/JP2014/059706, dated Oct. 6, 2015, 10 pages.
USPTO Restriction Requirement in U.S. Appl. No. 14/127,576, dated Jun. 1, 2016, 8 pages.
Fish & Richardson P.C., Reply to Restriction Requirement dated Jun. 1, 2016 in U.S. Appl. No. 14/127,576, filed Aug. 24, 2016, 2 pages.
USPTO Non-Final Office Action in U.S. Appl. No. 14/127,576, dated Sep. 20, 2016, 17 pages.
USPTO Interview Summary in U.S. Appl. No. 14/127,576, dated Dec. 23, 2016, 3 pages.
Fish & Richardson P.C., Reply to Non-Final Office Action of Sep. 20, 2016 in U.S. Appl. No. 14/127,576, dated Mar. 16, 2017, 21 pages.
USPTO Notice of Allowance in U.S. Appl. No. 14/127,576, dated Jun. 2, 2017, 13 pages.
USPTO Notice of Allowance in U.S. Appl. No. 14/127,576, dated Jun. 21, 2017, 9 pages.
USPTO Notice of Allowance in U.S. Appl. No. 14/127,576 dated Oct. 19, 2017, 7 pages.
USPTO Notice of Allowance in U.S. Appl. No. 14/127,576, dated Dec. 15, 2017, 8 pages.
USPTO Restriction Requirement in U.S. Appl. No. 14/406,232, dated Apr. 27, 2016, 15 pages.
Fish & Richardson P.C., Response to Restriction Requirement dated Apr. 27, 2016 in U.S. Appl. No. 14/406,232, filed Jul. 26, 2016, 2 pages.
USPTO Non-Final Office Action in U.S. Appl. No. 14/406,232, dated Oct. 20, 2016, 37 pages.
Fish & Richardson P.C., Response to Non-Final Office Action in U.S. Appl. No. 14/406,232, dated Apr. 20, 2017, 39 pages.
USPTO Notice of Non-Compliant Amendment in U.S. Appl. No. 14/406,232, dated Jul. 25, 2017, 3 pages.
USPTO Final Office Action in U.S. Appl. No. 14/406,232, dated Nov. 13, 2017, 26 pages.
USPTO Applicant-Initiated Interview Summary in U.S. Appl. No. 14/406,232, dated May 15, 2018, 3 pages.
USPTO Final Office Action in U.S. Appl. No. 14/406,232, dated Apr. 5, 2019, 38 pages.
USPTO Non-Final Office Action in U.S. Appl. No. 14/406,232, dated Aug. 11, 2020, 47 pages.
USPTO Final Office Action in U.S. Appl. No. 14/347,321 on Jan. 9, 2017, 60 pages.
USPTO Restriction Requirement in U.S. Appl. No. 14/347,321, dated Dec. 17, 2015, 10 pages.
Fish & Richardson P.C., Response to Restriction Requirement dated Dec. 17, 2015, in U.S. Appl. No. 14/347,321, filed Feb. 16, 2016, 3 pages.
USPTO Non Final Office Action in U.S. Appl. No. 14/347,321, dated May 2, 2016, 35 pages.
Fish & Richardson P.C., Response to Non Final Office Action dated May 2, 2016 in U.S. Appl. No. 14/347,321, filed Nov. 2, 2016, 35 pages.
USPTO Non-Final Office Action in U.S. Appl. No. 14/347.321, dated Nov. 13, 2017, 64 pages.
USPTO Restriction Requirement in U.S. Appl. No. 14/377,556, dated Dec. 15, 2016, 11 pages.

(56) References Cited

OTHER PUBLICATIONS

Fish & Richardson P.C., Response to Restriction Requirement dated Dec. 15, 2016, in U.S. Appl. No. 14/377,556, filed Feb. 13, 2017.
USPTO Non-Final Office Action in U.S. Appl. No. 14/377,556, dated Feb. 27, 2017, 10 pages.
USPTO Final Office Action in U.S. Appl. No. 14/377,556, dated Jul. 7, 2017, 12 pages.
USPTO Non-Final Office Action in U.S. Appl. No. 14/377,556, dated Dec. 12, 2017, 14 pages.
USPTO Final Office Action in U.S. Appl. No. 14/377,556, dated May 11, 2018, 19 pages.
USPTO Non-Final Office Action in U.S. Appl. No. 14/377,556, dated Apr. 18, 2019, 9 pages.
USPTO Final Office Action in U.S. Appl. No. 14/377,556, dated Sep. 24, 2019, 12 pages.
USPTO Restriction Requirement in U.S. Appl. No. 14/974,488, dated Jan. 24, 2017, 17 pages.
International Search Report for App. Ser. No. PCT/JP2016/003616, mailed Nov. 25, 2016, 4 pages.
USPTO Non-Final Office Action in U.S. Appl. No. 14/974,488, dated Aug. 16, 2017, 18 pages.
USPTO Notice of Allowance in U.S. Appl. No. 14/974,488, dated Mar. 13, 2018, 26 pages.
USPTO Restriction Requirement in U.S. Appl. No. 14/654,895, dated Sep. 21, 2017, 8 pages.
USPTO Non-final Office Action in U.S. Appl. No. 14/654,895, dated Feb. 7, 2018, 39 pages.
USPTO Final Office Action and Examiner-Initiated Interview Summary in U.S. Appl. No. 14/654,895, dated Oct. 11, 2018, 17 pages.
USPTO Applicant-Initiated Interview Summary in U.S. Appl. No. 14/654,895, dated Oct. 16, 2018, 3 pages.
USPTO Applicant-Initiated Interview Summary in U.S. Appl. No. 14/654,895, dated Nov. 19, 2018, 3 pages.
USPTO Advisory Action Before the Filing of an Appeal Brief in U.S. Appl. No. 14/654,895, dated Jan. 11, 2019, 3 pages.
USPTO Notice of Allowance in U.S. Appl. No. 14/654,895, dated Jun. 27, 2019, 12 pages.
USPTO Notice of Allowance in U.S. Appl. No. 14/654,895, dated Dec. 26, 2019, 7 pages.
USPTO Notice of Allowance in U.S. Appl. No. 14/654,895, dated May 26, 2020, 7 pages.
USPTO Final Office Action in U.S. Appl. No. 15/952,945, dated Jun. 3, 2019, 18 pages.
USPTO Final Office Action in U.S. Appl. No. 15/952,951, dated Jun. 3, 2019, 67 pages.
USPTO Advisory Action in U.S. Appl. No. 15/952,951, dated Aug. 19, 2019, 5 pages.
USPTO Non-final Office Action in U.S. Appl. No. 14/423,269, dated Oct. 2, 2019, 24 pages.
USPTO Restriction Requirement in U.S. Appl. No. 14/781,069, dated Dec. 7, 2017, 7 pages.
USPTO Non-final Office Action in U.S. Appl. No. 14/781,069, dated Aug. 27, 2018, 59 pages.
USPTO Final Office Action in U.S. Appl. No. 14/781,069, dated May 20, 2019, 29 pages.
USPTO Non-final Office Action in U.S. Appl. No. 14/781,069, dated Mar. 13, 2020, 21 pages.
U.S. Appl. No. 18/286,471, Koga, filed Oct. 11, 2023.
U.S. Appl. No. 18/286,471, filed Oct. 11, 2023, Koga.
Morris et al., "Signaling through the Inhibitory Fc Receptor FcγRIIB Induces CD8 T Cell Apoptosis to Limit T Cell Immunity," Immunity, Jan. 14, 2020, 52(1):136-150.
U.S. Appl. No. 18/022,342, Katada et al., filed Feb. 21, 2023.
U.S. Appl. No. 18/023,038, Katada et al., filed Feb. 24, 2023.
U.S. Appl. No. 18/022,342, filed Feb. 21, 2023, Katada et al.
U.S. Appl. No. 18/023,038, filed Feb. 24, 2023, Katada et al.
Bertolotti-Ciarlet et al., "Impact of methionine oxidation on the binding of human IgG1 to Fc Rn and Fc gamma receptors," Mol Immunol, May 2009, 46(8-9):1878-1882.
Wang et al., "Recent advances in detection of *k-ras* gene mutations and target therapy of colorectal cancer," World Chinese Journal of Digestology, Jan. 2011, 19(1):62-67 (with English translation).
U.S. Appl. No. 18/472,932, filed Sep. 22, 2023, Fukuzawa et al.
U.S. Appl. No. 15/860,163, Mimoto et al., filed Jan. 2, 2018.
U.S. Appl. No. 14/001,218, Mimoto et al., filed Aug. 23, 2013 (abandoned).
U.S. Appl. No. 14/347,321, Igawa et al., filed Mar. 26, 2014 (abandoned).
U.S. Appl. No. 15/977,757, Igawa et al., filed May 11, 2018 (abandoned).
U.S. Appl. No. 17/561,207, Igawa et al., filed Dec. 23, 2021.
U.S. Appl. No. 14/377,556, Kuramochi et al., filed Aug. 8, 2014 (abandoned).
U.S. Appl. No. 16/795,676, Kuramochi et al., filed Feb. 20, 2020.
U.S. Appl. No. 14/379,825, Igawa et al., filed Aug. 20, 2014 (abandoned).
U.S. Appl. No. 17/854,023, Igawa et al., filed Jun. 30, 2022.
U.S. Appl. No. 17/484,003, Igawa et al., filed Sep. 24, 2021.
U.S. Appl. No. 17/028,210, Katada et al., filed Sep. 20, 2020.
U.S. Appl. No. 17/671,185, Mimoto et al., filed Feb. 14, 2022.
U.S. Appl. No. 15/963,455, Ruike et al., filed Apr. 26, 2018.
U.S. Appl. No. 16/889,066, Ruike et al., filed Jun. 1, 2020.
U.S. Appl. No. 16/763,134, Feng et al., filed May 11, 2020.
U.S. Appl. No. 17/046,395, Fukuzawa et al., filed Oct. 9, 2020.
U.S. Appl. No. 17/266,024, Igawa et al., filed Feb. 4, 2021.
U.S. Appl. No. 17/333,256, Kakiuchi et al., filed May 28, 2021.
U.S. Appl. No. 17/494,199, Igawa et al., filed Oct. 5, 2021.
U.S. Appl. No. 17/602,196, Wakabayashi et al., filed Oct. 7, 2021.
U.S. Appl. No. 17/610,204, Koga, filed Nov. 10, 2021.
U.S. Appl. No. 17/742,824, Ruike et al., filed May 12, 2022.
U.S. Appl. No. 17/768,053, Koga et al., filed Apr. 11, 2022.
U.S. Appl. No. 14/001,218, filed Aug. 23, 2013, Mimoto et al.
U.S. Appl. No. 17/333,256, filed May 28, 2021, Kakiuchi et al.
U.S. Appl. No. 17/494,199, filed Oct. 5, 2021, Igawa et al.
U.S. Appl. No. 17/602,196, filed Oct. 7, 2021, Wakabayashi et al.
U.S. Appl. No. 17/610,204, filed Nov. 10, 2021, Koga.
U.S. Appl. No. 17/561,207, filed Dec. 23, 2021, Igawa et al.
U.S. Appl. No. 17/671,185, filed Feb. 14, 2022, Mimoto et al.
U.S. Appl. No. 17/742,824, filed May 12, 2022, Ruike et al.
U.S. Appl. No. 17/768,053, filed Apr. 11, 2022, Koga et al.
U.S. Appl. No. 17/854,023, filed Jun. 30, 2022, Igawa et al.
Deng et al., "Pharmacokinetics of Humanized Monoclonal Anti-Tumor Necrosis Factor-α Antibody and Its Neonatal Fc Receptor Variants in Mice and Cynomolgus Monkeys," Drug Metab Dispos, Apr. 2010, 38(4):600-605. doi: 10.1124/dmd.109.031310. Epub Jan. 13, 2010.
Fukuzawa et al., "Long lasting neutralization of C5 by SKY59, a novel recycling antibody, is a potential therapy for complement-mediated diseases," Sci Rep, Apr. 24, 2017, 7(1):1080. doi: 10.1038/s41598-017-01087-7.
Henne et al., "Anti-PCSK9 Antibody Pharmacokinetics and Low-Density Lipoprotein-Cholesterol Pharmacodynamics in Nonhuman Primates are Antigen Affinity-Dependent and Exhibit Limited Sensitivity to Neonatal Fc Receptor-Binding Enhancement," J Pharmacol Exp Ther, Apr. 2015, 353(1):119-131. doi: 10.1124/jpet.114.221242. Epub Feb. 4, 2015.
Huang et al., "Fully Humanized Neutralizing Antibodies to Interleukin-8 (ABX-IL8) Inhibit Angiogenesis, Tumor Growth, and Metastasis of Human Melanoma," Am J Pathol, Jul. 2002, 161(1):125-134.
Jakubke et al., "Physicochemical properties," Amino Acids, Peptides and Proteins, Moscow, Mir, 1985, pp. 356-363 (with English translation).
Nakagawa et al., "Complement C1s activation in degenerating articular cartilage of rheumatoid arthritis patients: immunohistochemical studies with an active form specific antibody," Ann Rheum Dis, Mar. 1999, 58(3):175-181.
Petkova et al., "Enhanced half-life of genetically engineered human IgG1 antibodies in a humanized FcRn mouse model: potential application in humorally mediated autoimmune disease," Int Immunol, Dec 2006, 18(12):1759-1769. Epub Oct. 31, 2006.

(56) References Cited

OTHER PUBLICATIONS

Ridgway et al., "'Knobs-into-holes' engineering of antibody $C_H3$ domains for heavy chain heterodimerization," Prot Eng, Jul. 1996, 9(7):617-621.
Xu, editor, Part III "Medicated Bath for Common Disease—Correct Medicated Bath Can Treat Various Diseases," Chinese Medicated Bath Encyclopedia, Golden Shield Press, Beijing, Oct. 31, 2013, p. 177.
Zwolak et al., "Rapid Purification of Human Bispecific Antibodies via Selective Modulation of Protein A Binding," Sci Rep, Nov. 14, 2017, 7(1):15521.
USPTO Restriction Requirement in U.S. Appl. No. 14/001,218, dated Dec. 2, 2015, 8 pages.
Fish & Richardson P.C., Reply to Restriction Requirement dated Dec. 2, 2015 in U.S. Appl. No. 14/001,218, filed Feb. 1, 2016, 1 page.
USPTO Non-Final Office Action in U.S. Appl. No. 14/001,218, dated Apr. 4, 2016, 13 pages.
Fish & Richardson P.C., Amendment and Reply to Office Action of Apr. 4, 2016 in U.S. Appl. No. 14/001,218, filed Oct. 3, 2016, 15 pages.
USPTO Final Office Action in U.S. Appl. No. 14/001,218, dated Dec. 16, 2016, 11 pages.
USPTO Interview Summary in U.S. Appl. No. 14/001,218, dated Jan. 12, 2017, 3 pages.
Fish & Richardson P.C., Amendment and Reply to Office Action dated Dec. 16, 2016 in U.S. Appl. No. 14/001,218, filed Jun. 16, 2017, 12 pages.
USPTO Non-Final Office Action in U.S. Appl. No. 14/001,218, dated Jun. 27, 2017, 12 pages.
Fish & Richardson P.C., Reply to Action of Jun. 27, 2017 in U.S. Appl. No. 14/001,218, filed Dec. 27, 2017, 7 pages.
USPTO Final Office Action in U.S. Appl. No. 14/001,218, dated Jan. 29, 2018, 8 pages.
Fish & Richardson P.C., Amendment and Reply to Final Action of Jan. 29, 2018 in U.S. Appl. No. 14/001,218, filed Mar. 28, 2018, 29 pages.
USPTO Advisory Action and Applicant-Initiated Interview Summary in U.S. Appl. No. 14/001,218, dated Apr. 11, 2018, 5 pages.
Fish & Richardson P.C, Request for Continued Examination and Declaration of Hitoshi Katada under 37 CFR. § 1.132 in U.S. Appl. No. 14/001,218, filed Feb. 22, 2019, 6 pages.
Fish & Richardson P.C., Substance of Interview of Apr. 3, 2018 in U.S. Appl. No. 14/001,218, filed Feb. 25, 2019, 1 page.
USPTO Non-Final Office Action in U.S. Appl. No. 14/001,218, dated Mar. 18, 2019, 22 pages.
Fish & Richardson P.C., Amendment and Reply to Action of Mar. 18, 2019 in U.S. Appl. No. 14/001,218, filed Sep. 18, 2019, 18 pages.
USPTO Final Office Action in U.S. Appl. No. 14/001,218, dated Nov. 21, 2019, 17 pages.
Fish & Richardson P.C., Amendment and Reply to Final Action of Nov. 21, 2019 in U.S. Appl. No. 14/001,218, filed May 20, 2020, 10 pages.
USPTO Non-Final Office Action in U.S. Appl. No. 14/001,218, dated Jun. 16, 2020, 9 pages.
Fish & Richardson P.C., Amendment and Reply to Non-Final Office Action in U.S. Appl. No. 14/001,218, filed Dec. 15, 2020, 15 pages.
USPTO Final Office Action in U.S. Appl. No. 14/001,218, dated Feb. 2, 2021, 11 pages.
Fish & Richardson P.C., Amendment and Reply to Final Office Action in U.S. Appl. No. 14/001,218, filed Oct. 28, 2021, 12 pages.
USPTO Non-Final Office Action in U.S. Appl. No. 14/001,218, dated Dec. 29, 2021, 10 pages.
USPTO Restriction Requirement in U.S. Appl. No. 14/423,269, dated May 4, 2017, 5 pages.
USPTO Non-final Office Action in U.S. Appl. No. 14/423,269, dated Nov. 28, 2017, 16 pages.
USPTO Final Office Action in U.S. Appl. No. 14/423,269, dated Aug. 15, 2018, 18 pages.
USPTO Restriction Requirement in U.S. Appl. No. 15/963,455, dated Jun. 13, 2019, 6 pages.
USPTO Non-Final Office Action in U.S. Appl. No. 15/963,455, dated Sep. 18, 2020, 20 pages.
USPTO Non-Final Office Action in U.S. Appl. No. 15/963,455, dated Dec. 6, 2021, 21 pages.
Katagiri et al., "Effects of SA237, a humanized anti-interleukin-6 receptor monoclonal antibody, on pre- and postnatal development in cynomolgus monkey," Birth Defects Res, Jul. 3, 2017, 109(11):843-856.
Kuznetsova, "Brackets in Text of Legal Document as a Linguo-Cognitive Phenomenon," Bulletin MGOU, Chapter: Russian philology, 2015, 3:37-43 (with English translation).
Singer et al., Chapter 1.3 "Structure of Proteins," Genes & Genomes, Moscow, Mir, 1998, pp. 63-66 (with what are believed to be the corresponding p. from an English version of Genes & Genomes).
U.S. Appl. No. 18/298,743, filed Apr. 11, 2023, Igawa et al.
U.S. Appl. No. 18/929,733, filed Oct. 29, 2024, Ruike et al.
Patton et al., "An acid dissociation bridging ELISA for detection of antibodies directed against therapeutic proteins in the presence of antigen," J Immunol Methods, Sep. 2005, 304(1-2):189-195.
USPTO Final Office Action in U.S. Appl. No. 15/963,455, dated Sep. 29, 2022, 17 pages.
USPTO Non-Final Office Action in U.S. Appl. No. 15/963,455, dated Sep. 26, 2023, 10 pages.
USPTO Restriction Requirement in U.S. Appl. No. 17/028,210, dated Oct. 13, 2023, 8 pages.
USPTO Office Action in U.S. Appl. No. 17/028,210, dated May 2, 2024, 5 pages.
U.S. Appl. No. 18/657,893, filed May 8, 2024, Fukuzawa et al.
U.S. Appl. No. 17/798,686, Sakurai et al., filed Aug. 10, 2011.
U.S. Appl. No. 17/798,686, filed Aug. 10, 2022, Sakurai et al.
Chen et al., "Advance in Research on Antibody Half-Life Related Engineering," China biotechnology, 2017, 37(5):87-96 (with English abstract).
Escobar-Cabrera et al., "Asymmetric Fc Engineering for Bispecific Antibodies with Reduced Effector Function," Antibodies (Basel), May 16, 2017, 6(2):7, 16 pages.
Tamura et al., "FcγR2A and 3A polymorphisms predict clinical outcome of trastuzumab in both neoadjuvant and metastatic settings in patients with HER2-positive breast cancer," Ann Oncol, Jun. 2011, 22(6):1302-1307.
Tsao et al., "CD47 blockade augmentation of trastuzumab antitumor efficacy dependent on antibody-dependent cellular phagocytosis," JCI Insight, Dec 19, 2019, 4(24):e131882, 21 pages.
Wang et al., "IgG Fc engineering to modulate antibody effector functions," Protein Cell, Jan. 2018, 9(1):63-73.
Yang et al., "Engineering of Fc Fragments with Optimized Physicochemical Properties Implying Improvement of Clinical Potentials for Fc-Based Therapeutics," Front Immunol, Jan. 8, 2018, 8:1860, 14 pages.
U.S. Appl. No. 19/644,413, filed Apr. 10, 2026, Igawa et al.

* cited by examiner

BLACK CRYSTAL STRUCTURE OF Fc(P238D)/FcγRIIb EXTRACELLULAR REGION COMPLEX
GRAY MODEL STRUCTURE OF Fc(WT)/FcγRIIb EXTRACELLULAR REGION COMPLEX

Fc-γ-RIIb-SPECIFIC Fc ANTIBODY

CROSS-REFERENCE TO RELATED APPLICATIONS

This application is a divisional of application Ser. No. 14/001,218, having a 371(c) filing date of Dec. 2, 2013, which is the National Stage of International Application No. PCT/JP2012/054624, filed on Feb. 24, 2012, which claims the benefit of Japanese Application No. 2011-040923, filed on Feb. 25, 2011, and Japanese Application No. 2011-219835, filed on Oct. 4, 2011. The entire contents of the foregoing US and PCT applications are incorporated by reference.

SEQUENCE LISTING

This application contains a Sequence Listing that has been submitted electronically as an ASCII text file named SequenceListing.txt. The ASCII text file, created on Jun. 22, 2022, is 460 kilobytes in size. The material in the ASCII text file is hereby incorporated by reference in its entirety.

TECHNICAL FIELD

The present invention relates to polypeptides comprising an IgG Fc region that have maintained or decreased binding activities towards both allotypes of FcγRIIa, H type and R type, in which the amino acid at position 131 (EU numbering) in FcγRIIa is His (type H) or Arg (type R), and having enhanced FcγRIIb-binding activity in comparison with a parent polypeptide by introducing amino acid substitutions into the IgG Fc region; pharmaceutical compositions comprising the polypeptide; therapeutic agents or preventive agents comprising the polypeptide for immunological inflammatory diseases; and methods for producing them. Furthermore, the present invention relates to methods for maintaining or decreasing binding activities towards both allotypes of FcγRIIa, H type and R type, in which the amino acid at position 131 (EU numbering) in FcγRIIa is His (type H) or Arg (type R), and enhancing FcγRIIb-binding activity in comparison with a parent polypeptide; and methods for suppressing antibody production compared with the parent polypeptide in in vivo administration. The present invention also relates to methods for producing a polypeptide having maintained or decreased binding activities towards both allotypes of FcγRIIa, H type and R type, in which the amino acid at position 131 (EU numbering) in FcγRIIa is His (type H) or Arg (type R), and having enhanced FcγRIIb-binding activity in comparison with a parent polypeptide; and methods for producing a polypeptide that suppresses antibody production compared with a parent polypeptide in in vivo administration.

BACKGROUND ART

Antibodies are drawing attention as pharmaceuticals since they are highly stable in blood and have few side effects (Non-patent Documents 1 and 2). Almost all antibody pharmaceuticals currently on the market are antibodies of the human IgG1 subclass. One of the known functions of IgG class antibodies is antibody-dependent cell-mediated cytotoxicity (hereinafter denoted as ADCC activity) (Non-patent Document 3). For an antibody to exhibit ADCC activity, the antibody Fc region must bind to an Fcγ receptor (hereinafter denoted as FcγR) which is an antibody-binding receptor present on the surface of effector cells such as killer cells, natural killer cells, and activated macrophages.

In humans, the FcγRIa (CD64A), FcγRIIa (CD32A), FcγRIIb (CD32B), FcγRIIIa (CD16A), and FcγRIIIb (CD16B) isoforms have been reported as the FcγR protein family, and the respective allotypes have also been reported (Non-patent Document 7). FcγRIa, FcγRIIa, and FcγRIIIa are called activating FcγR since they have immunologically active functions, and FcγRIIb is called inhibitory FcγR since it has immunosuppressive functions (Non-patent Document 8).

In the binding between the Fc region and FcγR, several amino acid residues in the antibody hinge region and CH2 domain, and a sugar chain attached to Asn at position 297 (EU numbering) bound to the CH2 domain have been shown to be important (Non-patent Documents 4, 5, and 6). Various variants having FcγR-binding properties, mainly antibodies with mutations introduced into these sites, have been studied so far; and Fc region variants having higher binding activities towards activating FcγR have been obtained (Patent Documents 1, 2, 3, and 4).

When activating FcγR is cross-linked with an immune complex, it phosphorylates immunoreceptor tyrosine-based activating motifs (ITAMs) contained in the intracellular domain or FcR common γ-chain (an interaction partner), activates a signal transducer SYK, and triggers inflammatory immune response by initiating an activation signal cascade (Non-patent Document 9).

FcγRIIb is the only FcγR expressed on B cells (Non-patent Document 10). Interaction of the antibody Fc region with FcγRIIb has been reported to suppress the primary immune response of B cells (Non-patent Document 11). Furthermore, it is reported that when FcγRIIb on B cells and a B cell receptor (BCR) are cross-linked via an immune complex in blood, B cell activation is suppressed, and antibody production by B cells is suppressed (Non-patent Document 12). In this immunosuppressive signal transduction mediated by BCR and FcγRIIb, the immunoreceptor tyrosine-based inhibitory motif (ITIM) contained in the intracellular domain of FcγRIIb is necessary (Non-patent Documents 13 and 14). When ITIM is phosphorylated upon signaling, SH2-containing inositol polyphosphate 5-phosphatase (SHIP) is recruited, transduction of other activating FcγR signal cascades is inhibited, and inflammatory immune response is suppressed (Non-patent Document 15). Furthermore, aggregation of FcγRIIb alone has been reported to transiently suppress calcium influx due to BCR cross-linking and B cell proliferation in a BCR-independent manner without inducing apoptosis of IgM-producing B cells (Non-patent Document 16).

Furthermore, FcγRIIb is also expressed on dendritic cells, macrophages, activated neutrophils, mast cells, and basophils. FcγRIIb inhibits the functions of activating FcγR such as phagocytosis and release of inflammatory cytokines in these cells, and suppresses inflammatory immune responses (Non-patent Document 8).

The importance of immunosuppressive functions of FcγRIIb has been elucidated so far through studies using FcγRIIb knockout mice. There are reports that in FcγRIIb knockout mice, humoral immunity is not appropriately regulated (Non-Patent Document 17), sensitivity towards collagen-induced arthritis (CIA) is increased (Non-patent Document 18), lupus-like symptoms are presented, and Goodpasture's syndrome-like symptoms are presented (Non-patent Document 19).

Furthermore, regulatory inadequacy of FcγRIIb has been reported to be related to human autoimmnue diseases. For example, the relationship between genetic polymorphism in the transmembrane region and promoter region of FcγRIIb, and the frequency of development of systemic lupus erythematosus (SLE) (Non-patent Documents 20, 21, 22, 23, and 24), and decrease of FcγRIIb expression on the surface of B cells in SLE patients (Non-patent Document 25 and 26) have been reported.

From mouse models and clinical findings as such, FcγRIIb is considered to play the role of controlling autoimmune diseases and inflammatory diseases mainly through involvement with B cells, and it is a promising target molecule for controlling autoimmune diseases and inflammatory diseases.

IgG1, mainly used as a commercially available antibody pharmaceutical, is known to bind not only to FcγRIIb, but also strongly to activating FcγR (Non-patent Document 27). It may be possible to develop antibody pharmaceuticals having greater immunosuppressive properties compared with those of IgG1, by utilizing an Fc region with enhanced FcγRIIb binding, or improved FcγRIIb-binding selectivity compared with activating FcγR. For example, it has been suggested that the use of an antibody having a variable region that binds to BCR and an Fc with enhanced FcγRIIb binding may inhibit B cell activation (Non-patent Document 28). It has been reported that crosslinking FcγRIIb on B cells and IgE bound to a B-cell receptor suppresses differentiation of B cells into plasma cells, which as a result causes suppression of IgE production; and in human PBMC-transplanted mice, human IgG and IgM concentrations are maintained whereas the human IgE concentration is decreased (Non-patent Document 29). Besides IgE, it has been reported that when FcγRIIb and CD79b forming a B-cell receptor complex are cross-linked by an antibody, B cell proliferation is suppressed in vitro, and symptoms are alleviated in the collagen arthritis model (Non-patent Document 30).

Besides B cells, it has been reported that crosslinking of FcεRI and FcγRIIb on mast cells using molecules, in which the Fc portion of an IgG with enhanced FcγRIIb binding is fused to the Fc portion of IgE that binds to an IgE receptor FcεRI, causes FcγRIIb phosphorylation of FcγRIIb, thereby suppressing FcεRI-dependent calcium influx. This suggests that inhibition of degranulation via FcγRIIb stimulation is possible by enhancing FcγRIIb binding (Non-patent Document 31).

Accordingly, an antibody having an Fc with improved FcγRIIb-binding activity is suggested to be promising as a therapeutic agent for inflammatory diseases such as autoimmune diseases.

Furthermore, mutants with enhanced FcγRIIb binding have been suggested to be promising therapeutic agents for cancer, as well as therapeutic agents for inflammatory diseases such as autoimmune diseases. So far, FcγRIIb has been found to play an important role in the agonistic activity of agonist antibodies against the anti-TNF receptor family. Specifically, it has been suggested that interaction with FcγRIIb is required for the agonistic activity of antibodies against CD40, DR4, DR5, CD30, and CD137, which are included in the TNF receptor family (Non-patent Documents 32, 33, 34, 35, 36, and 37). Non-patent Document 32 shows that the use of antibodies with enhanced FcγRIIb binding enhances the anti-tumor effect of anti-CD40 antibodies. Accordingly, antibodies with enhanced FcγRIIb are expected to have an effect of enhancing agonistic activity of agonist antibodies including antibodies against the anti-TNF receptor family.

Antibodies having an Fc with improved FcγRIIb-binding activity have been reported (Non-patent Document 28). In this Document, FcγRIIb-binding activity was improved by adding alterations such as S267E/L328F, G236D/S267E, and S239D/S267E to an antibody Fc region. Among them, the antibody introduced with the S267E/L328F mutation most strongly binds to FcγRIIb, and maintains the same level of binding to FcγRIa and FcγRIIa type H as that of a naturally-occurring IgG1. However, another report shows that this alteration enhances the binding to type-R FcγRIIa several hundred times to the same level of FcγRIIb binding, which means the FcγRIIb-binding selectivity is not improved in comparison with type-R FcγRIIa (Patent Document 5).

Even if FcγRIIb binding had been enhanced compared with that of IgG1, only the effect of enhancing FcγRIIa binding and not the enhancement of FcγRIIb binding is considered to have influence on cells such as platelets which express FcγRIIa but do not express FcγRIIb (Non-patent Document 8). For example, the group of patients who were administered bevacizumab, an antibody against VEGF, is known to have an increased risk for thromboembolism (Non-patent Document 38). Furthermore, thromboembolism has been observed in a similar manner in clinical development tests of antibodies against the CD40 ligand, and the clinical study was discontinued (Non-patent Document 39). In both cases of these antibodies, later studies using animal models and such have suggested that the administered antibodies aggregate platelets via FcγRIIa binding on the platelets, and form blood clots (Non-patent Documents 40 and 41). In systemic lupus erythematosus which is an autoimmune disease, platelets are activated via an FcγRIIa-dependent mechanism, and platelet activation has been reported to correlate with the severity of symptoms (Non-patent Document 42). Even if FcγRIIb binding is enhanced, administering an antibody with enhanced FcγRIIa binding to such patients who already have a high risk for developing thromboembolism will increase the risk for developing thromboembolism, thus is extremely dangerous.

Furthermore, antibodies with enhanced FcγRIIa binding have been reported to enhance macrophage-mediated antibody dependent cellular phagocytosis (ADCP) (Non-patent Document 43). When antibody's antigens are phagocytized by macrophages, antibodies themselves are also phagocytized at the same time. In that case, peptide fragments derived from those antibodies are also presented as an antigen and the antigenicity may become higher, thereby increasing the risk of production of antibodies against antibodies (anti-antibodies). More specifically, enhancing 20 FcγRIIa binding will increase the risk of production of antibodies against the antibodies, and this will remarkably decrease their value as pharmaceuticals.

More specifically, the value as pharmaceuticals will be considerably reduced when FcγRIIa binding is enhanced, which leads to increased risk of thrombus formation via platelet aggregation, higher antigenicity, and increased risk of anti-antibody production. 25

From such a viewpoint, the aforementioned Fc with enhanced FcγRIIb binding shows remarkably enhanced type-R FcγRIIa binding compared with that of a naturally-occurring IgG1. Therefore, its value as a pharmaceutical for patients carrying type-R FcγRIIa is considerably reduced. Types H and R of FcγRIIa are observed in Caucasians and African-Americans with approximately the same frequency (Non-patent Documents 44 and 45). Therefore, when this Fc 30 was used for treatment of autoimmune diseases, the number of patients who can safely use it while enjoying its effects as a pharmaceutical will be limited.

Furthermore, in dendritic cells deficient in FcγRIIb or dendritic cells in which the interaction between FcγRIIb and the antibody Fc portion is inhibited by an anti-FcγRIIb antibody, dendritic cells have been reported to mature spontaneously (Non-patent Documents 46 and 47). This report suggests that FcγRIIb is actively suppressing maturation of dendritic cells in a steady state where inflammation and such are not taking place. FcγRIIa is expressed on the dendritic cell surface in addition to FcγRIIb; therefore, even if binding to inhibitory FcγRIIb is enhanced and if binding to activating FcγR such as FcγRIIa is also enhanced, maturation of dendritic cells may be promoted as a result. More specifically, improving not only the FcγRIIb-binding activity but also the ratio of FcγRIIb-binding activity relative to FcγRIIa-binding activity is considered to be important in providing antibodies with an immunosuppressive action.

Therefore, when considering generation of pharmaceuticals that utilize the FcγRIIb binding-mediated immunosuppressive action, there is a need for an Fc that not only has enhanced FcγRIIb-binding activity, but also has binding to both FcγRIIa, types H and R allotypes, which is maintained at a similar level or is weakened to a lower level than that of a naturally-occurring IgG1.

Meanwhile, cases where amino acid alterations were introduced into the Fc region to increase the FcγRIIb-binding selectivity have been reported so far (Non-patent Document 48). However, all variants said to have improved FcγRIIb selectivity as reported in this document showed decreased FcγRIIb binding compared with that of a naturally-occurring IgG1. Therefore, it is considered to be difficult for these variants to actually induce an FcγRIIb-mediated immunosuppressive reaction more strongly than IgG1.

Furthermore, since FcγRIIb plays an important role in the agonist antibodies mentioned above, enhancing their binding activity is expected to enhance the agonistic activity. However, when FcγRIIa binding is similarly enhanced, unintended activities such as ADCC activity and ADCP activity will be exhibited, and this may cause side effects. Also from such viewpoint, it is preferable to be able to selectively enhance FcγRIIb-binding activity.

From these results, in producing antibody pharmaceuticals to be used for treating autoimmune diseases and cancer utilizing FcγRIIb, it is important that compared with those of a naturally-occurring IgG, the activities of binding to both FcγRIIa allotypes are maintained or decreased, and FcγRIIb binding is enhanced. However, FcγRIIb shares 93% sequence identity in the extracellular region with that of FcγRIIa which is one of the activating FcγRs, and they are very similar structurally. There are allotypes of FcγRIIa, H type and R type, in which the amino acid at position 131 is His (type H) or Arg (type R), and yet each of them reacts differently with the antibodies (Non-patent Document 49). Therefore, to produce an Fc region that selectively binds to FcγRIIb, the most difficult problem may be conferring to the antibody Fc region with the property of selectively improved FcγRIIb-binding activity, which involves distinguishing these homologous sequences, and decreasing or not increasing the binding activity towards each allotype of FcγRIIa, while increasing the binding activity towards FcγRIIb. So far, variants having sufficient FcγRIIb selectivity have not been obtained. Patent Document 5 reports variants with enhanced FcγRIIb-binding activity; however, the degree of enhancement is low, and there is a demand for development of variants having properties similar to those described above.

PRIOR ART DOCUMENTS

Patent Documents

[Patent Document 1] WO 2000/42072
[Patent Document 2] WO 2006/019447
[Patent Document 3] WO 2004/99249
[Patent Document 4] WO 2004/29207
[Patent Document 5] US2009/0136485

Non-Patent Documents

[Non-patent Document 1] Nat Biotechnol, 23 (9), 1073-1078, 2005
[Non-patent Document 2] Eur J Pharm Biopharm, 59 (3), 389-96, 2005
[Non-patent Document 3] Chem Immunol, 65, 88-110, 1997
[Non-patent Document 4] J Biol Chem, 276 (19), 16478-16483, 2001
[Non-patent Document 5] Eur J Immunol, 23 (5), 1098-1104, 1993
[Non-patent Document 6] Immunology, 86 (2), 319-324, 1995
[Non-patent Document 7] Immunol Lett, 82 (1-2), 57-65, 2002
[Non-patent Document 8] Nat Rev Immunol, 10 (5), 328-343, 2010
[Non-patent Document 9] Nat Rev Immunol, 8 (1), 34-47, 2008
[Non-patent Document 10] Eur J Immunol, 19 (8), 1379-1385, 1989
[Non-patent Document 11] J Exp Med, 129 (6), 1183-1201, 1969
[Non-patent Document 12] Immunol Lett, 88 (2), 157-161, 2003
[Non-patent Document 13] Science, 256 (5065), 1808-1812, 1992
[Non-patent Document 14] Nature, 368 (6466), 70-73, 1994
[Non-patent Document 15] Science, 290 (5489), 84-89, 2000
[Non-patent Document 16] J Immunol, 181 (8), 5350-5359 2008
[Non-patent Document 17] J Immunol, 163 (2), 618-622, 1999
[Non-patent Document 18] J Exp Med, 189 (1), 187-194, 1999
[Non-patent Document 19] J Exp Med, 191 (5), 899-906, 2000
[Non-patent Document 20] Hum Genet, 117 (2-3), 220-227, 2005
[Non-patent Document 21] J Biol Chem, 282 (3), 1738-1746, 2007
[Non-patent Document 22] Arthritis Rheum, 54 (12), 3908-3917, 2006
[Non-patent Document 23] Nat Med, 11 (10), 1056-1058, 2005
[Non-patent Document 24] J Immunol, 176 (9), 5321-5328, 2006
[Non-patent Document 25] J Exp Med, 203 (9), 2157-2164, 2006
[Non-patent Document 26] J Immunol, 178 (5), 3272-3280, 2007

[Non-patent Document 27] Blood, 113 (16), 3716-3725, 2009
[Non-patent Document 28] Mol Immunol, 45 (15), 3926-3933, 2008
[Non-patent Document 29] J Allergy Clin Immunol, 2012 Jan. 16. in press (PMID: 22257644)
[Non-patent Document 30] Arthritis Rheum, 62 (7), 1933-1943, 2010
[Non-patent Document 31] Immunol Lett, 2012 Jan. 25. in press (PMID: 22305932)
[Non-patent Document 32] Science, 333 (6045), 1030-1034, 2011
[Non-patent Document 33] Cancer Cell, 19 (1), 101-113, 2011
[Non-patent Document 34] J Clin Invest, 2012 Feb. 13. pii: 61226. doi: 10.1172/JCI61226. in press (PMID: 22326955)
[Non-patent Document 35] J Immunol, 171 (2), 562-568, 2003
[Non-patent Document 36] Blood, 108 (2), 705-710, 2006
[Non-patent Document 37] J Immunol, 166 (8), 4891-4898, 2001
[Non-patent Document 38] J Natl Cancer Inst, 99 (16), 1232-1239, 2007
[Non-patent Document 39] Arthritis Rheum, 48 (3), 719-727, 2003
[Non-patent Document 40] J Thromb Haemost, 7 (1), 171-181, 2008
[Non-patent Document 41] J Immunol, 185 (3), 1577-1583, 2010
[Non-patent Document 42] Sci Transl Med, 2 (47), 47-63, 2010
[Non-patent Document 43] Mol Cancer Ther, 7 (8), 2517-2527, 2008
[Non-patent Document 44] J Clin Invest, 97 (5), 1348-1354, 1996
[Non-patent Document 45] Arthritis Rheum, 41 (7), 1181-1189, 1998
[Non-patent Document 46] J Clin Invest, 115 (10), 2914-2923, 2005
[Non-patent Document 47] Proc Natl Acad Sci USA, 102 (8), 2910-2915, 2005
[Non-patent Document 48] Mol Immunol, 40 (9), 585-593, 2003
[Non-patent Document 49] J Exp Med, 172, 19-25, 1990

SUMMARY OF THE INVENTION

Problems to be Solved by the Invention

The present invention was achieved in view of the above circumstances. An objective of the present invention is to provide polypeptides comprising an IgG Fc region that have maintained or decreased binding activities towards both allotypes of FcγRIIa, H type and R type, in which the amino acid at position 131 (EU numbering) in FcγRIIa is His (type H) or Arg (type R), and having enhanced FcγRIIb-binding activity in comparison with a parent polypeptide through introduction of amino acid substitutions into the IgG Fc region; pharmaceutical compositions comprising the polypeptide; therapeutic agents or preventive agents comprising the polypeptide for immunological inflammatory diseases; and methods for producing them. Furthermore, an objective is to provide a method for maintaining or decreasing binding activities towards both allotypes of FcγRIIa, H type and R type, in which the amino acid at position 131 (EU numbering) in FcγRIIa is His (type H) or Arg (type R), and for enhancing FcγRIIb-binding activity in comparison with a parent polypeptide; and a method for suppressing antibody production in comparison with a parent polypeptide in in vivo administration. In addition, an objective is to provide methods for producing a polypeptide having maintained or decreased binding activities towards both allotypes of FcγRIIa, H type and R type, in which the amino acid at position 131 (EU numbering) in FcγRIIa is His (type H) or Arg (type R), and having enhanced FcγRIIb-binding activity in comparison with a parent polypeptide; and methods for producing a polypeptide with suppressed antibody production in comparison with a parent polypeptide when administered in vivo.

Means for Solving the Problems

The present inventors performed dedicated research on a polypeptide comprising an Fc region having decreased Fc-mediated binding to FcγRIIa, and increased binding to FcγRIIb in comparison with a parent polypeptide. As a result, the present inventors discovered that a polypeptide comprising an antibody Fc region that comprises an alteration produced by substituting Pro at position 238 (EU numbering) with Asp or Leu at position 328 (EU numbering) with Glu enhances FcγRIIb-binding activity, and decreases Fc region-mediated binding activity towards both allotypes of FcγRIIa, types H and R. Furthermore, the present inventors discovered that a polypeptide comprising an antibody Fc region that comprises an alteration of substituting Pro at position 238 (EU numbering) with Asp and several other alterations that enhance FcγRIIb-binding activity, and maintains or decreases Fc region-mediated binding activities towards both allotypes of FcγRIIa, types H and R.

More specifically, the present invention relates to the following:

[1] a polypeptide variant comprising an antibody Fc region with at least one amino acid alteration, which has maintained or decreased binding activities towards FcγRIIa (type R) and FcγRIIa (type H), and enhanced FcγRIIb-binding activity in comparison with a parent polypeptide, and wherein the value of [KD value of the polypeptide variant for FcγRIIa (type R)]/[KD value of the polypeptide variant for FcγRIIb] is 1.2 or more;

[2] the polypeptide of [1], wherein the value of [KD value of the polypeptide variant for FcγRIIa (type H)]/[KD value of the polypeptide variant for FcγRIIb] is 4.2 or more;

[3] the polypeptide of [1] or [2], wherein the value of [KD value of the parent polypeptide for FcγRIIb]/[KD value of the polypeptide variant for FcγRIIb] is 1.6 or more;

[4] the polypeptide of any one of [1] to [3], wherein the value of [KD value of the stronger of the binding activities of the polypeptide variant towards FcγRIIa (type R) and FcγRIIa (type H)]/[KD value of the stronger of the binding activities of the parent polypeptide towards FcγRIIa (type R) and FcγRIIa (type H)] is 0.7 or more;

[5] the polypeptide of any one of [1] to [4], which has maintained or decreased FcγRIIIa-binding activity compared with that of a parent polypeptide;

[6] the polypeptide of any one of [1] to [5], which has maintained or decreased FcγRIa-binding activity compared with that of a parent polypeptide;

[7] the polypeptide of any one of [1] to [6], wherein an amino acid alteration is substitution of Pro at position 238 (EU numbering) with Asp or substitution of Leu at position 328 (EU numbering) with Glu;

[8] the polypeptide of any one of [1] to [7], wherein an amino acid alteration is at least one substitution selected from the group consisting of:

substitution of Pro at position 238 (EU numbering) with Asp;
substitution of Gly at position 237 (EU numbering) with Trp;
substitution of Gly at position 237 (EU numbering) with Phe;
substitution of Ser at position 267 (EU numbering) with Val;
substitution of Ser at position 267 (EU numbering) with Gln;
substitution of His at position 268 (EU numbering) with Asn;
substitution of Pro at position 271 (EU numbering) with Gly;
substitution of Lys at position 326 (EU numbering) with Leu;
substitution of Lys at position 326 (EU numbering) with Gln;
substitution of Lys at position 326 (EU numbering) with Glu;
substitution of Lys at position 326 (EU numbering) with Met;
substitution of Ser at position 239 (EU numbering) with Asp;
substitution of Ser at position 267 (EU numbering) with Ala;
substitution of Leu at position 234 (EU numbering) with Trp;
substitution of Leu at position 234 (EU numbering) with Tyr;
substitution of Gly at position 237 (EU numbering) with Ala;
substitution of Gly at position 237 (EU numbering) with Asp;
substitution of Gly at position 237 (EU numbering) with Glu;
substitution of Gly at position 237 (EU numbering) with Leu;
substitution of Gly at position 237 (EU numbering) with Met;
substitution of Gly at position 237 (EU numbering) with Tyr;
substitution of Ala at position 330 (EU numbering) with Lys;
substitution of Ala at position 330 (EU numbering) with Arg;
substitution of Glu at position 233 (EU numbering) with Asp;
substitution of His at position 268 (EU numbering) with Asp;
substitution of His at position 268 (EU numbering) with Glu;
substitution of Lys at position 326 (EU numbering) with Asp;
substitution of Lys at position 326 (EU numbering) with Ser;
substitution of Lys at position 326 (EU numbering) with Thr;
substitution of Val at position 323 (EU numbering) with Ile;
substitution of Val at position 323 (EU numbering) with Leu;
substitution of Val at position 323 (EU numbering) with Met;
substitution of Tyr at position 296 (EU numbering) with Asp;
substitution of Lys at position 326 (EU numbering) with Ala;
substitution of Lys at position 326 (EU numbering) with Asn; and
substitution of Ala at position 330 (EU numbering) with Met;

[9] the polypeptide of any one of [1] to [8], wherein the polypeptide comprising the antibody Fc region is an IgG antibody;

[10] the polypeptide of any one of [1] to [8], wherein the polypeptide comprising the antibody Fc region is an Fc fusion protein molecule;

[11] a method for maintaining or decreasing binding activities towards FcγRIIa (type R) and FcγRIIa (type H) and enhancing FcγRIIb-binding activity of a polypeptide in comparison with a parent polypeptide, which comprises adding at least one amino acid alteration in the Fc region of the polypeptide comprising the antibody Fc region, wherein the amino acid alteration is substitution of Pro at position 238 (EU numbering) with Asp or substitution of Leu at position 328 (EU numbering) with Glu;

[12] a method for suppressing production of an antibody against a polypeptide comprising antibody Fc region in comparison with a parent polypeptide when administered in vivo, wherein the method comprises adding at least one amino acid alteration to the Fc region of the polypeptide, wherein the amino acid alteration is substitution of Pro at position 238 (EU numbering) with Asp or substitution of Leu at position 328 (EU numbering) with Glu;

[13] the method of or [12], wherein the amino acid alteration is at least one substitution selected from the group consisting of:

substitution of Pro at position 238 (EU numbering) with Asp;
substitution of Gly at position 237 (EU numbering) with Trp;
substitution of Gly at position 237 (EU numbering) with Phe;
substitution of Ser at position 267 (EU numbering) with Val;
substitution of Ser at position 267 (EU numbering) with Gln;
substitution of His at position 268 (EU numbering) with Asn;
substitution of Pro at position 271 (EU numbering) with Gly;
substitution of Lys at position 326 (EU numbering) with Leu;
substitution of Lys at position 326 (EU numbering) with Gln;
substitution of Lys at position 326 (EU numbering) with Glu;
substitution of Lys at position 326 (EU numbering) with Met;
substitution of Ser at position 239 (EU numbering) with Asp;
substitution of Ser at position 267 (EU numbering) with Ala;
substitution of Leu at position 234 (EU numbering) with Trp;
substitution of Leu at position 234 (EU numbering) with Tyr;

substitution of Gly at position 237 (EU numbering) with Ala;
substitution of Gly at position 237 (EU numbering) with Asp;
substitution of Gly at position 237 (EU numbering) with Glu;
substitution of Gly at position 237 (EU numbering) with Leu;
substitution of Gly at position 237 (EU numbering) with Met;
substitution of Gly at position 237 (EU numbering) with Tyr;
substitution of Ala at position 330 (EU numbering) with Lys;
substitution of Ala at position 330 (EU numbering) with Arg;
substitution of Glu at position 233 (EU numbering) with Asp;
substitution of His at position 268 (EU numbering) with Asp;
substitution of His at position 268 (EU numbering) with Glu;
substitution of Lys at position 326 (EU numbering) with Asp;
substitution of Lys at position 326 (EU numbering) with Ser;
substitution of Lys at position 326 (EU numbering) with Thr;
substitution of Val at position 323 (EU numbering) with Ile;
substitution of Val at position 323 (EU numbering) with Leu;
substitution of Val at position 323 (EU numbering) with Met;
substitution of Tyr at position 296 (EU numbering) with Asp;
substitution of Lys at position 326 (EU numbering) with Ala;
substitution of Lys at position 326 (EU numbering) with Asn; and
substitution of Ala at position 330 (EU numbering) with Met;

[14] the method of any one of to [13], wherein the polypeptide comprising the antibody Fc region is an IgG antibody;

[15] the method of any one of to [13], wherein the polypeptide comprising the antibody Fc region is an Fc fusion protein molecule;

[16] a method for producing a polypeptide having maintained or decreased binding activities towards FcγRIIa (type R) and FcγRIIa (type H) and having enhanced FcγRIIb-binding activity in comparison with a parent polypeptide, wherein the method comprises adding at least one amino acid alteration in the Fc region of a polypeptide comprising an antibody Fc region, wherein the amino acid alteration is substitution of Pro at position 238 (EU numbering) with Asp or substitution of Leu at position 328 (EU numbering) with Glu;

[17] a method for producing a polypeptide with suppressed production of an antibody against the polypeptide in comparison with a parent polypeptide when administered in vivo, wherein the method comprises adding at least one amino acid alteration in the Fc region of a polypeptide comprising an antibody Fc region, wherein the amino acid alteration is substitution of Pro at position 238 (EU numbering) with Asp or substitution of Leu at position 328 (EU numbering) with Glu;

[18] the method of or [17], wherein the amino acid alteration is at least one substitution selected from the group consisting of:
substitution of Pro at position 238 (EU numbering) with Asp;
substitution of Gly at position 237 (EU numbering) with Trp;
substitution of Gly at position 237 (EU numbering) with Phe;
substitution of Ser at position 267 (EU numbering) with Val;
substitution of Ser at position 267 (EU numbering) with Gln;
substitution of His at position 268 (EU numbering) with Asn;
substitution of Pro at position 271 (EU numbering) with Gly;
substitution of Lys at position 326 (EU numbering) with Leu;
substitution of Lys at position 326 (EU numbering) with Gln;
substitution of Lys at position 326 (EU numbering) with Glu;
substitution of Lys at position 326 (EU numbering) with Met;
substitution of Ser at position 239 (EU numbering) with Asp;
substitution of Ser at position 267 (EU numbering) with Ala;
substitution of Leu at position 234 (EU numbering) with Trp;
substitution of Leu at position 234 (EU numbering) with Tyr;
substitution of Gly at position 237 (EU numbering) with Ala;
substitution of Gly at position 237 (EU numbering) with Asp;
substitution of Gly at position 237 (EU numbering) with Glu;
substitution of Gly at position 237 (EU numbering) with Leu;
substitution of Gly at position 237 (EU numbering) with Met;
substitution of Gly at position 237 (EU numbering) with Tyr;
substitution of Ala at position 330 (EU numbering) with Lys;
substitution of Ala at position 330 (EU numbering) with Arg;
substitution of Glu at position 233 (EU numbering) with Asp;
substitution of His at position 268 (EU numbering) with Asp;
substitution of His at position 268 (EU numbering) with Glu;
substitution of Lys at position 326 (EU numbering) with Asp;
substitution of Lys at position 326 (EU numbering) with Ser;
substitution of Lys at position 326 (EU numbering) with Thr;
substitution of Val at position 323 (EU numbering) with Ile;

substitution of Val at position 323 (EU numbering) with Leu;

substitution of Val at position 323 (EU numbering) with Met;

substitution of Tyr at position 296 (EU numbering) with Asp;

substitution of Lys at position 326 (EU numbering) with Ala;

substitution of Lys at position 326 (EU numbering) with Asn; and substitution of Ala at position 330 (EU numbering) with Met;

[19] the method of any one of to [18], wherein the polypeptide comprising the antibody Fc region is an IgG antibody;

[20] the method of any one of to [18], wherein the polypeptide comprising the antibody Fc region is an Fc fusion protein molecule;

[21] a polypeptide produced by the method of any one of to [20];

[22] a pharmaceutical composition comprising the polypeptide of any one of [1] to and [21];

[23] an agent for suppressing activation of B cells, mast cells, dendritic cells, and/or basophils, which comprises the polypeptide of any one of [1] to and [21];

[24] an agent for treating or preventing an immunological inflammatory disease, which comprises the polypeptide of any one of [1] to and [21];

[25] the therapeutic agent or preventive agent of [24], wherein the immunological inflammatory disease is an autoimmune disease and is a disease which may be caused by production of an antibody against an autoantigen;

[26] an agent for treating a disease, which comprises the polypeptide of any one of [1] to and [21], wherein the disease is a disease with deficiency of a biologically essential protein; and

[27] an antiviral agent comprising the polypeptide of any one of [1] to and [21].

The present invention also relates to methods for treating or preventing immunological inflammatory diseases, which comprise the step of administering to a subject a polypeptide of the present invention or a polypeptide produced by the production methods of the present invention. Furthermore, the present invention relates to kits for use in the therapeutic methods or preventive methods of the present invention, which comprise a polypeptide of the present invention or a polypeptide produced by the production methods of the present invention, or a pharmaceutical composition of the present invention. The present invention also relates to use of a polypeptide of the present invention or a polypeptide produced by the production methods of the present invention in the production of therapeutic agents or preventive agents for immunological inflammatory diseases. In addition, the present invention relates to a polypeptide of the present invention or a polypeptide produced by the production methods of the present invention for use in a therapeutic method or a preventive method of the present invention. The present invention also relates to methods for suppressing activation of B cells, mast cells, dendritic cells, and/or basophils, which comprise the step of administering to a subject a polypeptide of the present invention or a polypeptide produced by the production methods of the present invention. The present invention relates to kits for use in the inhibition method of the present invention, which comprises a polypeptide of the present invention or a polypeptide produced by the production methods of the present invention, or a pharmaceutical composition of the present invention. The present invention relates to use of a polypeptide of the present invention or a polypeptide produced by the production methods of the present invention in the production of agents that suppress activation of B cells, mast cells, dendritic cells, and/or basophils. The present invention relates to polypeptides of the present invention or polypeptides produced by the production methods of the present invention for use in the inhibitory methods of the present invention. The present invention relates to methods for treating diseases with deficiency of biologically essential proteins, which comprises the step of administering to a subject a polypeptide of the present invention or a polypeptide produced by the production methods of the present invention. The present invention relates to kits for use in the therapeutic method of the present invention, which comprises a polypeptide of the present invention or a polypeptide produced by the production methods of the present invention, or a pharmaceutical composition of the present invention. The present invention relates to use of a polypeptide of the present invention or a polypeptide produced by the production methods of the present invention in the production of therapeutic agents for diseases with deficiency of biologically essential proteins. The present invention also relates to a polypeptide of the present invention or a polypeptide produced by the production methods of the present invention for use in a therapeutic method of the present invention. The present invention relates to methods for inhibiting viruses, which comprises the step of administering to a subject a polypeptide of the present invention or a polypeptide produced by the production methods of the present invention. The present invention relates to kits for use in the inhibition method of the present invention, which comprises a polypeptide of the present invention or a polypeptide produced by the production methods of the present invention, or a pharmaceutical composition of the present invention. Furthermore, the present invention relates to use of a polypeptide of the present invention or a polypeptide produced by the production methods of the present invention in the production of an antiviral agent. Furthermore, the present invention relates to a polypeptide of the present invention or a polypeptide produced by the production methods of the present invention for use in the inhibition method of the present invention.

Effects of the Invention

Polypeptides comprising an Fc region having maintained or decreased binding activities towards both allotypes of FcγRIIa, types R and H, and having enhanced FcγRIIb-binding activity in comparison with a parent polypeptide are provided by the present invention. By using the polypeptides with enhanced binding selectivity for FcγRIIb than for both allotypes of FcγRIIa (types H and R), it is possible to transmit inhibitory signals of inflammatory immune response mediated by phosphorylation of ITIM of FcγRIIb in patients carrying either of the allotypes, type R and type H. Furthermore, by conferring an antibody Fc with the property of selective FcγRIIb binding, it may be possible to suppress anti-antibody production through the FcγRIIb-mediated immunosuppressive action.

MODE FOR CARRYING OUT THE INVENTION

Figure 1:
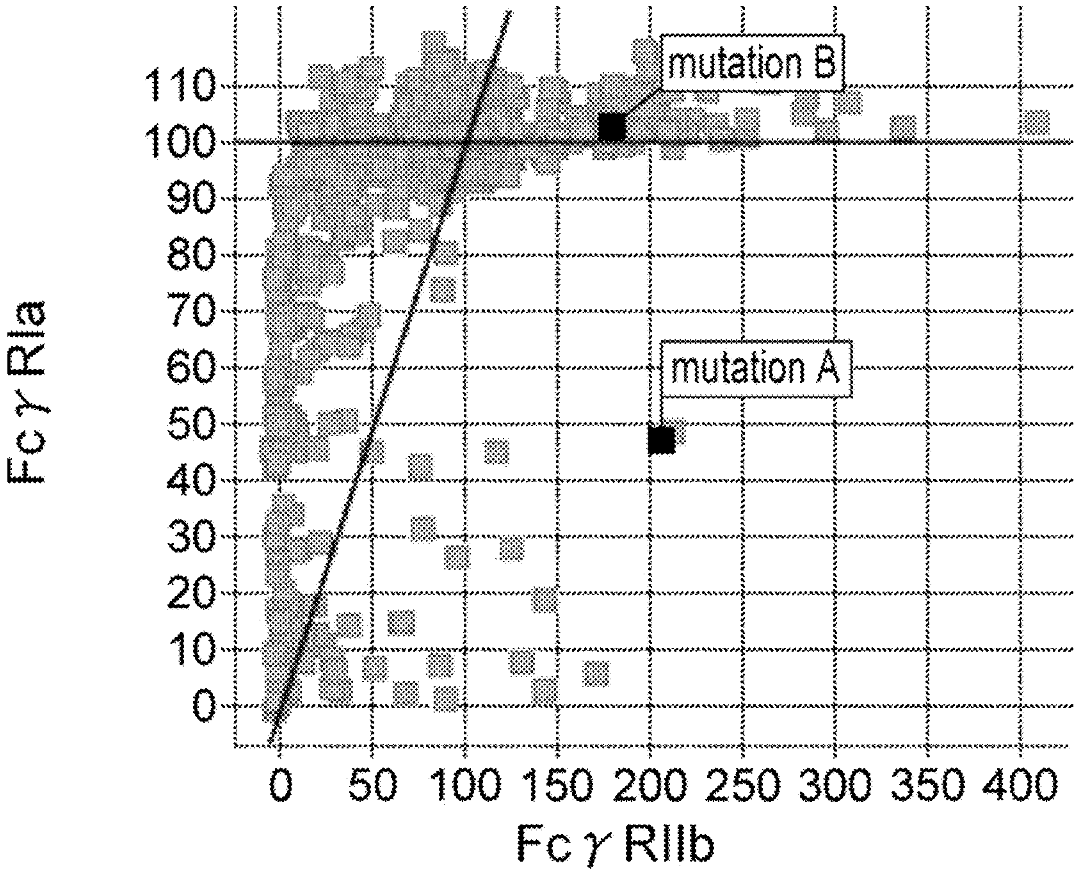
FIG. 1 shows comparison of FcγRIa binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp and "mutation B" refers to an alteration produced by substituting Leu at position 328 (EU numbering) with Glu.
Figure 2:
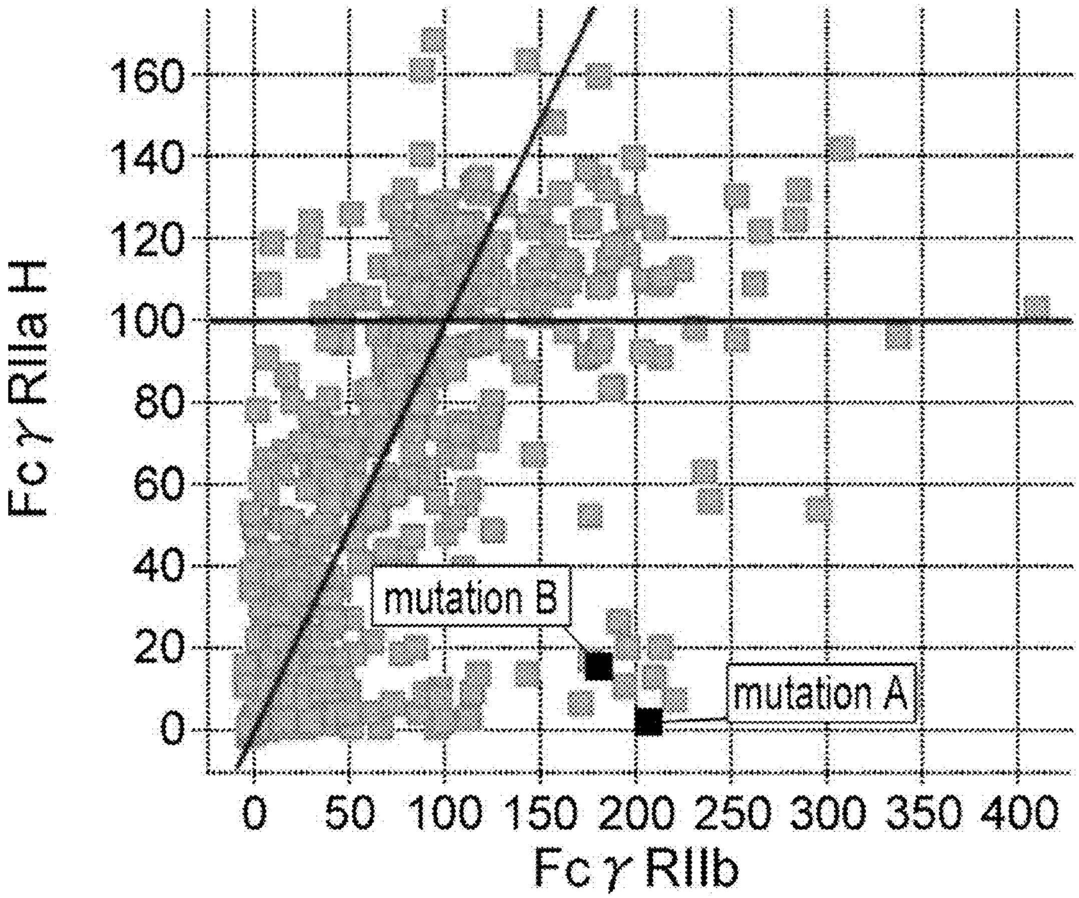
FIG. 2 shows comparison of FcγRIIa type H binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp, and "mutation B" refers to an alteration produced by substituting Leu at position 328 (EU numbering) with Glu.
Figure 3:
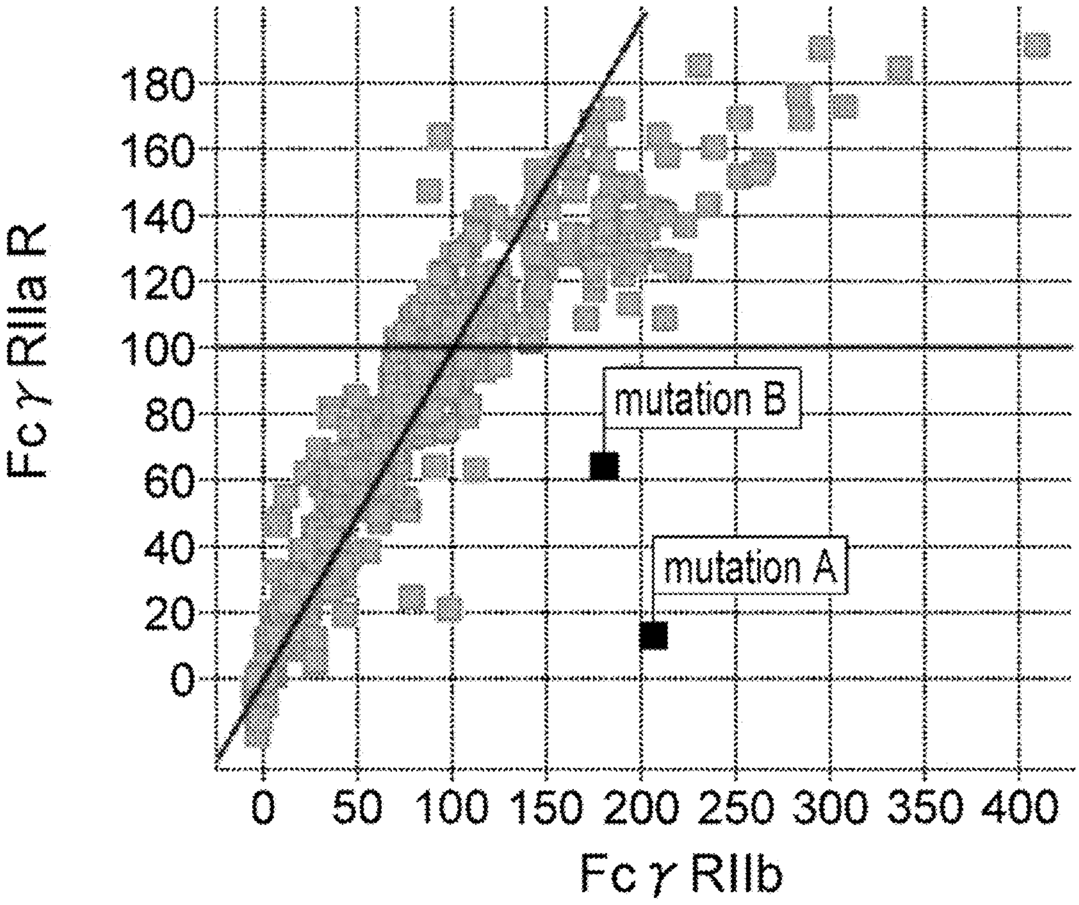
FIG. 3 shows comparison of FcγRIIa type R binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp, and "mutation B" refers to an alteration produced by substituting Leu at position 328 (EU numbering) with Glu.
Figure 4:
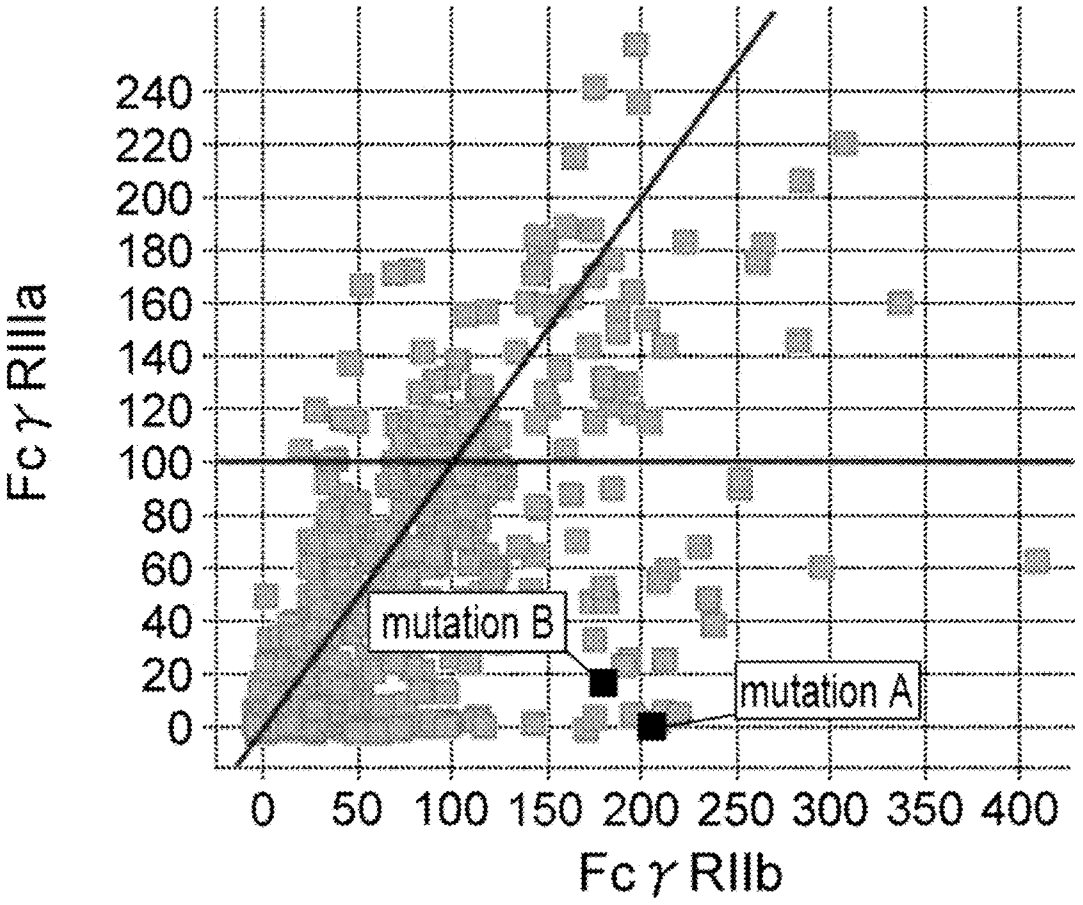
FIG. 4 shows comparison of FcγRIIIa binding and FcγRIIb binding. Binding of the antibody with substitution of Pro at position 238 (EU numbering) with Asp, and binding of the antibody with substitution of Leu at position 328 (EU numbering) with Glu have been labeled. "Mutation A" refers to an alteration produced by substituting Pro at position 238 (EU numbering) with Asp, and "mutation B" refers to an alteration produced by substituting Leu at position 328 (EU numbering) with Glu.

The present invention provides polypeptides comprising an IgG Fc region that have maintained or decreased FcγRIIa-binding, and having enhanced FcγRIIb-binding activity in comparison with a parent polypeptide by introducing amino acid substitution(s) into the IgG Fc region.

More specifically, the present invention provides a polypeptide comprising an antibody Fc region that comprises a substitution of Pro at position 238 (EU numbering) with Asp or substitution of Leu at position 328 (EU numbering) with Glu, and a polypeptide comprising an antibody Fc region that comprises combination of a substitution of Pro at position 238 (EU numbering) with Asp and several specific amino acid substitutions. Furthermore, the present invention provides a method for maintaining or decreasing binding activity towards both allotypes of FcγRIIa and enhancing the FcγRIIb-binding activity in comparison with a parent polypeptide. The present invention also provides a method for suppressing the antibody production in comparison with a parent polypeptide when the polypeptide is administered in vivo.

"Polypeptides of the present invention" generally refers to peptides or proteins approximately ten amino acids or more in length. Furthermore, they are generally polypeptides derived from organisms, but are not particularly limited, and for example, they may be polypeptides comprising an artificially designed sequence. Furthermore, they may be any of naturally-occurring polypeptides, synthetic polypeptides, recombinant polypeptides, or such.

"Fcγ receptors" (herein, referred to as Fcγ receptors or FcγR) refers to receptors that may bind to the Fc region of IgG1, IgG2, IgG3, and IgG4 monoclonal antibodies, and practically means any member of the family of proteins encoded by the Fcγ receptor genes. In humans, this family includes FcγRI (CD64) including isoforms FcγRIa, FcγRIb, and FcγRIc; FcγRII (CD32) including isoforms FcγRIIa (including allotypes H131 (type H) and $R^{131}$ (type R)), FcγRIIb (including FcγRIIb-1 and FcγRIIb-2), and FcγRIIc; and FcγRIII (CD16) including isoforms FcγRIIIa (including allotypes V158 and F158), and FcγRIIIb (including allotypes FcγRIIIb-NA1 and FcγRIIIb-NA2), and any human FcγRs, FcγR isoforms or allotypes yet to be discovered, but is not limited thereto. The FcγR includes human, mouse, rat, rabbit, and monkey-derived FcγRs but is not limited thereto, and may be derived from any organism. Mouse FcγRs include FcγRI (CD64), FcγRII (CD32), FcγRIII (CD16), and FcγRIII-2 (CD16-2), and any mouse FcγRs, or FcγR isoforms or allotypes yet to be discovered, but are not limited thereto. Favorable examples of such Fcγ receptors include human FcγRI (CD64), FcγRIIA (CD32), FcγRIIB (CD32), FcγRIIIA (CD16), and/or FcγRIIIB (CD16).

The polynucleotide sequence and amino acid sequence of FcγRI are set forth in SEQ ID NOs: 1 (NM_000566.3) and 2 (NP_000557.1), respectively;

- the polynucleotide sequence and amino acid sequence of FcγRIIA are set forth in SEQ ID NOs: 3 (BC020823.1) and 4 (AAH20823.1), respectively;
- the polynucleotide sequence and amino acid sequence of FcγRIIB are set forth in SEQ ID NOs: 5 (BC146678.1) and 6 (AAI46679.1), respectively;
- the polynucleotide sequence and amino acid sequence of FcγRIIIA are set forth in SEQ ID NOs: 7 (BC033678.1) and 8 (AAH33678.1), respectively; and
- the polynucleotide sequence and amino acid sequence of FcγRIIIB are set forth in SEQ ID NOs 9 (BC128562.1) and 10 (AAI28563.1), respectively (the RefSeq Registration number is indicated inside the parentheses).

In FcγRIIa, there are two allotypes, one where the amino acid at position 131 of FcγRIIa is histidine (type H) and the other where this amino acid is substituted with arginine (type R) (J. Exp. Med, 172:19-25, 1990).

Herein, "parent polypeptide" refers to a polypeptide that will serve as the basis for the production of polypeptides comprising an antibody Fc region of the present invention. More specifically, it is a polypeptide comprising an antibody Fc region and is the polypeptide prior to alteration of at least one amino acid in the Fc region. The parent polypeptide in the present invention may be, for example, a polypeptide comprising the Fc region of a naturally-occurring IgG, or it may be a polypeptide comprising an Fc region of an IgG to which an alteration other than the amino acid alterations of the present invention has been made to a naturally-occurring IgG.

"Naturally-occurring IgGs" refers to polypeptides belonging to a class of antibodies practically encoded by immunoglobulin gamma genes and comprising an amino acid sequence identical to those of IgGs found in nature. For example, a naturally-occurring human IgG means a naturally-occurring human IgG1, naturally-occurring human IgG2, naturally-occurring human IgG3, naturally-occurring human IgG4, or such. Naturally-occurring IgGs also include mutants spontaneously produced from them.

Figure 5:
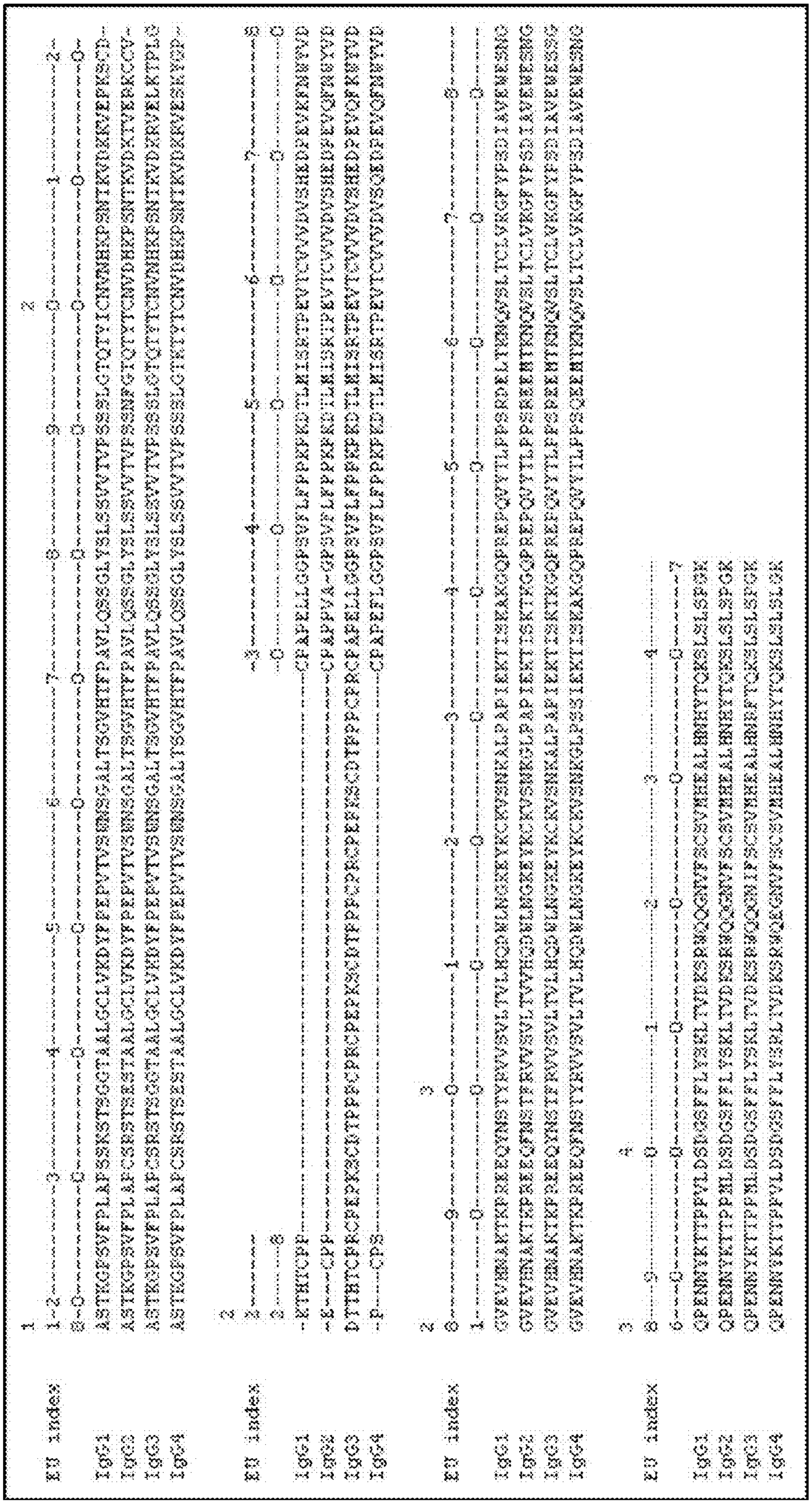
FIG. 5 shows the relationship between the amino acid residues constituting the Fc regions of IgG1 (SEQ ID NO: 11), IgG2 (SEQ ID NO: 12), IgG3 (SEQ ID NO: 13), and IgG4 (SEQ ID NO: 14), and EU numbering (herein, also referred to as EU INDEX).

The Fc region of a naturally-occurring IgG means an Fc region comprising an amino acid sequence identical to that of the Fc region derived from an IgG found in nature. The Fc region of a naturally-occurring IgG is shown in FIG. 5 (SEQ ID NOs: 11-14), and for example, it refers to Fc regions derived from naturally-occurring human IgG1, Fc regions derived from naturally-occurring human IgG2, Fc regions derived from naturally-occurring human IgG3, and Fc regions derived from naturally-occurring human IgG4. The Fc regions of naturally-occurring IgGs also include mutants spontaneously produced from them.

In the present invention, whether or not the binding activity towards each type of FcγR is enhanced, or maintained or decreased in a polypeptide or an Fc region of the present invention can be determined, for example, by observing whether there is a decrease or an increase in the dissociation constant (KD) value obtained from the results of sensorgram analysis, where various FcγRs are subjected to interaction as an analyte with antibodies immobilized onto the sensor chips or captured onto the sensor chips using Protein A, Protein L, Protein A/G, Protein G, anti-lamda chain antibodies, anti-kappa chain antibodies, antigenic peptides, antigenic proteins, or such using a BIACORE™ system which is an interaction analyzer that utilizes the surface plasmon resonance (SPR) phenomena, as shown in the Examples. Alternatively, it can also be determined by observing whether there is an increase or a decrease in the value obtained by dividing the amount of change in the resonance unit (RU) value on the sensorgram before and after various types of FcγRs are subjected to interaction as an analyte with antibodies immobilized onto the sensor chips or captured onto the sensor chips using Protein A, Protein L, Protein A/G, Protein G, anti-lamda chain antibodies, anti-kappa chain antibodies, antigenic peptides, antigenic proteins, or such, by the amount of change of resonance units (RU) before and after antibodies are immobilized or captured onto the sensor chip. Furthermore, it can be determined by observing an increase or a decrease in the dissociation constant (KD) values obtained from sensorgram analysis, where a sample such as an antibody to be evaluated is subjected to interaction as an analyte using a sensor chip onto which FcγR is immobilized directly or via an anti-tag antibody. Alternatively, it can be determined by observing whether the amount of change in sensorgram values increases or decreases before and after a sample such as an antibody to be evaluated is subjected to interaction as an analyte with the sensor chip onto which FcγR is immobilized directly or via an anti-tag antibody.

Specifically, the binding activity of an Fc region towards an Fcγ receptor can be measured by the Amplified Luminescent Proximity Homogeneous Assay (ALPHA) screening, the BIACORE™ method which utilizes the surface plasmon resonance (SPR) phenomena, or such, in addition to ELISA or fluorescence activated cell sorting (FACS) (Proc. Natl. Acad. Sci. USA (2006) 103 (11): 4005-4010).

ALPHA screening is performed by ALPHA technology which uses two beads, a donor and an acceptor, based on the following principles. Luminescent signals are detected only when molecules bound to donor beads physically interact with molecules bound to the acceptor beads, and the two beads are in close proximity to each other. Laser-excited photosensitizer in the donor beads converts ambient oxygen to excited-state singlet oxygen. Singlet oxygen is dispersed around the donor beads, and when it reaches the adjacent acceptor beads, chemiluminescent reaction is induced in the beads, and light is ultimately emitted. When the molecules bound to the donor beads do not interact with the molecules bound to the acceptor beads, the chemiluminescent reaction does not take place because singlet oxygen produced by the donor beads does not reach the acceptor beads.

For example, a biotinylated polypeptide complex is bound to the donor beads, and Fcγ receptor tagged with glutathione S transferase (GST) is linked to the acceptor beads. In the absence of a competing polypeptide complex comprising a mutant Fc region, the polypeptide complex comprising a wild-type Fc region interacts with the Fcγ receptor and produces 520-620 nm signals. The polypeptide complex comprising an untagged mutant Fc region competes with the polypeptide complex comprising a wild-type Fc region for interaction with the Fcγ receptor. Relative binding activities can be determined by quantifying the decrease in fluorescence observed as a result of the competition. Biotinylation of polypeptide complexes such as antibodies using Sulfo-NHS-biotin and such is well known. The method of expressing the Fcγ receptor and GST in a cell carrying a fusion gene produced by fusing a polynucleotide encoding the Fcγ receptor in frame with a polynucleotide encoding GST in an expressible vector, and performing purification using a glutathione column is appropriately adopted as a method for tagging an Fcγ receptor with GST. The obtained signals are preferably analyzed, for example, by fitting them to a one-site competition model which uses a non-linear regression analysis using software such as GRAPHPAD PRISM (GraphPad, San Diego).

One of the substances (the ligand) in observation of an interaction is immobilized onto a gold thin film on a sensor chip, and by shining light from the reverse side of the sensor chip so that total reflection takes place at the interface between the gold thin film and glass, a portion of reduced reflection intensity is formed in part of the reflected light (SPR signal). When the other one of the substances (the analyte) in observation of an interaction is made to flow on the sensor chip surface and the ligand binds to the analyte, the mass of the immobilized ligand molecule increases and the refractive index of the solvent on the sensor chip surface changes. The position of the SPR signal shifts as a result of this change in refractive index (on the other hand, the signal position returns when this binding dissociates). The Biacore™ system indicates the amount of shift mentioned above, or more specifically the time variable of mass by plotting the change in mass on the sensor chip surface on the ordinate as the measurement data (sensorgram). The amount of analyte bound to the ligand trapped on the sensor chip surface is determined from the sensorgram. Kinetic parameters such as association rate constants (ka) and dissociation rate constants (kd) are determined from the curves of the sensorgram, and the dissociation constants (KD) are determined from the ratio of these constants. In the BIACORE™ method, a method for measuring inhibition is preferably used. An example of the method for measuring inhibition is described in Proc. Natl. Acad. Sci USA (2006) 103 (11): 4005-4010.

A polypeptide with decreased FcγR-binding activity refers to a polypeptide that binds to FcγR with a substantially lower binding activity than the parent polypeptide when assay is performed by keeping the amount of the parent polypeptide and the amount of the polypeptide comprising at least one amino acid alteration in the Fc region of the parent polypeptide (also called a polypeptide variant) practically the same.

For example, in the KD values measured by the above-mentioned measurement method, the KD value ratio (KD value of a polypeptide variant/KD value of a parent polypeptide) is preferably 1.25 or more, 2 or more, or 3 or more, and more preferably, 5 or more, 10 or more, 100 or more, 1,000 or more, or 10,000 or more.

Furthermore, in the KD values measured by the above-mentioned measurement method, the KD value is preferably increased by 1 μM or more, and more preferably increased by 2 μM or more, 3 μM or more, 5 μM or more, 10 UM or more, 20 UM or more, 50 μM or more, and 100 μM or more. Furthermore, in the KD values measured by the above-mentioned measurement method, the KD value is preferably 0.0001 UM or more, and more preferably 0.001 UM or more, 0.01 μM or more, 0.1 μM or more, 0.5 μM or more, 1 μM or more, 2 μM or more, 3 μM or more, 5 μM or more, 10 μM or more, 100 μM or more, or 1,000 μM or more.

A polypeptide with enhanced FcγR-binding activity refers to a polypeptide that binds to FcγR with a substantially higher binding activity than the parent polypeptide when assay is performed by keeping the amount of the parent polypeptide and the amount of the polypeptide variant practically the same.

For example, in the KD values measured by the above-mentioned measurement method, the KD value ratio (KD value of a parent polypeptide/KD value of a polypeptide variant) is preferably 1.25 or more, 2 or more, or 3 or more, and more preferably, 5 or more, 10 or more, 100 or more, 1,000 or more, or 10,000 or more.

Furthermore, in the KD values measured by the above-mentioned measurement method, the KD value is preferably decreased by 0.001 UM or more, and more preferably decreased by 0.01 μM, 0.1μ, 1 μM or more, 2 μM or more, 3 μM or more, 5 μM or more, 10 μM or more, 20 μM or more, 50 μM or more, and 100 μM or more.

Furthermore, in the KD values measured by the above-mentioned measurement method, the KD value is preferably 5 μM or less, and more preferably 3 μM or less, 1 μM or less, 0.5 μM or less, 0.1 μM or less, 0.01 μM or less, 0.001 μM or less, or 0.0001 μM or less.

A polypeptide with unchanged (maintained) FcγR-binding activity refers to a polypeptide that binds to FcγR with a binding activity practically unchanged from or equivalent to the parent polypeptide when assay is performed by keeping the amount of the parent polypeptide and the amount of the polypeptide comprising at least one amino acid alteration in the Fc region of the parent polypeptide (also called a polypeptide variant) practically the same.

Whether or not a polypeptide is a polypeptide having maintained or decreased FcγRIIa-binding activity and having enhanced FcγRIIb-binding activity can be determined using the KD value of this polypeptide for FcγRIIa and the KD value of this polypeptide for FcγRIIb determined according to the above-mentioned examples. An example is the case where the KD value of the polypeptide of the present invention for FcγRIIb is decreased compared with the KD value of the parent polypeptide for FcγRIIb; and the KD value of the polypeptide of the present invention for FcγRIIa (type R and type H) is increased or maintained compared with the KD value of the parent polypeptide for FcγRIIa (type R and type H). Furthermore, it is possible to determine by appropriately combining the KD value of the polypeptide for FcγRIa and the KD value of the polypeptide for FcγRIIIa, which were determined according to the above-mentioned example.

In the present invention, an increased FcγRIIb-binding activity means that, for example, in the KD values measured by the measurement method described above, the KD ratio of [KD value of the parent polypeptide]/[KD value of the polypeptide variant] is preferably 1.6 or more, 2 or more, or 3 or more, and more preferably 5 or more, 10 or more, 20 or more, 30 or more, and 50 or more.

Maintained or decreased binding activities towards FcγRIIa (type R) and FcγRIIa (type H) means that, for example, in the KD values measured by the measurement method described above, the KD ratio of [KD value for the stronger of the binding activities of a polypeptide variant towards FcγRIIa (type R) and FcγRIIa (type H)]/[KD value for the stronger of the binding activities of a parent polypeptide towards FcγRIIa (type R) and FcγRIIa (type H)] is preferably 0.7 or more, 1 or more, 2 or more, or 3 or more, and more preferably 5 or more, 10 or more, 20 or more, 30 or more, and 50 or more.

Polypeptides of the present invention preferably have maintained or decreased binding activities towards FcγRIIa type R and FcγRIIa type H. Furthermore, they preferably have maintained or decreased binding activities towards FcγRIIa type R and FcγRIIa type H, as well as a maintained or decreased FcγRIIIa-binding activity. In addition, they preferably have a maintained or decreased binding activity towards FcγRIa.

A maintained or decreased binding activity towards FcγRIIIa or FcγRIa means that, for example, in the KD values measured by the measurement method described above, the KD ratio of [KD value of the polypeptide variant]/[KD value of the parent polypeptide] is preferably 1 or more, 2 or more, or 3 or more, and more preferably 5 or more, 10 or more, 20 or more, 30 or more, and 50 or more.

Furthermore, whether or not a polypeptide of the present invention is a polypeptide with improved binding selectivity for FcγRIIb rather than for FcγRIIa can be determined by comparing the ratio of the KD value for FcγRIIa to the KD value for FcγRIIb of the polypeptide. of the present invention (KD value for FcγRIIa/KD value for FcγRIIb) with the ratio of the KD value for FcγRIIa to the KD value for FcγRIIb of the parent peptide (KD value for FcγRIIa/KD value for FcγRIIb), which were determined according to the above-mentioned examples. Specifically, when the value of the KD ratio for the polypeptide of the present invention is greater than that of the parent polypeptide, the polypeptide of the present invention can be determined to have an improved binding selectivity for FcγRIIb rather than for FcγRIIa in comparison with the parent polypeptide.

The binding selectivity between FcγRIIa (type R) and FcγRIIb is, for example, a KD value ratio [KD value of the polypeptide variant for FcγRIIa (type R)]/[KD value of the polypeptide variant for FcγRIIb] of preferably 1.2 or more, 2 or more, or 3 or more for the KD values measured by the measurement method described above, and more preferably 5 or more, 10 or more, 20 or more, or 30 or more.

The binding selectivity between FcγRIIa (type H) and FcγRIIb is, for example, a KD value ratio [KD value of the polypeptide variant for FcγRIIa (type H)]/[KD value of the polypeptide variant for FcγRIIb] of preferably 4.2 or more, 5 or more, or 10 or more for the KD values measured by the measurement method described above, and more preferably 20 or more, 30 or more, 50 or more, 100 or more, or 200 or more.

Furthermore, whether or not the binding activities of the polypeptides of the present invention towards various FcγRs were maintained, enhanced, or decreased can be determined from the increase or decrease in the amount of binding of the various FcγRs to the polypeptides of the present invention, which were determined according to the examples described above. Here, the amount of binding of the various FcγRs to the polypeptides refers to values obtained by determining the difference in the RU values of sensorgrams that changed before and after interaction of various FcγRs as the analyte with each polypeptide, and dividing them by differences in the RU values of sensorgrams that changed before and after capturing polypeptides to the sensor chips.

Whether or not the polypeptides of the present invention is a polypeptide having maintained or decreased binding activities towards FcγRIIa (type R and type H), and having increased binding activity towards FcγRIIb can be determined by using the amount of FcγRIIa binding of the polypeptide and the amount of FcγRIIb binding of the polypeptide, which were determined according to the examples described above.

An example is the case where the amount of FcγRIIb binding of a polypeptide of the present invention is increased compared with the amount of FcγRIIb binding of a parent polypeptide, and the amount of FcγRIIa (type R and type H) binding of a polypeptide of the present invention is equivalent to (maintained at) or preferably decreased from the amount of binding of a parent polypeptide towards FcγRIIa (type R and type H). Furthermore, it is possible to determine by appropriately combining the amount of FcγRIa binding and the amount of FcγRIIIa binding of the polypeptide determined according to the examples described above.

"Fc region" refers to the region comprising a fragment consisting of a hinge portion or a part thereof, CH2 domain, or CH3 domain in an antibody molecule. According to EU numbering (herein, also called the EU INDEX) (see FIG. 5), an IgG-class Fc region refers to, for example, the region from cysteine at position 226 to the C terminus, or from proline at position 230 to the C terminus, but is not limited thereto.

The Fc region may be obtained preferably by re-eluting the fraction adsorbed onto protein A column after partially digesting IgG1, IgG2, IgG3, IgG4 monoclonal antibodies or such using a protease such as pepsin. The protease is not particularly limited as long as it can digest a full-length antibody so that Fab and F(ab')2 will be produced in a restrictive manner by appropriately setting the enzyme reaction conditions such as pH, and examples include pepsin and papain.

The present invention provides an antibody constant region comprising an Fc region which comprises an alteration produced by substituting Pro at position 238 (EU numbering) with Asp or substituting Leu at position 328 (EU numbering) with Glu in human IgG (IgG1, IgG2, IgG3, and IgG4). Polypeptides with maintained or decreased binding activities towards FcγRIa, FcγRIIIa, and both allotypes of FcγRIIa, types R and H, as well as enhanced FcγRIIb-binding activity in comparison with a parent polypeptide can be provided by introducing alteration of substituting Pro at position 238 (EU numbering) with Asp or substituting Leu at position 328 (EU numbering) with Glu in human IgG.

In the present invention, at least one alteration can be further added to the human IgG Fc region comprising the alteration produced by substituting Pro at position 238 (EU numbering) with Asp or substituting Leu at position 328 (EU numbering) with Glu. Here, alteration refers to any one of, or a combination of substitutions, deletions, additions, and insertions. Additional alterations can be further included with these alterations. The additional alteration can be selected from any one of, or combinations of amino acid substitutions, deletions, or modifications. For example, alterations that enhance the binding activity to FcγRIIb, as well as maintain or decrease binding activities towards FcγRIIa (type H) and FcγRIIa (type R) can be added. Adding such alterations improves the binding selectivity for FcγRIIb rather than for FcγRIIa.

Among them, alterations that improve the binding selectivity for FcγRIIb rather than for FcγRIIa (type R) are preferred, and alterations that improve the binding selectivity for FcγRIIb rather than for FcγRIIa (type H) are more preferred. Preferred examples of alterations of substituting an amino acid include, the alteration of substituting Gly at position 237 (EU numbering) with Trp,
the alteration of substituting Gly at position 237 (EU numbering) with Phe,
the alteration of substituting Pro at position 238 (EU numbering) with Phe,
the alteration of substituting Asn at position 325 (EU numbering) with Met,
the alteration of substituting Ser at position 267 (EU numbering) with Ile,
the alteration of substituting Leu at position 328 (EU numbering) with Asp,
the alteration of substituting Ser at position 267 (EU numbering) with Val,
the alteration of substituting Leu at position 328 (EU numbering) with Trp,
the alteration of substituting Ser at position 267 (EU numbering) with Gln,
the alteration of substituting Ser at position 267 (EU numbering) with Met,
the alteration of substituting Gly at position 236 (EU numbering) with Asp,
the alteration of substituting Ala at position 327 (EU numbering) with Asn,
the alteration of substituting Asn at position 325 (EU numbering) with Ser,
the alteration of substituting Leu at position 235 (EU numbering) with Tyr,
the alteration of substituting Val at position 266 (EU numbering) with Met,
the alteration of substituting Leu at position 328 (EU numbering) with Tyr,
the alteration of substituting Leu at position 235 (EU numbering) with Trp,
the alteration of substituting Leu at position 235 (EU numbering) with Phe,
the alteration of substituting Ser at position 239 (EU numbering) with Gly,
the alteration of substituting Ala at position 327 (EU numbering) with Glu,
the alteration of substituting Ala at position 327 (EU numbering) with Gly,
the alteration of substituting Pro at position 238 (EU numbering) with Leu,
the alteration of substituting Ser at position 239 (EU numbering) with Leu,
the alteration of substituting Leu at position 328 (EU numbering) with Thr,
the alteration of substituting Leu at position 328 (EU numbering) with Ser,
the alteration of substituting Leu at position 328 (EU numbering) with Met,
the alteration of substituting Pro at position 331 (EU numbering) with Trp,
the alteration of substituting Pro at position 331 (EU numbering) with Tyr,
the alteration of substituting Pro at position 331 (EU numbering) with Phe,
the alteration of substituting Ala at position 327 (EU numbering) with Asp,
the alteration of substituting Leu at position 328 (EU numbering) with Phe,
the alteration of substituting Pro at position 271 (EU numbering) with Leu,
the alteration of substituting Ser at position 267 (EU numbering) with Glu,
the alteration of substituting Leu at position 328 (EU numbering) with Ala,
the alteration of substituting Leu at position 328 (EU numbering) with Ile,
the alteration of substituting Leu at position 328 (EU numbering) with Gln,
the alteration of substituting Leu at position 328 (EU numbering) with Val,
the alteration of substituting Lys at position 326 (EU numbering) with Trp,
the alteration of substituting Lys at position 334 (EU numbering) with Arg,
the alteration of substituting His at position 268 (EU numbering) with Gly,
the alteration of substituting His at position 268 (EU numbering) with Asn,
the alteration of substituting Ser at position 324 (EU numbering) with Val,
the alteration of substituting Val at position 266 (EU numbering) with Leu,
the alteration of substituting Pro at position 271 (EU numbering) with Gly,
the alteration of substituting Ile at position 332 (EU numbering) with Phe,
the alteration of substituting Ser at position 324 (EU numbering) with Ile,
the alteration of substituting Glu at position 333 (EU numbering) with Pro,
the alteration of substituting Tyr at position 300 (EU numbering) with Asp,
the alteration of substituting Ser at position 337 (EU numbering) with Asp,
the alteration of substituting Tyr at position 300 (EU numbering) with Gln,
the alteration of substituting Thr at position 335 (EU numbering) with Asp,
the alteration of substituting Ser at position 239 (EU numbering) with Asn,
the alteration of substituting Lys at position 326 (EU numbering) with Leu,
the alteration of substituting Lys at position 326 (EU numbering) with Ile,
the alteration of substituting Ser at position 239 (EU numbering) with Glu,
the alteration of substituting Lys at position 326 (EU numbering) with Phe, the alteration of substituting Lys at position 326 (EU numbering) with Val,
the alteration of substituting Lys at position 326 (EU numbering) with Tyr,
the alteration of substituting Ser at position 267 (EU numbering) with Asp,
the alteration of substituting Lys at position 326 (EU numbering) with Pro,
the alteration of substituting Lys at position 326 (EU numbering) with His,
the alteration of substituting Lys at position 334 (EU numbering) with Ala,
the alteration of substituting Lys at position 334 (EU numbering) with Trp,
the alteration of substituting His at position 268 (EU numbering) with Gln,
the alteration of substituting Lys at position 326 (EU numbering) with Gln,
the alteration of substituting Lys at position 326 (EU numbering) with Glu,
the alteration of substituting Lys at position 326 (EU numbering) with Met,
the alteration of substituting Val at position 266 (EU numbering) with Ile,
the alteration of substituting Lys at position 334 (EU numbering) with Glu,
the alteration of substituting Tyr at position 300 (EU numbering) with Glu,
the alteration of substituting Lys at position 334 (EU numbering) with Met,
the alteration of substituting Lys at position 334 (EU numbering) with Val,
the alteration of substituting Lys at position 334 (EU numbering) with Thr,
the alteration of substituting Lys at position 334 (EU numbering) with Ser,
the alteration of substituting Lys at position 334 (EU numbering) with His,
the alteration of substituting Lys at position 334 (EU numbering) with Phe,
the alteration of substituting Lys at position 334 (EU numbering) with Gln,
the alteration of substituting Lys at position 334 (EU numbering) with Pro,
the alteration of substituting Lys at position 334 (EU numbering) with Tyr,
the alteration of substituting Lys at position 334 (EU numbering) with Ile,
the alteration of substituting Gln at position 295 (EU numbering) with Leu,
the alteration of substituting Lys at position 334 (EU numbering) with Leu,
the alteration of substituting Lys at position 334 (EU numbering) with Asn,
the alteration of substituting His at position 268 (EU numbering) with Ala,
the alteration of substituting Ser at position 239 (EU numbering) with Asp,
the alteration of substituting Ser at position 267 (EU numbering) with Ala,
the alteration of substituting Leu at position 234 (EU numbering) with Trp,
the alteration of substituting Leu at position 234 (EU numbering) with Tyr,
the alteration of substituting Gly at position 237 (EU numbering) with Ala,
the alteration of substituting Gly at position 237 (EU numbering) with Asp,
the alteration of substituting Gly at position 237 (EU numbering) with Glu,
the alteration of substituting Gly at position 237 (EU numbering) with Leu,
the alteration of substituting Gly at position 237 (EU numbering) with Met,
the alteration of substituting Gly at position 237 (EU numbering) with Tyr,
the alteration of substituting Ala at position 330 (EU numbering) with Lys,
the alteration of substituting Ala at position 330 (EU numbering) with Arg,
the alteration of substituting Glu at position 233 (EU numbering) with Asp,
the alteration of substituting His at position 268 (EU numbering) with Asp,
the alteration of substituting His at position 268 (EU numbering) with Glu,
the alteration of substituting Lys at position 326 (EU numbering) with Asp,
the alteration of substituting Lys with Ser at position 326 (EU numbering),
the alteration of substituting Lys with Thr at position 326 (EU numbering),
the alteration of substituting Val with Ile at position 323 (EU numbering),
the alteration of substituting Val with Leu at position 323 (EU numbering),
the alteration of substituting Val at position 323 (EU numbering) with Met,
the alteration of substituting Tyr at position 296 (EU numbering) with Asp,
the alteration of substituting Lys at position 326 (EU numbering) with Ala,
the alteration of substituting Lys at position 326 (EU numbering) with Asn, and
the alteration of substituting Ala at position 330 (EU numbering) with Met.

Furthermore, examples of preferred amino acid substitutions among these alterations include
the alteration of substituting Gly at position 237 (EU numbering) with Trp,
the alteration of substituting Gly at position 237 (EU numbering) with Phe,
the alteration of substituting Ser at position 267 (EU numbering) with Val,
the alteration of substituting Ser at position 267 (EU numbering) with Gln,
the alteration of substituting His at position 268 (EU numbering) with Asn,
the alteration of substituting Pro at position 271 (EU numbering) with Gly,
the alteration of substituting Lys at position 326 (EU numbering) with Leu,
the alteration of substituting Lys at position 326 (EU numbering) with Gln,
the alteration of substituting Lys at position 326 (EU numbering) with Glu,
the alteration of substituting Lys at position 326 (EU numbering) with Met,
the alteration of substituting Ser at position 239 (EU numbering) with Asp,
the alteration of substituting Ser at position 267 (EU numbering) with Ala, the alteration of substituting Leu at position 234 (EU numbering) with Trp,
the alteration of substituting Leu at position 234 (EU numbering) with Tyr,
the alteration of substituting Gly at position 237 (EU numbering) with Ala,
the alteration of substituting Gly at position 237 (EU numbering) with Asp,
the alteration of substituting Gly at position 237 (EU numbering) with Glu,
the alteration of substituting Gly at position 237 (EU numbering) with Leu,
the alteration of substituting Gly at position 237 (EU numbering) with Met,
the alteration of substituting Gly at position 237 (EU numbering) with Tyr,
the alteration of substituting Ala at position 330 (EU numbering) with Lys,
the alteration of substituting Ala at position 330 (EU numbering) with Arg,
the alteration of substituting Glu at position 233 (EU numbering) with Asp,
the alteration of substituting His at position 268 (EU numbering) with Asp,
the alteration of substituting His at position 268 (EU numbering) with Glu,
the alteration of substituting Lys at position 326 (EU numbering) with Asp,
the alteration of substituting Lys at position 326 (EU numbering) with Ser,
the alteration of substituting Lys at position 326 (EU numbering) with Thr,
the alteration of substituting Val at position 323 (EU numbering) with Ile,
the alteration of substituting Val at position 323 (EU numbering) with Leu,
the alteration of substituting Val at position 323 (EU numbering) with Met,
the alteration of substituting Tyr at position 296 (EU numbering) with Asp,
the alteration of substituting Lys at position 326 (EU numbering) with Ala,
the alteration of substituting Lys at position 326 (EU numbering) with Asn, and
the alteration of substituting Ala at position 330 (EU numbering) with Met.

The alteration mentioned above may be an alteration introduced at one position, and alternatively, or alterations at two or more positions can be combined. Preferred examples of such alterations include those mentioned in Tables 6-7 and Tables 9-12.

Furthermore, for example, amino acid substitutions that improve FcRn-binding activity (J. Immunol. 2006 Jan. 1; 176(1): 346-56; J Biol Chem. 2006 Aug. 18; 281(33): 23514-24; Int. Immunol. 2006 December; 18(12): 1759-69; Nat Biotechnol. 2010 February; 28(2): 157-9.; WO 2006/019447; WO 2006/053301; and WO 2009/086320), and amino acid substitutions for improving antibody heterogeneity or stability (WO 2009/041613) may be introduced into an antibody constant region portion. Alternatively, polypeptides produced by conferring polypeptides of the present invention with the property of promoting disappearance of antigens, which are described in WO 2011/122011 or PCT/JP2011/072550, and polypeptides conferring the property for repeated binding to a plurality of antigen molecules, which are described in WO 2009/125825 or PCT/JP2011/077619, are also included in the present invention.

Preferred examples of polypeptides of the present invention include IgG antibodies. When an IgG antibody is used as the antibody, the type of constant region is not limited, and an IgG isotypes (subclasses) such as IgG1, IgG2, IgG3, and IgG4 can be used. IgG antibodies of the present invention are preferably human IgG, and more preferably human IgG1 and human IgG4. The amino acid sequences of the heavy-chain constant regions of human IgG1 and human IgG4 are known. A plurality of allotype sequences due to genetic polymorphisms have been described in Sequences of Proteins of Immunological Interest, NIH Publication No. 91-3242 for the human IgG1 constant region, and any of the sequences may be used in the present invention.

<Substitution>

When substituting amino acid residues, substitution to a different amino acid residue is carried out with the objective of altering aspects such as (a)-(c) described below:

(a) polypeptide backbone structure in the sheet-structure or helical-structure region;
(b) electric charge or hydrophobicity at the target site; or
(c) size of the side chain.

Amino acid residues are classified into the following groups based on their general side chain properties:

(1) hydrophobic: norleucine, met, ala, val, leu, and ile;
(2) neutral hydrophilic: cys, ser, thr, asn, and gln;
(3) acidic: asp and glu;
(4) basic: his, lys, and arg;
(5) residues that affect the chain orientation: gly and pro; and
(6) aromatic: trp, tyr, and phe.

Substitution between amino acid residues within each of these amino acid groups is referred to as conservative substitution, and amino acid residue substitution between different groups is referred to as non-conservative substitution. Substitutions in the present invention may be conservative substitutions or non-conservative substitutions, or a combination of conservative substitutions and non-conservative substitutions.

Amino acid sequence alterations are produced by various methods known to those skilled in the art. Such methods include the site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152:271-275; Zoller, M J, and Smith, M. (1983) Oligonucleotide-directed mutagenesis of DNA fragments cloned into M13 vectors. Methods Enzymol. 100:468-500; Kramer, W, Drutsa, V, Jansen, HW, Kramer, B, Pflugfelder, M, and Fritz, HJ (1984) The gapped duplex DNA approach to oligonucleotide-directed mutation construction. Nucleic Acids Res. 12:9441-9456; Kramer W, and Fritz H J (1987) Oligonucleotide-directed construction of mutations via gapped duplex DNA Methods. Enzymol. 154, 350-367; and Kunkel, TA (1985) Rapid and efficient site-specific mutagenesis without phenotypic selection. Proc Natl Acad Sci USA. 82:488-492), the PCR mutation method, and the cassette mutation method, but are not limited thereto.

Amino acid modification of the present invention includes post-translational modification. A specific post-translational modification may be addition or deletion of a sugar chain. For example, in the IgG1 constant region consisting of the amino acid sequence of SEQ ID NO: 11, the amino acid residue at position 297 (EU numbering) may be sugar chain-modified. The sugar-chain structure for the modification is not limited. Generally, antibodies expressed in eukaryotic cells comprise glycosylation in the constant region. Therefore, antibodies expressed in cells such as those below are normally modified by some type of sugar chain:

antibody-producing cells of mammals eukaryotic cells transformed with an expression vector comprising a DNA encoding an antibody Eukaryotic cells shown here include yeast and animal cells. For example, CHO cells and HEK293H cells are representative animal cells used in transformation with an expression vector comprising an antibody-encoding DNA. On the other hand, those without glycosylation at this site are also included in the constant region of the present invention. Antibodies whose constant region is not glycosylated can be obtained by expressing an antibody-encoding gene in prokaryotic cells such as *Escherichia coli.*

Specifically, for example, sialic acid may be added to the sugar chain of an Fc region (MAbs. 2010 September-October; 2(5): 519-27).

<Antibody>

Furthermore, the present invention provides antibodies comprising an Fc region in which any of the above-mentioned amino acid sequences is altered.

The term "antibody/antibodies" in the present invention is used in the broadest sense, and as long as the desired biological activity is shown, it comprises any antibody such as monoclonal antibodies (including full-length monoclonal antibodies), polyclonal antibodies, antibody variants, antibody fragments, polyspecific antibodies (multi-specific antibodies) (for example, bispecific antibodies (diabodies)), chimeric antibodies, and humanized antibodies.

Regarding the antibodies of the present invention, the antigen type and antibody origin are not limited, and they may be any type of antibodies. The origin of the antibodies is not particularly limited, but examples include human antibodies, mouse antibodies, rat antibodies, and rabbit antibodies.

Methods for producing the antibodies are well known to those skilled in the art, and for example, monoclonal antibodies may be produced by the hybridoma method (Kohler and Milstein, Nature 256:495 (1975)), or the recombination method (U.S. Pat. No. 4,816,567). Alternatively, they may be isolated from a phage antibody library (Clackson et al., Nature 352:624-628 (1991); Marks et al., J.Mol.Biol. 222: 581-597 (1991)).

A humanized antibody is also called a reshaped human antibody. Specifically, humanized antibodies prepared by grafting the CDRs of a non-human animal antibody such as a mouse antibody to a human antibody and such are known. Common genetic engineering techniques for obtaining humanized antibodies are also known. Specifically, for example, overlap extension PCR is known as a method for grafting mouse antibody CDRs to human FRs.

A vector for expressing a humanized antibody can be produced by inserting a DNA encoding an antibody variable region in which three CDRs and four FRs are ligated and a DNA encoding a human antibody constant region into an expression vector so that these DNAs are fused in frame. After this integration vector is transfected into a host to establish recombinant cells, these cells are cultured, and the DNA encoding the humanized antibody is expressed to produce the humanized antibody in the culture of the cells (see, European Patent Publication No. EP 239,400, and International Patent Publication No. WO 1996/002576).

As necessary, an amino acid residue in an FR may be substituted so that the CDRs of a reshaped human antibody form an appropriate antigen-binding site. For example, a mutation can be introduced into the amino acid sequence of an FR by applying the PCR method used for grafting mouse CDRs to human FRs.

A desired human antibody can be obtained by DNA immunization using a transgenic animal having the complete repertoire of human antibody genes (see International Publication Nos. WO 1993/012227, WO 1992/003918, WO 1994/002602, WO 1994/025585, WO 1996/034096, and WO 1996/033735) as an animal for immunization.

Furthermore, technologies for obtaining a human antibody by panning using a human antibody library are known. For example, a human antibody V region is expressed on the surface of a phage as a single-chain antibody (scFv) by the phage display method. The scFv-expressing phage that binds to the antigen can be selected. The DNA sequence that encodes the V region of the antigen-bound human antibody can be determined by analyzing the genes of the selected phage. After determining the DNA sequence of the scFv that binds to the antigen, an expression vector can be prepared by fusing the V-region sequence in-frame with the sequence of a desired human antibody C region, and then inserting this into a suitable expression vector. The expression vector is introduced into suitable expression cells such as those described above, and the human antibody can be obtained by expressing the human antibody-encoding gene. These methods are already known (see, International Publication Nos. WO 1992/001047, WO 1992/020791, WO 1993/006213, WO 1993/011236, WO 1993/019172, WO 1995/001438, and WO 1995/15388).

Variable regions constituting the antibodies of the present invention can be variable regions that recognize any antigen.

Herein, there is no particular limitation on the antigen, and it may be any antigens. Examples of such antigens preferably include ligands (cytokines, chemokines, and such), receptors, cancer antigens, MHC antigens, differentiation antigens, immunoglobulins, and immune complexes partly containing immunoglobulins.

Examples of cytokines include interleukins 1 to 18, colony stimulating factors (G-CSF, M-CSF, GM-CSF, etc.), interferons (IFN-α, IFN-β, IFN-γ, etc.), growth factors (EGF, FGF, IGF, NGF, PDGF, TGF, HGF, etc.), tumor necrosis factors (TNF-α and TNF-β), lymphotoxin, erythropoietin, leptin, SCF, TPO, MCAF, and BMP.

Examples of chemokines include CC chemokines such as CCL1 to CCL28, CXC chemokines such as CXCL1 to CXCL17, C chemokines such as XCL1 and XCL2, and CX3C chemokines such as CX3CL1.

Examples of receptors include receptors belonging to receptor families such as the hematopoietic growth factor receptor family, cytokine receptor family, tyrosine kinase-type receptor family, serine/threonine kinase-type receptor family, TNF receptor family, G protein-coupled receptor family, GPI anchor-type receptor family, tyrosine phosphatase-type receptor family, adhesion factor family, and hormone receptor family. The receptors belonging to these receptor families and their characteristics have been described in many documents such as Cooke B A., King R J B., van der Molen H J. ed. New Comprehensive Biochemistry Vol.18B "Hormones and their Actions Part II" pp. 1-46 (1988) Elsevier Science Publishers BV; Patthy (Cell (1990) 61 (1): 13-14); Ullrich et al. (Cell (1990) 61 (2): 203-212); Massagué (Cell (1992) 69 (6): 1067-1070); Miyajima et al. (Annu. Rev. Immunol. (1992) 10:295-331); Taga et al. (FASEB J. (1992) 6, 3387-3396); Fantl et al. (Annu. Rev. Biochem. (1993), 62:453-481); Smith et al. (Cell (1994) 76 (6): 959-962); and Flower DR. Flower (Biochim. Biophys. Acta (1999) 1422 (3): 207-234).

Examples of specific receptors belonging to the above-mentioned receptor families preferably include human or mouse erythropoietin (EPO) receptors (Blood (1990) 76 (1): 31-35; and Cell (1989) 57 (2): 277-285), human or mouse granulocyte-colony stimulating factor (G-CSF) receptors (Proc. Natl. Acad. Sci. USA. (1990) 87 (22): 8702-8706, mG-CSFR; Cell (1990) 61 (2): 341-350), human or mouse thrombopoietin (TPO) receptors (Proc Natl Acad Sci USA. (1992) 89 (12): 5640-5644; EMBO J. (1993) 12 (7): 2645-53), human or mouse insulin receptors (Nature (1985) 313 (6005): 756-761), human or mouse Flt-3 ligand receptors (Proc. Natl. Acad. Sci. USA. (1994) 91 (2): 459-463), human or mouse platelet-derived growth factor (PDGF) receptors (Proc. Natl. Acad. Sci. USA. (1988) 85 (10): 3435-3439), human or mouse interferon (IFN)-$\alpha$ and $\beta$ receptors (Cell (1990) 60 (2): 225-234; and Cell (1994) 77 (3): 391-400), human or mouse leptin receptors, human or mouse growth hormone (GH) receptors, human or mouse interleukin (IL)-10 receptors, human or mouse insulin-like growth factor (IGF)-I receptors, human or mouse leukemia inhibitory factor (LIF) receptors, and human or mouse ciliary neurotrophic factor (CNTF) receptors.

Cancer antigens are antigens that are expressed as cells become malignant, and they are also called tumor-specific antigens. Abnormal sugar chains that appear on cell surfaces or protein molecules when cells become cancerous are also cancer antigens, and they are also called sugar-chain cancer antigens. Examples of cancer antigens preferably include GPC3 which is a receptor belonging to the GPI anchor-type receptor family mentioned above, and is also expressed in several cancers including liver cancer (Int J Cancer. (2003) 103 (4): 455-65), as well as EpCAM which is expressed in several cancers including lung cancer (Proc Natl Acad Sci USA. (1989) 86 (1): 27-31), CA19-9, CA15-3, and sialyl SSEA-1 (SLX).

MHC antigens are roughly classified into MHC class I antigens and MHC class II antigens. MHC class I antigens include HLA-A, -B, -C, -E, -F, -G, and -H, and MHC class II antigens include HLA-DR, -DQ, and -DP.

Differentiation antigens may include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Immunoglobulins include IgA, IgM, IgD, IgG, and IgE. Immunocomplexes include a component of at least any of the immunoglobulins.

Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7,alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Axl, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-IR, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N—C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGGI, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alpha-beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137. ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, AB, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, Clq, Clr, Cls, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and S1P; and receptors for hormone and growth factors.

One or more amino acid residue alterations are allowed in the amino acid sequences constituting the variable regions as long as their antigen-binding activities are maintained. When altering a variable region amino acid sequence, there is no particularly limitation on the site of alteration and number of amino acids altered. For example, amino acids present in CDR and/or FR can be altered appropriately. When altering amino acids in a variable region, the binding activity is preferably maintained without particular limitation; and for example, as compared to before alteration, the binding activity is 50% or more, preferably 80% or more, and more preferably 100% or more. Furthermore, the binding activity may be increased by amino acid alterations. For example, the binding activity may be 2-, 5-, 10-times higher or such than that before alteration. In the antibodies of the present invention, alteration of amino acid sequence may be at least one of amino acid residue substitution, addition, deletion, and modification.

For example, the modification of the N-terminal glutamine of a variable region into pyroglutamic acid by pyroglutamylation is a modification well known to those skilled in the art. Thus, when the heavy-chain N terminus is glutamine, the antibodies of the present invention comprise the variable regions in which the glutamine is modified to pyroglutamic acid.

Antibody variable regions of the present invention may have any sequences, and they may be antibody variable regions of any origin, such as mouse antibodies, rat antibodies, rabbit antibodies, goat antibodies, camel antibodies, humanized antibodies produced by humanizing these non-human antibodies, and human antibodies. "Humanized antibodies", also referred to as "reshaped human antibodies", are antibodies in which the complementarity determining regions (CDRs) of an antibody derived from a non-human mammal, for example, a mouse antibody, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342:877). Their common genetic recombination techniques are also known (see, European Patent Application Publication No. EP 125023 and WO 96/02576). Furthermore, these antibodies may have various amino acid substitutions introduced into their variable regions to improve their antigen binding, pharmacokinetics, stability, and antigenicity. Variable regions of the antibodies of the present invention may be able to bind antigens repeatedly due to their pH dependability in antigen binding (WO 2009/125825).

κ chain and λ chain-type constant regions are present in antibody light-chain constant regions, but either one of the light chain constant regions is acceptable. Furthermore, light-chain constant regions of the present invention may be light-chain constant regions with amino acid alterations such as substitutions, deletions, additions, and/or insertions.

For example, for the heavy chain constant regions of an antibody of the present invention, heavy chain constant regions of human IgG antibodies may be used and heavy chain constant regions of human IgG1 antibodies and those of human IgG4 antibodies are preferred.

Furthermore, polypeptides of the present invention may be made into Fc fusion protein molecules by linking to other proteins, physiologically active peptides, and such.

Examples of the other proteins and biologically active peptides include receptors, adhesion molecules, ligands, and enzymes, but are not limited thereto.

Preferred examples of Fc fusion protein molecules of the present invention include proteins with Fc domain fused to a receptor protein that binds to a target, and such examples include TNFR-Fc fusion protein, IL1R-Fc fusion protein, VEGFR-Fc fusion protein, and CTLA4-Fc fusion protein (Nat Med. 2003 January; 9(1): 47-52; BioDrugs. 2006; 20(3): 151-60). Furthermore, a protein to be fused to a polypeptide of the present invention may be any molecule as long as it binds to a target molecule, and examples include scFv molecules (WO 2005/037989), single-domain antibody molecules (WO 2004/058821; WO 2003/002609), antibody-like molecules (Current Opinion in Biotechnology 2006, 17:653-658; Current Opinion in Biotechnology 2007, 18:1-10; Current Opinion in Structural Biology 1997, 7:463-469; and Protein Science 2006, 15:14-27) such as DARPins (WO 2002/020565), Affibody (WO 1995/001937), Avimer (WO 2004/044011; WO 2005/040229), and Adnectin (WO 2002/032925). Furthermore, antibodies and Fc fusion protein molecules may be multispecific antibodies that bind to multiple types of target molecules or epitopes.

Furthermore, the antibodies of the present invention include antibody modification products. Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single molecule variable regions that recognize different epitopes. The epitopes may be present in a single molecule or in different molecules.

The polypeptides of the present invention can be prepared by the methods known to those skilled in the art. For example, the antibodies can be prepared by the methods described below, but the methods are not limited thereto.

A DNA encoding an antibody heavy chain in which one or more amino acid residues in the Fc region have been substituted with other amino acids of interest and DNA encoding an antibody light chain, are expressed. A DNA encoding a heavy chain in which one or more amino acid residues in the Fc region are substituted with other amino acids of interest can be prepared, for example, by obtaining a DNA encoding the Fc region of a natural heavy chain, and introducing an appropriate substitution so that a codon encoding a particular amino acid in the Fc region encodes another amino acid of interest.

Alternatively, a DNA encoding a heavy chain in which one or more amino acid residues in the Fc region are substituted with other amino acids of interest can also be prepared by designing and then chemically synthesizing a DNA encoding a protein in which one or more amino acid residues in the Fc region of the natural heavy chain are substituted with other amino acids of interest. The position and type of amino acid substitution are not particularly limited. Furthermore, alteration is not limited to substitution, and alteration may be any of deletion, addition, or insertion, or combination thereof.

Alternatively, a DNA encoding a heavy chain in which one or more amino acid residues in the Fc region are substituted with other amino acids of interest can be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto. Furthermore, a DNA encoding a light chain can similarly be prepared as a combination of partial DNAs.

Methods for expressing the above-described DNAs include the methods described below. For example, a heavy chain expression vector is constructed by inserting a DNA encoding a heavy chain variable region into an expression vector along with a DNA encoding a heavy chain constant region. Likewise, a light chain expression vector is constructed by inserting a DNA encoding a light chain variable region into an expression vector along with a DNA encoding a light chain constant region. Alternatively, these heavy and light chain genes may be inserted into a single vector.

When inserting a DNA encoding the antibody of interest into an expression vector, the DNA is inserted so that the antibody is expressed under the control of an expression-regulating region such as an enhancer or promoter. Next, host cells are transformed with this expression vector to express the antibody. In such cases, an appropriate combination of host and expression vector may be used.

Examples of the vectors include M13 vectors, pUC vectors, pBR322, pBluescript, and pCR-Script. Alternatively, when aiming to subclone and excise cDNA, in addition to the vectors described above, pGEM-T, pDIRECT, pT7, and such can be used.

Expression vectors are particularly useful when using vectors for producing the polypeptides of the present invention. For example, when a host cell is *E. coli* such as JM109, DH5a, HB101, and XL1-Blue, the expression vectors must carry a promoter that allows efficient expression in *E. coli*, for example, lacZ promoter (Ward et al., Nature (1989) 341:544-546; FASEB J. (1992) 6:2422-2427; its entirety are incorporated herein by reference), araB promoter (Better et al., Science (1988) 240:1041-1043; its entirety are incorporated herein by reference), T7 promoter, or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The vectors may contain signal sequences for polypeptide secretion. As a signal sequence for polypeptide secretion, a pelB signal sequence (Lei, S. P. et al J. Bacteriol. (1987) 169:4379; its entirety are incorporated herein by reference) may be used when a polypeptide is secreted into the *E. coli* periplasm. The vector can be introduced into host cells by lipofectin method, calcium phosphate method, and DEAE-Dextran method, for example.

In addition to *E. coli* expression vectors, the vectors for producing the polypeptides of the present invention include mammalian expression vectors (for example, pcDNA3 (Invitrogen), pEGF-BOS (Nucleic Acids. Res. 1990, 18(17): p5322; its entirety are incorporated herein by reference), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "*Pichia* Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277:108; its entirety are incorporated herein by reference), MMTV-LTR promoter, EF1α promoter (Mizushima et al., Nucleic Acids Res. (1990) 18:5322; its entirety are incorporated herein by reference), CAG promoter (Gene. (1990) 18:5322; its entirety are incorporated herein by reference), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP13, for example.

In addition, the following method can be used for stable gene expression and gene copy number amplification in cells: CHO cells deficient in a nucleic acid synthesis pathway are introduced with a vector that carries a DHFR gene which compensates for the deficiency (for example, pCHOI), and the vector is amplified using methotrexate (MTX). Alternatively, the following method can be used for transient gene expression: COS cells with a gene expressing SV40 T antigen on their chromosome are transformed with a vector with an SV40 replication origin (pcD and such). Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Antibodies can be collected, for example, by culturing transformed cells, and then separating the antibodies from the inside of the transformed cells or from the culture media. Antibodies can be separated and purified using an appropriate combination of methods such as centrifugation, ammonium sulfate fractionation, salting out, ultrafiltration, 1q, FcRn, protein A, protein G column, affinity chromatography, ion exchange chromatography, and gel filtration chromatography.

Furthermore, the present invention provides methods for producing a polypeptide comprising an antibody Fc region having maintained or decreased FcγRIIa-binding activity, and enhanced FcγRIIb-binding activity in comparison with a parent polypeptide, which comprises adding at least one amino acid alteration to the Fc region of the polypeptide.

Examples include production methods comprising the following steps:

(a) adding at least one amino acid alteration to the Fc region of polypeptides comprising an antibody Fc region;

(b) measuring the FcγRIIa-binding activity and FcγRIIb-binding activity of the polypeptides altered in step (a); and (c) selecting polypeptides having maintained or decreased FcγRIIa-binding activity, and enhanced FcγRIIb-binding activity in comparison with a parent polypeptide.

A preferred embodiment is a method for producing a polypeptide comprising an antibody Fc region, which comprises the steps of:

(a) altering a nucleic acid encoding the polypeptide so that the FcγRIIa-binding activity is maintained or decreased, and the FcγRIIb-binding activity is enhanced in comparison with the parent peptide;

(b) introducing the nucleic acid into host cells and culturing them to induce expression; and (c) collecting the polypeptide from the host cell culture.

Furthermore, antibodies and Fc fusion protein molecules produced by this production method are also included in the present invention.

The present invention also provides methods for producing a polypeptide in which antibody production against the polypeptide is suppressed compared with its parent polypeptide when administered in vivo, which comprise adding at least one amino acid alteration in the Fc region of a polypeptide comprising an antibody Fc region.

Examples include a production method comprising the following steps:

(a) adding at least one amino acid alteration in the Fc region of a polypeptide comprising an antibody Fc region; and (b) confirming that antibody production is suppressed when the polypeptide altered in step (a) is administered in vivo in comparison with a parent polypeptide.

Whether or not production of antibodies against the polypeptide has been suppressed can be confirmed by methods of administering the polypeptide to an animal and such. Alternatively, suppression of antibody production can be determined by measuring the binding activities towards FcγRIIa and FcγRIIb, and observing an increase in the value obtained by dividing the KD value for FcγRIIa by the KD value for FcγRIIb. Such polypeptides are considered to be useful as pharmaceuticals since they can suppress antibody production without activating activating FcγR.

In the above-mentioned production method, it is preferable to enhance the FcγRIIb-binding activity, and maintain or decrease the binding activities towards FcγRIIa (type R) and FcγRIIa (type H); and it is preferable to additionally reduce binding activities towards FcγRIa and/or FcγRIIIa.

In a preferred embodiment in the above-mentioned production method, for example, a polypeptide comprising a human IgG Fc region is altered so that Pro at position 238 (EU numbering) is substituted with Asp or Leu at position 328 (EU numbering) is substituted with Glu. Other preferred embodiments include altering the polypeptide so that at least one substitution selected from the group consisting of:

substitution of Gly at position 237 (EU numbering) with Trp;
substitution of Gly at position 237 (EU numbering) with Phe;
substitution of Ser at position 267 (EU numbering) with Val;
substitution of Ser at position 267 (EU numbering) with Gln;
substitution of His at position 268 (EU numbering) with Asn;
substitution of Pro at position 271 (EU numbering) with Gly;
substitution of Lys at position 326 (EU numbering) with Leu;
substitution of Lys at position 326 (EU numbering) with Gln;
substitution of Lys at position 326 (EU numbering) with Glu;
substitution of Lys at position 326 (EU numbering) with Met;
substitution of Ser at position 239 (EU numbering) with Asp;
substitution of Ser at position 267 (EU numbering) with Ala;
substitution of Leu at position 234 (EU numbering) with Trp;
substitution of Leu at position 234 (EU numbering) with Tyr;
substitution of Gly at position 237 (EU numbering) with Ala;
substitution of Gly at position 237 (EU numbering) with Asp;
substitution of Gly at position 237 (EU numbering) with Glu;
substitution of Gly at position 237 (EU numbering) with Leu;
substitution of Gly at position 237 (EU numbering) with Met;
substitution of Gly at position 237 (EU numbering) with Tyr;
substitution of Ala at position 330 (EU numbering) with Lys;
substitution of Ala at position 330 (EU numbering) with Arg;
substitution of Glu at position 233 (EU numbering) with Asp;
substitution of His at position 268 (EU numbering) with Asp;
substitution of His at position 268 (EU numbering) with Glu;
substitution of Lys at position 326 (EU numbering) with Asp;
substitution of Lys at position 326 (EU numbering) with Ser;
substitution of Lys at position 326 (EU numbering) with Thr;
substitution of Val at position 323 (EU numbering) with Ile;
substitution of Val at position 323 (EU numbering) with Leu;
substitution of Val at position 323 (EU numbering) with Met;
substitution of Tyr at position 296 (EU numbering) with Asp;
substitution of Lys at position 326 (EU numbering) with Ala;
substitution of Lys at position 326 (EU numbering) with Asn; and
substitution of Ala at position 330 (EU numbering) with Met, in addition to substitution of Pro at position 238 (EU numbering) with Asp.

Furthermore, the present invention provides methods for altering a polypeptide for the production of a polypeptide having maintained or decreased FcγRIIa-binding activity, and having enhanced FcγRIIb-binding activity in comparison with its parent polypeptide.

The present invention also provides methods for altering a polypeptide for the production of a polypeptide whose antibody production is suppressed compared with that of a parent polypeptide when it is administered in vivo.

In a preferred embodiment, for example, a polypeptide comprising a human IgG Fc region is altered so that Pro at position 238 (EU numbering) is substituted with Asp or Leu at position 328 (EU numbering) is substituted with Glu. Other preferred embodiments include altering the polypeptide so that at least one substitution selected from the group consisting of: substitution of Gly at position 237 (EU numbering) with Trp;

substitution of Gly at position 237 (EU numbering) with Phe;
substitution of Ser at position 267 (EU numbering) with Val;
substitution of Ser at position 267 (EU numbering) with Gln;
substitution of His at position 268 (EU numbering) with Asn;
substitution of Pro at position 271 (EU numbering) with Gly;
substitution of Lys at position 326 (EU numbering) with Leu;
substitution of Lys at position 326 (EU numbering) with Gln;
substitution of Lys at position 326 (EU numbering) with Glu;
substitution of Lys at position 326 (EU numbering) with Met;
substitution of Ser at position 239 (EU numbering) with Asp;
substitution of Ser at position 267 (EU numbering) with Ala;
substitution of Leu at position 234 (EU numbering) with Trp;
substitution of Leu at position 234 (EU numbering) with Tyr;
substitution of Gly at position 237 (EU numbering) with Ala;
substitution of Gly at position 237 (EU numbering) with Asp;
substitution of Gly at position 237 (EU numbering) with Glu;
substitution of Gly at position 237 (EU numbering) with Leu;

substitution of Gly at position 237 (EU numbering) with Met;
substitution of Gly at position 237 (EU numbering) with Tyr;
substitution of Ala at position 330 (EU numbering) with Lys;
substitution of Ala at position 330 (EU numbering) with Arg;
substitution of Glu at position 233 (EU numbering) with Asp;
substitution of His at position 268 (EU numbering) with Asp;
substitution of His at position 268 (EU numbering) with Glu;
substitution of Lys at position 326 (EU numbering) with Asp;
substitution of Lys at position 326 (EU numbering) with Ser;
substitution of Lys at position 326 (EU numbering) with Thr;
substitution of Val at position 323 (EU numbering) with Ile;
substitution of Val at position 323 (EU numbering) with Leu;
substitution of Val at position 323 (EU numbering) with Met;
substitution of Tyr at position 296 (EU numbering) with Asp;
substitution of Lys at position 326 (EU numbering) with Ala;
substitution of Lys at position 326 (EU numbering) with Asn; and
substitution of Ala at position 330 (EU numbering) with Met, in addition to substitution of Pro at position 238 (EU numbering) with Asp.

Furthermore, the present invention provides a nucleic acid encoding a polypeptide comprising an antibody Fc region with at least one amino acid alteration, which has maintained or decreased FcγRIIa-binding activity, and enhanced FcγRIIb-binding activity in comparison with a parent polypeptide. The nucleic acid of the present invention may be in any form such as DNA or RNA.

The present invention also provides vectors carrying the above-described nucleic acids of the present invention. The type of vector can be appropriately selected by those skilled in the art depending on the host cells to be introduced with the vector. The vectors include, for example, those described above.

Furthermore, the present invention relates to host cells transformed with the above-described vectors of the present invention. Appropriate host cells can be selected by those skilled in the art. The host cells include, for example, those described above.

Furthermore, the present invention provides methods for maintaining or decreasing FcγRIIa-binding activity and enhancing FcγRIIb-binding activity of a polypeptide comprising an antibody Fc region in comparison with a parent polypeptide, wherein the method comprises adding at least one amino acid alteration to the Fc region.

The present invention also provides methods for suppressing production of antibodies against a polypeptide compared with a parent polypeptide when the polypeptide is administered in vivo, wherein the method comprises adding at least one amino acid alteration in the Fc region of the polypeptide comprising an antibody Fc region.

In a preferred embodiment, for example, a polypeptide comprising a human IgG Fc region is altered so that Pro at position 238 (EU numbering) is substituted with Asp or Leu at position 328 (EU numbering) is substituted with Glu. Other preferred embodiments include altering the polypeptide so that at least one substitution selected from the group consisting of: substitution of Gly at position 237 (EU numbering) with Trp;

substitution of Gly at position 237 (EU numbering) with Phe;
substitution of Ser at position 267 (EU numbering) with Val;
substitution of Ser at position 267 (EU numbering) with Gln;
substitution of His at position 268 (EU numbering) with Asn;
substitution of Pro at position 271 (EU numbering) with Gly;
substitution of Lys at position 326 (EU numbering) with Leu;
substitution of Lys at position 326 (EU numbering) with Gln;
substitution of Lys at position 326 (EU numbering) with Glu;
substitution of Lys at position 326 (EU numbering) with Met;
substitution of Ser at position 239 (EU numbering) with Asp;
substitution of Ser at position 267 (EU numbering) with Ala;
substitution of Leu at position 234 (EU numbering) with Trp;
substitution of Leu at position 234 (EU numbering) with Tyr;
substitution of Gly at position 237 (EU numbering) with Ala;
substitution of Gly at position 237 (EU numbering) with Asp;
substitution of Gly at position 237 (EU numbering) with Glu;
substitution of Gly at position 237 (EU numbering) with Leu;
substitution of Gly at position 237 (EU numbering) with Met;
substitution of Gly at position 237 (EU numbering) with Tyr;
substitution of Ala at position 330 (EU numbering) with Lys;
substitution of Ala at position 330 (EU numbering) with Arg;
substitution of Glu at position 233 (EU numbering) with Asp;
substitution of His at position 268 (EU numbering) with Asp;
substitution of His at position 268 (EU numbering) with Glu;
substitution of Lys at position 326 (EU numbering) with Asp;
substitution of Lys at position 326 (EU numbering) with Ser;
substitution of Lys at position 326 (EU numbering) with Thr;
substitution of Val at position 323 (EU numbering) with Ile;
substitution of Val at position 323 (EU numbering) with Leu;
substitution of Val at position 323 (EU numbering) with Met;

substitution of Tyr at position 296 (EU numbering) with Asp;
substitution of Lys at position 326 (EU numbering) with Ala;
substitution of Lys at position 326 (EU numbering) with Asn; and
substitution of Ala at position 330 (EU numbering) with Met, in addition to substitution of Pro at position 238 (EU numbering) with Asp.

In the above-mentioned method, it is preferable to enhance the FcγRIIb-binding activity, and maintain or decrease binding activities towards FcγRIIa (type R) and FcγRIIa (type H); and it is preferable to additionally maintain or decrease binding activities towards FcγRIa and/or FcγRIIIa.

Polypeptides produced by any of the above-mentioned methods are also included in the present invention.

<Pharmaceutical Compositions>

The present invention provides pharmaceutical compositions comprising the polypeptide of the present invention.

The pharmaceutical compositions of the present invention can be formulated, in addition to the antibody or Fc-fusion protein molecules of the present invention described above, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies or Fc-fusion protein molecules with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ non-ionic surfactant and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dosage of the pharmaceutical composition containing an antibody or a polynucleotide encoding an antibody can be selected, for example, from the range of 0.0001 to 1,000 mg per kg of body weight. Alternatively, the dosage may be, for example, in the range of 0.001 to 100,000 mg/patient. However, the dosage is not limited to these values. The dosage and method of administration vary depending on the patient's body weight, age, and symptoms, and can be appropriately selected by those skilled in the art.

The above-mentioned polypeptides of the present invention are useful as active ingredients of pharmaceutical agents that suppress the activation of B cells, mast cells, dendritic cells, and/or basophils. Polypeptides of the present invention can suppress the activation of B cells, mast cells, dendritic cells, and/or basophils, by selectively working on FcγRIIb without activating activating FcγR. B cell activation includes proliferation, IgE production, IgM production, and IgA production. The above-mentioned polypeptides of the present invention cross-link FcγRIIb with IgE to suppress IgE production of B cells, with IgM to suppress IgM production of B cells, and with IgA to suppress IgA production. Other than the above, suppressive effects similar to those mentioned above are exhibited by directly or indirectly cross-linking FcγRIIb with molecules that are expressed on B cells and comprise the ITAM domain inside the cell or interact with the ITAM domain such as BCR, CD19, and CD79b. Furthermore, activation of mast cells includes proliferation, activation by IgE and such, and degranulation. In mast cells, the above-mentioned polypeptides of the present invention can suppress proliferation, activation by IgE and such, and degranulation by directly or indirectly cross-linking FcγRIIb with IgE receptor molecules that are expressed on mast cells and comprise the ITAM domain or interact with the ITAM domain such as FcεRI, DAP12, and CD200R3. Activation of basophils includes proliferation and degranulation of basophils. Also in basophils, the above-mentioned polypeptides of the present invention can suppress proliferation, activation, and degranulation by directly or indirectly cross-linking FcγRIIb with molecules on the cell membrane, which comprise the ITAM domain inside the cell or interact with the ITAM domain. Activation of dendritic cells includes proliferation and degranulation of dendritic cells. Also in dendritic cells, the above-mentioned polypeptides of the present invention can suppress activation, degranulation, and proliferation by directly or indirectly cross-linking FcγRIIb with molecules on the cell membrane, which comprise the ITAM domain inside the cell or interact with the ITAM domain.

In the present invention, the polypeptides of the present invention mentioned above are useful as an active ingredient of therapeutic agents or preventive agents for immunological inflammatory diseases. As described above, since polypeptides of the present invention can suppress activation of B cells, mast cells, dendritic cells and/or basophils, administration of the polypeptides of the present invention as a result can treat or prevent immunological inflammatory diseases. Without being limited thereto, the term "immunological inflammatory diseases" comprises, rheumatoid arthritis, autoimmune hepatitis, autoimmune thyroiditis, autoimmune blistering diseases, autoimmune adrenocortical disease, autoimmune hemolytic anemia, autoimmune thrombocytopenia purpura, megalocytic anemia, autoimmune atrophic gastritis, autoimmune neutropenia, autoimmune orchitis, autoimmune encephalomyelitis, autoimmune receptor disease, autoimmune infertility, chronic active hepatitis, glomerulonephritis, interstitial pulmonary fibrosis, multiple sclerosis, Paget's disease, osteoporosis, multiple myeloma, uveitis, acute and chronic spondylitis, gouty arthritis, inflammatory bowel disease, adult respiratory distress syndrome (ARDS), psoriasis, Crohn's disease, Basedow's disease, juvenile diabetes, Addison's disease, myasthenia gravis, lens-induced uveitis, systemic lupus erythematosus, allergic rhinitis, allergic dermatitis, ulcerative colitis, hypersensitivity, muscle degeneration, cachexia, systemic scleroderma, localized scleroderma, Sjogren's syndrome, Behchet's disease, Reiter's syndrome, type I and type II diabetes, bone resorption disorder, graft-versus-host reaction, ischemia-reperfusion injury, atherosclerosis, brain trauma, cerebral malaria, sepsis, septic shock, toxic shock syndrome, fever, malgias due to staining, aplastic anemia, hemolytic anemia, idiopathic thrombocytopenia, Goodpasture's syndrome, Guillain-Barre syndrome, Hashimoto's thyroiditis, pemphigus, IgA nephropathy, pollinosis, antiphospholipid antibody syndrome, polymyositis, Wegener's granulomatosis, arteritis nodosa, mixed connective tissue disease, fibromyalgia, asthma, atopic dermatitis, chronic atrophic gastritis, primary biliary cirrhosis, primary sclerosing cholangitis, autoimmune pancreatitis, aortitis syndrome, rapidly progressive glomerulonephritis, megaloblastic anemia, idiopathic thrombocytopenia purpura, primary hypothyroidism, idiopathic Addison's disease, insulin-dependent diabetes mellitus, chronic discoid lupus erythematosus, pemphigoid, herpes gestationis, linear IgA bullous dermatosis, epidermolysis bullosa acquisita, alopecia areata, vitiligo vulgaris, leukoderma acquisitum *centrifugum* of Sutton, Harada's disease, autoimmune optic neuropathy, idiopathic azoospermia, habitual abortion, hypoglycemia, chronic urticaria, ankylosing spondylitis, psoriatic arthritis, enteropathic arthritis, reactive arthritis, spondyloarthropathy, enthesopathy, irritable bowel syndrome, chronic fatigue syndrome, dermatomyositis, inclusion body myositis, Schmidt's syndrome, Graves' disease, pernicious anemia, lupoid hepatitis, presenile dementia, Alzheimer's disease, demyelinating disorder, amyotrophic lateral sclerosis, hypoparathyroidism, Dressler's syndrome, Eaton-Lambert syndrome, dermatitis herpetiformis, alopecia, progressive systemic sclerosis, CREST syndrome (calcinosis, Raynaud's phenomenon, esophageal dysmotility, sclerodactyly, and telangiectasia), sarcoidosis, rheumatic fever, erythema multiforme, Cushing's syndrome, transfusion reaction, Hansen's disease, Takayasu arteritis, polymyalgia rheumatica, temporal arteritis, giant cell arthritis, eczema, lymphomatoid granulomatosis, Kawasaki disease, endocarditis, endomyocardial fibrosis, endophthalmitis, fetal erythroblastosis, eosinophilic fasciitis, Felty syndrome, Henoch-Schonlein purpura, transplant rejection, mumps, cardiomyopathy, purulent arthritis, familial Mediterranean fever, Muckle-Wells syndrome, and hyper-IgD syndrome.

Furthermore, in autoimmune diseases which may be caused by production of antibodies against autoantigens (autoantibodies), the polypeptides of the present invention mentioned above are useful as an active ingredient of pharmaceutical agents for treating or preventing the autoimmune diseases by suppressing production of those autoantibodies. Use of a molecule produced by fusing an antibody Fc portion with AchR (an autoantigen of myasthenia gravis) has been reported to suppress proliferation of B cells which express AchR-recognizing BCR, and induce apoptosis (J. Neuroimmunol, 227:35-43, 2010). Use of a fusion protein formed between an antigen recognized by an autoantibody and an antibody Fc region of the present invention enables crosslinking of FcγRIIb with BCR of a B cell expressing BCR for that autoantigen, suppression of proliferation of B cells expressing BCR for the autoantigen, and induction of apoptosis. Such autoimmune diseases include Guillain-Barre syndrome, myasthenia gravis, chronic atrophic gastritis, autoimmune hepatitis, primary biliary cirrhosis, primary sclerosing cholangitis, autoimmune pancreatitis, aortitis syndrome, Goodpasture's syndrome, rapidly progressive glomerulonephritis, megaloblastic anemia, autoimmune hemolytic anemia, autoimmune neutropenia, idiopathic thrombocytopeniarpura, Basedow's disease, Hashimoto's thyroiditis, primary hypothyroidism, idiopathic Addison's disease, insulin-dependent diabetes mellitus, chronic discoid lupus erythematosus, localized scleroderma, pemphigus, pemphigoid, herpes gestationis, linear IgA bullous dermatosis, epidermolysis bullosa acquisita, alopecia areata, vitiligo vulgaris, leukoderma acquisitum *centrifugum* of Sutton, Harada's disease, autoimmune optic neuropathy, idiopathic azoospermia, habitual abortion, type II diabetes, hypoglycemia, and chronic urticaria; but are not limited thereto.

Furthermore, the above-mentioned polypeptides of the present invention are useful as an active ingredient in therapeutic agents for diseases with deficiency of a biologically essential protein. For diseases with deficiency of a biologically essential protein, therapeutic methods that administer and supplement the protein as a pharmaceutical agent are used. However, since the patient lacks the protein from the beginning, the externally supplemented protein is recognized as a foreign substance and antibodies against that protein are produced. As a result, the protein becomes easily removed, and the effect as a pharmaceutical is reduced. Use of a fusion protein comprising such a protein and an antibody Fc region of the present invention enables crosslinking between FcγRIIb and BCR on B cells that recognize the protein, and enables suppression of antibody production against the protein. The proteins to be supplemented include Factor VIII, Factor IX, TPO, EPO, a-iduronidase, iduronate sulfatase, A-type heparan N-sulfatase, B type a-N-acetylglucosaminidase, C type acetyl COA: α-glucosaminidase acetyltransferase, D type N-acetylglucosamine 6-sulfatase, galactose 6-sulfatase, N-acetylgalactosamine 4-sulfatase, β-glucuronidase, α-galactosidase, acidic α-galactosidase, and glucocerebrosidase. These proteins may be supplemented for diseases such as hemophilia, idiopathic thrombocytopenia purpura, renal anemia, and lysosomal disease (mucopolysaccharidosis, Fabry's disease, Pompe disease, and Gaucher's disease), without being limited thereto.

Furthermore, the above-mentioned polypeptides of the present invention are useful as an active ingredient for antiviral agents. Antibodies that comprise an Fc region of the present invention and are anti-virus antibodies can suppress antibody-dependent enhancement observed with anti-virus antibodies. Antibody-dependent enhancement is a phenomenon where a virus uses neutralizing antibodies against the virus to become phagocytosed via activating FcγRs, and infects FcγR-expressing cells so that the infection spreads. Binding of anti-dengue-virus neutralizing antibodies to FcγRIIb has been reported to play an important role in suppressing antibody-dependent enhancement (Proc. Natl. Acad. Sci. USA, 108:12479-12484, 2011). Crosslinking FcγRIIb with an immunocomplex with dengue virus, which is formed by the anti-dengue-virus neutralizing antibodies, inhibits FcγR-mediated phagocytosis, resulting in the suppression of antibody-dependent enhancement. Examples of such viruses include dengue virus (DENV1, DENV2, and DENV4) and HIV, but are not limited thereto.

Furthermore, polypeptides of the present invention described above are useful as an active ingredient in preventive agents or therapeutic agents for arteriosclerosis. Antibodies against oxidized LDL, i.e., a cause for arteriosclerosis, which are antibodies comprising an Fc region of the present invention, can prevent FcγRIIa-dependent adhesion of inflammatory cells. It has been reported that while anti-oxidized LDL antibodies inhibit the interaction between oxidized LDL and CD36, anti-oxidized LDL antibodies bind to endothelial cells, and monocytes recognize their Fc portion in an FcγRIIa-dependent or FcγRI-dependent manner; and this leads to adhesion (Immunol. Lett., 108:52-61, 2007). Using antibodies comprising an Fc region of the present invention for such antibodies may inhibit FcγRIIa-dependent binding and suppress monocyte adhesion by FcγRIIb-mediated inhibitory signals.

Herein, polypeptides of the present invention described above are useful as an active ingredient in therapeutic agents or preventive agents for cancer. As described above, it is known that enhancing the FcγRIIb binding enhances the agonistic activity of an agonist antibody, and enhances the antitumor effect of the antibody. Therefore, agonist antibodies using the Fc region of the present invention are useful for treatment or prevention of cancer. The Fc region of the present invention enhances the agonistic activity of agonist antibodies against receptors of the TNF receptor family such as Aliases, CD120a, CD120b, Lymphotoxin β receptor, CD134, CD40, FAS, TNFRSF6B, CD27, CD30, CD137, TNFRSF10A, TNFRSF10B, TNFRSF10C, TNFRSF10D, RANK, Osteoprotegerin, TNFRSF12A, TNFRSF13B, TNFRSF13C, TNFRSF14, Nerve growth factor receptor, TNFRSF17, TNFRSF18, TNFRSF19, TNFRSF21, TNFRSF25, and Ectodysplasin A2 receptor. Furthermore, the agonistic activity of agonist antibodies other than those described above is also enhanced. Without being limited thereto, cancer includes lung cancer (including small cell lung cancer, non-small cell lung cancer, pulmonary adenocarcinoma, and squamous cell carcinoma of the lung), large intestine cancer, rectal cancer, colon cancer, breast cancer, liver cancer, gastric cancer, pancreatic cancer, renal cancer, prostate cancer, ovarian cancer, thyroid cancer, cholangiocarcinoma, peritoneal cancer, mesothelioma, squamous cell carcinoma, cervical cancer, endometrial cancer, bladder cancer, esophageal cancer, head and neck cancer, nasopharyngeal cancer, salivary gland tumor, thymoma, skin cancer, basal cell tumor, malignant melanoma, anal cancer, penile cancer, testicular cancer, Wilms' tumor, acute myeloid leukemia (including acute myeloleukemia, acute myeloblastic leukemia, acute promyelocytic leukemia, acute myelomonocytic leukemia, and acute monocytic leukemia), chronic myelogenous leukemia, acute lymphoblastic leukemia, chronic lymphatic leukemia, Hodgkin's lymphoma, non-Hodgkin's lymphoma (Burkitt's lymphoma, chronic lymphocytic leukemia, mycosis fungoides, mantle cell lymphoma, follicular lymphoma, diffuse large-cell lymphoma, marginal zone lymphoma, pilocytic leukemia plasmacytoma, peripheral T-cell lymphoma, and adult T cell leukemia/lymphoma), Langerhans cell histiocytosis, multiple myeloma, myelodysplastic syndrome, brain tumor (including glioma, astroglioma, glioblastoma, meningioma, and ependymoma), neuroblastoma, retinoblastoma, osteosarcoma, Kaposi's sarcoma, Ewing's sarcoma, angiosarcoma, and hemangiopericytoma.

Furthermore, the present invention relates to methods for treating or preventing immunological inflammatory diseases, which comprise the step of administering to a subject (patient) a polypeptide of the present invention or a polypeptide produced by production methods of the present invention.

The present invention also provides kits for use in the therapeutic methods or preventive methods of the present invention, which comprises at least a polypeptide of the present invention or a polypeptide produced by production methods of the present invention, or a pharmaceutical composition of the present invention. In addition, pharmaceutically acceptable carriers, media, instructions on the method of use, and such may be included in the kit. Furthermore, the present invention relates to use of a polypeptide of the present invention or a polypeptide produced by production methods of the present invention in the production of agents for treating or preventing immunological inflammatory diseases. The present invention also relates to polypeptides of the present invention or polypeptides produced by production methods of the present invention for use in the therapeutic methods or preventive methods of the present invention.

As used herein, the three-letter and single-letter codes for respective amino acids are as follows:

Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser(S)
Threonine: Thr (T)
Tryptophan: Trp (W)
Tyrosine: Tyr (Y)
Valine: Val (V) All prior art documents cited herein are incorporated by reference in their entirety.

EXAMPLES

Herein below, the present invention will be specifically described further with reference to the Examples, but it is not to be construed as being limited thereto.

[Example 1] Comprehensive Analysis of the Binding of Fc Variants to FcγR

Mutations were introduced into IgG1 antibodies to generate antibodies that have decreased Fc-mediated binding towards activating FcγR, specifically both allotypes of FcγRIIa, types H and R, as well as enhanced FcγRIIb binding relative to IgG1; and binding to each FcγR was analyzed comprehensively.

The variable region (SEQ ID NO: 15) of a glypican 3 antibody comprising the CDR of GpH7 which is an anti-glypican 3 antibody with improved plasma kinetics disclosed in WO 2009/041062 was used as the common antibody H chain. Similarly, for the common antibody L chain, GpL16-k0 (SEQ ID NO: 16) of the glypican 3 antibody with improved plasma kinetics disclosed in WO 2009/041062 was used. Furthermore, B3 (SEQ ID NO: 17) in which a K439E mutation has been introduced into G1d produced by removing the C terminal Gly and Lys of IgG1 was used as the antibody H chain constant region. This H chain is referred to as GpH7-B3 (SEQ ID NO: 18), and the L chain is referred to as GpL16-k0 (SEQ ID NO: 16).

With respect to GpH7-B3, the amino acids that are considered to be involved in FcγR binding and the surrounding amino acids (positions 234 to 239, 265 to 271, 295, 296, 298, 300, and 324 to 337, according to EU numbering) were substituted respectively with 18 types of amino acids excluding the original amino acids and Cys. These Fc variants are referred to as B3 variants. B3 variants were expressed and purified using the method of Reference Example 1, and the binding to each FcγR (FcγRIa, FcγRIIa type H, FcγRIIa type R, FcγRIIb, and FcγRIIIa) was comprehensively evaluated using the method of Reference Example 2.

Figures were produced based on the results of interaction analysis with each FcγR by the method below. The value of the amount of FcγR binding of each B3 variant-derived antibody was divided by the value of the amount of FcγR binding of the antibody used for comparison which does not have mutations introduced into B3 (an antibody having the sequence of a naturally-occurring human IgG1 at positions 234 to 239, 265 to 271, 295, 296, 298, 300, and 324 to 337, according to EU numbering). The value obtained by multiplying this value by 100 was used as an indicator of the relative FcγR-binding activity of each variant. The horizontal axis shows the value of the relative FcγRIIb-binding activity of each variant, and the vertical axis shows the value of the respective relative binding activity of each variant towards activating FcγRs: FcγRIa, FcγRIIa type H, FcγRIIa type R, and FcγRIIIa (FIGS. 1, 2, 3, and 4).

As shown by labels in FIGS. 1-4, the results show that of all alterations, when only mutations called mutation A (alteration produced by substituting Pro at position 238 (EU numbering) with Asp) and mutation B (alteration produced by substituting Leu at position 328 (EU numbering) with Glu) were introduced, there were remarkable enhancement of binding to FcγRIIb and remarkable suppression of binding to both types of FcγRIIa compared with before the introduction.

[Example 2] SPR Analysis of Variants that Selectively Bind to FcγRIIb

With regard to the alteration identified in Example 1 where Pro at position 238 (EU numbering) is substituted with Asp, the binding to each FcγR was analyzed in detail.

The variable region of IL6R-H (SEQ ID NO: 19), which is the variable region of the antibody against the human interleukin 6 receptor disclosed in WO 2009/125825, was used as the antibody H chain variable region, and IL6R-G1d (SEQ ID NO: 20) which comprises G1d with deletion of C-terminal Gly and Lys of human IgG1 was used as the antibody H chain constant region in the IgG1 H chain. Pro at position 238 (EU numbering) in IL6R-Gld was substituted with Asp to produce IL6R-G1d-v1 (SEQ ID NO: 21). Next, Leu at position 328 (EU numbering) in IL6R-Gld was substituted with Glu to produce IL6R-G1d-v2 (SEQ ID NO: 23). Furthermore, for comparison, Ser at position 267 (EU numbering) was substituted with Glu, and Leu at position 328 (EU numbering) was substituted with Phe in IL6R-Gld to produce IL6R-G1d-v3 (SEQ ID NO: 24) as described in Non-patent Document 27. IL6R-L (SEQ ID NO: 22), which is the L chain of tocilizumab, was utilized as a mutual antibody L chain; and together with each H chain, the antibodies were expressed and purified according to the method of Reference Example 1. The obtained antibodies which comprise an amino acid sequence derived from IL6R-G1d, IL6R-G1d-v1, IL6R-G1d-v2, or IL6R-G1d-v3 as the antibody H chain are referred to as IgG1, IgG1-v1, IgG1-v2, and IgG1-v3, respectively.

Next, kinetic analysis of interactions between these antibodies and FcγR was carried out using Biacore™ T100 surface plasmon resonance system (GE Healthcare). HBS-EP+ (0.01 M HEPES pH 7.4, 0.15 M NaCl, 3 mM ethylene diamine tetraacetic acid (EDTA), 0.05% polysorbate 20) (GE Healthcare) was used as the running buffer, and the measurement temperature was set to 25° C. A chip produced by immobilizing Protein A onto a Series S Sensor Chip CM5 (GE Healthcare) by the amine-coupling method was used. An antibody of interest was captured onto this chip to interact with each FcγR that had been diluted with the running buffer, and binding to the antibody was measured. After the measurement, the antibody captured on the chip was washed off by allowing reaction with 10 mM glycine-HCl, pH 1.5, and the chip was regenerated and used repeatedly. The sensorgrams obtained as measurement results were analyzed by the 1:1 Langmuir binding model using the Biacore™ Evaluation Software to calculate the binding rate constant ka (L/mol/s) and dissociation rate constant kd (1/s), and the dissociation constant KD (mol/L) was calculated from these values.

This time, since the binding of IgG1-v1 and IgG1-v2 to FcγRIIa type H and to FcγRIIIa was weak, kinetic parameters such as KD could not be calculated from the above-mentioned analytical method. Regarding such interactions, KD values were calculated using the following 1:1 binding model described in Biacore™ T100 surface plasmon resonance system Software Handbook BR1006-48 Edition AE.

The behavior of interacting molecules according to the 1:1 binding model using the Biacore™ surface plasmon resonance technique can be described by Equation 1 shown below.

$$R_{eq}=C\cdot R_{max}/(KD+C)+RI \quad \text{[Equation 1]}$$

$R_{eq}$: a plot of steady-state binding levels against analyte concentration

C: concentration

RI: bulk refractive index contribution in the sample $R_{max}$: analyte binding capacity of the surface When this equation is rearranged, KD can be expressed as Equation 2 shown below.

$$KD=C\cdot R_{max}/(R_{eq}-RI)-C \quad \text{[Equation 2]}$$

KD can be calculated by substituting the values of $R_{max}$, RI, and C into this equation. From the current measurement conditions, RI=0, C=2 μmol/L can be used. Furthermore, the $R_{max}$ value obtained when globally fitting the sensorgram obtained as a result of analyzing the interaction of each FcγR with IgG1 using the 1:1 Langmuir binding model was divided by the amount of IgG1 captured, this was multiplied by the amount of IgG1-v1 and IgG1-v2 captured, and the resulting value was used as $R_{max}$. This calculation is based on the hypothesis that the limit quantity of each FcγR that can be bound by IgG1 remains unchanged for all variants produced by introducing mutations into IgG1, and the $R_{max}$ at the time of measurement is proportional to the amount of antibody bound on the chip at the time of measurement. $R_{eq}$ Was defined as the amount of binding of each FcγR to each variant on the sensor chip observed at the time of measurement.

Under these measurement conditions, the amount of binding ($R_{eq}$) of IgG1-v1 and IgG1-v2 to FcγRIIa type H was approximately 2.5 RU and 10 RU, respectively, and the amount of binding ($R_{eq}$) of IgG1-v1 and IgG1-v2 to FcγRIIIa was approximately 2.5 RU and 5 RU, respectively. The amount of IgG1, IgG1-v1, and IgG1-v2 captured in the analysis of interactions with H-type FcγRIIa was 452 RU, 469.2 RU, and 444.2 RU, respectively, and the amount of IgG1, IgG1-v1, and IgG1-v2 captured in the analysis of interactions with FcγRIIIa was 454.5 RU, 470.8 RU, and 447.1 RU, respectively. The $R_{max}$ values obtained from global fitting of sensorgrams obtained as a result of analyzing the interaction of IgG1 with H-type FcγRIIa and FcγRIIIa using the 1:1 Langmuir binding model were 69.8 RU and 63.8 RU, respectively. When these values were used, the calculated $R_{max}$ values of IgG1-v1 and IgG1-v2 to FcγRIIa type H were 72.5 RU and 68.6 RU, respectively, and the calculated $R_{max}$ values of IgG1-v1 and IgG1-v2 to FcγRIIIa were 66.0 RU and 62.7 RU, respectively. These values were substituted into Equation 2 to calculate the KD of IgG1-v1 and IgG1-v2 for FcγRIIa type H and FcγRIIIa.

$$KD = C \bullet R_{max}/(R_{eq} - RI) - C \quad \text{[Equation 2]}$$

The KD values of IgG1, IgG1-v1, IgG1-v2, and IgG1-v3 for each FcγR (the KD values of each antibody for each FcγR) are shown in Table 1, and the relative KD values of IgG1-v1, IgG1-v2, and IgG1-v3 obtained by taking the KD values of IgG1 for each FcγR and dividing them by the KD values of IgG1-v1, IgG1-v2, and IgG1-v3 for each FcγR (the relative KD values of each antibody for each FcγR) are shown in Table 2.

TABLE 1

| | IgG1 | IgG1-v1 | IgG1-v2 | IgG1-v3 |
|---|---|---|---|---|
| FcγRIa | 3.4E−10 | 7.3E−09 | 4.6E−10 | 1.9E−10 |
| FcγRIIa R | 1.2E−06 | 1.2E−05 | 2.9E−06 | 2.3E−09 |
| FcγRIIa H | 7.7E−07 | 5.6E−05* | 1.2E−05* | 1.5E−06 |
| FcγRIIb | 5.3E−06 | 1.1E−06 | 2.3E−06 | 1.3E−08 |
| FcγRIIIa | 3.1E−06 | 5.1E−05* | 2.3E−05* | 8.8E−06 |

(mol/L)

In Table 1 shown above, "*" means that the KD value was calculated using Equation 2 because binding of FcγR to IgG was not sufficiently observed.

$$KD = C \bullet R_{max}/(R_{eq} - RI) - C \quad \text{[Equation 2]}$$

TABLE 2

| | IgG1-v1 | IgG1-v2 | IgG1-v3 |
|---|---|---|---|
| FcγRIa | 0.047 | 0.74 | 1.8 |
| FcγRIIa R | 0.10 | 0.41 | 522 |
| FcγRIIa H | 0.014 | 0.064 | 0.51 |
| FcγRIIb | 4.8 | 2.3 | 408 |
| FcγRIIIa | 0.061 | 0.14 | 0.35 |

(THE VALUE OBTAINED BY DIVIDING THE KD VALUE OF IgG1 FOR EACH FcγR BY THE KD VALUE OF EACH ANTIBODY IgG1 FOR EACH FcγR)

According to Table 2, when compared with that of IgG1, the binding activity of IgG1-v1 was decreased to 0.047-fold for FcγRIa, decreased to 0.10-fold for FcγRIIa type R, decreased to 0.014-fold for FcγRIIa type H, decreased to 0.061-fold for FcγRIIIa, and increased to 4.8-fold for FcγRIIb.

Furthermore, according to Table 2, when compared with that of IgG1, the binding activity of IgG1-v2 was decreased to 0.74-fold for FcγRIa, decreased to 0.41-fold for FcγRIIa type R, decreased to 0.064-fold for FcγRIIa type H, decreased to 0.14-fold for FcγRIIIa, and increased to 2.3-fold for FcγRIIb.

More specifically, these results demonstrated that IgG1-v1 having an alteration of substituting Pro at position 238 (EU numbering) with Asp and IgG1-v2 having an alteration of substituting Leu at position 328 (EU numbering) with Glu have the properties of weakening the binding to all activating FcγRs including both allotypes of FcγRIIa, while enhancing the binding to FcγRIIb which is an inhibitory FcγR.

Next, selectivity of the obtained variant to FcγRIIb was evaluated by using the ratio of FcγRIIb-binding activity to the binding activity towards type R or type H of FcγRIIa as the indicator. Specifically, I/A(R) or I/A(H), which is a value obtained by dividing the KD value for FcγRIIa type R or type H by the KD value for FcγRIIb, was used as an indicator for the selectivity of FcγRIIb with respect to each FcγRIIa. This indicator has a greater value when the KD value for FcγRIIb becomes smaller or when the KD value for FcγRIIa becomes larger. That is, a variant that shows a larger value shows an increased binding activity for FcγRIIb relative to FcγRIIa. These indicators are summarized in Table 3 for each variant.

TABLE 3

| | IgG1 | IgG1-v1 | IgG1-v2 | IgG1-v3 |
|---|---|---|---|---|
| I/A (R) | 0.23 | 11 | 1.3 | 0.18 |
| I/A (H) | 0.15 | 51 | 5.2 | 115 |

According to the results of Table 3, in comparison with IgG1, IgG1-v3 which was produced by applying the existing technology showed a greater 1/A(H) value than that of IgG1 and a greater selectivity for FcγRIIb, but a smaller 1/A(R) value than that of IgG1 and an improved selectivity for FcγRIIb. On the other hand, IgG1-v1 and IgG1-v2 found in the Examples have larger I/A(R) and I/A(H) values than those of IgG1, and improved selectivity for FcγRIIb over both allotypes of FcγRIIa.

So far, alterations having such properties have not been reported, and they are in fact very rare as shown in FIGS. 1, 2, 3, and 4. Alterations produced by substituting Pro at position 238 (EU numbering) with Asp or substituting Leu at position 328 (EU numbering) with Glu are very useful for the development of therapeutic agents for immunological inflammatory diseases and such.

Furthermore, Table 2 shows that IgG1-v3 described in Non-Patent Document 27 certainly shows a 408-fold enhanced binding to FcγRIIb, while the binding to FcγRIIa type H is decreased to 0.51 fold, and the binding to FcγRIIa type R is enhanced to 522 fold. According to these results, since IgG1-v1 and IgG1-v2 suppress their binding to both FcγRIIa types R and H, and enhance their binding to FcγRIIb, they are considered to be variants that bind with a greater FcγRIIb selectivity compared with IgG1-v3. Specifically, alterations produced by substituting Pro at position 238 (EU numbering) with Asp or substituting Leu at position 328 (EU numbering) with Glu are very useful for the development of therapeutic agents for immunological inflammatory diseases and such.

[Example 3] Effects of Combining FcγRIIb-Selective Binding Alterations with Other Fc Region Amino Acid Substitutions Further enhancement of the selectivity for FcγRIIb was attempted based on the variant which has improved selectivity for FcγRIIb and has a substitution of Pro at position 238 (EU numbering) with Asp found in Examples 1 and 2.

First, into IL6R-G1d_v1 (SEQ ID NO: 21) produced by introducing into IL6R-G1d the alteration produced by substituting Pro at position 238 (EU numbering) with Asp, the substitution of Leu at position 328 (EU numbering) with Glu as described in Example 2 which enhances selectivity for FcγRIIb was introduced to produce the IL6R-G1d-v4 variant (SEQ ID NO: 25). This was combined with IL6R-L (SEQ ID NO: 22) and prepared according to the method of Reference Example 1. The obtained antibody having the amino acid sequence derived from IL6R-G1d-v4 as the antibody H chain has been named IgG1-v4. The binding activities of IgG1, IgG1-v1, IgG1-v2, and IgG1-v4 to FcγRIIb were evaluated according to the method of Reference Example 2, and those results are shown in Table 4.

TABLE 4

| Variant | Alteration | KD for FcγRIIb (mol/L) | Relative KD for FcγRIIb (KD of IgG1/KD of each variant) |
|---|---|---|---|
| IgG1 | — | 5.30E−06 | 1 |
| IgG1-v1 | Substitution of Pro at position 238 (EU numbering) with Asp | 1.10E−06 | 4.8 |
| IgG1-v2 | Substitution of Leu at position 328 (EU numbering) with Glu | 2.30E−06 | 2.3 |
| IgG1-v4 | Substitution of Pro at position 238 (EU numbering) with Asp and substitution of Leu at position 328 (EU numbering) with Glu | 1.10E−05 | 0.47 |

From the results of Table 4, since L328E improves the FcγRIIb-binding activity by 2.3 fold compared with IgG1, combining it with P238D which similarly improves the FcγRIIb-binding activity by 4.8 fold compared with IgG1 was anticipated to further increase the degree of improvement of FcγRIIb-binding activity; however, in reality, the FcγRIIb-binding activity of the variant containing a combination of these alterations was decreased to 0.47 fold compared with that of IgG1. This result is an effect that could not have been predicted from the respective alterations.

Similarly, into IL6R-G1d-v1 (SEQ ID NO: 21) produced by introducing into IL6R-Gld the alteration produced by substituting Pro at position 238 (EU numbering) with Asp, the substitutions of Ser at position 267 (EU numbering) with Glu and of Leu at position 328 (EU numbering) with Phe as described in Example 2 which improve FcγRIIb-binding activity were introduced, and the IL6R-Gld-v5 variant (SEQ ID NO: 26) was prepared according to the method of Reference Example 1. The obtained antibody having the amino acid sequence derived from IL6R-Gld-v5 as the antibody H chain has been named IgG1-v5. The FcγRIIb-binding activities of IgG1, IgG1-v1, IgG1-v3, and IgG1-v5 were evaluated according to the method of Reference Example 2, and those results are shown in Table 5.

S267E/L328F which had an enhancing effect on FcγRIIb in Example 2 was introduced into the P238D variant, and its FcγRIIb-binding activities before and after introducing this alteration were evaluated. The results are shown in Table 5.

TABLE 5

| Variant | Alteration | KD for FcγRIIb (mol/L) | Relative KD for FcγRIIb (KD of IgG1/KD of each variant) |
|---|---|---|---|
| IgG1 | — | 5.30E−06 | 1 |
| IgG1-v1 | Substitution of Pro at position 238 (EU numbering) with Asp | 1.10E−06 | 4.8 |
| IgG1-v3 | Substitution of Ser at position 267 (EU numbering) with Glu and substitution of Leu at position 328 (EU numbering) with Phe | 1.30E−08 | 408 |
| IgG1-v5 | Substitution of Pro at position 238 (EU numbering) with Asp, substitution of Ser at position 267 (EU numbering) with Glu, and substitution of Leu at position 328 (EU numbering) with Phe | 4.50E−07 | 12 |

From the results of Table 5, since S267E/L328F improves the FcγRIIb-binding activity by 408 fold compared with IgG1, combining it with P238D which similarly improves the FcγRIIb-binding activity by 4.8 fold as compared with IgG1 was anticipated to further increase the degree of improvement of FcγRIIb-binding activity; however, in reality, in a similar manner to the former example, the FcγRIIb-binding activity of the variant containing a combination of these alterations was improved only 12 fold or so as compared with that of IgG1. This result is also an effect that could not have been predicted from the effects of the respective alterations.

These results showed that while the substitution of Pro at position 238 (EU numbering) with Asp alone improves FcγRIIb-binding activity, the effect is not exhibited when it is combined with other alterations that improve the FcγRIIb-binding activity. A reason for this may be that the structure at the interacting interface between Fc and FcγR is changed by introducing the substitution of Pro at position 238 (EU numbering) with Asp and the effects of alterations observed in the naturally-occurring antibody are no longer reflected in the results. Accordingly, it was considered to be extremely difficult to create an Fc with excellent selectivity for FcγRIIb using an Fc comprising substitution of Pro at position 238 (EU numbering) with Asp as a template, since the information on effects of alterations obtained with naturally-occurring antibodies could not be applied.

[Example 4] Comprehensive Analysis of FcγRIIb Binding of Variants Introduced with an Alteration at the Hinge Portion in Addition to the P238D Alteration As shown in Example 3, in an Fc produced by substituting Pro at position 238 (EU numbering) with Asp in a naturally-occurring human IgG1, an anticipated combinatorial effect could not be obtained even by combining it with another alteration predicted to further increase FcγRIIb binding. Therefore, based on the altered Fc produced by substituting Pro at position 238 (EU numbering) with Asp, examination was carried out by comprehensively introducing alterations into the Fc to find variants that further enhance FcγRIIb binding. For the antibody H chains, IL6R-F11 (SEQ ID NO: 27) was produced by introducing an alteration of substituting Met at position 252 (EU numbering) with Tyr and an alteration of substituting Asn at position 434 (EU numbering) with Tyr into IL6R-Gld (SEQ ID NO: 20), and IL6R-F652 (SEQ ID NO: 28) was prepared by introducing an additional alteration of substituting Pro at position 238 (EU numbering) with Asp. Expression plasmids containing an antibody H chain sequence were prepared for each of the antibody H chain sequences produced by substituting the region near the residue at position 238 (EU numbering) (positions 234 to 237, and 239 (EU numbering)) in IL6R-F652 each with 18 amino acids excluding the original amino acids and Cys. IL6R-L (SEQ ID NO: 22) was utilized as a common antibody L chain for all of the antibodies. These variants were expressed, purified, and expressed by the method of Reference Example 1. These Fc variants are called PD variants. Interactions of each PD variant with FcγRIIa type R and FcγRIIb were comprehensively evaluated by the method of Reference Example 2.

Figure 6:
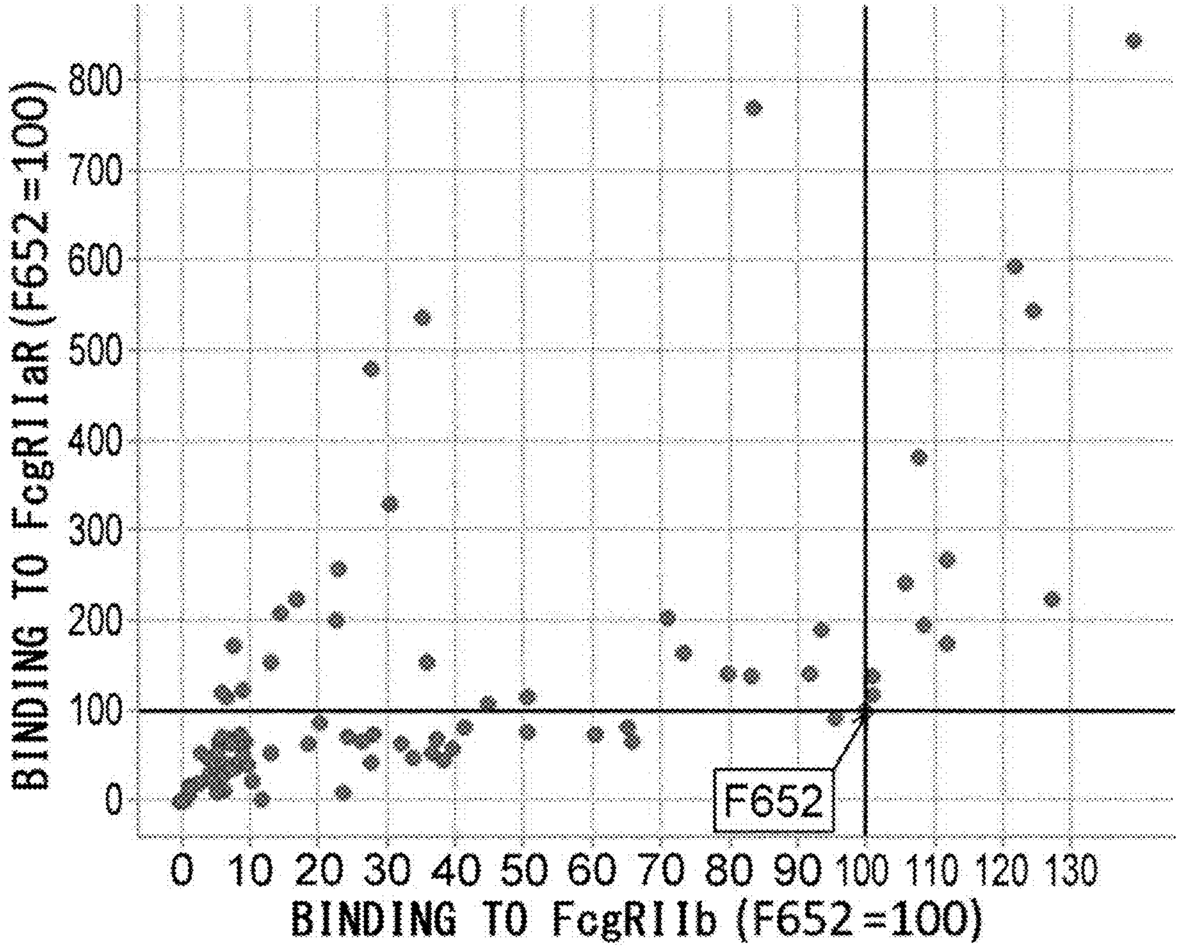
FIG. 6 shows a graph in which the horizontal axis shows the relative value of FcγRIIb-binding activity of each PD variant, and the vertical axis shows the relative value of FcγRIIa type R-binding activity of each PD variant. The value for the amount of binding of each PD variant to each FcγR was divided by the value for the amount of binding of IL6R-F652, which is a control antibody prior to introduction of the alteration (altered Fc with substitution of Pro at position 238 (EU numbering) with Asp), to each FcγR; and then the obtained value was multiplied by 100, and used as the relative binding activity value for each PD variant to each FcγR. The F652 plot in the figure shows the value for IL6R-F652.

With regard to the results of analyzing the interaction with the respective FcγRs, a figure was produced according to the following method. The value obtained by dividing the value for the amount of binding of each PD variant to each FcγR by the value for the amount of FcγR binding of the pre-altered antibody which is used as the control (IL6R-F652/IL6R-L, which has an alteration of substituting Pro at position 238 (EU numbering) with Asp and then multiplying the result by 100, was used as the relative binding activity value of each PD variant to each FcγR. The horizontal axis shows relative values of the FcγRIIb-binding activity of each PD variant, and the vertical axis shows relative values of the FcγRIIa type R-binding activity values of each PD variant (FIG. 6).

As a result, eleven types of alterations were found to have the effects of enhancing FcγRIIb binding and maintaining or enhancing FcγRIIa type R-binding in comparison with the antibody before introducing alterations. The activities of these eleven variants to bind FcγRIIb and FcγRIIa R are summarized in Table 6. In the table, SEQ ID NO refers to the SEQ ID NO of the H chain of the evaluated variant, and alteration refers to the alteration introduced into IL6R-F11 (SEQ ID NO: 27).

TABLE 6

| SEQ ID NO | VARIANT NAME | ALTERATION | RELATIVE FcγRIIb-BINDING ACTIVITY | RELATIVE FcγRIIaR-BINDING ACTIVITY |
|---|---|---|---|---|
| 28 | IL6R-F652/IL6R-L | P238D | 100 | 100 |
| 29 | IL6R-PD042/IL6R-L | P238D/L234W | 106 | 240 |
| 30 | IL6R-PD043/IL6R-L | P238D/L234Y | 112 | 175 |
| 31 | IL6R-PD079/IL6R-L | P238D/G237A | 101 | 138 |
| 32 | IL6R-PD080/IL6R-L | P238D/G237D | 127 | 222 |
| 33 | IL6R-PD081/IL6R-L | P238D/G237E | 101 | 117 |
| 34 | IL6R-PD082/IL6R-L | P238D/G237F | 108 | 380 |
| 35 | IL6R-PD086/IL6R-L | P238D/G237L | 112 | 268 |
| 36 | IL6R-PD087/IL6R-L | P238D/G237M | 109 | 196 |
| 37 | IL6R-PD094/IL6R-L | P238D/G237W | 122 | 593 |
| 38 | IL6R-PD095/IL6R-L | P238D/G237Y | 124 | 543 |
| 39 | IL6R-PD097/IL6R-L | P238D/S239D | 139 | 844 |

Figure 7:
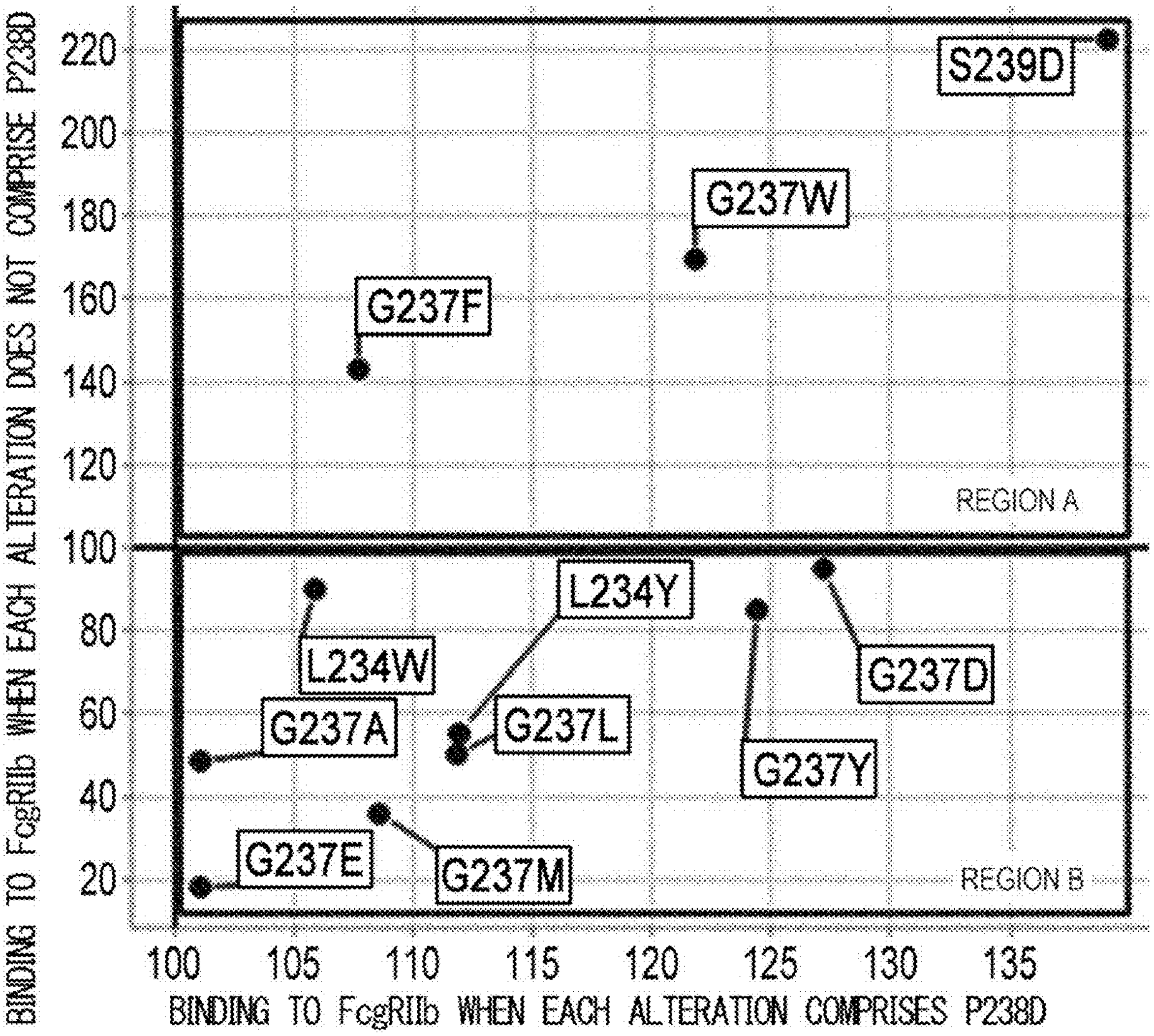
FIG. 7 shows a graph in which the vertical axis shows the relative value of FcγRIIb-binding activity of variants produced by introducing each alteration into GpH7-B3 which does not have the P238D alteration, and the horizontal axis shows the relative value of FcγRIIb-binding activity of variants produced by introducing each alteration into IL6R-F652 which has the P238D alteration. The value for the amount of FcγRIIb binding of each variant was divided by the value for the amount of FcγRIIb binding of the pre-altered antibody; and then the obtained value was multiplied by 100, and used as the value of relative binding activity. Here, region A contains alterations that exhibit the effect of enhancing FcγRIIb binding in both cases where an alteration is introduced into GpH7-B3 which does not have P238D and where an alteration is introduced into IL6R-F652 which has P238D. Region B contains alterations that exhibit the effect of enhancing FcγRIIb binding when introduced into GpH7-B3 which does not have P238D, but do not exhibit the effect of enhancing FcγRIIb binding when introduced into IL6R-F652 which has P238D.

FIG. 7 shows relative values for the FcγRIIb-binding activity obtained by additionally introducing these eleven alterations into a variant carrying the P238D alteration, and relative values for the FcγRIIb-binding activity obtained by introducing these alterations into an Fc that does not contain the P238D alteration in Example 1. These eleven alterations enhanced the amount of FcγRIIb binding compared with before introduction when they were further introduced into the P238D variant, but on the contrary, the effect of lowering FcγRIIb binding was observed for eight of those alterations except G237F, G237W, and S239D, when they were introduced into the variant that does not contain P238D (GpH7-B3/GpL16-k0) used in Example 1. Example 3 and these results showed that from the effects of introducing alterations into a naturally-occurring IgG1, it is difficult to predict the effects of introducing the same alterations into the variant containing an Fc with the P238D alteration. In other words, it would not have been possible to discover these eight alterations identified this time without this investigation.

The results of measuring KD values of the variants indicated in Table 6 for FcγRIa, FcγRIIaR, FcγRIIaH, FcγRIIb, and FcγRIIIaV by the method of Reference Example 2 are summarized in Table 7. In the table, SEQ ID NO refers to the SEQ ID NO of the H chain of the evaluated variant, and alteration refers to the alteration introduced into IL6R-F11 (SEQ ID NO: 27). The template used for producing IL6R-F11, IL6R-G1d/IL6R-L, is indicated with an asterisk (*). Furthermore, KD(IIaR)/KD(IIb) and KD(IIaH)/KD (IIb) in the table respectively show the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD(IIb) of the altered polypeptide refers to a value obtained by dividing the KD value of the parent polypeptide for FcγRIIb by the KD value of each variant for FcγRIIb. In addition, Table 7 shows KD values for the stronger of the FcγRIIaR- and FcγRIIaH-binding activities of each variant/KD values for the stronger of the FcγRIIaR- and FcγRIIaH-binding activities of the parent polypeptide. Here, parent polypeptide refers to a variant which has IL6R-F11 (SEQ ID NO: 27) as the H chain. It was determined that, due to weak binding of FcγR to IgG, it was impossible to accurately analyze some binding by kinetic analysis, and thus the cells outlined in heavy lines in Table 7 show values calculated by using Equation 2 of Reference Example 2.

$$KD = C \bullet R_{max}/(R_{eq} - RI) - C \quad \text{[Equation 2]}$$

Table 7 shows that all variants improved their affinity for FcγRIIb in comparison with IL6R-F11, and the range of improvement was 1.9 fold to 5.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a larger value indicates a higher binding selectivity for FcγRIIb. For the parent polypeptide IL6R-F11/IL6R-L, the ratio of KD value for FcγRIIaR/KD value for FcγRIIb and the ratio of KD value for FcγRIIaH/KD value for FcγRIIb are both 0.7, and accordingly all variants in Table 7 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or reduced binding compared with the binding by the stronger of the FcγRIIaR- and FcγRIIaH-binding activities of the parent polypeptide. Since this value was 0.7 to 5.0 for the variants obtained this time, one may say that binding by the stronger of the FcγRIIaR- and FcγRIIaH-binding activities of the variants obtained this time was nearly the same or decreased in comparison with the parent polypeptide. These results showed that compared with the parent polypeptide, the variants obtained this time have maintained or decreased binding activities to FcγRIIa type R and type H, and improved selectivity for FcγRIIb. Furthermore, compared with IL6R-F11, all variants had lower affinity to FcγRIa and FcγRIIIaV.

(hereinafter, Fc(P238D)) and the extracellular region of FcγRIIb was elucidated by X-ray crystallographic analysis, and the three-dimensional structure and binding mode were compared to those of the complex formed between the Fc of a naturally-occurring IgG1 (hereinafter, Fc(WT)) and the extracellular region of FcγRIIb. Many reports have been made on the three-dimensional structure of a complex formed between an Fc and an FcγR extracellular region; and the three-dimensional structures of the Fc(WT)/FcγRIIIb extracellular region complex (Nature, 2000, 400:267-273; J. Biol. Chem. 2011, 276:16469-16477), the Fc(WT)/FcγRIIIa extracellular region complex (Proc. Natl. Acad. Sci. USA, 2011, 108:12669-126674), and the Fc(WT)/FcγRIIa extracellular region complex (J. Imunol. 2011, 187:3208-3217) have been analyzed. While the three-dimensional structure of the Fc(WT)/FcγRIIb extracellular region complex has not

TABLE 7

| SEQ ID NO | VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) |
|---|---|---|---|---|---|---|---|
| 20 | IL6R-G1d/IL6R-L | * | 3.2E−10 | 1.0E−06 | 6.7E−07 | 2.6E−06 | 3.5E−07 |
| 27 | IL6R-F11/IL6R-L | | 9.0E−10 | 5.0E−06 | 5.0E−06 | 6.8E−06 | 1.5E−06 |
| 28 | IL6R-PD042/ILR-L | L234W/P238D | 6.3E−08 | 1.6E−05 | 1.9E−05 | 2.0E−05 | 3.7E−05 |
| 30 | IL6R-PD043/IL6R-L | L234Y/P238D | 7.5E−08 | 2.6E−05 | 2.3E−05 | 1.6E−06 | 4.5E−05 |
| 31 | IL6R-PD079/IL6R-L | G237A/P238D | 1.4E−07 | 3.2E−05 | 2.1E−05 | 3.0E−06 | 3.7E−05 |
| 32 | IL6R-PD080/IL6R-L | G237D/P238D | 1.4E−07 | 2.1E−05 | 2.5E−05 | 2.0E−06 | 4.3E−05 |
| 33 | IL6R-PD081/IL6R-L | G237E/P23BD | 3.4E−07 | 3.8E−05 | 2.5E−05 | 3.6E−06 | 4.1E−05 |
| 34 | IL6R-PD082/IL6R-L | G237F/P238D | 5.2E−08 | 1.4E−05 | 1.6E−05 | 3.4E−06 | 4.3E−05 |
| 35 | IL6R-PD086/IL6R-L | G237L/P238D | 1.2E−07 | 1.8E−05 | 1.8E−05 | 2.6E−06 | 4.1E−05 |
| 36 | ILDR-PD087/IL6R-L | G237M/P238D | 5.2E−08 | 2.2E−05 | 2.0E−05 | 2.9E−06 | 3.7E−05 |
| 37 | IL6R-PD084/IL6R-L | G237W/P238D | 3.6E−08 | 7.2E−06 | 1.2E−05 | 2.3E−06 | 3.8E−05 |
| 38 | IL6R-PF095/IL6R-L | G237Y/P238D | 9.3E−08 | 7.9E−06 | 1.5E−05 | 2.3E−06 | 4.2E−05 |
| 39 | IL6R/PD097/IL6R-L | P238D/S239D | 4.9E−09 | 3.5E−06 | 1.9E−05 | 1.4E−06 | 1.7E−05 |

| SEQ ID NO | KDIIaR)/ KD(IIb) | KD(IIaH)/ KD(IIb) | KD (IIb) OF PARENT POLYPEPTIDE/ KD (IIb) OF ALTERED POLYPEPTIDE | KD VALUE FOR THE STRONGER OF THE BINDING ACTIVITIES OF A VARIANT TO FcgRIIaR AND FcgRIIaH/ KD VALUE FOR THE STRONGER OF THE BINDING ACTIVITIES OF THE PARENT POLYPEPTIDE TO FcgRIIaR AND FcgRIIaH |
|---|---|---|---|---|
| 20 | 0.4 | 0.3 | 2.6 | 0.1 |
| 27 | 0.7 | 0.7 | 1.0 | 1.0 |
| 28 | 8.1 | 9.5 | 3.4 | 3.2 |
| 30 | 15.9 | 14.4 | 4.2 | 4.6 |
| 31 | 10.5 | 7.0 | 2.3 | 4.2 |
| 32 | 10.7 | 12.8 | 3.5 | 4.2 |
| 33 | 10.6 | 7.0 | 1.9 | 5.0 |
| 34 | 4.1 | 4.7 | 2.0 | 2.8 |
| 35 | 6.9 | 7.1 | 2.7 | 3.5 |
| 36 | 7.7 | 7.0 | 2.4 | 4.0 |
| 37 | 3.1 | 5.2 | 2.9 | 1.4 |
| 38 | 3.4 | 5.4 | 2.9 | 1.6 |
| 39 | 2.6 | 14.0 | 5.0 | 0.7 |

[Example 5] X-Ray Crystallographic Analysis of a Complex Formed Between an Fc Containing P238D and an Extracellular Region of FcγRIIb As indicated earlier in Example 3, even though an alteration that improves FcγRIIb-binding activity or selectivity for FcγRIIb is introduced into an Fc containing P238D, the FcγRIIb-binding activity was found to decrease, and the reason for this may be that the structure at the interacting interface between Fc and FcγRIIb is changed due to introduction of P238D. Therefore, to pursue the reason for this phenomena, the three-dimensional structure of the complex formed between an IgG1 Fc containing the P238D mutation been analyzed, the three-dimensional structure of a complex formed with Fc(WT) is known for FcγRIIa, and the extracellular regions of FcγRIIa and FcγRIIb match 93% in amino acid sequence and have very high homology. Thus, the three-dimensional structure of the Fc(WT)/FcγRIIb extracellular region complex was predicted by modeling using the crystal structure of the Fc(WT)/FcγRIIa extracellular region complex.

Figure 8:
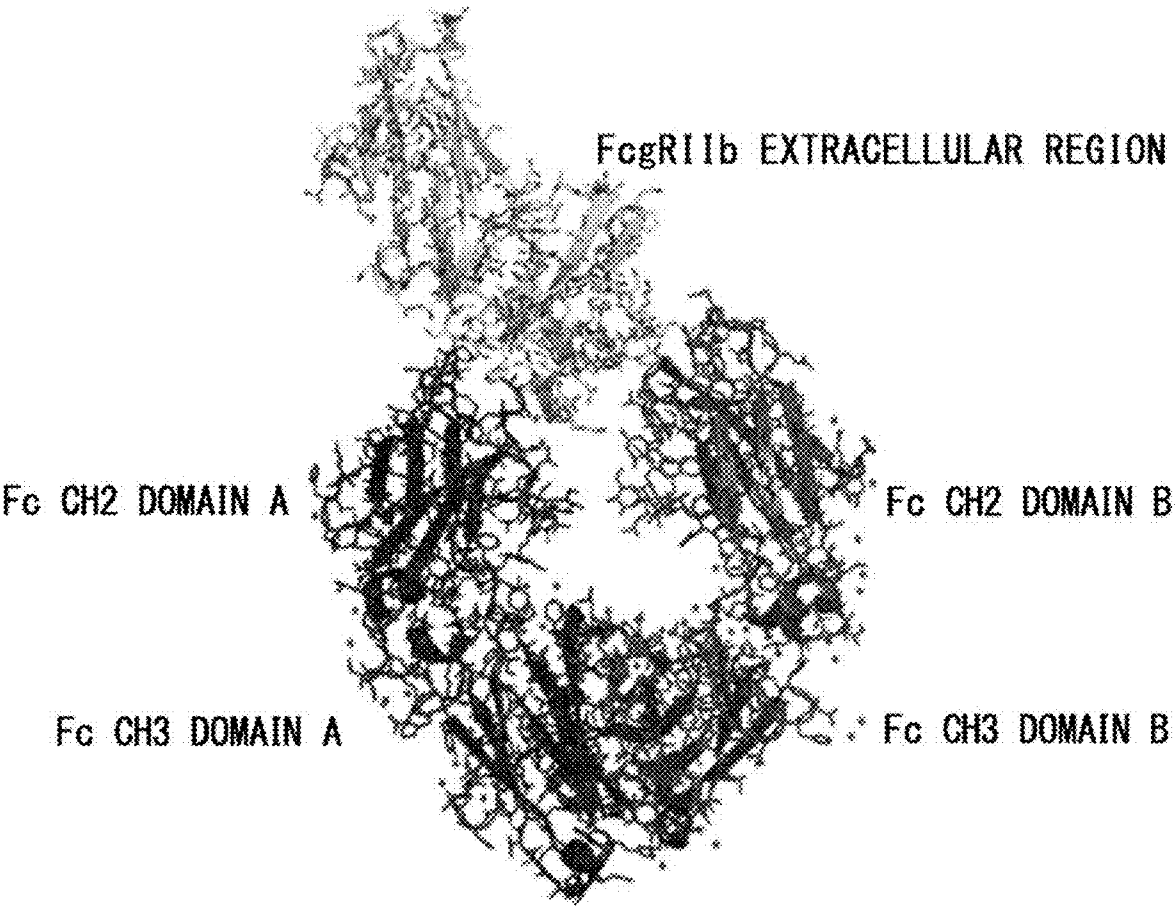
FIG. 8 shows a crystal structure of the Fc(P238D)/FcγRIIb extracellular region complex.

The three-dimensional structure of the Fc(P238D)/FcγRIIb extracellular region complex was determined by X-ray crystallographic analysis at 2.6 Å resolution. The structure obtained as a result of this analysis is shown in FIG. 8. The FcγRIIb extracellular region is bound between two Fc CH2 domains, and this is similar to the three-dimensional structures of complexes formed between Fc(WT) and the respective extracellular region of FcγRIIIa, FcγRIIIb, or FcγRIIa analyzed so far.

Figure 9:
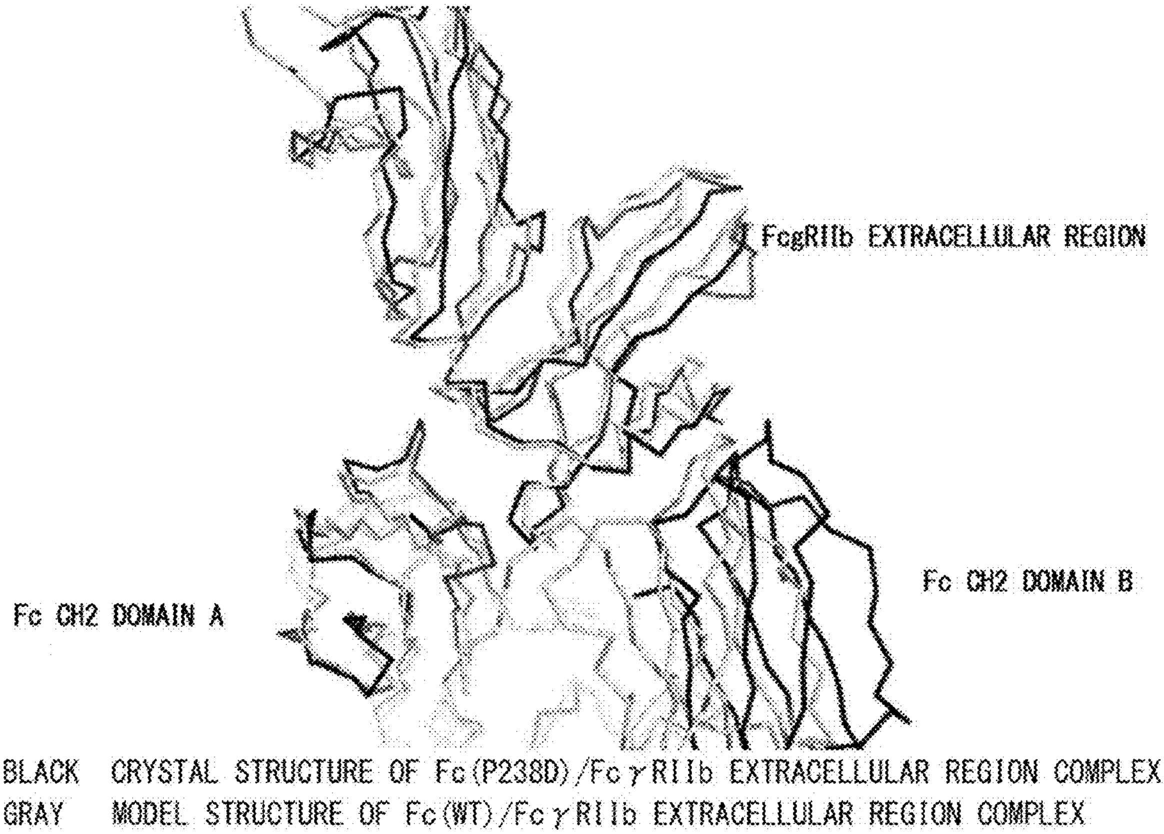
FIG. 9 shows an image of superimposing the crystal structure of the Fc(P238D)/FcγRIIb extracellular region complex and the model structure of the Fc(WT)/FcγRIIb extracellular region complex, with respect to the FcγRIIb extracellular region and the Fc CH2 domain A by the least squares fitting based on the Ca atom pair distances.

Next, for detailed comparison, the crystal structure of the Fc(P238D)/FcγRIIb extracellular region complex and the model structure of the Fc(WT)/FcγRIIb extracellular region complex were superimposed by the least squares fitting based on the Cα atom pair distances with respect to the FcγRIIb extracellular region and the Fc CH2 domain A (FIG. 9). In that case, the degree of overlap between Fc CH2 domains B was not satisfactory, and conformational differences were found in this portion. Furthermore, using the crystal structure of the Fc(P238D)/FcγRIIb extracellular region complex and the model structure of the Fc(WT)/FcγRIIb extracellular region complex, pairs of atoms that have a distance of 3.7 Å or less between the FcγRIIb extracellular region and Fc CH2 domain B were extracted and compared in order to observe the differences in interatomic interactions between FcγRIIb and Fc CH2 domain B in Fc(WT) and Fc(P238D). As shown in Table 8, the interatomic interactions between Fc CH2 domain B and FcγRIIb in Fc(P238D) and Fc(WT) do not match.

TABLE 8

| FcgRIIb ATOM | Fc (P238D) CH2 DOMAIN B INTERACTION PARTNER (DISTANCE BETWEEN ATOMS, Å) | Fc (WT) CH2 DOMAIN B INTERACTION PARTNER (DISTANCE BETWEEN ATOMS, Å) |
|---|---|---|
| Val 116 CG2 | | Asp 265 OD2 (3.47) |
| | | Gly 237 O (3.65) |
| Ser 126 OG | Ser 298 N (3.31) | |
| | Ser 298 CB (3.32) | |
| | Tyr 296 O (3.05) | |
| Lys 128 CA | Ser 298 OG (3.50) | |
| Phe 129 CB | Ser 298 O (3.36) | |
| Phe 129 CD2 | | Asn 297 CB (3.50) |
| | | Asn 297 CG (3.43) |
| Lys 128 C | Ser 298 OG (3.47) | |
| Phe 129 N | Ser 298 OG (3.30) | |
| Phe 129 O | Ser 267 OG (3.54) | |
| Arg 131 CB | | Val 266 O (3.02) |
| Arg 131 CG | | Val 266 O (3.22) |
| Arg 131 CD | | Val 266 CG1 (3.45) |
| | | Val 266 C (3.55) |
| | | Val 266 O (3.10) |
| Arg 131 NE | Ala 327 O (3.60) | Val 266 C (3.66) |
| | | Val 266 O (3.01) |
| | | Val 266 N (3.49) |
| Arg 131 CZ | Asp 270 CG (3.64) | Val 266 N (3.13) |
| | Asp 270 OD2 (3.22) | |
| | Asp 270 OD1 (3.27) | |
| | Ala 327 CB (3.63) | |
| Arg 131 NH1 | Asp 270 CG (3.19) | Val 266 CG1 (3.47) |
| | Asp 270 OD2 (2.83) | Val 266 N (3.43) |
| | Asp 270 OD1 (2.99) | Thr 299 OG1 (3.66) |
| | Ser 267 CB (3.56) | Ser 298 O (3.11) |
| Arg 131 NH2 | Asp 270 CG (3.20) | Asp 265 CA (3.16) |
| | Asp 270 OD2 (2.80) | Val 266 N (3.37) |
| | Asp 270 OD1 (2.87) | |
| | Asp 327 CB (3.66) | |
| Tyr 157 CE1 | | Leu 234 CG (3.64) |
| | | Leu 234 CD1 (3.61 |
| Tyr 157 OH | | Gly 236 O (3.62) |
| | | Leu 234 CA (3.48) |
| | | Leu 234 CG (3.45) |

Figure 10:
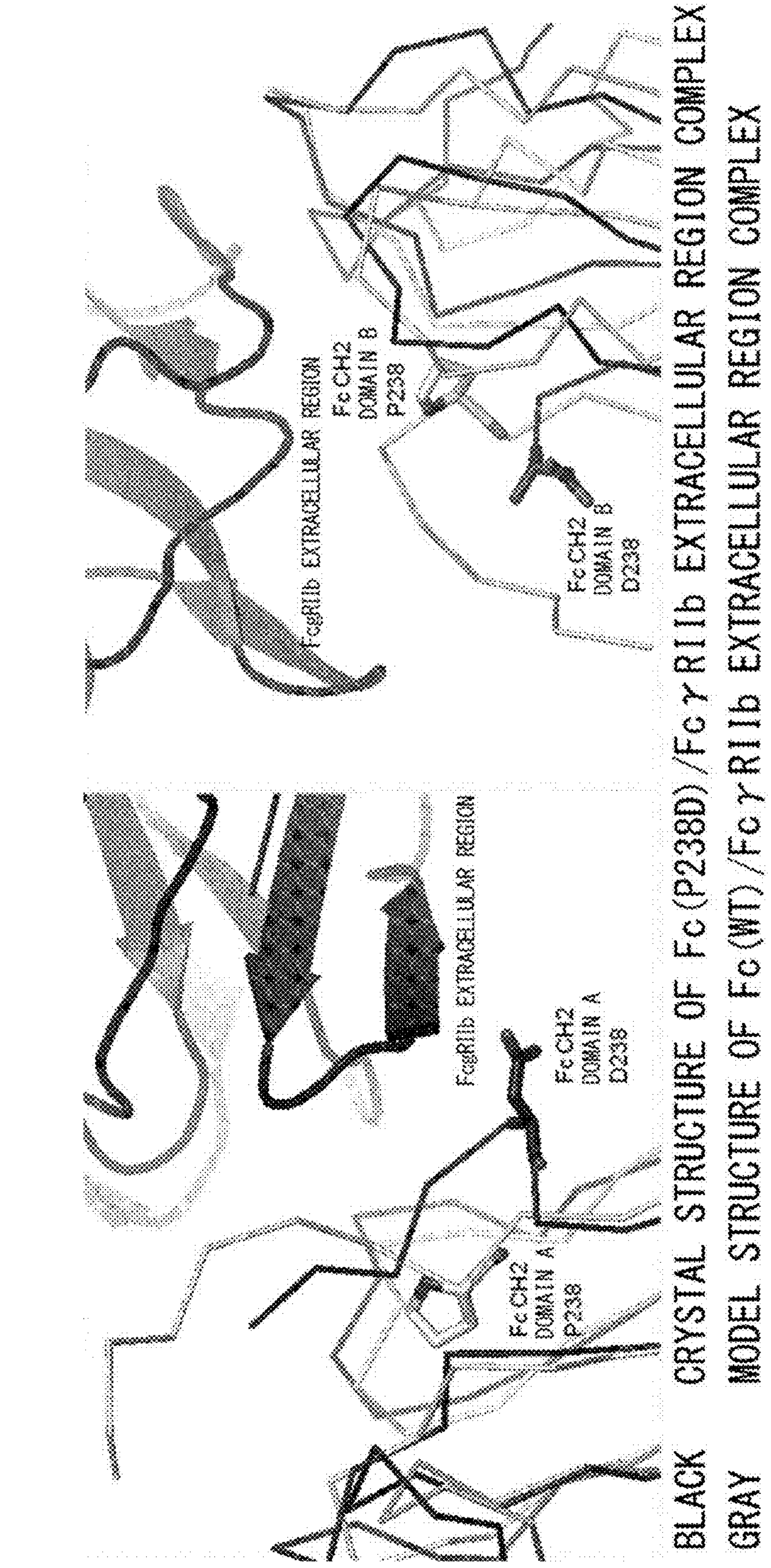
FIG. 10 shows comparison of the detailed structure around P238D after superimposing the crystal structure of the Fc(P238D)/FcγRIIb extracellular region complex and the model structure of the Fc(WT)/FcγRIIb extracellular region complex with respect to the only Fc CH2 domain A or the only Fc CH2 domain B by the least squares fitting based on the Cα atom pair distances.

Furthermore, the X-ray crystal structure of the Fc(P238D)/FcγRIIb extracellular region complex and the model structure of the Fc(WT)/FcγRIIb extracellular region complex were superimposed by the least squares fitting based on the Ca atom pair distances with respect to the only Fc CH2 domain A or the only Fc CH2 domain B, and the detailed structures near P238D were compared. The location of the amino acid residue at position 238 (EU numbering), which is mutation introduction position, is changed between Fc(P238D) and Fc(WT), one can see that along with this change, the nearby loop structure continuing from this hinge region is changed between Fc(P238D) and Fc(WT) (FIG. 10). Originally in Fc(WT), Pro at position 238 (EU numbering) is present on the inner side of the protein, and forms a hydrophobic core with the surrounding residues. However, when this residue is changed to a charged and very hydrophilic Asp, the presence in the same hydrophobic core would cause energetical disadvantage in terms of desolvation. Therefore, in Fc(P238D), to cancel this energetically disadvantageous situation, the amino acid residue at position 238 (EU numbering) changes its orientation to face the solvent side, and this may have caused this change in the nearby loop structure. Furthermore, since this loop continues from the hinge region crosslinked by an S—S bond, its structural change will not be limited to a local change, and will affect the relative positioning of the FcCH2 domain A and domain B. As a result, the interatomic interactions between FcγRIIb and Fc CH2 domain B have been changed. Therefore, predicted effects could not be observed when alterations that improve selectivity and binding activity towards FcγRIIb in a naturally-occurring IgG were combined with an Fc containing the P238D alteration.

Figure 11:
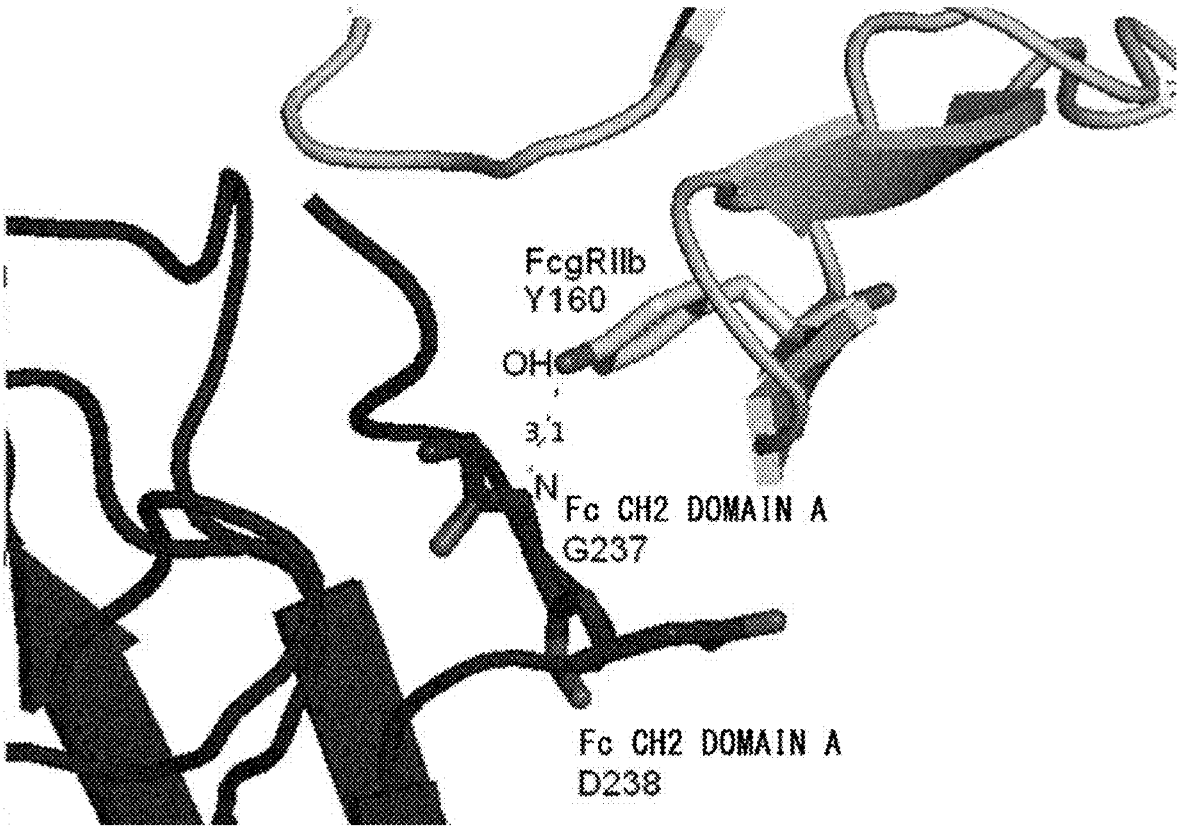
FIG. 11 shows that a hydrogen bond can be found between the main chain of Gly at position 237 (EU numbering) in Fc CH2 domain A, and Tyr at position 160 in FcγRIIb in the crystal structure of the Fc(P238D)/FcγRIIb extracellular region complex.
Figure 12:
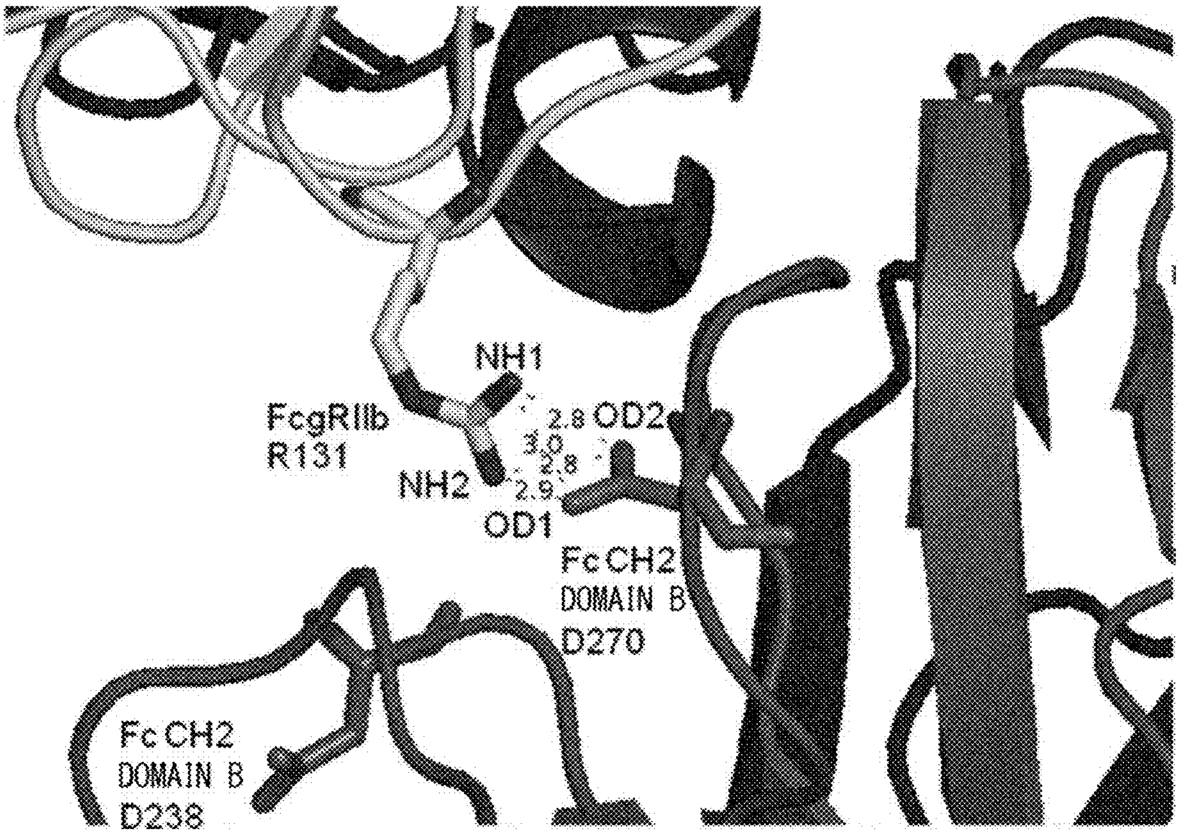
FIG. 12 shows that an electrostatic interaction can be found between Asp at position 270 (EU numbering) in Fc CH2 domain B, and Arg at position 131 in FcγRIIb in the crystal structure of the Fc(P238D)/FcγRIIb extracellular region complex.

Furthermore, as a result of structural changes due to introduction of P238D in Fc CH2 domain A, a hydrogen bond has been found between the main chain of Gly at adjacent position 237 (EU numbering) and Tyr at position 160 in FcγRIIb (FIG. 11). The residue in FcγRIIa that corresponds to this Tyr 160 is Phe; and when the binding is to FcγRIIa, this hydrogen bond is not formed. The amino acid at position 160 is one of the few differences between FcγRIIa and FcγRIIb at the interface of interaction with Fc, the presence of this hydrogen bond which is specific to FcγRIIb is presumed to have led to improvement of FcγRIIb-binding activity and decrease of FcγRIIa-binding activity in Fc(P238D), and improvement of its selectivity. Furthermore, in Fc CH2 domain B, an electrostatic interaction is observed between Asp at position 270 (EU numbering) and Arg at position 131 in FcγRIIb (FIG. 12). In FcγRIIa type H, which is one of the allotypes of FcγRIIa, the corresponding residue is His, and therefore cannot form this electrostatic interaction. This can explain why the Fc(P238D)-binding activity is lowered in FcγRIIa type H compared with FcγRIIa type R. Observations based on such results of X-ray crystallographic analysis showed that the change of the loop structure beside P238D due to P238D introduction and the accompanying change in the relative domain positioning causes formation of new interactions not found in the naturally-occurring IgG, and this led to a selective binding profile of P238D variants for FcγRIIb.

[Expression and Purification of Fc(P238D)]

An Fc containing the P238D alteration was prepared as follows. First, Cys at position 220 (EU numbering) of hIL6R-IgG1-v1 (SEQ ID NO: 21) was substituted with Ser. Then, genetic sequence of Fc(P238D) from Glu at position 236 (EU numbering) to its C terminal was cloned by PCR. Using this cloned genetic sequence, production of expression vectors, and expression and purification of Fc(P238D) were carried out according to the method of Reference Example 1. Cys at position 220 (EU numbering) forms a disulfide bond with Cys of the L chain in general IgG1. The L chain is not co-expressed when Fc alone is prepared, and therefore, this residue was substituted with Ser to avoid formation of unnecessary disulfide bonds.

[Expression and Purification of the FcγRIIb Extracellular Region]

This was prepared according to the method of Reference Example 2.

[Purification of the Fc(P238D)/FcγRIIb Extracellular Region Complex]

To 2 mg of the FcγRIIb extracellular region sample obtained for crystallization, 0.29 mg of Endo F1 (Protein Science 1996, 5:2617-2622) expressed and purified from *Escherichia coli* as a glutathione S-transferase fusion protein was added. This was allowed to remain at room temperature for three days in 0.1 M Bis-Tris buffer at pH 6.5, and the N-linked oligosaccharide was cleaved, leaving N-acetylglucosamine directly bound to Asn. Next, this FcγRIIb extracellular domain sample subjected to carbohydrate cleavage treatment was concentrated by ultrafiltration with 5000 MWCO, and purified by gel filtration chromatography (Superdex™200 10/300 size exclusion chromatography) using a column equilibrated in 20 mM HEPS at pH 7.5 containing 0.05 M NaCl. Furthermore, to the obtained carbohydrate-cleaved FcγRIIb extracellular region fraction, Fc(P238D) was added so that the molar ratio of the FcγRIIb extracellular region would be present in slight excess, and after concentration by ultrafiltration with 10,000 MWCO, a sample of the Fc(P238D)/FcγRIIb extracellular region complex was obtained through purification by gel filtration chromatography (Superdex™ 200 10/300 size exclusion chromatography) using a column equilibrated in 20 mM HEPS at pH 7.5 containing 0.05 M NaCl.

[Crystallization of the Fc(P238D)/FcγRIIb Extracellular Region Complex]

A sample of the Fc(P238D)/FcγRIIb extracellular region complex was concentrated to approximately 10 mg/mL by ultrafiltration with 10,000 MWCO, and crystallization was carried out by the sitting drop vapor diffusion method. Matrix® Hydra® II-Plus-One pipetting robot was used for crystallization; and for a reservoir solution containing 100 mM Bis-Tris pH 6.5, 17% PEG3350, 0.2 M ammonium acetate, and 2.7% (w/v) D-Galactose, a crystallization drop was produced by mixing at a ratio of reservoir solution: crystallization sample=0.2 μL: 0.2 μL, and after sealing, this was allowed to remain at 20° C., and thin plate-like crystals were successfully obtained.

[Measurement of X-Ray Diffraction Data from an Fc(P238D)/FcγRIIb Extracellular Region Complex Crystal]

One of the obtained single crystals of the Fc(P238D)/FcγRIIb extracellular region complex was soaked into a solution of 100 mM Bis-Tris pH 6.5, 20% PEG3350, ammonium acetate, 2.7% (w/v) D-Galactose, 22.5% (v/v) ethylene glycol. The crystal was fished out of the solution using a pin with attached tiny nylon loop, and frozen in liquid nitrogen; and then X-ray diffraction data was measured at synchrotron radiation facility Photon Factory BL-1A in High Energy Accelerator Research Organization. During the measurement, the crystal was constantly placed in a nitrogen stream at −178° C. to maintain in a frozen state, and a total of 225 X ray diffraction images were collected using Quantum 270 CCD detector (ADSC) attached to a beam line with rotating the crystal 0.8° at a time. Determination of cell parameters, indexing of diffraction spots, and diffraction data processing from the obtained diffraction images were performed using the Xia2 program (CCP4 Software Suite), XDS Package (Walfgang Kabsch) and Scala (CCP4 Software Suite); and finally, diffraction intensity data up to 2.46 Å resolution was obtained. The crystal belongs to the space group P21, and has the following cell parameters; a=48.85 Å, b=76.01 Å, c=115.09 Å, α=90°, β=100.70°, γ=90°.

[X Ray Crystallographic Analysis of the Fc(P238D)/FcγRIIb Extracellular Region Complex]

Crystal structure of the Fc(P238D)/FcγRIIb extracellular region complex was determined by the molecular replacement method using the program Phaser (CCP4 Software Suite). From the size of the obtained crystal lattice and the molecular weight of the Fc(P238D)/FcγRIIb extracellular region complex, the number of complexes in the asymmetric unit was predicted to be one. From the structural coordinates of PDB code: 3SGJ which is the crystal structure of the Fc(WT)/FcγRIIIa extracellular region complex, the amino acid residue portions of the A chain positions 239-340 and the B chain positions 239-340 were taken out as separate coordinates, and they were used respectively as models for searching the Fc CH2 domains. The amino acid residue portions of the A chain positions 341-444 and the B chain positions 341-443 were taken out as a single set of coordinates from the same structural coordinates of PDB code: 3SGJ; and this was used as a model for searching the Fc CH3 domains. Finally, from the structural coordinates of PDB code: 2FCB which is a crystal structure of the FcγRIIb extracellular region, the amino acid residue portions of the A chain positions 6-178 was taken out and used as a model for searching the FcγRIIb extracellular region. The orientation and position of each search model in the crystal lattice were determined in the order of Fc CH3 domain, FcγRIIb extracellular region, and Fc CH2 domain, based on the rotation function and translation function to obtain the initial model for the crystal structure of the Fc(P238D)/FcγRIIb extracellular region complex. When rigid body refinement which moves the two Fc CH2 domains, the two Fc CH3 domains, and the FcγRIIb extracellular region was performed on the obtained initial model, the crystallographic reliability factor, R value became 40.4%, and the Free R value became 41.9% to diffraction intensity data from 25 Å to 3.0 Å at this point. Furthermore, structural refinement using the program Refmac5 (CCP4 Software Suite), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Paul Emsley), and model refinement was carried out by repeating these steps. Finally, as a result of incorporation of water molecules into the model based on the electron density maps which use 2Fo-Fc or Fo-Fc as the coefficient, and the following refinement, the crystallographic reliability factor, R values and the Free R value of the model containing 4846 non-hydrogen atoms became 23.7% and 27.6% to 24291 diffraction intensity data from 25 Å to 2.6 Å resolution, respectively.

[Production of a Model Structure of the Fc(WT)/FcγRIIb Extracellular Region Complex]

Based on the structural coordinates of PDB code: 3RY6 which is a crystal structure of the Fc(WT)/FcγRIIa extracellular region complex, the Build Mutants function of the Discovery Studio 3.1 program (Accelrys) was used to introduce mutations to match the amino acid sequence of FcγRIIb into FcγRIIa in this structural coordinates. In that case, the Optimization Level was set to High, Cut Radius was set to 4.5, five models were generated, and the one with the best energy score from among them was employed as the model structure for the Fc(WT)/FcγRIIb extracellular region complex.

[Example 6] Analysis of FcγR Binding of Fc Variants Whose Alteration Sites were Determined Based on Crystal Structures Based on the results of X-ray crystallographic analysis on the complex formed between Fc(P238D) and the FcγRIIb extracellular region obtained in Example 5, comprehensive alterations were introduced into sites on the altered Fc having substitution of Pro at position 238 (EU numbering) with Asp that were predicted to affect interaction with FcγRIIb, (residues of positions 233, 240, 241, 263, 265, 266, 267, 268, 271, 273, 295, 296, 298, 300, 323, 325, 326, 327, 328, 330, 332, and 334 (EU numbering)) and variants with a combination of alterations that enhance FcγRIIb binding were examined.

IL6R-B3 (SEQ ID NO: 40) was produced by introducing into IL6R-G1d (SEQ ID NO: 20) produced in Example 2, the alteration produced by substituting Lys at position 439 (EU numbering) with Glu. Next, IL6R-BF648 (SEQ ID NO: 41) was produced by introducing into IL6R-B3, the alteration produced by substituting Pro at position 238 (EU numbering) with Asp. IL6R-L (SEQ ID NO: 22) was utilized as the common antibody L chain for all of the antibodies. These antibody variants were expressed and purified according to the method of Reference Example 1, and binding to each of the FcγRs (FcγRIa, FcγRIIa type H, FcγRIIa type R, FcγRIIb, and FcγRIIIa type V) was comprehensively evaluated by the method of Reference Example 2.

A figure was produced according to the following method for the results of analyzing the interactions with the respective FcγRs. The value for the amount of binding of each variant to each FcγR was divided by the value for the amount of binding of the pre-altered control antibody (IL6R-BF648/IL6R-L with Pro at position 238 (EU numbering) substituted with Asp) to each FcγR, and the obtained was then multiplied by 100 and used as the relative binding activity value of each variant to each FcγR. The horizontal axis shows the relative binding activity value of each variant to FcγRIIb, and the vertical axis shows the relative binding activity value of each variant to FcγRIIa type R (FIG. 13).

Figure 13:
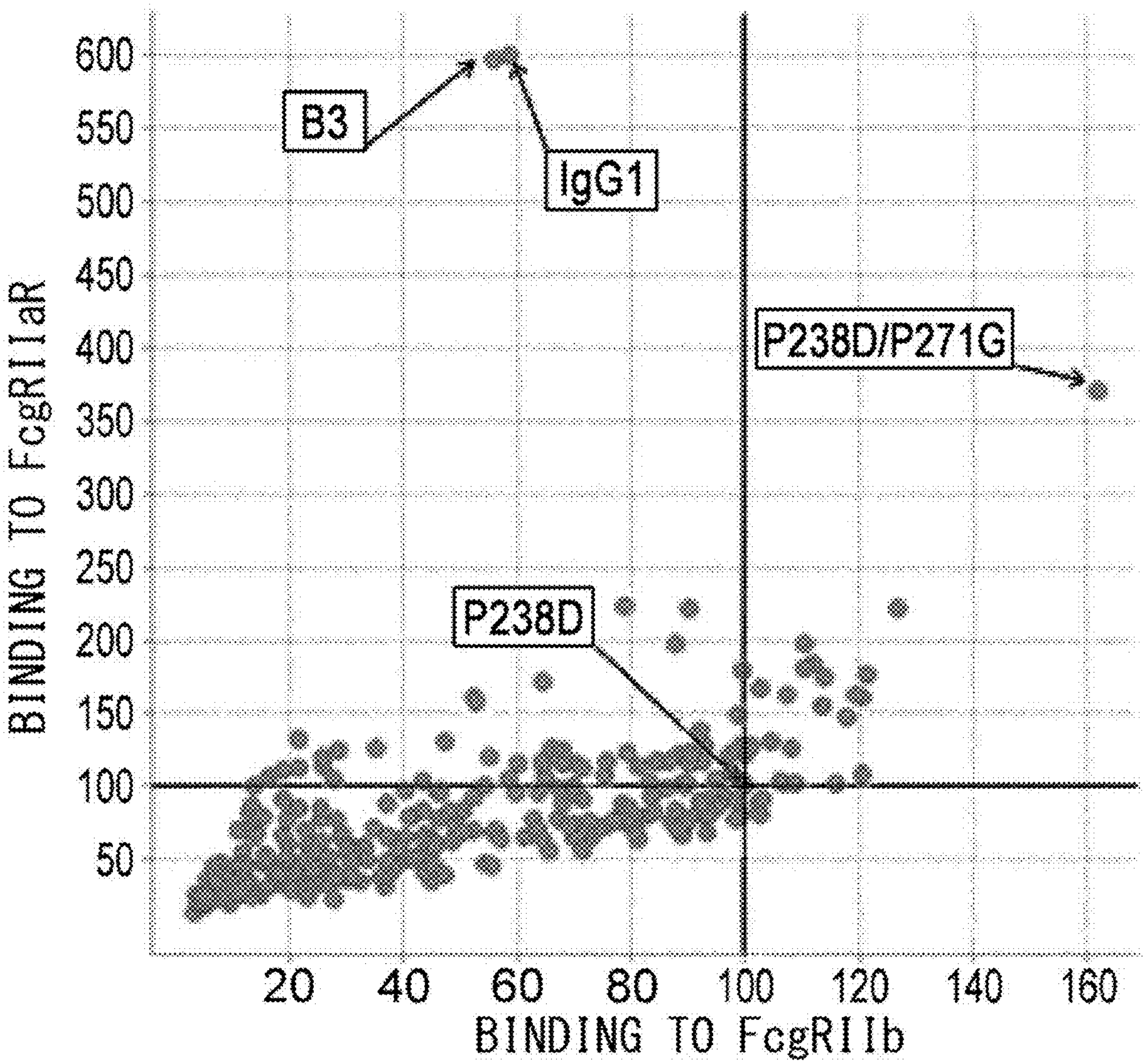
FIG. 13 shows a graph in which the horizontal axis shows the relative value of FcγRIIb-binding activity of each 2B variant, and the vertical axis shows the relative value of FcγRIIa type R-binding activity of each 2B variant. The value for the amount of binding of each 2B variant to each FcγR was divided by the value for the amount of binding of a control antibody prior to alteration (altered Fc with substitution of Pro at position 238 (EU numbering) with Asp) to each FcγR; and then the obtained value was multiplied by 100, and used as the value of relative binding activity of each 2B variant towards each FcγR.

As shown in FIG. 13, the results show that of all the alterations, 24 types of alterations were found to have an effect of maintaining or enhancing FcγRIIb binding in comparison with the pre-altered antibody. The binding of these variants to each of the FcγRs are shown in Table 9. In the table, SEQ ID NO refers to the SEQ ID NO of the H chain of the evaluated variant, and alteration refers to the alteration introduced into IL6R-B3 (SEQ ID NO: 40). The template used for producing IL6R-B3, IL6R-G1d/IL6R-L, is indicated with an asterisk (*).

TABLE 9

| SEQ ID NO | VARIANT NAME | ALTERNATION | RELATIVE FcgRIa-BINDING ACTIVITY | RELATIVE FcgRIIaR-BINDING ACTIVITY | RELATIVE FcgRIIaH-BINDING ACTIVITY | RELATIVE FcgRIIb-BINDING ACTIVITY | RELATIVE FcgRIIIaV-BINDING ACTIVITY |
|---|---|---|---|---|---|---|---|
| 20 | IL6R-G1d/IL6R-L | * | 140 | 650 | 1670 | 62 | 3348 |
| 40 | IL6R-2B999/IL6R-L | | 145 | 625 | 1601 | 58 | 3264 |
| 41 | IL6R-BF648/IL6R-L | P238D | 100 | 100 | 100 | 100 | 100 |
| 42 | IL6R-2B002/IL6R-L | P238D/E233D | 118 | 103 | 147 | 116 | 147 |
| 43 | IL6R-BP100/IL6R-L | P238D/S267A | 121 | 197 | 128 | 110 | 138 |
| 44 | IL6R-BP102/IL6R-L | P238D/S267Q | 104 | 165 | 66 | 106 | 86 |
| 45 | IL6R-BP103/IL6R-L | P238D/S267V | 56 | 163 | 69 | 107 | 77 |
| 46 | IL6R-BP106/IL6R-L | P238D/H268D | 127 | 150 | 110 | 116 | 127 |
| 47 | IL6R-BP107/IL6R-L | P238D/H268E | 123 | 147 | 114 | 118 | 129 |
| 48 | IL6R-BP110/IL6R-L | P238D/H268N | 105 | 128 | 127 | 101 | 127 |
| 49 | IL6R-BP112/IL6R-L | P238D/P271G | 119 | 340 | 113 | 157 | 102 |
| 50 | 1L6R-2B128/IL6R-L | P238D/Y296D | 95 | 87 | 37 | 103 | 96 |
| 51 | IL6R-2B169/IL6R-L | P238D/V323I | 73 | 92 | 83 | 104 | 94 |
| 52 | IL6R-2B171/IL6R-L | P238D/V323L | 116 | 117 | 115 | 113 | 122 |
| 53 | IL6R-2B172/IL6R-L | P238D/V323M | 140 | 244 | 179 | 132 | 144 |
| 54 | IL6R-BP136/IL6R-L | P238D/K326A | 117 | 159 | 103 | 119 | 102 |
| 55 | IL6R-BP117/IL6R-L | P238D/K326D | 124 | 166 | 96 | 118 | 105 |
| 56 | IL6R-BP120/IL6R-L | P238D/K326E | 125 | 175 | 92 | 114 | 103 |

TABLE 9-continued

| SEQ ID NO | VARIANT NAME | ALTERNATION | RELATIVE FcgRIa-BINDING ACTIVITY | RELATIVE FcgRIIaR-BINDING ACTIVITY | RELATIVE FcgRIIaH-BINDING ACTIVITY | RELATIVE FcgRIIb-BINDING ACTIVITY | RELATIVE FcgRIIIaV-BINDING ACTIVITY |
|---|---|---|---|---|---|---|---|
| 57 | IL6R-BP126/IL6R-L | P238D/K326L | 113 | 167 | 132 | 103 | 146 |
| 58 | IL6R-BP119/IL6R-L | P238D/K326M | 117 | 181 | 133 | 110 | 145 |
| 59 | IL6R-BP142/IL6R-L | P238D/K326N | 98 | 103 | 97 | 106 | 102 |
| 60 | IL6R-BP121/IL6R-L | P238D/K326Q | 118 | 155 | 135 | 113 | 157 |
| 61 | IL6R-BP118/IL6R-L | P238D/K326S | 101 | 132 | 128 | 104 | 144 |
| 62 | IL6R-BP116/IL6R-L | P238D/K326T | 110 | 126 | 110 | 108 | 114 |
| 63 | IL6R-BP911 /IL6R-L | P238D/A330K | 52 | 101 | 108 | 119 | 120 |
| 64 | IL6R-BP078/IL6R-L | P238D/A330M | 106 | 101 | 89 | 105 | 91 |
| 65 | IL6R-BP912/IL6R-L | P238D/A330R | 60 | 81 | 93 | 103 | 97 |

The results of measuring KD values of the variants shown in Table 9 for FcγRIa, FcγRIIaR, FcγRIIaH, FcγRIIb, and FcγRIIIa type V by the method of Reference Example 2 are summarized in Table 10. In the table, SEQ ID NO refers to the SEQ ID NO of the H chain of the evaluated variant, and alteration refers to the alteration introduced into IL6R-B3 (SEQ ID NO: 40). The template used for producing IL6R-B3, IL6R-G1d/IL6R-L, is indicated with an asterisk (*). Furthermore, KD(IIaR)/KD(IIb) and KD(IIaH)/KD(IIb) in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD(IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Table 10. Here, parent polypeptide refers to the variant which has IL6R-B3 (SEQ ID NO: 40) as the H chain. It was determined that, due to weak binding of FcγR to IgG, it was impossible to accurately analyze some binding by kinetic analysis, and thus the cells outlined in heavy lines in Table 10 show values calculated by using Equation 2 of Reference Example 2.

$$KD = C \bullet R_{max}/(R_{eq} - RI) - C \qquad \text{[Equation 2]}$$

Table 10 shows that in comparison with IL6R-B3, all variants showed improvement of affinity for FcγRIIb, and the range of improvement was 2.1 fold to 9.7 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb in the parent polypeptide IL6R-B3/IL6R-L were 0.3 and 0.2, respectively, all variants in Table 10 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 4.6 to 34.0 for the variants obtained this time, one may say that in comparison with the parent polypeptide, the variants obtained this time had reduced binding by the stronger of the FcγRIIaR- and FcγRIIaH-binding activities. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity to FcγRIa and FcγRIIIaV.

TABLE 10

| SEQ ID NO | VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) |
|---|---|---|---|---|---|---|---|
| 20 | IL6R-G1d/IL6R-L | * | 3.2E−10 | 1.0E−06 | 6.7E−07 | 2.6E−06 | 3.5E−07 |
| 40 | IL6R-2B999/IL6R-L | | 4.2E−10 | 1.1E−06 | 7.7E−07 | 3.1E−06 | 3.3E−07 |
| 41 | IL6R-BF648/ILR-L | P238D | 1.1E−06 | 1.5E−05 | 4.0E−05 | 1.2E−06 | 7.1E−05 |
| 42 | IL6R-2B002/IL6R-L | P238D/E233D | 6.4E−09 | 1.9E−05 | 8.6E−05 | 9.3E−07 | 5.3E−05 |
| 43 | IL6R-BP100/IL6R-L | F238D/8267A | 1.1E−09 | 7.8E−06 | 4.6E−05 | 1.1E−06 | 5.9E−05 |
| 44 | IL6R-BP102/IL6R-L | P238D/S267Q | 8.2E−09 | 8.4E−06 | 6.1E−05 | 9.0E−07 | 8.2E−06 |
| 45 | IL6R-BP103/IL6R-L | P2380/S267V | 3.5E−08 | 1.1.E−05 | 8.8E−05 | 1.2E−06 | 1.1E−04 |
| 46 | IL6R-BP106/IL6R-L | P238D/H268D | 4.0E−09 | 1.1E−05 | 3.6E−05 | 9.3E−07 | 5.5E−05 |
| 47 | IL6R-BP107/IL6R-L | P238D/H268E | 1.5E−09 | 1.2E−05 | 5.2E−05 | 9.3E−07 | 6.3E−05 |
| 48 | IL6R-BP110/IL6R-L | F238D/H266N | 7.3E−09 | 1.7E−05 | 4.7E−05 | 1.5E−06 | 6.4E−05 |
| 49 | IL6R-BP112/IL6R-L | P238D/P271G | 6.5E−09 | 3.5E−06 | 3.5E−05 | 3.2E−07 | 6.9E−05 |
| 50 | IL6R-2B128/IL6R-L | F238D/Y296D | 1.3E−08 | 2.6E−05 | 3.4E−05 | 1.4E−06 | 7.2E−05 |

TABLE 10-continued

| | | | | | | | |
|---|---|---|---|---|---|---|---|
| 51 | IL6R-2E169/IL6R-L | P238D/V3231 | 2.5E−08 | 1.9E−05 | 4.6E−05 | 1.2E−06 | 7.5E−05 |
| 52 | IL6R-2B171/L6R-L | P238D/V323L | 9.1E−09 | 1.6E−05 | 3.4E−05 | 1.1E−06 | 5.7E−05 |
| 53 | IL6R-2B172/L6R-L | F238D/V323M | 3.0E−09 | 6.1E−06 | 2.1E−05 | 7.7E−07 | 4.8E−05 |
| 54 | IL6R-BP136/IL6R-L | P238D/K326A | 6.6E−09 | 9.1E−06 | 3.8E−05 | 8.0E−07 | 6.9E−05 |
| 55 | IL6R-BP117/IL6R-L | P238D/K326D | 4.1E−09 | 9.2E−06 | 4.1E−05 | 8.0E−07 | 6.7E−05 |
| 56 | IL6R-BP120/IL6R-L | F238D/K326E | 6.6E−09 | 9.6E−06 | 6.5E−05 | 1.0E−06 | 7.9E−05 |
| 57 | IL6R-BP126/IL6R-L | P238D/K326L | 7.4E−09 | 1.1E−05 | 4.5E−05 | 1.4E−06 | 5.6E−05 |
| 58 | IL6R-BP119/IL6R-L | P238D/K326M | 7.0E−09 | 9.9E−06 | 4.5E−05 | 1.1E−06 | 5.6E−05 |
| 59 | IL6R-BP142/IL6R-L | P238D/K326N | 5.3E−09 | 1.6E−05 | 9.3E−05 | 1.2E−06 | 1.1E−04 |
| 60 | IL6R-BP121/IL6R-L | P238D/K3260 | 1.1E−08 | 1.3E−05 | 4.4E−05 | 1.1E−06 | 5.2E−05 |
| 61 | IL6R-BP118/IL6R-L | F238D/K326S | 1.2E−08 | 1.5E−05 | 4.6E−05 | 1.2E−06 | 5.6E−05 |
| 62 | IL6R-BP116/IL6R-L | P238D/K326T | 2.6E−09 | 1.5E−05 | 5.4E−05 | 1.1E−06 | 7.2E−05 |
| 63 | IL6R-BP911/IL6R-L | P2380/4330K | 4.9E−08 | 1.6E−05 | 3.7E−05 | 8.9E−07 | 5.8E−05 |
| 64 | IL6R-BP07B/IL6R-L | P238D/A330M | 8.2E−09 | 1.5E−05 | 4.5E−05 | 1.1E−06 | 7.8E−05 |
| 65 | IL6R-BP912/IL6R-L | P238D/A330R | 3.8E−08 | 2.6E−05 | 3.8E−05 | 1.5E−06 | 7.8E−05 |

| SEQ ID NO | KDIIaR)/ KD(IIb) | KD(IIaH)/ KD(IIb) | KD (IIb) OF PARENT POLYPEPTIDE/ KD (IIb) OF ALTERED POLYPEPTIDE | KD VALUE FOR THE STRONGER OF THE BINDING ACTIVITIES OF A VARIANT TO FcgRIIaR AND FcgRIIaH/ KD VALUE FOR THE STRONGER OF THE BINDING ACTIVITIES OF THE PARENT POLYPEPTIDE TO FcgRIIaR AND FcgRIIaH |
|---|---|---|---|---|
| 20 | 0.4 | 0.3 | 1.2 | 0.9 |
| 40 | 0.3 | 0.2 | 1.0 | 1.0 |
| 41 | 13.0 | 33.9 | 2.6 | 19.9 |
| 42 | 20.4 | 92.3 | 3.3 | 24.7 |
| 43 | 7.3 | 42.6 | 2.9 | 10.2 |
| 44 | 9.4 | 67.6 | 3.4 | 11.0 |
| 45 | 9.0 | 71.5 | 2.5 | 14.4 |
| 46 | 11.6 | 38.7 | 3.3 | 14.0 |
| 47 | 12.7 | 56.1 | 3.3 | 15.3 |
| 48 | 11.7 | 31.5 | 2.1 | 22.6 |
| 49 | 11.0 | 109.4 | 9.7 | 4.6 |
| 50 | 17.7 | 23.6 | 2.1 | 33.1 |
| 51 | 15.8 | 40.7 | 2.6 | 24.3 |
| 52 | 15.0 | 31.3 | 2.9 | 20.8 |
| 53 | 8.0 | 27.3 | 4.0 | 8.0 |
| 54 | 11.4 | 47.8 | 3.9 | 11.8 |
| 55 | 11.6 | 51.4 | 3.9 | 12.0 |
| 56 | 9.3 | 63.1 | 3.0 | 12.5 |
| 57 | 7.8 | 31.7 | 2.2 | 14.4 |
| 58 | 8.7 | 38.5 | 2.7 | 12.8 |
| 59 | 15.5 | 79.5 | 2.6 | 23.5 |
| 60 | 11.7 | 40.4 | 2.8 | 16.6 |
| 61 | 13.2 | 40.0 | 2.7 | 19.7 |
| 62 | 13.3 | 48.2 | 2.8 | 19.4 |
| 63 | 18.5 | 41.7 | 3.5 | 21.3 |
| 64 | 13.4 | 41.3 | 2.8 | 19.0 |
| 65 | 17.8 | 25.9 | 2.1 | 34.0 |

Figure 14:
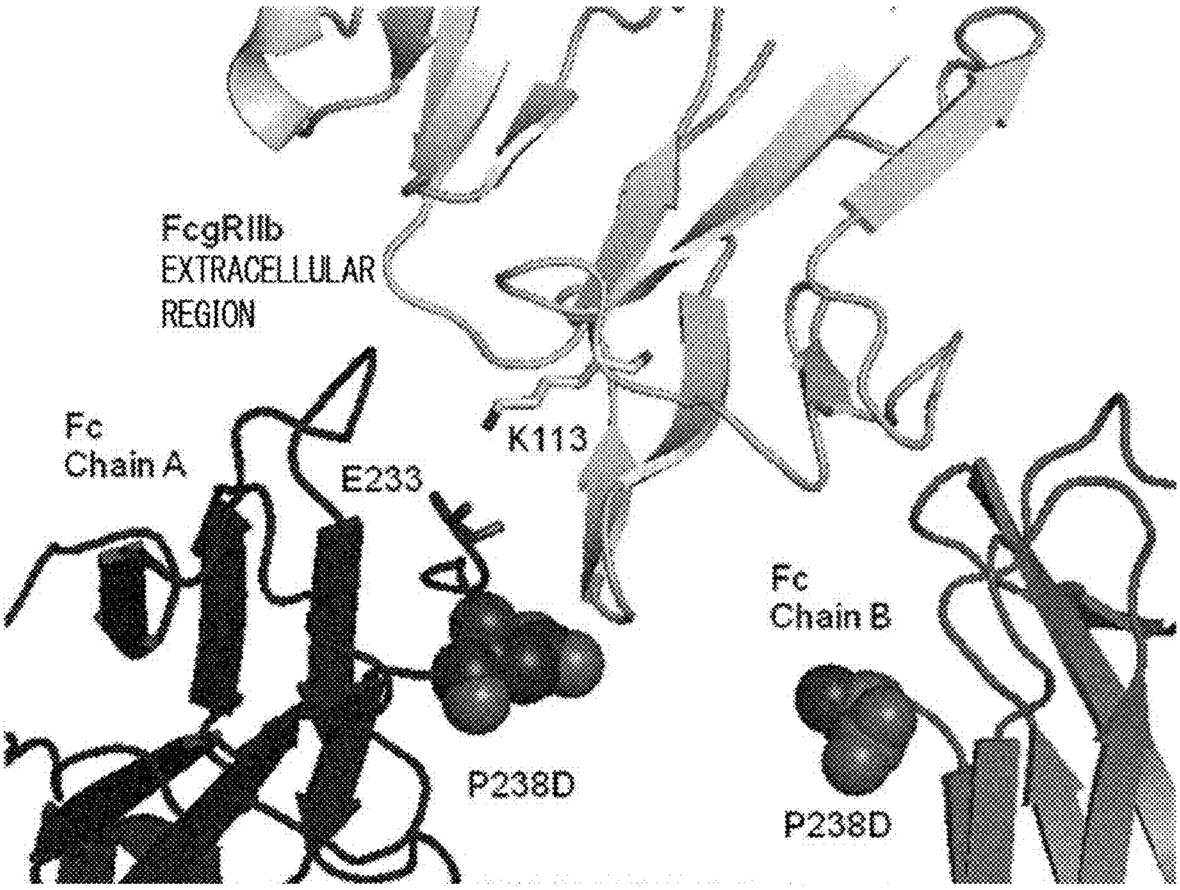
FIG. 14 shows Glu at position 233 (EU numbering) in Fc Chain A and the surrounding residues in the extracellular region of FcγRIIb in the crystal structure of the Fc(P238D)/FcγRIIb extracellular region complex.

With regard to the promising variants among the obtained combination variants, the factors leading to their effects were studied using the crystal structure. FIG. 14 shows the crystal structure of the Fc(P238D)/FcγRIIb extracellular region complex. In this figure, the H chain positioned on the left side is Fc Chain A, and the H chain positioned on the right side is Fc Chain B. Here, one can see that the site at position 233 (EU numbering) in Fc Chain A is located near Lys at position 113 (EU numbering) of FcγRIIb. However, in this crystal structure, the E233 side chain is in a condition of considerably high mobility, and its electron density is not well observed. Therefore, the alteration produced by substituting Glu at position 233 (EU numbering) with Asp leads to decrease in the degree of freedom of the side chain since the side chain becomes one carbon shorter. As a result, the entropy loss when forming an interaction with Lys at position 113 (EU numbering) of FcγRIIb may be decreased, and consequently this is speculated to contribute to improvement of binding free energy.

Figure 15:
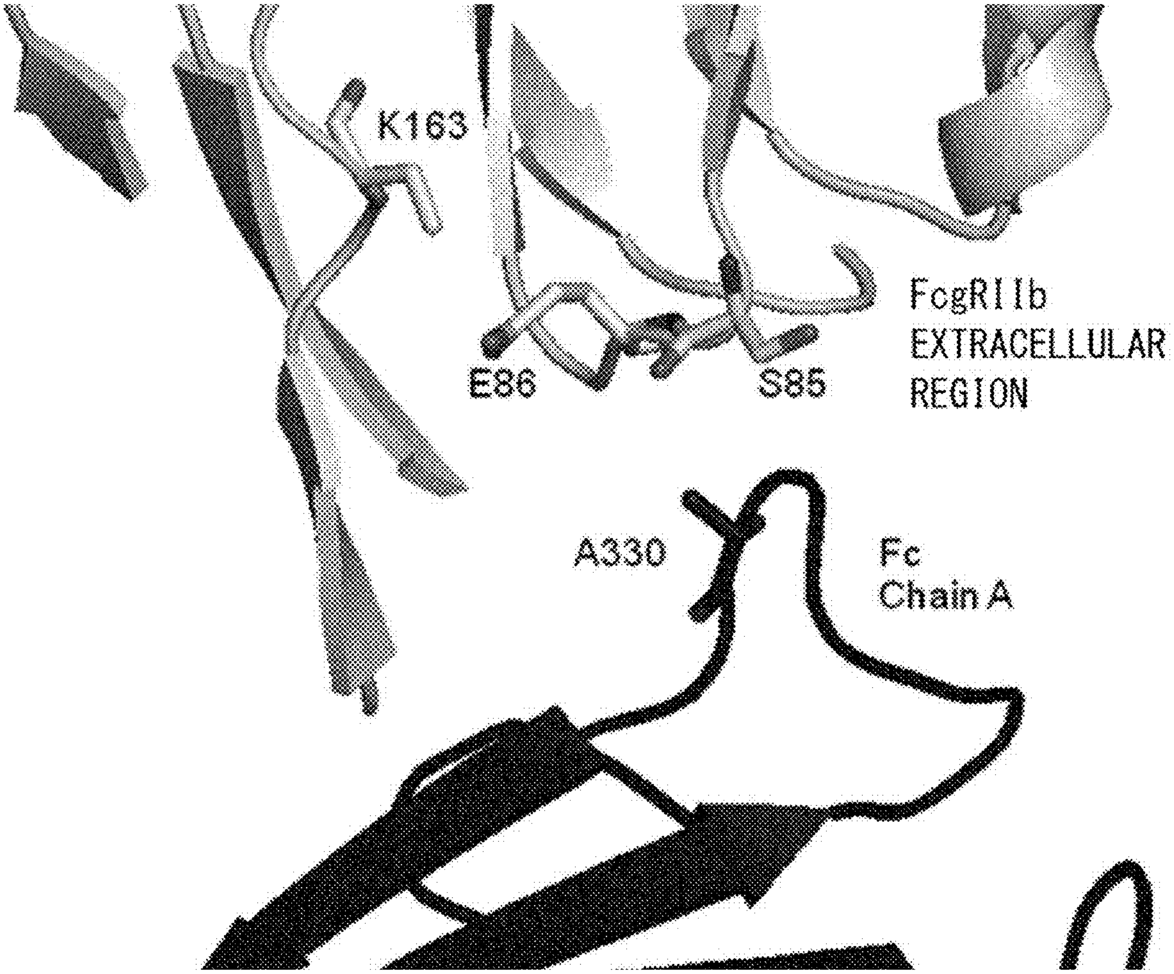
FIG. 15 shows Ala at position 330 (EU numbering) in Fc Chain A and the surrounding residues in the extracellular region of FcγRIIb in the crystal structure of the Fc(P238D)/FcγRIIb extracellular region complex.

Similarly, FIG. 15 shows the environment near the site at position 330 (EU numbering) in the structure of the Fc(P238D)/FcγRIIb extracellular region complex. This figure shows that the environment around the site at position 330 (EU numbering) of Fc Chain A of Fc(P238D) is a hydrophilic environment composed of Ser at position 85, Glu at position 86, Lys at position 163, and such (EU numbering) of FcγRIIb. Therefore, the alteration produced by substituting Ala at position 330 (EU numbering) with Lys or Arg is speculated to contribute to strengthening the interaction with Ser at position 85 (EU numbering) or Glu at position 86 (EU numbering) in FcγRIIb.

Figure 16:
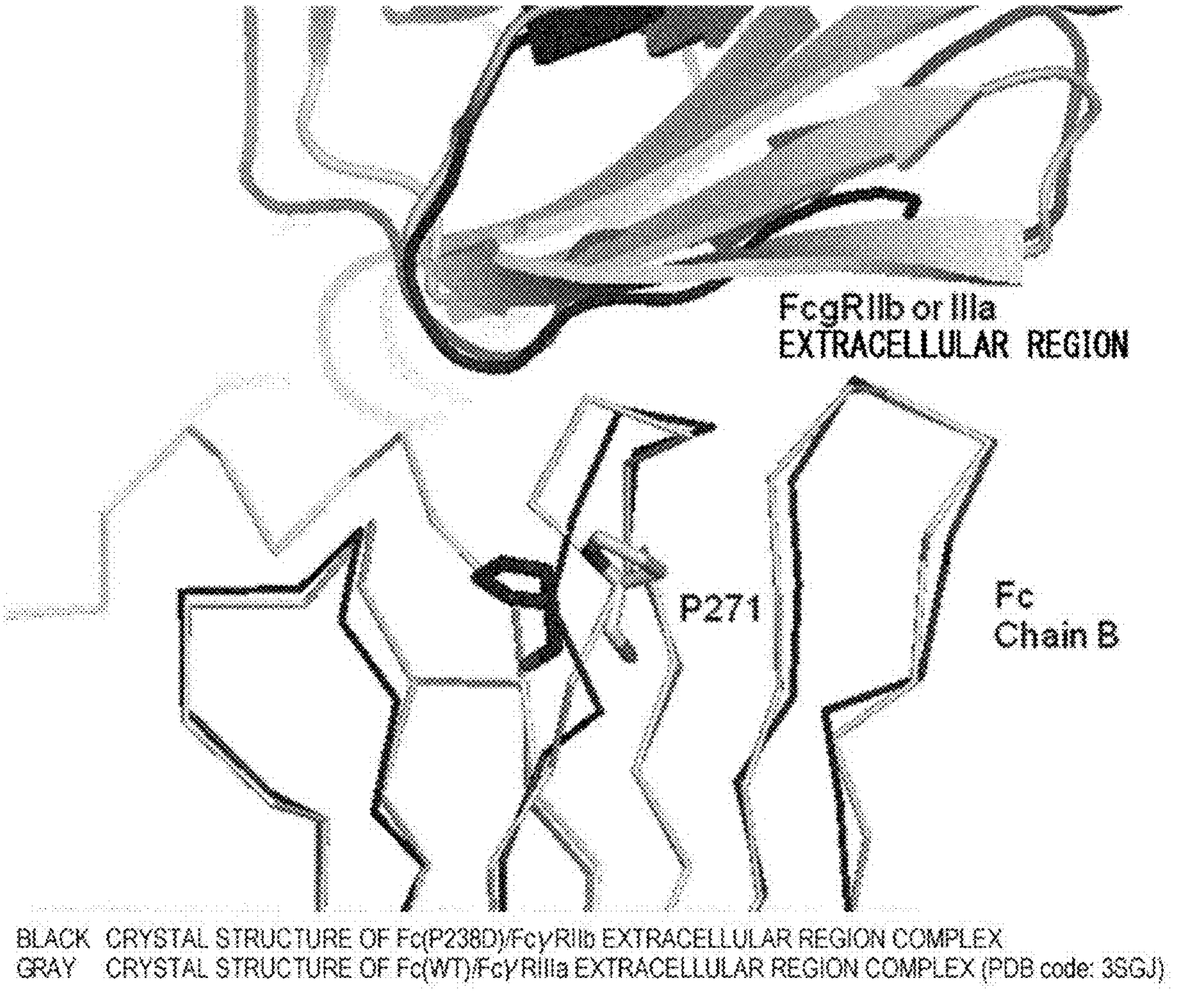
FIG. 16 shows the structures of Pro at position 271 (EU numbering) of Fc Chain B after superimposing the crystal structures of the Fc(P238D)/FcγRIIb extracellular region complex and the Fc(WT)/FcγRIIIa extracellular region complex by the least squares fitting based on the Ca atom pair distances with respect to Fc Chain B.

FIG. 16 depicts the structures of Pro at position 271 (EU numbering) of Fc Chain B after superimposing the crystal structures of the Fc(P238D)/FcγRIIb extracellular region complex and the Fc(WT)/FcγRIIIa extracellular region complex by the least squares fitting based on the Ca atom pair distances with respect to Fc Chain B. These two structures match well, but have different three-dimensional structures of Pro at position 271 (EU numbering). When the weak electron density around this area in the crystal structure of the Fc(P238D)/FcγRIIb extracellular region complex is also taken into consideration, it is suggested that there is possibility that Pro at position 271 (EU numbering) in Fc(P238D)/FcγRIIb causes a large strain on the structure, thus disturbing the loop structure to attain an optimal structure. Therefore, the alteration produced by substituting Pro at position 271 (EU numbering) with Gly gives flexibility to this loop structure, and is speculated to contribute to enhancement of binding by reducing the energetic barrier when allowing an optimum structure to form during interaction with FcγRIIb.

[Example 7] Examination of the Combinatorial Effect of Alterations that Enhance FcγRIIb Binding When Combined with P238D Of the alterations obtained in Examples 4 and 6, those that enhanced FcγRIIb binding or maintained FcγRIIb binding and showed effects of suppressing binding to other FcγRs were combined with each other, and their effects were examined.

Particularly good alterations were selected from Tables 6 and 9, and they were combined and introduced into the antibody H chain IL6R-BF648 in a similar manner to the method of Example 6. IL6R-L was utilized as the common antibody L chain for all of the antibodies, the antibodies were expressed and purified according to the method of Reference Example 1, and binding to each of the FcγRs (FcγRIa, FcγRIIa H type, FcγRIIa R type, FcγRIIb, and FcγRIIIa V type) was comprehensively evaluated by the method of Reference Example 2.

Relative binding activities were calculated for the results of analyzing interactions with the respective FcγRs according to the following method. The value for the amount of binding of each variant to each FcγR was divided by the value for the amount of binding of the pre-altered control antibody (IL6R-BF648/IL6R-L with substitution of Pro at position 238 (EU numbering) with Asp to each FcγR, and multiplied by 100; and then the value was used as the relative binding activity value of each variant to each FcγR. The horizontal axis shows the relative binding activity value of each variant to FcγRIIb, and the vertical axis shows the relative binding activity value of each variant to FcγRIIa type R (Table 11).

In the table, SEQ ID NO refers to the SEQ ID NO of the H chain of the evaluated variant, and alteration refers to the alteration introduced into IL6R-B3 (SEQ ID NO: 40). The template used for producing IL6R-B3, IL6R-G1d/IL6R-L, is indicated with an asterisk (*).

TABLE 11

| SEQ ID NO | VARIANT NAME | ALTERNATION | RELATIVE FcgRIa-BINDING ACTIVITY | RELATIVE FcgRIIaR-BINDING ACTIVITY | RELATIVE FcgRIIaH-BINDING ACTIVITY | RELATIVE FegRIIb-BINDING ACTIVITY | RELATIVE FegRIIIaV-BINDING ACTIVITY |
|---|---|---|---|---|---|---|---|
| 20 | IL6R-G1d/IL6R-L | * | 140 | 650 | 1670 | 62 | 3348 |
| 40 | IL6R-B3/IL6R-L | | 145 | 625 | 1601 | 58 | 3264 |
| 41 | IL6R-BF548/IL6R-L | P238D | 100 | 100 | 100 | 100 | 100 |
| 66 | IL6R-2B253/IL6R-L | B233D/P238D/V323M | 155 | 288 | 207 | 156 | 126 |
| 67 | ILGR-2B261/IL6R-L | B233D/P238D/Y296D | 100 | 94 | 81 | 115 | 87 |
| 68 | IL6R-BP082/IL6R-L | B233D/P238D/A330K | 74 | 125 | 106 | 136 | 87 |
| 69 | IL6R-BF083/IL6R-L | B233D/P238D/A330K | 50 | 87 | 81 | 122 | 107 |
| 70 | IL6R-BF084/IL6R-L | B233D/P238D/A330K | 109 | 203 | 162 | 141 | 105 |
| 71 | IL6R-BF065/IL6R-L | G237D/P233D/A330K | 19 | 279 | 158 | 152 | 104 |
| 72 | IL6R-BF086/IL6R-L | P236D/K326A/A330K | 72 | 155 | 116 | 137 | 123 |
| 73 | IL6R-BF087/IL6R-L | L234Y/P238D/A330K | 33 | 153 | 179 | 137 | 158 |
| 74 | IL6R-BF088/IL6R-L | G237D/P238D/K326A/A330K | 25 | 377 | 156 | 161 | 122 |
| 75 | IL6R-BF089/IL6R-L | L234Y/P238D/K326A/A330K | 49 | 222 | 156 | 147 | 136 |
| 76 | IL6R-BF129/IL6R-L | B233D/P238D/Y296D/A330K | 68 | 111 | 58 | 138 | 85 |
| 77 | IL6R-BF130/IL6R-L | B233D/P238D/Y323M/A330K | 104 | 272 | 224 | 160 | 115 |
| 78 | IL6R-BF131/IL6R-L | B233D/G237D/P238D/A330K | 83 | 364 | 253 | 160 | 118 |
| 79 | IL6R-BF192/IL6R-L | B233D/P238D/K326A/A330K | 91 | 181 | 130 | 150 | 120 |
| 80 | IL6R-BF133/IL6R-L | B233D/L234Y/P233D/A330K | 41 | 174 | 151 | 197 | 114 |
| 81 | IL6R-BF148/IL6R-L | L234Y/P238D/K325A | 85 | 238 | 143 | 133 | 114 |
| 82 | IL6R-BF144/IL6R-L | G237D/P233D/K326A | 64 | 204 | 108 | 121 | 128 |
| 83 | IL6R-BF145/IL6R-L | L234Y/G237D/P238D | 41 | 350 | 224 | 152 | 153 |
| 84 | IL6R-BF146/IL6R-L | L234Y/G237D/P238D/K326A | 50 | 445 | 203 | 156 | 180 |
| 85 | IL6R-BF147/IL6R-L | L234Y/G287D/P238D/K326A/A330K | 24 | 650 | 552 | 177 | 209 |
| 86 | IL6R-BF148/IL6R-L | B233D/L234Y/G237D/P238D/K326A/A330K | 38 | 603 | 462 | 176 | 227 |
| 87 | IL6R-BF149/IL6R-L | B233D/L234Y/G237D/P238D/K326A/A330K | 29 | 539 | 401 | 173 | 186 |
| 88 | IL6R-BF150/IL6R-L | L234Y/G237D/P238D/K326A/A330R | 30 | 757 | 770 | 183 | 204 |
| 89 | IL6R-BF151/IL6R-L | B233D/L234Y/G237D/P238D/K326A/A330R | 39 | 705 | 621 | 180 | 221 |
| 90 | IL6R-BF152/IL6R-L | B233D/L234Y/G237D/P238D/Y296D/K326A/ A330K | 34 | 638 | 548 | 178 | 146 |
| 91 | IL6R-BF175/IL6R-L | B233D/P238D/K326D/A330K | 102 | 201 | 128 | 147 | 131 |
| 92 | IL6R-BF177/IL6R-L | B233D//L294Y/G237D/P238D/P271G/K326D/ A330K | 57 | 691 | 408 | 177 | 186 |
| 93 | IL6R-BF178/IL6R-L | B233D/G237D/P238D/P271G/A330K | 51 | 653 | 259 | 179 | 110 |
| 94 | IL6R-BF179/IL6R-L | G237D/P238D/P271G/K326A/A330K | 39 | 570 | 226 | 177 | 125 |
| 95 | IL6R-BF180/IL6R-L | G237D/P238D/P271G/A330K | 29 | 502 | 203 | 178 | 100 |
| 96 | IL6R-BF161/IL6R-L | B233D/P238D/P271G/K326A/A330K | 108 | 362 | 150 | 170 | 122 |
| 97 | IL6R-BF182/IL6R-L | B233D/P238D/P271G/Y296D/A330K | 95 | 413 | 159 | 173 | 120 |
| 98 | IL6R-BF138/IL6R-L | B233D/L234Y/P233D/P271G/K326A/A330K | 83 | 423 | 181 | 164 | 113 |
| 99 | IL6R-BF184/IL6R-L | B233D/P238D/P271G/A330K | 96 | 435 | 131 | 171 | 105 |
| 100 | IL6R-BF185/IL6R-L | B233D/L234Y/G237D/P238D/P271G/K326A/ A333K | 47 | 670 | 446 | 178 | 191 |
| 101 | IL6R-BF186/IL6R-L | B233D/L234Y/G237D/P238D/P271G/Y236D/ K326A/A330K | 43 | 514 | 368 | 175 | 143 |
| 102 | IL6R-BF187/IL6R-L | L234Y/P238D/P271G/K326A/A330K | 66 | 357 | 205 | 157 | 124 |
| 103 | IL6R-BF188/IL6R-L | B233D/G237D/P238D/H268D/P271G/A330K | 74 | 636 | 234 | 179 | 121 |

TABLE 11-continued

| SEQ ID NO | VARIANT NAME | ALTERNATION | RELATIVE FcgRIa-BINDING ACTIVITY | RELATIVE FcgRIIaR-BINDING ACTIVITY | RELATIVE FcgRIIaH-BINDING ACTIVITY | RELATIVE FegRIIb-BINDING ACTIVITY | RELATIVE FegRIIIaV-BINDING ACTIVITY |
|---|---|---|---|---|---|---|---|
| 104 | IL6R-BF189/IL6R-L | G237D/P288D/H208D/P271G/K326A/A330K | 56 | 557 | 183 | 177 | 141 |
| 105 | IL6R-BF190/IL6R-L | G237D/P238D/H268D/P271G/A330K | 50 | 015 | 224 | 181 | 155 |
| 106 | IL6R-BF191/IL6R-L | B233D/P298D/H268D/P271G/K326A/A330K | 125 | 382 | 145 | 170 | 142 |
| 107 | IL6R-BF192/IL6R-L | B233D/P238D/H268D/P271G/Y236D/A330K | 109 | 406 | 122 | 172 | 118 |
| 108 | IL6R-BF193/IL6R-L | B233D/P238D/H268D/P271G/A330K | 113 | 449 | 154 | 173 | 135 |
| 109 | IL6R-BF194/IL6R-L | B233D/L234Y/G237D/P238D/H268D/P271G/K326A/A330K | 69 | 672 | 385 | 170 | 249 |
| 110 | IL6R-BF195/IL6R-L | B233D/L234Y/G237D/P238D/H268D/P271G/Y296D/K326A/A330K | 68 | 651 | 344 | 181 | 221 |
| 111 | IL6R-BF196/IL6R-L | L234Y/P238D/H268D/P271G/K326A/A330K | 89 | 402 | 185 | 157 | 137 |
| 112 | IL6R-BF197/IL6R-L | B233D/L234Y/G237D/P238D/H268D/P271G/Y296D/K326A/A330K | 71 | 542 | 254 | 179 | 205 |
| 113 | IL6R-BF198/IL6R-L | B233D/L234Y/P233D/H268D/P271G/K326A/A330K | 104 | 449 | 188 | 164 | 157 |
| 114 | IL6R-BF199/IL6R-L | B233D/P238D/K326D/A330K | 112 | 172 | 116 | 144 | 108 |
| 115 | IL6R-BF200/IL6R-L | B233D/L234Y/G237D/P238D/P271G/K326D/A330R | 90 | 754 | 517 | 188 | 154 |
| 116 | IL6R-BF201/IL6R-L | B233D/G297D/P238D/P271G/A330R | 57 | 636 | 359 | 186 | 121 |
| 117 | IL6R-BF202/IL6R-L | G237D/P238D/P271G/K326A/A330R | 43 | 615 | 265 | 185 | 108 |
| 118 | IL6R-BF203/IL6R-L | G237D/P233D/P271G/A330R | 35 | 637 | 255 | 185 | 86 |
| 119 | IL6R-BF204/IL6R-L | B233D/P238D/P271G/K326A/A330R | 110 | 301 | 127 | 165 | 121 |
| 120 | IL6R-BF205/IL6R-L | B233D/P238D/P271G/Y296D/A300R | 87 | 335 | 108 | 167 | 93 |
| 121 | IL6R-BF206/IL6R-L | B233D/P236D/P271G/A330R | 101 | 362 | 123 | 166 | 92 |
| 122 | IL6R-BF207/IL6R-L | B233D/P238D/A330R | 74 | 103 | 103 | 124 | 97 |
| 123 | IL6R-BF208/IL6R-L | B233D/G237D/P238D/H268D/P271G/A330R | 81 | 690 | 310 | 188 | 118 |
| 124 | IL6R-BF209/IL6R-L | G237D/P238D/H268D/P271G/K326A/A330R | 68 | 625 | 257 | 186 | 153 |
| 125 | IL6R-BF210/IL6R-L | G237D/P238D/H268D/P271G/A330R | 57 | 651 | 278 | 187 | 135 |
| 126 | IL6R-BF211/IL6R-L | B233D/P238D/H268D/P271G/K326A/A330R | 126 | 312 | 111 | 165 | 87 |
| 127 | IL6R-BF212/IL6R-L | B233D/P238D/H268D/P271G/Y296D/A330R | 117 | 353 | 135 | 173 | 122 |
| 128 | IL6R-BF218/IL6R-L | B233D/P238D/H268D/P271G/A330R | 118 | 382 | 123 | 168 | 100 |
| 129 | IL6R-BF214/IL6R-L | B233D/L234Y/G237D/P238D/Y296D/K326A/A330K | 36 | 498 | 255 | 174 | 165 |

The results of measuring KD values of the variants shown in Table 11 for FcγRIa, FcγRIIaR, FcγRIIaH, FcγRIIb, and FcγRIIIa type V by the method of Reference Example 2 are summarized in Table 12. In the table, SEQ ID NO refers to the SEQ ID NO of the H chain of the evaluated variant, and alteration refers to the alteration introduced into IL6R-B3 (SEQ ID NO: 40). The template used for producing IL6R-B3, IL6R-Gld/IL6R-L, is indicated with an asterisk (*). Furthermore, KD(IIaR)/KD(IIb) and KD(IIaH)/KD(IIb) in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD(IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Table 12. Here, parent polypeptide refers to the variant which has IL6R-B3 (SEQ ID NO: 40) as the H chain. It was determined that, due to weak binding of FcγR to IgG, it was impossible to accurately analyze some of the binding by kinetic analysis, and thus the cells outlined in heavy lines in Table 12 show values calculated by using Equation 2 of Reference Example 2.

$$KD = C \bullet R_{max}/(R_{eq} - RI) - C \quad \text{[Equation 2]}$$

Table 12 shows that in comparison with IL6R-B3, all variants showed improvement of affinity for FcγRIIb, and the range of improvement was 3.0 fold to 99.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, those values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb of the parent polypeptide IL6R-B3/IL6R-L were 0.3 and 0.2, respectively, all variants in Table 12 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 0.7 to 29.9 for the variants obtained this time, one may say that binding by the stronger of the FcγRIIaR- and FcγRIIaH-binding activities of the variants obtained this time was nearly equivalent or decreased compared with that of the parent polypeptide. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity for FcγRIa and FcγRIIIaV.

TABLE 12

| SEQ ID NO | VARIANT NAME | ALTERATION | KD AGAINST FcRIa (mol/L) | KD AGAINST FcRIIaR (mol/L) | KD AGAINST FcRIIaH (mol/L) | KD AGAINST FcRIIb (mol/L) | KD AGAINST FcIIIaV (mol/L) | KD(IIaR)/ KD(IIb) | KD(IIaH)/ KD(IIb) | KD (IIb) OF PARENT POLYPEPTIDE/ K0 (IIB) OF ALTERED POLYPEPTIDE | KD VALUE FOR THE STRONGER OF THE BINDING ACTIVITIES OF A VARIANT TO FcgRIIaR AND FcgRIIaH/ KD VALUE FOR THE STRONGER OF THE BINDING ACTIVITIES OF THE PARENT POLY-PEPTIDE TO FcgRIIaR AND FcgRIIaH |
|---|---|---|---|---|---|---|---|---|---|---|---|
| 20 | IL6R-G1d/IL6R-L | * | 3.2E−10 | 1.0E−06 | 6.7E−07 | 2.6E−05 | 3.5E−08 | 0.4 | 0.3 | 12 | 0.9 |
| 40 | IL6R-B3/IL6R-L | | 4.2E−10 | 1.1E−06 | 7.7E−07 | 3.1E−06 | 3.3E−07 | 0.3 | 0.2 | 10 | 1.0 |
| 41 | IL6R-BF648/IL6R-L | P238D | 1.1E−08 | 1.5E−05 | 4.0E−05 | 1.2E−06 | 7.1E−05 | 13.0 | 339 | 28 | 13.3 |
| 66 | IL6R-2B253/IL6R-L | B233D/P238D/V323M | 1.4E−09 | 5.0E−08 | 1.3E−05 | 4.3E−07 | 5.0E−06 | 11.5 | 301 | 7.2 | 6.5 |
| 67 | IL6R-2B251/IL6R-L | B233D/P238D/Y296D | 9.0E−09 | 2.2E−05 | 3.3E−05 | 1.0E−05 | 7.3E−05 | 21.0 | 32.4 | 3.0 | 28.8 |
| 68 | IL6R-BF082/IL6R-L | B233D/P238D/A330K | 1.8E−08 | 1.2E−05 | 3.7E−05 | 5.4E−07 | 8.1E−05 | 22.8 | 69.0 | 5.8 | 15.8 |
| 69 | IL6R-BF083/IL6R-L | 9238D/Y296D/A330K | 3.8E−08 | 2.3E−05 | 4.4E−05 | 7.9E−07 | 6.6E−05 | 29.0 | 55.5 | 3.9 | 29.9 |
| 70 | IL6R-BF084/IL6R-L | 9238D/Y325M/A330K | 7.0E−09 | 7.2E−06 | 2.4E−05 | 5.0E−07 | 6.7E−06 | 14.8 | 47.6 | 6.1 | 8.4 |
| 71 | IL6R-BF085/IL6R-L | G237D/P238D/A330K | 2.9E−07 | 4.2E−06 | 2.4E−05 | 3.2E−07 | 6.8E−05 | 13.1 | 74.5 | 9.6 | 5.5 |
| 72 | IL6R-BF085/IL6R-L | P238D/K326A/A330K | 2.7E−08 | 9.7E−08 | 3.4E−05 | 5.7E−07 | 5.7E−05 | 17.1 | 59.9 | 5.4 | 12.5 |
| 73 | IL6R-BF067/IL6R-L | L234Y/P236D/A330K | 3.8E−08 | 9.7E−06 | 2.1E−05 | 6.1E−07 | 4.4E−05 | 16.0 | 34.7 | 5.1 | 12.5 |
| 74 | IL6R-BF088/IL6R-L | G287D/P238D/K326A/A330K | 3.9E−07 | 2.9E−06 | 2.3E−05 | 2.2E−07 | 5.7E−05 | 13.3 | 106.5 | 14.3 | 3.7 |
| 75 | IL6R-BF063/IL6R-L | L234Y/P236D/K326A/A330K | 6.3E−08 | 6.4E−08 | 2.0E−05 | 3.9E−07 | 5.1E−05 | 16.6 | 51.9 | 6.0 | 8.3 |
| 76 | IL6R-BF129/IL6R-L | B233D/P238D/Y296D/A330K | 2.5E−06 | 1.5E−05 | 4.0E−05 | 5.2E−07 | 7.5E−05 | 29.8 | 77.5 | 6.0 | 19.5 |
| 77 | IL6R-BF130/IL6R-L | B233D/P238D/V323M/A330K | 1.8E−09 | 5.3E−06 | 2.5E−05 | 3.0E−07 | 7.1E−05 | 17.5 | 85.5 | 10.2 | 6.8 |
| 78 | IL6R-BF131/IL6R-L | B233D/G237D/P238D/A330K | 1.2E−07 | 3.1E−06 | 1.4E−05 | 2.5E−07 | 5.8E−05 | 12.5 | 56.9 | 12.6 | 4.0 |
| 79 | IL6R-BF132/IL6R-L | B233D/P236D/K326A/A330K | 1.5E−00 | 8.0E−06 | 3.0E−05 | 3.7E−07 | 5.0E−05 | 21.5 | 51.1 | 8.4 | 10.3 |
| 80 | IL6R-BF133/IL6R-L | B233D/L234Y/P238D/A330K | 1.3E−07 | 8.5E−06 | 2.6E−05 | 5.6E−07 | 6.2E−05 | 15.5 | 46.8 | 5.6 | 11.2 |
| 81 | IL6R-BF143/IL6R-L | L234Y/P238D/K326A | 1.6E−06 | 5.7E−06 | 2.7E−05 | 5.7E−07 | 6.2E−05 | 10.0 | 47.1 | 5.4 | 7.5 |
| 82 | IL6R-BF144/IL6R-L | G237D/P238D/K326A | 3.7E−08 | 6.9E−06 | 3.6E−05 | 7.9E−07 | 5.5E−05 | 8.7 | 45.8 | 3.9 | 8.9 |
| 83 | IL6R-BF145/IL6R-L | L234Y/G237D/P238D | 1.2E−07 | 3.4E−06 | 1.7E−05 | 3.4E−07 | 4.5E−05 | 8.8 | 49.9 | 9.1 | 4.4 |
| 84 | IL6R-BF146/IL6R-L | L234Y/G237D/P238D/K326A | 7.4E−08 | 2.1E−06 | 1.0E−05 | 2.3E−07 | 3.8E−05 | 9.3 | 80.0 | 13.7 | 2.7 |
| 85 | IL6R-BF147/IL6R-L | L234Y/G237D/P238D/K326A/A330K | 1.4E−07 | 8.3E−07 | 5.1E−06 | 6.6E−08 | 3.3E−05 | 13.6 | 77.7 | 47.1 | 1.2 |
| 86 | IL6R-BF148/IL6R-L | B233D/L234Y/G237D/P238D/K326A/A330K | 5.9E−08 | 1.1E−06 | 7.0E−06 | 7.5E−08 | 3.0E−05 | 14.5 | 33.8 | 41.4 | 1.4 |
| 87 | IL6R-BF149/IL6R-L | B233D/L234Y/G237D/P238D/ Y296D/K326A/A330K | 1.2E−07 | 1.4E−0 | 8.4E−05 | 9.3E−08 | 3.7E−05 | 15.0 | 89.9 | 33.1 | 1.8 |
| 88 | IL6R-BF150/IL6R-L | L234Y/G237D/P238D/K326A/A330R | 3.2E−07 | 5.5E−07 | 3.4E−08 | 3.1E−08 | 3.4E−05 | 17.7 | 109.0 | 99.0 | 0.7 |
| 89 | IL6R-BF151/IL6R-L | B233D/L234Y/G237D/P238D/K326A/A330K | 8.4E−00 | 6.7E−07 | 4.7E−08 | 4.0E−08 | 3.1E−05 | 16.9 | 117.0 | 77.4 | 0.9 |
| 90 | IL6R-BF152/IL6R-L | B233D/L234Y/G237D/ P238D/Y296D/K326A/A330R | 7.3E−08 | 8.1E−07 | 5.5E−06 | 4.1E−08 | 4.8E−05 | 19.5 | 135.9 | 75.0 | 1.0 |
| 91 | IL6R-BF176/IL6R-L | B233D/P238D/K326D/A330K | 7.3E−09 | 6.9E−05 | 3.6E−07 | 3.6E−07 | 5.4E−05 | 19.1 | 83.1 | 8.6 | 8.9 |
| 92 | IL6R-BF177/IL6R-L | B233D/L234Y/G237D/ P238D/P271G/K326A/A330K | 3.3E−08 | 7.1E−07 | 8.2E−06 | 5.2E−09 | 3.7E−05 | 13.8 | 159.2 | 60.0 | 0.9 |
| 93 | IL6R-BF178/IL6R-L | B233D/G237D/P238D/P271G/A330K | 4.3E−08 | 9.3E−07 | 1.4E−05 | 5.1E−09 | 6.4E−05 | 18.1 | 272.4 | 50.1 | 1.2 |
| 94 | IL6R-BF179/IL6R-L | G237D/P238D/P271G/K326A/A330K | 6.4E−08 | 1.4E−08 | 1.6E−05 | 8.4E−08 | 5.6E−05 | 16.7 | 180.8 | 36.9 | 1.8 |
| 95 | IL6R-BF180/IL6R-L | G237D/P238D/P271G/A330K | 8.8E−08 | 1.2E−06 | 1.8E−05 | 6.2E−08 | 7.0E−06 | 18.6 | 280.8 | 49.9 | 1.5 |
| 96 | IL6R-BF181/IL6R-L | B233D/P298D/P271G/K326A/A330K | 7.5E−09 | 3.2E−06 | 2.6E−05 | 1.6E−07 | 5.7E−05 | 20.3 | 162.5 | 19.3 | 4.2 |
| 97 | IL6R-BF182/IL6R-L | B233D/P298D/P271G/Y296D/A330K | 1.0E−08 | 2.6E−06 | 2.3E−05 | 1.1E−07 | 5.8E−05 | 23.5 | 256.9 | 28.3 | 3.3 |
| 98 | IL6R-BF185/IL6R-L | B233D/L234Y/P238D/P271G/K326A/A330K | 1.7E−08 | 2.6E−05 | 1.5E−05 | 2.4E−07 | 5.6E−05 | 10.7 | 62.5 | 12.9 | 3.3 |

TABLE 12-continued

| SEQ ID NO | VARIANT NAME | ALTERATION | KD AGAINST FcRIa (mol/L) | KD AGAINST FcRIIaR (mol/L) | KD AGAINST FcRIIaH (mol/L) | KD AGAINST FcRIIb (mol/L) | KD AGAINST FcIIIaV (mol/L) | KD(IIaR)/ KD(IIb) | KD(IIaH)/ KD(IIb) | KD (IIb) OF PARENT POLYPEPTIDE/ K0 (IIB) OF ALTERED POLYPEPTIDE | KD VALUE FOR THE STRONGER OF THE BINDING ACTIVITIES OF A VARIANT TO FcgRIIaR AND FcgRIIaH/ KD VALUE FOR THE STRONGER OF THE BINDING ACTIVITIES OF THE PARENT POLY-PEPTIDE TO FcgRIIaR AND FcgRIIaH |
|---|---|---|---|---|---|---|---|---|---|---|---|
| 99 | IL6R-BF184/IL6R-L | B233D/P238D/P271G/A330K | 1.1E−08 | 2.3E−05 | 3.0E−05 | 1.3E−07 | 6.6E−05 | 18.2 | 238.1 | 24.5 | 3.0 |
| 100 | IL6R-BF185/IL6R-L | B233D/L234Y/G237D/ P238D/P271G/K326A/A330K | 6.3E−08 | 8.8E−07 | 7.3E−06 | 6.9E−06 | 3.6E−05 | 12.6 | 105.2 | 44.5 | 1.1 |
| 101 | IL6R-BF186/IL6R-L | B233D/L234Y/G237D/P238D/ P271G/Y298D/K326A/A330K | 4.5E−08 | 9.5E−07 | 9.3E−06 | 6.1E−08 | 4.9E−05 | 15.9 | 152.5 | 50.7 | 1.3 |
| 102 | IL6R-BF187/IL6R-L | L234Y/P238D/P271G/K326A/A330K | 2.5E−06 | 2.8E−06 | 1.8E−05 | 2.9E−07 | 5.6E−05 | 9.7 | 62.3 | 10.7 | 3.6 |
| 103 | IL6R-BF188/IL6R-L | B233D/G237D/P238D/H268D/P271G/A330K | 2.1E−08 | 1.0E−06 | 1.6E−05 | 4.6E−08 | 5.8E−05 | 21.9 | 350.1 | 67.6 | 1.3 |
| 104 | IL6R-BF189/IL6R-L | G237D/P238D/H268D/P271D/K326A/A330K | 4.2E−09 | 1.4E−06 | 2.1E−05 | 7.4E−08 | 4.9E−05 | 18.5 | 283.8 | 41.8 | 1.8 |
| 105 | IL6R-BF190/IL6R-L | G237D/P238D/H268D/P271G/A330K | 6.3E−08 | 1.1E−06 | 1.7E−05 | 5.8E−08 | 4.5E−05 | 19.3 | 282.6 | 53.2 | 1.5 |
| 106 | IL6R-BF191/IL6R-L | B233D/P238D/H268D/P271G/K326A/A330K | 4.0E−09 | 3.0E−06 | 2.7E−05 | 1.5E−07 | 4.9E−05 | 20.3 | 184.9 | 21.2 | 3.8 |
| 107 | IL6R-BF192/IL6R-L | B233D/P238D/H268D/P271G/Y296D/A330K | 8.3E−09 | 2.8E−06 | 3.2E−05 | 1.1E−07 | 5.9E−05 | 29.1 | 283.2 | 27.3 | 3.4 |
| 108 | IL6R-BF193/IL6R-L | B233D/P238D/H268D/P271G/A330K | 6.3E−09 | 2.2E−05 | 2.5E−05 | 1.2E−07 | 5.2E−05 | 16.3 | 206.8 | 25.5 | 2.9 |
| 109 | IL6R-BF194/IL6R-L | B233D/L234Y/G237D/P238D/ H268D/P271G/K326A/A330K | 2.4E−08 | 8.2E−07 | 8.5E−06 | 5.2E−08 | 2.7E−05 | 15.8 | 163.5 | 59.4 | 1.1 |
| 110 | IL6R-BF195/IL6R-L | B233D/L234Y/G237D/ P238D/H268D/P271G/K326A/A330K | 2.3E−08 | 9.1E−07 | 1.0E−05 | 5.0E−05 | 3.1E−06 | 18.2 | 200.8 | 62.0 | 1.2 |
| 111 | IL6R-BF196/IL6R-L | L234Y/P236D/H258D/P271G/K326A/A330K | 1.4E−08 | 3.0E−08 | 1.9E−05 | 2.2E−07 | 5.1E−06 | 13.4 | 85.2 | 13.9 | 3.9 |
| 112 | IL6R-BF197/IL6R-L | B233D/L234Y/G237D/P238D/H268D/ P271G/Y296D/Y326D/A330K | 1.9E−08 | 8.8E−07 | 1.2E−05 | 5.8E−08 | 3.3E−05 | 17.1 | 208.7 | 58.7 | 1.3 |
| 113 | IL6R-BF188/IL6R-L | B233D/L234Y/P238D/H268D/ P271G/K326A/A330K | 1.1E−06 | 2.2E−06 | 2.0E−05 | 2.0E−07 | 4.4E−05 | 11.0 | 101.5 | 15.7 | 2.8 |
| 114 | IL6R-BF198/IL6R-L | B233D/P238D/K326A/A330R | 6.4E−09 | 8.6E−06 | 2.6E−05 | 4.9E−07 | 6.1E−05 | 17.5 | 53.0 | 6.3 | 11.1 |
| 115 | IL6R-BF200/IL6R-L | B233D/L234Y/G297D/P238D/ P271G/K326A/A330R | 3.3E−08 | 6.3E−07 | 4.2E−06 | 8.4E−08 | 3.8E−05 | 18.6 | 123.9 | 91.2 | 0.8 |
| 116 | IL6R-BF201/IL6R-L | E233D/G237D/P238D/P271G/A330R | 5.1E−08 | 8.4E−07 | 6.9E−06 | 4.0E−05 | 5.2E−05 | 21.0 | 172.1 | 77.1 | 1.1 |
| 117 | IL6R-BF202/IL6R-L | G237D/P238D/P271G/K326A/A330R | 8.5E−08 | 1.2E−08 | 8.2E−06 | 6.4E−08 | 5.9E−05 | 19.2 | 144.0 | 48.4 | 1.6 |
| 118 | IL6R-BF203/IL6R-L | G237D/P238D/P271G/A330K | 1.3E−07 | 9.9E−07 | 1.1E−05 | 4.9E−08 | 7.2E−05 | 20.5 | 226.8 | 53.7 | 1.3 |
| 119 | IL6R-BF204/IL6R-L | B233D/P238D/P271G/K326A/A330R | 7.6E−09 | 4.5E−06 | 2.1E−05 | 2.5E−07 | 5.2E−05 | 17.0 | 82.7 | 12.2 | 5.8 |
| 120 | IL6R-BF205/IL6R-L | B233D/P298D/P271G/Y296D/A330R | 7.7E−09 | 3.5E−06 | 2.8E−05 | 1.6E−07 | 6.8E−06 | 21.8 | 176.1 | 19.4 | 4.5 |
| 121 | IL6R-BF206/IL6R-L | BB233D/P238D/P271G/A330R | 8.2E−09 | 3.1E−06 | 2.4E−05 | 2.0E−07 | 6.9E−06 | 16.1 | 123.1 | 15.8 | 4.1 |
| 122 | IL6R-BF207/IL6R-L | B233D/P298D/A330R | 2.2E−08 | 1.9E−05 | 2.9E−05 | 8.4E−07 | 6.5E−05 | 23.0 | 34.5 | 3.7 | 25.1 |
| 123 | IL6R-BF208/IL6R-L | B233D/G237D/P238D/H268D/P271G/A330R | 1.9E−08 | 8.5E−07 | 8.3E−08 | 3.2E−08 | 5.3E−05 | 26.3 | 256.2 | 95.4 | 1.1 |
| 124 | IL6R-BF208/IL6R-L | G237D/P238D/H265D/P271G/K326A/A330R | 3.9E−06 | 1.2E−05 | 1.0E−05 | 5.1E−06 | 4.1E−05 | 22.7 | 185.3 | 50.4 | 1.5 |
| 125 | IL6R-BF210/IL6R-L | G237D/P238D/H268D/P271G/A330R | 6.5E−08 | 1.0E−05 | 9.5E−06 | 3.9E−08 | 4.6E−05 | 25.4 | 241.1 | 78.4 | 1.3 |
| 126 | IL6R-BF211/IL6R-L | B233D/P238D/H268D/P271G/K326A/A330R | 4.2E−09 | 4.1E−06 | 2.7E−05 | 2.2E−07 | 7.3E−05 | 18.5 | 120.5 | 13.8 | 5.4 |
| 127 | IL6R-BF212/IL6R-L | B233D/P238D/H268D/P271G/Y295D/A330R | 5.2E−09 | 3.5E−08 | 2.2E−05 | 1.7E−07 | 5.2E−05 | 21.1 | 133.3 | 16.7 | 4.5 |
| 128 | IL6R-BF213/IL6R-L | B233D/P238D/H268D/P271G/A330R | 4.1E−09 | 3.1E−06 | 2.4E−05 | 1.8E−07 | 6.3E−06 | 17.7 | 136.4 | 17.6 | 4.0 |
| 129 | IL6R-BF214/IL6R-L | B233D/L234Y/G237D/P238D/ Y296D/K326A/A330K | 5.9E−08 | 1.7E−06 | 9.2E−06 | 1.2E−07 | 3.8E−05 | 14.5 | 78.0 | 26.2 | 2.2 |

[Reference Example 1] Construction of Antibody Expression Vectors; and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using PCR or such. The obtained plasmid fragment was inserted into an animal cell expression vector, and the H-chain expression vector and L-chain expression vector were produced. The nucleotide sequence of the obtained expression vector was determined by methods known to those skilled in the art. The produced plasmids were introduced transiently into the HEK293H cell line derived from human embryonic kidney cancer cells (Invitrogen) or into FreeStyle™ 293 human embryonic kidney cells (Invitrogen) for antibody expression. The obtained culture supernatant was collected, and then passed through a 0.22 μm MILLEX® GV filter (Millipore), or through a 0.45 μm MILLEX® GV filter (Millipore) to obtain the culture supernatant. Antibodies were purified from the obtained culture supernatant by methods known to those skilled in the art using rProtein A Sepharose™ Fast Flow column chromatography (GE Healthcare) or Protein G Sepharose™ 4 Fast Flow column chromatography (GE Healthcare). For the concentration of the purified antibodies, their absorbance at 280 nm was measured using a spectrophotometer. From the obtained value, the extinction coefficient calculated by the methods such as PACE was used to calculate the antibody concentration (Protein Science 1995; 4:2411-2423).

[Reference Example 2] Method for Preparing FcγR and Method for Analyzing the Interaction Between an Altered Antibody and FcγR Extracellular domains of FcγRs were prepared by the following method. First, a gene of the extracellular domain of FcγR was synthesized by a method well known to those skilled in the art. At that time, the sequence of each FcγR was produced based on the information registered at NCBI. Specifically, FcγRI was produced based on the sequence of NCBI Accession No. NM_000566.3, FcγRIIa was produced based on the sequence of NCBI Accession No. NM_001136219.1, FcγRIIb was produced based on the sequence of NCBI Accession No. NM_004001.3, FcγRIIIa was produced based on the sequence of NCBI Accession No. NM_001127593.1, and FcγRIIIb was produced based on the sequence of NCBI Accession No. NM_000570.3, and a His tag was attached to the C terminus. Furthermore, polymorphism is known for FcγRIIa, FcγRIIIa, and FcγRIIIb, and the polymorphic sites were produced by referring to J. Exp. Med., 1990, 172:19-25 for FcγRIIa; J. Clin. Invest., 1997, 100 (5): 1059-1070 for FcγRIIIa; and J. Clin. Invest., 1989, 84, 1688-1691 for FcγRIIIb.

The obtained gene fragments were inserted into an animal cell expression vector, and expression vectors were produced. The produced expression vectors were introduced transiently into human embryonic kidney cancer cell line-derived FreeStyle™ 293 human embryonic kidney cells (Invitrogen) to express the proteins of interest. Regarding FcγRIIb used for crystallographic analysis, the protein of interest was expressed in the presence of kifunensine at a final concentration of 10 μg/mL, so that the sugar chain added to FcγRIIb will be the high-mannose type. Cells were cultured, and after collection of the obtained culture supernatant, this was passed through a 0.22 μm filter to obtain the culture supernatant. In principle, the obtained culture supernatants were purified in the following four steps. The steps carried out were, cation exchange column chromatography (SP Sepharose™ FF column chromatography) in step 1, affinity column chromatography (HisTrap™ HP column chromatography) for His tag in step 2, gel filtration column chromatography (Superdex™200 size exclusion chromatography) in step 3, and aseptic chromatography in step 4. However, for FcγRI, anion exchange column chromatography using Q Sepharose™ FF column chromatography was performed as step 1. The purified proteins were subjected to absorbance measurements at 280 nm using a spectrophotometer; and from the obtained values, the concentrations of the purified proteins were calculated using the absorption coefficient calculated using methods such as PACE (Protein Science 1995; 4:2411-2423).

Analysis of interaction between each altered antibody and the Fcγ receptor prepared as mentioned above was carried out using a Biacore™ T100 surface plasmon resonance system (GE Healthcare), Biacore™ T200 surface plasmon resonance system (GE Healthcare), Biacore™ A100 surface plasmon resonance system, and Biacore™ 4000 surface plasmon resonance system. HBS-EP+ (GE Healthcare) was used as the running buffer, and the measurement temperature was set to 25° C. Chips produced by immobilizing the antigen peptide, Protein A (Thermo Scientific), Protein A/G (Thermo Scientific), and Protein L (ACTIGEN® protein (Alltech) or BioVision) by the amine coupling method to a Series S sensor Chip CM5 (GE Healthcare) or Series S sensor Chip CM4 (GE Healthcare), or alternatively, chips produced by allowing preliminarily biotinylated antigen peptides to interact with and immobilize onto a Series S Sensor Chip SA (certified) (GE Healthcare) were used.

After capturing of antibodies of interest onto these sensor chips, an Fcγ receptor diluted with the running buffer was allowed to interact, the amount bound to an antibody was measured, and the antibodies were compared. However, since the amount of Fcγ receptor bound depends on the amount of the captured antibodies, the amount of Fcγ receptor bound was divided by the amount of each antibody captured to obtain corrected values, and these values were compared. Furthermore, antibodies captured onto the chips were washed by reaction with 10 mM glycine-HCl, pH 1.5, and the chips were regenerated and used repeatedly.

Kinetic analyses for calculating the KD values of each altered antibody for FcγR were performed according to the following method. First, antibodies of interest were captured onto the above-mentioned sensor chips, and an Fcγ receptor diluted with the running buffer was allowed to interact. The Biacore™ Evaluation Software was used to globally fit the measured results to the obtained sensorgram using the 1:1 Langmuir binding model, and the association rate constant ka (L/mol/s) and the dissociation rate constant kd (1/s) were calculated; and from those values the dissociation constants KD (mol/L) were calculated.

When the interaction between each of the altered antibodies and FcγR was weak, and correct analysis was determined to be impossible by the above-mentioned kinetic analysis, the KD for such interactions were calculated using the following 1:1 binding model equation described in the Biacore™ T100 surface plasmon resonance system Software Handbook BR1006-48 Edition AE.

The behavior of interacting molecules according to the 1:1 binding model on a Biacore™ surface plasmon resonance system can be described by Equation 1 shown below.

$$R_{eq}=C\bullet R_{max}/(KD+C)+RI \quad \text{[Equation 1]}$$

$R_{eq}$: a plot of steady-state binding levels against analyte concentration

C: concentration

RI: bulk refractive index contribution in the sample $R_{max}$: analyte binding capacity of the surface When this equation is rearranged, KD can be expressed as Equation 2 shown below.

$$KD=C\bullet R_{max}/(R_{eq}-RI)-C \quad \text{[Equation 2]}$$

KD can be calculated by substituting the values of $R_{max}$, RI, and C into this equation. The values of RI and C can be determined from the sensorgram of the measurement results and measurement conditions. $R_{max}$ was calculated according to the following method. As a target of comparison, for antibodies that had sufficiently strong interactions as evaluated simultaneously in the same round of measurement, the $R_{max}$ value was obtained through global fitting using the 1:1 Langmuir binding model, and then it was divided by the amount of the comparison antibody captured onto the sensor chip, and multiplied by the captured amount of an altered antibody to be evaluated.

INDUSTRIAL APPLICABILITY

Polypeptides comprising an Fc region that have maintained or decreased binding activities towards both allotypes of FcγRIIa, types R and H, and having enhanced FcγRIIb-binding activity in comparison with the parent polypeptide are provided by the present invention. By using the polypeptides with enhanced binding selectivity for FcγRIIb rather than for both allotypes of FcγRIIa (types R and H), it is possible to transmit inhibitory signal of inflammatory immune response mediated by phosphorylation of ITIM of FcγRIIb in patients carrying either of the allotypes, types R and H. Furthermore, by conferring an antibody Fc with the property of selective FcγRIIb binding, anti-antibody production may be suppressed through FcγRIIb-mediated immunosuppressive actions.

The invention claimed is:

1. A polypeptide comprising a modified human Fc region identical to a naturally occurring human IgG1 Fc region except that (a) each of the following EU numbering positions is substituted with the indicated amino acid:
position 237 is substituted with Asp,
position 238 is substituted with Asp,
position 268 is substituted with Asp,
position 271 is substituted with Gly, and
position 330 is substituted with Lys or Arg; and (b) the residues at EU numbering positions 446 and 447 are optionally deleted.

2. The polypeptide of claim 1, wherein the amino acid residue at EU numbering position 330 is Arg.

3. The polypeptide of claim 1, wherein the amino acid residue at EU numbering position 330 is Lys.

4. The polypeptide of claim 1, wherein the residues at EU numbering positions 446 and 447 are deleted.

5. The polypeptide of claim 1, wherein the residues at EU numbering positions 446 and 447 are not deleted.

6. The polypeptide of claim 2, wherein the residues at EU numbering positions 446 and 447 are deleted.

7. The polypeptide of claim 2, wherein the residues at EU numbering positions 446 and 447 are not deleted.

8. The polypeptide of claim 3, wherein the residues at EU numbering positions 446 and 447 are deleted.

9. The polypeptide of claim 3, wherein the residues at EU numbering positions 446 and 447 are not deleted.

10. A polypeptide comprising a human IgG1 Fc region that comprises:
Asp at EU numbering position 237,
Asp at EU numbering position 238,
Asp at EU numbering position 268,
Gly at EU numbering position 271, and
Lys or Arg at EU numbering position 330,
wherein the polypeptide's carboxy terminal amino acid is at EU numbering position 445 or 447.

11. The polypeptide of claim 10, wherein the amino acid residue at EU numbering position 330 is Arg.

12. The polypeptide of claim 10, wherein the amino acid residue at EU numbering position 330 is Lys.

13. The polypeptide of claim 10, wherein the polypeptide's carboxy terminal amino acid is at EU numbering position 445.

14. The polypeptide of claim 10, wherein the polypeptide's carboxy terminal amino acid is at EU numbering position 447.

15. The polypeptide of claim 11, wherein the polypeptide's carboxy terminal amino acid is at EU numbering position 445.

16. The polypeptide of claim 11, wherein the polypeptide's carboxy terminal amino acid is at EU numbering position 447.

17. The polypeptide of claim 12, wherein the polypeptide's carboxy terminal amino acid is at EU numbering position 445.

18. The polypeptide of claim 12, wherein the polypeptide's carboxy terminal amino acid is at EU numbering position 447.

* * * * *

SEQUENCE LISTING

```
<160> NUMBER OF SEQ ID NOS: 129

<210> SEQ ID NO 1
<211> LENGTH: 1125
<212> TYPE: DNA
<213> ORGANISM: Homo sapiens

<400> SEQUENCE: 1

atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg accccataca gctggaaatc     300
cacagaggct ggctactact gcaggtctcc agcagagtct tcacggaagg agaacctctg     360
gccttgaggt gtcatgcgtg gaaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caaagttgct cttgcagagg     660
cctggtttgc agctttactt ctccttctac atgggcagca agaccctgcg aggcaggaac     720
acatcctctg aataccaaat actaactgct agaagagaag actctgggtt atactggtgc     780
gaggctgcca cagaggatgg aaatgtcctt aagcgcagcc ctgagttgga gcttcaagtg     840
cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag ggtgcaccgg gaaggagccc caggggggcca cgtag                   1125
```

<210> SEQ ID NO 2
<211> LENGTH: 374
<212> TYPE: PRT
<213> ORGANISM: Homo sapiens

<400> SEQUENCE: 2

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370
```

370

<210> SEQ ID NO 3
<211> LENGTH: 951
<212> TYPE: DNA
<213> ORGANISM: Homo sapiens

<400> SEQUENCE: 3
atgactatgg agacccaaat gtctcagaat gtatgtccca gaaacctgtg gctgcttcaa 60
ccattgacag ttttgctgct gctggcttct gcagacagtc aagctgctcc cccaaaggct 120
gtgctgaaac ttgagccccc gtggatcaac gtgctccagg aggactctgt gactctgaca 180
tgccaggggg ctcgcagccc tgagagcgac tccattcagt ggttccacaa tgggaatctc 240
attcccaccc acacgcagcc cagctacagg ttcaaggcca acaacaatga cagcggggag 300
tacacgtgcc agactggcca gaccagcctc agcgaccctg tgcatctgac tgtgctttcc 360
gaatggctgg tgctccagac ccctcacctg gagttccagg agggagaaac catcatgctg 420
aggtgccaca gctggaagga caagcctctg gtcaaggtca cattcttcca gaatggaaaa 480
tcccagaaat tctcccattt ggatcccacc ttctccatcc cacaagcaaa ccacagtcac 540
agtggtgatt accactgcac aggaaacata ggctacacgc tgttctcatc caagcctgtg 600
accatcactg tccaagtgcc cagcatgggc agctcttcac caatgggggt cattgtggct 660
gtggtcattg cgactgctgt agcagccatt gttgctgctg tagtggcctt gatctactgc 720
aggaaaaagc ggatttcagc caattccact gatcctgtga aggctgccca atttgagcca 780
cctggacgtc aaatgattgc catcagaaag agacaacttg aagaaaccaa caatgactat 840
gaaacagctg acggcggcta catgactctg aaccccaggg cacctactga cgatgataaa 900
aacatctacc tgactcttcc tcccaacgac catgtcaaca gtaataacta a 951

<210> SEQ ID NO 4
<211> LENGTH: 316
<212> TYPE: PRT
<213> ORGANISM: Homo sapiens

<400> SEQUENCE: 4

Met Thr Met Glu Thr Gln Met Ser Gln Asn Val Cys Pro Arg Asn Leu
1 5 10 15

Trp Leu Leu Gln Pro Leu Thr Val Leu Leu Leu Leu Ala Ser Ala Asp
20 25 30

Ser Gln Ala Ala Pro Pro Lys Ala Val Leu Lys Leu Glu Pro Pro Trp
35 40 45

Ile Asn Val Leu Gln Glu Asp Ser Val Thr Leu Thr Cys Gln Gly Ala
50 55 60

Arg Ser Pro Glu Ser Asp Ser Ile Gln Trp Phe His Asn Gly Asn Leu
65 70 75 80

Ile Pro Thr His Thr Gln Pro Ser Tyr Arg Phe Lys Ala Asn Asn Asn
85 90 95

Asp Ser Gly Glu Tyr Thr Cys Gln Thr Gly Gln Thr Ser Leu Ser Asp
100 105 110

Pro Val His Leu Thr Val Leu Ser Glu Trp Leu Val Leu Gln Thr Pro
115 120 125

His Leu Glu Phe Gln Glu Gly Glu Thr Ile Met Leu Arg Cys His Ser
130 135 140

Trp Lys Asp Lys Pro Leu Val Lys Val Thr Phe Phe Gln Asn Gly Lys
145 150 155 160

Ser Gln Lys Phe Ser His Leu Asp Pro Thr Phe Ser Ile Pro Gln Ala
165 170 175

Asn His Ser His Ser Gly Asp Tyr His Cys Thr Gly Asn Ile Gly Tyr
180 185 190

Thr Leu Phe Ser Ser Lys Pro Val Thr Ile Thr Val Gln Val Pro Ser
195 200 205

Met Gly Ser Ser Ser Pro Met Gly Val Ile Val Ala Val Val Ile Ala
210 215 220

Thr Ala Val Ala Ala Ile Val Ala Ala Val Val Ala Leu Ile Tyr Cys
225 230 235 240

Arg Lys Lys Arg Ile Ser Ala Asn Ser Thr Asp Pro Val Lys Ala Ala
245 250 255

Gln Phe Glu Pro Pro Gly Arg Gln Met Ile Ala Ile Arg Lys Arg Gln
260 265 270

Leu Glu Glu Thr Asn Asn Asp Tyr Glu Thr Ala Asp Gly Gly Tyr Met
275 280 285

Thr Leu Asn Pro Arg Ala Pro Thr Asp Asp Asp Lys Asn Ile Tyr Leu
290 295 300

Thr Leu Pro Pro Asn Asp His Val Asn Ser Asn Asn
305 310 315

<210> SEQ ID NO 5
<211> LENGTH: 876
<212> TYPE: DNA
<213> ORGANISM: Homo sapiens

<400> SEQUENCE: 5
atgggaatcc tgtcattctt acctgtcctt gccactgaga gtgactgggc tgactgcaag 60
tccccccagc cttggggtca tatgcttctg tggacagctg tgctattcct ggctcctgtt 120
gctgggacac ctgcagctcc cccaaaggct gtgctgaaac tcgagcccca gtggatcaac 180
gtgctccagg aggactctgt gactctgaca tgccggggga ctcacagccc tgagagcgac 240
tccattcagt ggttccacaa tgggaatctc attcccaccc acacgcagcc cagctacagg 300
ttcaaggcca acaacaatga cagcggggag tacacgtgcc agactggcca gaccagcctc 360
agcgaccctg tgcatctgac tgtgctttct gagtggctgg tgctccagac ccctcacctg 420
gagttccagg agggagaaac catcgtgctg aggtgccaca gctggaagga caagcctctg 480
gtcaaggtca cattcttcca gaatggaaaa tccaagaaat tttcccgttc ggatcccaac 540
ttctccatcc cacaagcaaa ccacagtcac agtggtgatt accactgcac aggaaacata 600
ggctacacgc tgtactcatc caagcctgtg accatcactg tccaagctcc cagctcttca 660
ccgatgggga tcattgtggc tgtggtcact gggattgctg tagcggccat tgttgctgct 720
gtagtggcct tgatctactg caggaaaaag cggatttcag ccaatcccac taatcctgat 780
gaggctgaca aagttggggc tgagaacaca atcacctatt cacttctcat gcacccggat 840
gctctggaag agcctgatga ccagaaccgt atttag 876

<210> SEQ ID NO 6
<211> LENGTH: 291
<212> TYPE: PRT
<213> ORGANISM: Homo sapiens

<400> SEQUENCE: 6

Met Gly Ile Leu Ser Phe Leu Pro Val Leu Ala Thr Glu Ser Asp Trp
1 5 10 15

```
Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290
```

<210> SEQ ID NO 7
<211> LENGTH: 765
<212> TYPE: DNA
<213> ORGANISM: Homo sapiens

<400> SEQUENCE: 7

```
atgtggcagc tgctcctccc aactgctctg ctacttctag tttcagctgg catgcggact     60

gaagatctcc caaaggctgt ggtgttcctg gagcctcaat ggtacagggt gctcgagaag    120

gacagtgtga ctctgaagtg ccagggagcc tactcccctg aggacaattc cacacagtgg    180

tttcacaatg agagcctcat ctcaagccag gcctcgagct acttcattga cgctgccaca    240

gttgacgaca gtggagagta caggtgccag acaaacctct ccaccctcag tgacccggtg    300

cagctagaag tccatatcgg ctggctgttg ctccaggccc ctcggtgggt gttcaaggag    360

gaagacccta ttcacctgag gtgtcacagc tggaagaaca ctgctctgca taaggtcaca    420

tatttacaga atggcaaagg caggaagtat tttcatcata attctgactt ctacattcca    480
```

```
aaagccacac tcaaagacag cggctcctac ttctgcaggg ggcttgttgg gagtaaaaat    540

gtgtcttcag agactgtgaa catcaccatc actcaaggtt tgtcagtgtc aaccatctca    600

tcattctttc cacctgggta ccaagtctct ttctgcttgg tgatggtact ccttttttgca   660

gtggacacag gactatattt ctctgtgaag acaaacattc gaagctcaac aagagactgg    720

aaggaccata aatttaaatg gagaaaggac cctcaagaca aatga                    765
```

<210> SEQ ID NO 8
<211> LENGTH: 254
<212> TYPE: PRT
<213> ORGANISM: Homo sapiens

<400> SEQUENCE: 8

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 9
<211> LENGTH: 702
<212> TYPE: DNA
<213> ORGANISM: Homo sapiens

<400> SEQUENCE: 9

```
atgtggcagc tgctcctccc aactgctctg ctacttctag tttcagctgg catgcggact     60

gaagatctcc caaaggctgt ggtgttcctg gagcctcaat ggtacagcgt gcttgagaag    120

gacagtgtga ctctgaagtg ccagggagcc tactcccctg aggacaattc cacacagtgg    180
```

```
tttcacaatg agagcctcat ctcaagccag gcctcgagct acttcattga cgctgccaca    240

gtcaacgaca gtggagagta caggtgccag acaaacctct ccaccctcag tgacccggtg    300

cagctagaag tccatatcgg ctggctgttg ctccaggccc ctcggtgggt gttcaaggag    360

gaagacccta ttcacctgag gtgtcacagc tggaagaaca ctgctctgca taaggtcaca    420

tatttacaga atggcaaaga caggaagtat tttcatcata attctgactt ccacattcca    480

aaagccacac tcaaagatag cggctcctac ttctgcaggg ggcttgttgg gagtaaaaat    540

gtgtcttcag agactgtgaa catcaccatc actcaaggtt tggcagtgtc aaccatctca    600

tcattctctc cacctgggta ccaagtctct ttctgcttgg tgatggtact cctttttgca    660

gtggacacag gactatattt ctctgtgaag acaaacattt ga                       702
```

```
<210> SEQ ID NO 10
<211> LENGTH: 233
<212> TYPE: PRT
<213> ORGANISM: Homo sapiens

<400> SEQUENCE: 10

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230


<210> SEQ ID NO 11
<211> LENGTH: 330
<212> TYPE: PRT
<213> ORGANISM: Artificial
<220> FEATURE:
<223> OTHER INFORMATION: an artificially synthesized sequence
```

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 12
<211> LENGTH: 326
<212> TYPE: PRT
<213> ORGANISM: Artificial
<220> FEATURE:
<223> OTHER INFORMATION: an artificially synthesized sequence

<400> SEQUENCE: 12

```
Ala Ser Thr Lys Gly Pro Ser Val Phe Pro Leu Ala Pro Cys Ser Arg
1               5                   10                  15
```

-continued

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 13
<211> LENGTH: 377
<212> TYPE: PRT
<213> ORGANISM: Artificial
<220> FEATURE:
<223> OTHER INFORMATION: an artificially synthesized sequence

<400> SEQUENCE: 13

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 14
<211> LENGTH: 327
<212> TYPE: PRT
<213> ORGANISM: Artificial
<220> FEATURE:
<223> OTHER INFORMATION: an artificially synthesized sequence

<400> SEQUENCE: 14

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 15
<211> LENGTH: 115
<212> TYPE: PRT
<213> ORGANISM: Artificial
<220> FEATURE:
<223> OTHER INFORMATION: an artificially synthesized sequence

<400> SEQUENCE: 15

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60
```

Gln Asp Arg Val Thr Leu Thr Ala Asp Lys Ser Thr Ser Thr Ala Tyr
65 70 75 80

Met Glu Leu Ser Ser Leu Thr Ser Glu Asp Thr Ala Val Tyr Tyr Cys
85 90 95

Thr Arg Phe Tyr Ser Tyr Thr Tyr Trp Gly Gln Gly Thr Leu Val Thr
100 105 110

Val Ser Ser
115

<210> SEQ ID NO 16
<211> LENGTH: 219
<212> TYPE: PRT
<213> ORGANISM: Artificial
<220> FEATURE:
<223> OTHER INFORMATION: an artificially synthesized sequence

<400> SEQUENCE: 16

Asp Ile Val Met Thr Gln Ser Pro Leu Ser Leu Pro Val Thr Pro Gly
1 5 10 15

Glu Pro Ala Ser Ile Ser Cys Gln Ala Ser Glu Ser Leu Val His Ser
20 25 30

Asn Arg Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Asn
85 90 95

Thr His Val Pro Pro Thr Phe Gly Gln Gly Thr Lys Val Glu Ile Glu
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 17
<211> LENGTH: 328
<212> TYPE: PRT
<213> ORGANISM: Artificial
<220> FEATURE:
<223> OTHER INFORMATION: an artificially synthesized sequence

<400> SEQUENCE: 17

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325


<210> SEQ ID NO 18
<211> LENGTH: 443
<212> TYPE: PRT
<213> ORGANISM: Artificial
<220> FEATURE:
<223> OTHER INFORMATION: an artificially synthesized sequence

<400> SEQUENCE: 18

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60
```

```
Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440
```

<210> SEQ ID NO 19
<211> LENGTH: 119
<212> TYPE: PRT
<213> ORGANISM: Artificial
<220> FEATURE:

<223> OTHER INFORMATION: an artificially synthesized sequence

<400> SEQUENCE: 19

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser
115

<210> SEQ ID NO 20
<211> LENGTH: 447
<212> TYPE: PRT
<213> ORGANISM: Artificial
<220> FEATURE:
<223> OTHER INFORMATION: an artificially synthesized sequence

<400> SEQUENCE: 20

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 21
<211> LENGTH: 447
<212> TYPE: PRT
<213> ORGANISM: Artificial
<220> FEATURE:
<223> OTHER INFORMATION: an artificially synthesized sequence

<400> SEQUENCE: 21

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 22
<211> LENGTH: 214
<212> TYPE: PRT
<213> ORGANISM: Artificial
<220> FEATURE:
<223> OTHER INFORMATION: an artificially synthesized sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60
```

```
Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 23
<211> LENGTH: 447
<212> TYPE: PRT
<213> ORGANISM: Artificial
<220> FEATURE:
<223> OTHER INFORMATION: an artificially synthesized sequence

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Glu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 24
<211> LENGTH: 447
<212> TYPE: PRT
<213> ORGANISM: Artificial
<220> FEATURE:
<223> OTHER INFORMATION: an artificially synthesized sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 25
<211> LENGTH: 447
<212> TYPE: PRT
<213> ORGANISM: Artificial
<220> FEATURE:
<223> OTHER INFORMATION: an artificially synthesized sequence

<400> SEQUENCE: 25

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45
```

```
Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Glu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 26
<211> LENGTH: 447

<212> TYPE: PRT
<213> ORGANISM: Artificial
<220> FEATURE:
<223> OTHER INFORMATION: an artificially synthesized sequence

<400> SEQUENCE: 26

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 27
<211> LENGTH: 447
<212> TYPE: PRT
<213> ORGANISM: Artificial
<220> FEATURE:
<223> OTHER INFORMATION: an artificially synthesized sequence

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 28
<211> LENGTH: 447
<212> TYPE: PRT
<213> ORGANISM: Artificial
<220> FEATURE:
<223> OTHER INFORMATION: an artificially synthesized sequence

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

-continued

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Tyr Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Tyr His Tyr Thr Gln Lys Ser Leu Ser Leu Ser Pro
435 440 445

<210> SEQ ID NO 29
<211> LENGTH: 447
<212> TYPE: PRT
<213> ORGANISM: Artificial
<220> FEATURE:
<223> OTHER INFORMATION: an artificially synthesized sequence

<400> SEQUENCE: 29

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Trp Leu Gly Gly Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 30
<211> LENGTH: 447
<212> TYPE: PRT
<213> ORGANISM: Artificial
<220> FEATURE:
<223> OTHER INFORMATION: an artificially synthesized sequence

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60
```

```
Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445
```

<210> SEQ ID NO 31
<211> LENGTH: 447
<212> TYPE: PRT
<213> ORGANISM: Artificial
<220> FEATURE:
<223> OTHER INFORMATION: an artificially synthesized sequence

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Ala Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 32
<211> LENGTH: 447
<212> TYPE: PRT
<213> ORGANISM: Artificial
<220> FEATURE:
<223> OTHER INFORMATION: an artificially synthesized sequence

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 33
<211> LENGTH: 447
<212> TYPE: PRT
<213> ORGANISM: Artificial
<220> FEATURE:
<223> OTHER INFORMATION: an artificially synthesized sequence

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Glu Asp
225                 230                 235                 240

Ser Val Phe Leu Phe Pro Pro Lys Pro Lys Asp Thr Leu Tyr Ile Ser
```

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 34
<211> LENGTH: 447
<212> TYPE: PRT
<213> ORGANISM: Artificial
<220> FEATURE:
<223> OTHER INFORMATION: an artificially synthesized sequence

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Phe Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 35
<211> LENGTH: 447
<212> TYPE: PRT
<213> ORGANISM: Artificial
<220> FEATURE:
<223> OTHER INFORMATION: an artificially synthesized sequence

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Leu Asp
225                 230                 235                 240

Ser Val Phe Leu Phe Pro Pro Lys Pro Lys Asp Thr Leu Tyr Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 36
<211> LENGTH: 447
<212> TYPE: PRT
<213> ORGANISM: Artificial
<220> FEATURE:
<223> OTHER INFORMATION: an artificially synthesized sequence

<400> SEQUENCE: 36

Gln Val Gln Leu Gln Glu Ser Gly Pro Gly Leu Val Lys Pro Ser Glu
```

-continued

```
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Met Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Tyr His Tyr Thr Gln Lys Ser Leu Ser Leu Ser Pro
        435                 440                 445


<210> SEQ ID NO 37
<211> LENGTH: 447
<212> TYPE: PRT
<213> ORGANISM: Artificial
<220> FEATURE:
<223> OTHER INFORMATION: an artificially synthesized sequence

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Trp Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 38
<211> LENGTH: 447
<212> TYPE: PRT
<213> ORGANISM: Artificial
<220> FEATURE:
<223> OTHER INFORMATION: an artificially synthesized sequence

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Tyr Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 39
<211> LENGTH: 447
<212> TYPE: PRT
<213> ORGANISM: Artificial
<220> FEATURE:
<223> OTHER INFORMATION: an artificially synthesized sequence

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Asp Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445
```

<210> SEQ ID NO 40
<211> LENGTH: 447
<212> TYPE: PRT
<213> ORGANISM: Artificial
<220> FEATURE:
<223> OTHER INFORMATION: an artificially synthesized sequence

<400> SEQUENCE: 40

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 41
<211> LENGTH: 447
<212> TYPE: PRT
<213> ORGANISM: Artificial
<220> FEATURE:
<223> OTHER INFORMATION: an artificially synthesized sequence

<400> SEQUENCE: 41

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30
```

```
His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 42
<211> LENGTH: 447
<212> TYPE: PRT
<213> ORGANISM: Artificial
<220> FEATURE:
<223> OTHER INFORMATION: an artificially synthesized sequence

<400> SEQUENCE: 42

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 43
<211> LENGTH: 447
<212> TYPE: PRT
<213> ORGANISM: Artificial
<220> FEATURE:
<223> OTHER INFORMATION: an artificially synthesized sequence

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ala His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 44
<211> LENGTH: 447
<212> TYPE: PRT
<213> ORGANISM: Artificial
<220> FEATURE:
<223> OTHER INFORMATION: an artificially synthesized sequence

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Gln His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 45
<211> LENGTH: 447
<212> TYPE: PRT
<213> ORGANISM: Artificial
<220> FEATURE:
<223> OTHER INFORMATION: an artificially synthesized sequence

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Val His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 46
<211> LENGTH: 447
<212> TYPE: PRT
<213> ORGANISM: Artificial
<220> FEATURE:
<223> OTHER INFORMATION: an artificially synthesized sequence

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45
```

```
Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 47
<211> LENGTH: 447
<212> TYPE: PRT

<213> ORGANISM: Artificial
<220> FEATURE:
<223> OTHER INFORMATION: an artificially synthesized sequence

<400> SEQUENCE: 47

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Glu Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu 385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 48
<211> LENGTH: 447
<212> TYPE: PRT
<213> ORGANISM: Artificial
<220> FEATURE:
<223> OTHER INFORMATION: an artificially synthesized sequence

<400> SEQUENCE: 48

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Asn Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu

```
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 49
<211> LENGTH: 447
<212> TYPE: PRT
<213> ORGANISM: Artificial
<220> FEATURE:
<223> OTHER INFORMATION: an artificially synthesized sequence

<400> SEQUENCE: 49

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
```

```
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 50
<211> LENGTH: 447
<212> TYPE: PRT
<213> ORGANISM: Artificial
<220> FEATURE:
<223> OTHER INFORMATION: an artificially synthesized sequence

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Asp Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 51
<211> LENGTH: 447
<212> TYPE: PRT
<213> ORGANISM: Artificial
<220> FEATURE:
<223> OTHER INFORMATION: an artificially synthesized sequence

<400> SEQUENCE: 51

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr

```
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Ile Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 52
<211> LENGTH: 447
<212> TYPE: PRT
<213> ORGANISM: Artificial
<220> FEATURE:
<223> OTHER INFORMATION: an artificially synthesized sequence

<400> SEQUENCE: 52

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Leu Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 53
<211> LENGTH: 447
<212> TYPE: PRT
<213> ORGANISM: Artificial
<220> FEATURE:
<223> OTHER INFORMATION: an artificially synthesized sequence

<400> SEQUENCE: 53

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Met Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 54
<211> LENGTH: 447
<212> TYPE: PRT
<213> ORGANISM: Artificial
<220> FEATURE:
<223> OTHER INFORMATION: an artificially synthesized sequence

<400> SEQUENCE: 54

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Met Ile Ser
245 250 255

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 55
<211> LENGTH: 447
<212> TYPE: PRT
<213> ORGANISM: Artificial
<220> FEATURE:
<223> OTHER INFORMATION: an artificially synthesized sequence

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 56
<211> LENGTH: 447
<212> TYPE: PRT
<213> ORGANISM: Artificial
<220> FEATURE:
<223> OTHER INFORMATION: an artificially synthesized sequence

<400> SEQUENCE: 56

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Glu Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

```
<210> SEQ ID NO 57
<211> LENGTH: 447
<212> TYPE: PRT
<213> ORGANISM: Artificial
<220> FEATURE:
<223> OTHER INFORMATION: an artificially synthesized sequence

<400> SEQUENCE: 57

Gln Val Gln Leu Gln Glu Ser Gly Pro Gly Leu Val Lys Pro Ser Glu
1               5                   10                  15
```

```
Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Leu Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Glu Ser Leu Ser Leu Ser Pro
        435                 440                 445


<210> SEQ ID NO 58
<211> LENGTH: 447
<212> TYPE: PRT
<213> ORGANISM: Artificial
<220> FEATURE:
<223> OTHER INFORMATION: an artificially synthesized sequence

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Met Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 59
<211> LENGTH: 447
<212> TYPE: PRT
<213> ORGANISM: Artificial
<220> FEATURE:
<223> OTHER INFORMATION: an artificially synthesized sequence

<400> SEQUENCE: 59

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asn Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 60
<211> LENGTH: 447
<212> TYPE: PRT
<213> ORGANISM: Artificial
<220> FEATURE:
<223> OTHER INFORMATION: an artificially synthesized sequence

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Gln Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 61
<211> LENGTH: 447
<212> TYPE: PRT
<213> ORGANISM: Artificial
<220> FEATURE:
<223> OTHER INFORMATION: an artificially synthesized sequence

<400> SEQUENCE: 61

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ser Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 62
<211> LENGTH: 447
<212> TYPE: PRT
<213> ORGANISM: Artificial
<220> FEATURE:
<223> OTHER INFORMATION: an artificially synthesized sequence

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30
```

-continued

```
His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Thr Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

```
<210> SEQ ID NO 63
<211> LENGTH: 447
<212> TYPE: PRT
<213> ORGANISM: Artificial
<220> FEATURE:
<223> OTHER INFORMATION: an artificially synthesized sequence

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

```
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 64
<211> LENGTH: 447
<212> TYPE: PRT
<213> ORGANISM: Artificial
<220> FEATURE:
<223> OTHER INFORMATION: an artificially synthesized sequence

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Met Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 65
<211> LENGTH: 447
<212> TYPE: PRT
<213> ORGANISM: Artificial
<220> FEATURE:
<223> OTHER INFORMATION: an artificially synthesized sequence

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 66
<211> LENGTH: 447
<212> TYPE: PRT
<213> ORGANISM: Artificial
<220> FEATURE:
<223> OTHER INFORMATION: an artificially synthesized sequence

<400> SEQUENCE: 66

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Met Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 67
<211> LENGTH: 447
<212> TYPE: PRT
<213> ORGANISM: Artificial
<220> FEATURE:
<223> OTHER INFORMATION: an artificially synthesized sequence

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
```

```
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 68
<211> LENGTH: 447
<212> TYPE: PRT
<213> ORGANISM: Artificial

<220> FEATURE:
<223> OTHER INFORMATION: an artificially synthesized sequence

<400> SEQUENCE: 68

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 69
<211> LENGTH: 447
<212> TYPE: PRT
<213> ORGANISM: Artificial
<220> FEATURE:
<223> OTHER INFORMATION: an artificially synthesized sequence

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Lys Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 70
<211> LENGTH: 447
<212> TYPE: PRT
<213> ORGANISM: Artificial
<220> FEATURE:
<223> OTHER INFORMATION: an artificially synthesized sequence

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240
```

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Met Ser Asn Lys Ala Leu Pro Lys Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 71
<211> LENGTH: 447
<212> TYPE: PRT
<213> ORGANISM: Artificial
<220> FEATURE:
<223> OTHER INFORMATION: an artificially synthesized sequence

<400> SEQUENCE: 71

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 72
<211> LENGTH: 447
<212> TYPE: PRT
<213> ORGANISM: Artificial
<220> FEATURE:
<223> OTHER INFORMATION: an artificially synthesized sequence

<400> SEQUENCE: 72

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 73
<211> LENGTH: 447
<212> TYPE: PRT
<213> ORGANISM: Artificial
<220> FEATURE:
<223> OTHER INFORMATION: an artificially synthesized sequence

<400> SEQUENCE: 73

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 74
<211> LENGTH: 447
<212> TYPE: PRT
<213> ORGANISM: Artificial
<220> FEATURE:
<223> OTHER INFORMATION: an artificially synthesized sequence

<400> SEQUENCE: 74

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 75
<211> LENGTH: 447
<212> TYPE: PRT
<213> ORGANISM: Artificial
<220> FEATURE:
<223> OTHER INFORMATION: an artificially synthesized sequence

<400> SEQUENCE: 75

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 76
<211> LENGTH: 447
<212> TYPE: PRT
<213> ORGANISM: Artificial
<220> FEATURE:
<223> OTHER INFORMATION: an artificially synthesized sequence

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 77
<211> LENGTH: 447
<212> TYPE: PRT
<213> ORGANISM: Artificial
<220> FEATURE:
<223> OTHER INFORMATION: an artificially synthesized sequence

<400> SEQUENCE: 77

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Met Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 78
<211> LENGTH: 447
<212> TYPE: PRT
<213> ORGANISM: Artificial
<220> FEATURE:
<223> OTHER INFORMATION: an artificially synthesized sequence

<400> SEQUENCE: 78

```
Gln Val Gln Leu Gln Glu Ser Gly Pro Gly Leu Val Lys Pro Ser Glu
1               5                   10                  15
```

```
Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
```

435 440 445

<210> SEQ ID NO 79
<211> LENGTH: 447
<212> TYPE: PRT
<213> ORGANISM: Artificial
<220> FEATURE:
<223> OTHER INFORMATION: an artificially synthesized sequence

<400> SEQUENCE: 79

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 80
<211> LENGTH: 447
<212> TYPE: PRT
<213> ORGANISM: Artificial
<220> FEATURE:
<223> OTHER INFORMATION: an artificially synthesized sequence

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 81
<211> LENGTH: 447
<212> TYPE: PRT
<213> ORGANISM: Artificial
<220> FEATURE:
<223> OTHER INFORMATION: an artificially synthesized sequence

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 82
<211> LENGTH: 447
<212> TYPE: PRT
<213> ORGANISM: Artificial
<220> FEATURE:
<223> OTHER INFORMATION: an artificially synthesized sequence

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
```

```
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 83
<211> LENGTH: 447
<212> TYPE: PRT
<213> ORGANISM: Artificial
<220> FEATURE:
<223> OTHER INFORMATION: an artificially synthesized sequence

<400> SEQUENCE: 83

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
```

-continued

```
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 84

<211> LENGTH: 447
<212> TYPE: PRT
<213> ORGANISM: Artificial
<220> FEATURE:
<223> OTHER INFORMATION: an artificially synthesized sequence

<400> SEQUENCE: 84

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Tyr Leu Gly Asp Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Ala Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 85
<211> LENGTH: 447
<212> TYPE: PRT
<213> ORGANISM: Artificial
<220> FEATURE:
<223> OTHER INFORMATION: an artificially synthesized sequence

<400> SEQUENCE: 85

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Tyr Leu Gly Asp Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Ala Ala Leu Pro Lys Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 86
<211> LENGTH: 447
<212> TYPE: PRT
<213> ORGANISM: Artificial
<220> FEATURE:
<223> OTHER INFORMATION: an artificially synthesized sequence

<400> SEQUENCE: 86

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Asp Tyr Leu Gly Asp Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Ala Ala Leu Pro Lys Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 87
<211> LENGTH: 447
<212> TYPE: PRT
<213> ORGANISM: Artificial
<220> FEATURE:
<223> OTHER INFORMATION: an artificially synthesized sequence

<400> SEQUENCE: 87

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 88
<211> LENGTH: 447
<212> TYPE: PRT
<213> ORGANISM: Artificial
<220> FEATURE:
<223> OTHER INFORMATION: an artificially synthesized sequence

<400> SEQUENCE: 88

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60
```

```
Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 89
<211> LENGTH: 447
<212> TYPE: PRT
<213> ORGANISM: Artificial
<220> FEATURE:

<223> OTHER INFORMATION: an artificially synthesized sequence

<400> SEQUENCE: 89

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 90
<211> LENGTH: 447
<212> TYPE: PRT
<213> ORGANISM: Artificial
<220> FEATURE:
<223> OTHER INFORMATION: an artificially synthesized sequence

<400> SEQUENCE: 90

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 91
<211> LENGTH: 447
<212> TYPE: PRT
<213> ORGANISM: Artificial
<220> FEATURE:
<223> OTHER INFORMATION: an artificially synthesized sequence

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 92
<211> LENGTH: 447
<212> TYPE: PRT
<213> ORGANISM: Artificial
<220> FEATURE:
<223> OTHER INFORMATION: an artificially synthesized sequence

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 93
<211> LENGTH: 447
<212> TYPE: PRT
<213> ORGANISM: Artificial
<220> FEATURE:
<223> OTHER INFORMATION: an artificially synthesized sequence

<400> SEQUENCE: 93

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 94
<211> LENGTH: 447
<212> TYPE: PRT
<213> ORGANISM: Artificial
<220> FEATURE:
<223> OTHER INFORMATION: an artificially synthesized sequence

<400> SEQUENCE: 94

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
            420                 425                 430

Ala Leu His Asn His Tyr Thr Gln Glu Ser Leu Ser Leu Ser Pro
        435                 440                 445


<210> SEQ ID NO 95
<211> LENGTH: 447
<212> TYPE: PRT
<213> ORGANISM: Artificial
<220> FEATURE:
<223> OTHER INFORMATION: an artificially synthesized sequence

<400> SEQUENCE: 95

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
```

```
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 96
<211> LENGTH: 447
<212> TYPE: PRT
<213> ORGANISM: Artificial
<220> FEATURE:
<223> OTHER INFORMATION: an artificially synthesized sequence

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 97
<211> LENGTH: 447
<212> TYPE: PRT
<213> ORGANISM: Artificial
<220> FEATURE:
<223> OTHER INFORMATION: an artificially synthesized sequence

<400> SEQUENCE: 97

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 98
<211> LENGTH: 447
<212> TYPE: PRT
<213> ORGANISM: Artificial
<220> FEATURE:
<223> OTHER INFORMATION: an artificially synthesized sequence

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
```

```
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 99
<211> LENGTH: 447
<212> TYPE: PRT
<213> ORGANISM: Artificial
<220> FEATURE:
<223> OTHER INFORMATION: an artificially synthesized sequence

<400> SEQUENCE: 99

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
```

```
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 100
<211> LENGTH: 447
<212> TYPE: PRT
<213> ORGANISM: Artificial
<220> FEATURE:
<223> OTHER INFORMATION: an artificially synthesized sequence

<400> SEQUENCE: 100

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Asp Tyr Leu Gly Asp Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Gly Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Ala Ala Leu Pro Lys Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 101
<211> LENGTH: 447
<212> TYPE: PRT
<213> ORGANISM: Artificial
<220> FEATURE:
<223> OTHER INFORMATION: an artificially synthesized sequence

<400> SEQUENCE: 101

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

```
Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 102
<211> LENGTH: 447
<212> TYPE: PRT
<213> ORGANISM: Artificial
<220> FEATURE:
<223> OTHER INFORMATION: an artificially synthesized sequence

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 103
<211> LENGTH: 447
<212> TYPE: PRT
<213> ORGANISM: Artificial
<220> FEATURE:
<223> OTHER INFORMATION: an artificially synthesized sequence

<400> SEQUENCE: 103

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 104
<211> LENGTH: 447
<212> TYPE: PRT
<213> ORGANISM: Artificial
<220> FEATURE:
<223> OTHER INFORMATION: an artificially synthesized sequence

<400> SEQUENCE: 104

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45
```

```
Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 105
<211> LENGTH: 447

<212> TYPE: PRT
<213> ORGANISM: Artificial
<220> FEATURE:
<223> OTHER INFORMATION: an artificially synthesized sequence

<400> SEQUENCE: 105

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 106
<211> LENGTH: 447
<212> TYPE: PRT
<213> ORGANISM: Artificial
<220> FEATURE:
<223> OTHER INFORMATION: an artificially synthesized sequence

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 107
<211> LENGTH: 447
<212> TYPE: PRT
<213> ORGANISM: Artificial
<220> FEATURE:
<223> OTHER INFORMATION: an artificially synthesized sequence

<400> SEQUENCE: 107

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 108
<211> LENGTH: 447
<212> TYPE: PRT
<213> ORGANISM: Artificial
<220> FEATURE:
<223> OTHER INFORMATION: an artificially synthesized sequence

<400> SEQUENCE: 108

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 109
<211> LENGTH: 447
<212> TYPE: PRT
<213> ORGANISM: Artificial
<220> FEATURE:
<223> OTHER INFORMATION: an artificially synthesized sequence

<400> SEQUENCE: 109

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60
```

```
Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 110
<211> LENGTH: 447
<212> TYPE: PRT
<213> ORGANISM: Artificial
<220> FEATURE:
<223> OTHER INFORMATION: an artificially synthesized sequence

<400> SEQUENCE: 110

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 111
<211> LENGTH: 447
<212> TYPE: PRT
<213> ORGANISM: Artificial
<220> FEATURE:
<223> OTHER INFORMATION: an artificially synthesized sequence

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
```

```
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 112
<211> LENGTH: 447
<212> TYPE: PRT
<213> ORGANISM: Artificial
<220> FEATURE:
<223> OTHER INFORMATION: an artificially synthesized sequence

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 113
<211> LENGTH: 447
<212> TYPE: PRT
<213> ORGANISM: Artificial
<220> FEATURE:
<223> OTHER INFORMATION: an artificially synthesized sequence

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 114
<211> LENGTH: 447
<212> TYPE: PRT
<213> ORGANISM: Artificial
<220> FEATURE:
<223> OTHER INFORMATION: an artificially synthesized sequence

<400> SEQUENCE: 114

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 115
<211> LENGTH: 447
<212> TYPE: PRT
<213> ORGANISM: Artificial
<220> FEATURE:
<223> OTHER INFORMATION: an artificially synthesized sequence

<400> SEQUENCE: 115

```
Gln Val Gln Leu Gln Glu Ser Gly Pro Gly Leu Val Lys Pro Ser Glu
```

```
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Glu Ser Leu Ser Leu Ser Pro
435 440 445

<210> SEQ ID NO 116
<211> LENGTH: 447
<212> TYPE: PRT
<213> ORGANISM: Artificial
<220> FEATURE:
<223> OTHER INFORMATION: an artificially synthesized sequence

<400> SEQUENCE: 116

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Asp Leu Leu Gly Asp Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Gly Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Arg Pro Ile Glu Lys
325 330 335

Thr Ile Ser Lys Ala Lys Gly Gln Pro Arg Glu Pro Gln Val Tyr Thr
340 345 350

```
Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 117
<211> LENGTH: 447
<212> TYPE: PRT
<213> ORGANISM: Artificial
<220> FEATURE:
<223> OTHER INFORMATION: an artificially synthesized sequence

<400> SEQUENCE: 117

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 118
<211> LENGTH: 447
<212> TYPE: PRT
<213> ORGANISM: Artificial
<220> FEATURE:
<223> OTHER INFORMATION: an artificially synthesized sequence

<400> SEQUENCE: 118

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 119
<211> LENGTH: 447
<212> TYPE: PRT
<213> ORGANISM: Artificial
<220> FEATURE:
<223> OTHER INFORMATION: an artificially synthesized sequence

<400> SEQUENCE: 119

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 120
<211> LENGTH: 447
<212> TYPE: PRT
<213> ORGANISM: Artificial
<220> FEATURE:
<223> OTHER INFORMATION: an artificially synthesized sequence

<400> SEQUENCE: 120

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30
```

```
His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 121
<211> LENGTH: 447
<212> TYPE: PRT
<213> ORGANISM: Artificial
<220> FEATURE:
<223> OTHER INFORMATION: an artificially synthesized sequence

<400> SEQUENCE: 121

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Asp Leu Leu Gly Gly Asp
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Gly Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Arg Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

```
<210> SEQ ID NO 122
<211> LENGTH: 447
<212> TYPE: PRT
<213> ORGANISM: Artificial
<220> FEATURE:
<223> OTHER INFORMATION: an artificially synthesized sequence

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 123
<211> LENGTH: 447
<212> TYPE: PRT
<213> ORGANISM: Artificial
<220> FEATURE:
<223> OTHER INFORMATION: an artificially synthesized sequence

<400> SEQUENCE: 123

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 124
<211> LENGTH: 447
<212> TYPE: PRT
<213> ORGANISM: Artificial
<220> FEATURE:
<223> OTHER INFORMATION: an artificially synthesized sequence

<400> SEQUENCE: 124

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 125
<211> LENGTH: 447
<212> TYPE: PRT
<213> ORGANISM: Artificial
<220> FEATURE:
<223> OTHER INFORMATION: an artificially synthesized sequence

<400> SEQUENCE: 125

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45
```

```
Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 126
<211> LENGTH: 447
<212> TYPE: PRT

<213> ORGANISM: Artificial
<220> FEATURE:
<223> OTHER INFORMATION: an artificially synthesized sequence

<400> SEQUENCE: 126

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 127
<211> LENGTH: 447
<212> TYPE: PRT
<213> ORGANISM: Artificial
<220> FEATURE:
<223> OTHER INFORMATION: an artificially synthesized sequence

<400> SEQUENCE: 127

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
```

305 310 315 320

Tyr Lys Cys Lys Val Ser Asn Lys Ala Leu Pro Arg Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Glu Ser Leu Ser Leu Ser Pro
435 440 445

<210> SEQ ID NO 128
<211> LENGTH: 447
<212> TYPE: PRT
<213> ORGANISM: Artificial
<220> FEATURE:
<223> OTHER INFORMATION: an artificially synthesized sequence

<400> SEQUENCE: 128

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Asp Leu Leu Gly Gly Asp

```
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Arg Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 129
<211> LENGTH: 447
<212> TYPE: PRT
<213> ORGANISM: Artificial
<220> FEATURE:
<223> OTHER INFORMATION: an artificially synthesized sequence

<400> SEQUENCE: 129

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

-continued

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Tyr Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Asp Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Lys Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```